(12) United States Patent
Dawson et al.

(10) Patent No.: US 8,921,042 B2
(45) Date of Patent: Dec. 30, 2014

(54) TRANSCRIPTIONAL REPRESSION LEADING TO PARKINSON'S DISEASE

(71) Applicant: Valted, LLC, Baltimore, MD (US)

(72) Inventors: Ted M. Dawson, Baltimore, MD (US); Valina L. Dawson, Baltimore, MD (US); Han Seok Ko, Lutherville Timonium, MD (US); Jooho Shin, Ellicott City, MD (US)

(73) Assignee: Valted LLC, Baltimore, MD (US)

(*) Notice: Subject to any disclaimer, the term of this patent is extended or adjusted under 35 U.S.C. 154(b) by 0 days.

(21) Appl. No.: 14/056,409

(22) Filed: Oct. 17, 2013

(65) Prior Publication Data

US 2014/0045921 A1     Feb. 13, 2014

Related U.S. Application Data

(63) Continuation of application No. 13/294,909, filed on Nov. 11, 2011, now Pat. No. 8,603,994.

(60) Provisional application No. 61/412,426, filed on Nov. 11, 2010.

(51) Int. Cl.
| | |
|---|---|
| *C12Q 1/68* | (2006.01) |
| *C12N 5/00* | (2006.01) |
| *C12N 5/02* | (2006.01) |
| *C12P 19/34* | (2006.01) |

(52) U.S. Cl.
USPC ............ 435/6.1; 435/91.1; 435/325; 435/375

(58) Field of Classification Search
USPC .................. 435/6.1, 91.1, 325, 375
See application file for complete search history.

(56) References Cited

PUBLICATIONS

Shin et al. (Cell, 2011 vol. 144:689-702).*

* cited by examiner

*Primary Examiner* — Terra Cotta Gibbs
(74) *Attorney, Agent, or Firm* — Hogan Lovells US LLP

(57) ABSTRACT

Parkinson's disease is caused by the preferential loss of substantia nigra dopamine neurons. A Parkin Interacting Substrate, PARIS (ZNF746) is identified. The levels of PARIS are regulated by the ubiquitin proteasome system via binding to and ubiquitination by the E3 ubiquitin ligase, parkin. PARIS is a KRAB and zinc finger protein that accumulates in models of parkin inactivation and in human brain Parkinson's disease patients. PARIS represses the expression of the transcriptional co-activator, PGC-1α and the PGC-1α target gene, NRF-1 by binding to insulin response sequences in the PGC-1α promoter. Conditional knockout of parkin in adult animals leads to progressive loss of dopamine (DA) neurons that is PARIS dependent. Overexpression of PARIS causes selective loss of DA neurons in the substantia nigra, which is reversed by either parkin or PGC-1α co-expression. The identification of PARIS provides a molecular mechanism for neurodegeneration due to parkin inactivation.

3 Claims, 93 Drawing Sheets
(29 of 93 Drawing Sheet(s) Filed in Color)

US 8,921,042 B2

TRANSCRIPTIONAL REPRESSION LEADING TO PARKINSON'S DISEASE

RELATED APPLICATIONS

This is application is a continuation of U.S. application Ser. No. 13/294,909, filed on Nov. 11, 2011, now U.S. Pat. No. 8,603,994, which claims priority to provisional application No. 61/412,426, filed on Nov. 11, 2010, both of which are hereby incorporated by reference in their entirety.

STATEMENT REGARDING FEDERALLY SPONSORED RESEARCH OR DEVELOPMENT

This invention was made with government support under grant award numbers NS38377, NS048206 and NS051764 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 22, 2014, is named 039321-0003CON_SL.txt and is 58,802 bytes in size.

FIELD OF THE INVENTION

The present invention relates the detection, diagnosis, and treatment of Parkinson's disease and related disorders. More particularly, the present invention relates to isolated polypeptides, isolated polynucleotides, compositions, methods and kits for the detection, diagnosis, and treatment of Parkinson's disease and related disorders. Additionally, the present invention relates to the biochemical factors and biochemistry of the causative agents of Parkinson's disease and related disorders.

BACKGROUND OF THE INVENTION

Parkinson's disease (PD) is a progressive neurodegenerative disorder that is characterized phenotypically by bradykinesia, rigidity, tremor, and neuropsychiatric disturbances (Savitt et al., 2006). Although the cause of PD in the majority of cases is unknown, there are rare familial cases for which the genes have been identified. There are at least sixteen PD associated loci (Gasser, 2007). Mutations in α-synuclein and leucine rich repeat kinase 2 (LRRK2) cause autosomal dominant PD. Four genes have been linked to autosomal recessive PD (AR-PD) and include mutations in parkin, DJ-1, PINK1, and ATP13A2. Investigating the biology of these genes and their mutant protein has provided tremendous insight into the pathogenesis of both familial and sporadic PD (Gasser, 2007; Savitt et al., 2006).

Parkin is an ubiquitin E3 ligase (Shimura et al., 2000; Zhang et al., 2000). In general, PD-associated mutations in parkin lead to loss of its E3 ligase function (Tanaka et al., 2004). Moreover, oxidative, nitrosative, and dopaminergic stress, which play important pathogenic roles in PD, inactivate parkin, suggesting that parkin inactivation may play a role in sporadic PD (Chung et al., 2004; LaVoie et al., 2005; Winklhofer et al., 2003). Thus, substrates of parkin that are subject to proteasomal degradation should accumulate in animal and cellular models of parkin inactivation and AR-PD due to parkin mutations, and also in sporadic PD. There are a diverse array of parkin substrates that has hindered the generation of a consensus in the field on parkin's physiologic function and pathologic role in PD. Moreover, parkin's ability to mono- and poly-ubiquitinate, as well as, ubiquitinate proteins with both lysine-48 and lysine-63 chains has made it difficult to reconcile a common biochemical pathway for parkin's role in PD (Dawson and Dawson, 2010).

A new Parkin Interacting Substrate, PARIS, has been identified, which provides a molecular mechanism for neurodegeneration due to parkin inactivation in PD. Parkin regulates the levels of PARIS via the ubiquitin proteasome system (UPS). PARIS is a major transcriptional repressor of peroxisome proliferator-activated receptor gamma (PPARγ) coactivator-1α (PGC-1α) expression and that conditional knockout (KO) of parkin in adult mice leads to progressive loss of dopamine (DA) neurons through PARIS overexpression and transcriptional repression of PGC-1α.

SUMMARY OF THE INVENTION

A hallmark of Parkinson's disease (PD) is the preferential loss of substantia nigra dopamine neurons. A new Parkin Interacting Substrate, PARIS (ZNF746), is identified whose levels are regulated by the ubiquitin proteasome system via binding to and ubiquitination by the E3 ubiquitin ligase, parkin. PARIS is a novel KRAB and zinc finger protein that accumulates in models of parkin inactivation and in human PD brain. PARIS represses the expression of the transcriptional co-activator, PGC-1α and the PGC-1α target gene, NRF-1 by binding to insulin response sequences in the PGC-1α promoter. Conditional knockout of parkin in adult animals leads to progressive loss of dopamine (DA) neurons that is PARIS dependent. Moreover overexpression of PARIS leads to the selective loss of DA neurons in the substantia nigra, which is reversed by either parkin or PGC-1α co-expression. The identification of PARIS provides a molecular mechanism for neurodegeneration due to parkin inactivation.

Applications of the disclosed discoveries include the testing for elevated levels of PARIS or reduced levels of PGC-1α and NRF-1 as a diagnostic test in Parkinson's disease. Any bodily fluid (e.g. urine, blood, cerebra-spinal fluid and brain) or tissue could be tested by measuring protein and/or mRNA levels of PARIS, PGC-1α and NRF-1, or their metabolites.

PARIS can be used to identify small molecule inhibitors to treat Parkinson's disease and related disorders. Additionally, PARIS can be used to identify small molecule inhibitors that leave unaffected other important regulatory signaling of PGC-1α that is PARIS independent.

Reporter constructs for PGC-1α (pGL3-h PGC-1α) are repressed by PARIS. Plus, SK-SHSY cell lines are created to stably express PARIS and pGL3-h PGC-1α and GL3-h PGC-1α alone to be used to screen for PARIS inhibitors.

In vitro and in vivo models of PARIS overexpression and Parkin inactivation can be used to validate and optimize the PARIS inhibitors. The disclosed experiments demonstrate the functions of PARIS, which enables the selection of inhibitors. Positive results will identify the molecules for biologic assays to confirm and characterize PARIS inhibitors and to determine their effect on neuronal viability in models of Parkinson's disease.

Short hair-pin RNA (shRNA) and anti-sense microRNA inhibitors of PARIS can be used to treat Parkinson's disease and Parkinson's disease related disorders.

Inhibitors of PARIS will have broad therapeutic potential on neurodegenerative and related neurologic diseases. Essentially any indication that has been touted for PPARγ agonists or PGC-1α activators will be targets of PARIS inhibition. Some of the neurodegenerative and related neurologic diseases are Alexander's disease, Alper's disease, Alzheimer's disease, amyotrophic lateral sclerosis, ataxia telangiectasia, Batten disease, bovine spongiform encephalopathy, Canavan disease, Cockayne syndrome, corticobasal degeneration, Creutzfeldt-Jakob disease, Huntington's disease, HIV associated dementia, Kennedy's disease, Krabbe's disease, lewy body dementia, Machado-Joseph disease, multiple sclerosis, multiple system atrophy, narcolepsy, neuroborreliosis, Parkinson's disease, Pelizaeus-Merzbacher Disease, Pick's disease, primary lateral sclerosis, prion diseases, Refsum's disease, Sandhoff's disease, Schilder's disease, subacute combined degeneration of spinal cord secondary to pernicious anemia, schizophrenia, spinocerebellar ataxia, spinal muscular atrophy, Steele-Richardson-Olszewski disease, and tabes dorsalis.

Additionally, inhibitors of PARIS will enable the treatment of a broad spectrum of diseases and disorder. These include:

metabolic disorders, such as, diabetes mellitus, dyslipidemia, and obesity;

atherosclerosis, cardiovascular disease, and cardiac ischemia;

inflammatory conditions, such as, inflammatory bowel diseases, colitis and psoriasis;

cancer;

kidney disease, including glomerulonephritis, glomerulosclerosis and diabetic nephropathy;

mitochondrial disorders;

muscle disorders, including muscular dystrophies and disorders of circadian rhythms and sleep.

BRIEF DESCRIPTION OF THE DRAWINGS

The patent of application file contains at least one drawing executed in color. Copies of this patent or patent application publication with color drawing(s) will be provided by the Office upon request and payment of the necessary fee.

FIG. 29—10 μM MG-132 increases PARIS steady state levels compared to DMSO control. Bottom panel, relative PARIS levels normalized to β-actin, n=3. [mean±S.E.M., $*p<0.05$, $p<0.01$ and $*p<0.001$, Student's t-test].

FIG. 70 discloses the full-length sequence as SEQ ID NO: 154.

FIGS. 2, 85-89, 93 and 94 illustrate introduction of AAV1-Parkin or Lenti-PGC-1α in mice SN protects from AAV1-PARIS-mediated selective dopaminergic neuronal toxicity.

FIGS. 3 and 9-11 illustrate the identification of a novel parkin interacting substrate, PARIS.

FIGS. 4-8 illustrate characterization of PARIS.

FIGS. 12-15 and 17 illustrate Parkin interacts with PARIS.

FIGS. 16 and 18-20 illustrates Protein interaction mapping between parkin and PARIS.

FIGS. 21, 22 and 29-33 illustrate Parkin ubiquitinates and regulates the ubiquitin proteasomal degradation of PARIS.

FIGS. 23-28 illustrate Parkin ubiquitinates PARIS in vitro.

FIGS. 30, 41, 56, 57, 59, 64, 66-68, 74 and 75 illustrate PARIS acts as transcriptional repressor of PGC-1α.

FIGS. 34-37 illustrate PARIS accumulates in AR-PD, sporadic PD and in animal models of parkin inactivation.

FIGS. 38, 43, 44, 76-79 and 84 illustrate identification of PGC-1α and NRF-1 as pathological in vivo targets of accumulated PARIS in PD brain and conditional parkin KO mice.

FIGS. 39, 42, 45-47 and 80-83 illustrate identification of PGC-1α and NRF-1 as in vivo targets of accumulated PARIS in PD brain.

FIGS. 48, 55, 58, 60-63 and 69-72 illustrate PARIS is a transcriptional repressor.

FIGS. 90-92 illustrates lack of degeneration of GABAergic neurons.

DETAILED DESCRIPTION OF THE PREFERRED EMBODIMENTS

Figure 1:
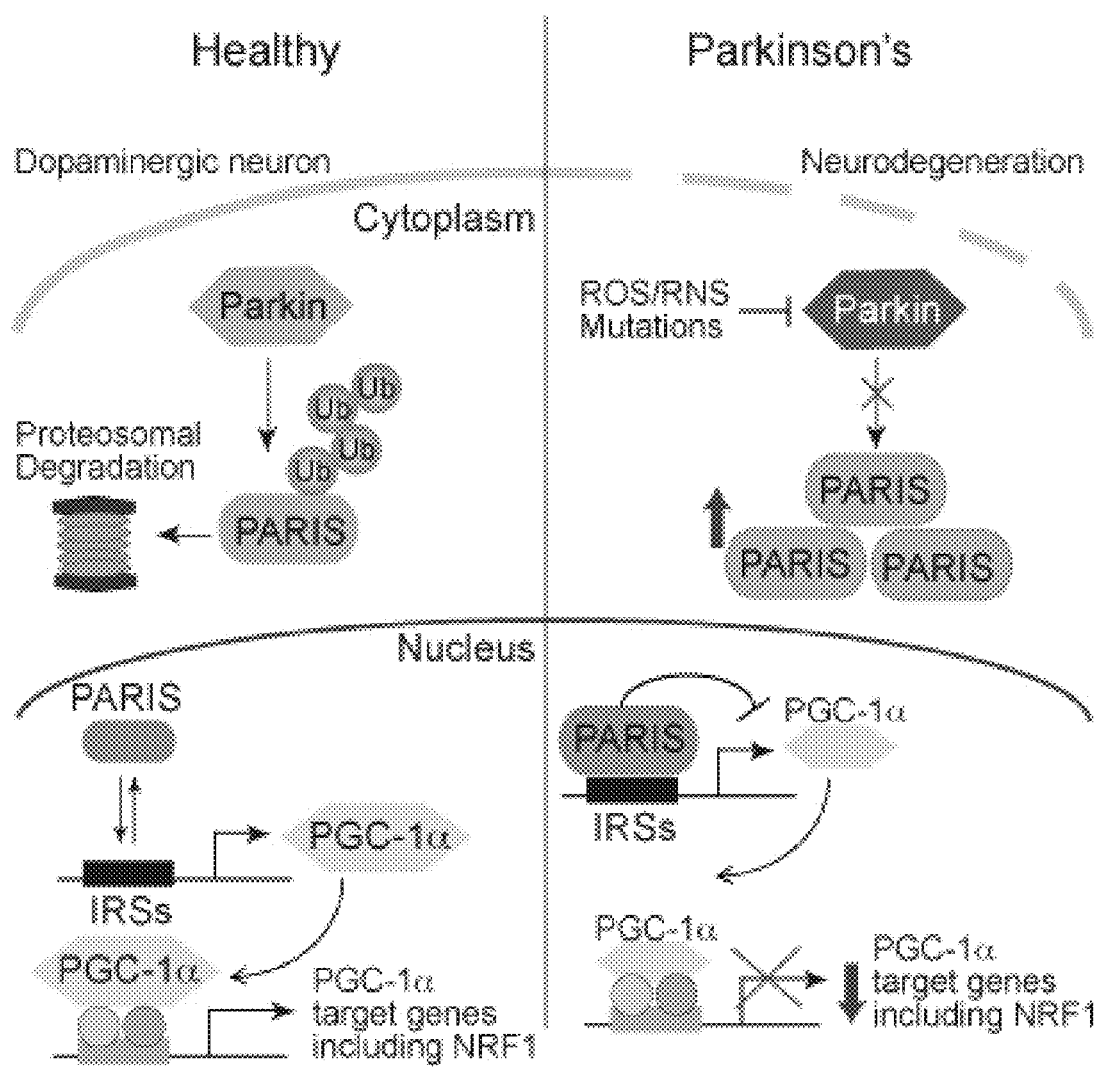
FIG. 1 illustrates a summary of the invention.

In one embodiment the invention is drawn to a method to diagnose Parkinson's disease by testing for an elevated level of PARIS.

In one embodiment the invention is drawn to a method to diagnose Parkinson's disease by testing for an elevated level of PARIS in urine.

In one embodiment the invention is drawn to a method to diagnose Parkinson's disease by testing for an elevated level of PARIS in blood.

In one embodiment the invention is drawn to a method to diagnose Parkinson's disease by testing for an elevated level of PARIS in cerebra-spinal fluid.

In one embodiment the invention is drawn to a method to diagnose Parkinson's disease by testing for an elevated level of PARIS in the brain.

In one embodiment the invention is drawn to a method to diagnose Parkinson's disease by testing for an elevated level of PARIS in a bodily fluid.

In one embodiment the invention is drawn to a method to diagnose Parkinson's disease by measuring a protein level of PARIS.

In one embodiment the invention is drawn to a method to diagnose Parkinson's disease by measuring a protein level of PARIS in urine.

In one embodiment the invention is drawn to a method to diagnose Parkinson's disease by measuring a protein level of PARIS in blood.

In one embodiment the invention is drawn to a method to diagnose Parkinson's disease by measuring a protein level of PARIS in cerebra-spinal fluid.

In one embodiment the invention is drawn to a method to diagnose Parkinson's disease by measuring a protein level of PARIS in the brain.

In one embodiment the invention is drawn to a method to diagnose Parkinson's disease by measuring a protein level of PARIS in a bodily fluid.

In one embodiment the invention is drawn to a method to diagnose Parkinson's disease by testing for an elevated level of a metabolite of PARIS.

In one embodiment the invention is drawn to a method to diagnose Parkinson's disease by testing for an elevated level of a metabolite of PARIS in urine.

In one embodiment the invention is drawn to a method to diagnose Parkinson's disease by testing for an elevated level of a metabolite of PARIS in blood.

In one embodiment the invention is drawn to a method to diagnose Parkinson's disease by testing for an elevated level of a metabolite of PARIS in cerebra-spinal fluid.

In one embodiment the invention is drawn to a method to diagnose Parkinson's disease by testing for an elevated level of a metabolite of PARIS in the brain.

In one embodiment the invention is drawn to a method to diagnose Parkinson's disease by testing for an elevated level of a metabolite of PARIS in a bodily fluid.

In one embodiment the invention is drawn to a method to diagnose Parkinson's disease by measuring a protein level of a metabolite of PARIS.

In one embodiment the invention is drawn to a method to diagnose Parkinson's disease by measuring a protein level of a metabolite of PARIS in urine.

In one embodiment the invention is drawn to a method to diagnose Parkinson's disease by measuring a protein level of a metabolite of PARIS in blood.

In one embodiment the invention is drawn to a method to diagnose Parkinson's disease by measuring a protein level of a metabolite of PARIS in cerebra-spinal fluid.

In one embodiment the invention is drawn to a method to diagnose Parkinson's disease by measuring a protein level of a metabolite of PARIS in the brain.

In one embodiment the invention is drawn to a method to diagnose Parkinson's disease by measuring a protein level of a metabolite of PARIS in a bodily fluid.

In one embodiment the invention is drawn to a method to diagnose Parkinson's disease by measuring level of an mRNA coding for PARIS.

In one embodiment the invention is drawn to a method to diagnose Parkinson's disease by measuring level of an mRNA coding for PARIS in urine.

In one embodiment the invention is drawn to a method to diagnose Parkinson's disease by measuring level of an mRNA coding for PARIS in blood.

In one embodiment the invention is drawn to a method to diagnose Parkinson's disease by measuring level of an mRNA coding for PARIS in cerebra-spinal fluid.

In one embodiment the invention is drawn to a method to diagnose Parkinson's disease by measuring level of an mRNA coding for PARIS in blood the brain.

In one embodiment the invention is drawn to a method to diagnose Parkinson's disease by measuring level of a mRNA coding for PARIS in a bodily fluid.

In one embodiment the invention is drawn to a method to diagnose Parkinson's disease by testing for a reduced level of PGC-1$\alpha$.

In one embodiment the invention is drawn to a method to diagnose Parkinson's disease by testing for a reduced level of PGC-1$\alpha$ in urine.

In one embodiment the invention is drawn to a method to diagnose Parkinson's disease by testing for a reduced level of PGC-1$\alpha$ in blood.

In one embodiment the invention is drawn to a method to diagnose Parkinson's disease by testing for a reduced level of PGC-1$\alpha$ in cerebra-spinal fluid.

In one embodiment the invention is drawn to a method to diagnose Parkinson's disease by testing for a reduced level of PGC-1$\alpha$ in the brain.

In one embodiment the invention is drawn to a method to diagnose Parkinson's disease by testing for a reduced level of PGC-1$\alpha$ in a bodily fluid.

In one embodiment the invention is drawn to a method to diagnose Parkinson's disease by measuring a protein level of PGC-1$\alpha$.

In one embodiment the invention is drawn to a method to diagnose Parkinson's disease by measuring a protein level of PGC-1$\alpha$ in urine.

In one embodiment the invention is drawn to a method to diagnose Parkinson's disease by measuring a protein level of PGC-1$\alpha$ in blood.

In one embodiment the invention is drawn to a method to diagnose Parkinson's disease by measuring a protein level of PGC-1$\alpha$ in cerebra-spinal fluid.

In one embodiment the invention is drawn to a method to diagnose Parkinson's disease by measuring a protein level of PGC-1$\alpha$ in the brain.

In one embodiment the invention is drawn to a method to diagnose Parkinson's disease by measuring a protein level of PGC-1α in a bodily fluid.

In one embodiment the invention is drawn to a method to diagnose Parkinson's disease by measuring level of an mRNA coding for PGC-1α.

In one embodiment the invention is drawn to a method to diagnose Parkinson's disease by measuring level of an mRNA coding for PGC-1α in urine.

In one embodiment the invention is drawn to a method to diagnose Parkinson's disease by measuring level of an mRNA coding for PGC-1α in blood.

In one embodiment the invention is drawn to a method to diagnose Parkinson's disease by measuring level of an mRNA coding for PGC-1α in cerebra-spinal fluid.

In one embodiment the invention is drawn to a method to diagnose Parkinson's disease by measuring level of an mRNA coding for PGC-1α in the brain.

In one embodiment the invention is drawn to a method to diagnose Parkinson's disease by measuring level of an mRNA coding for PGC-1α in a bodily fluid.

In one embodiment the invention is drawn to a method to identify small molecular compound that can be used to treat Parkinson's disease.

In one embodiment the invention is drawn to a method to identify small molecular compound that can be used to treat Parkinson's disease related disorders.

In one embodiment the invention is drawn to a reporter construct for PGC-1α (pGL3-h PGC-1α) that is repressed by PARIS.

In one embodiment the invention is drawn to a SK-SHSY cell line to stably express PARIS and pGL3-h PGC-1α, and GL3-h PGC-1α alone, wherein PARIS and pGL3-h PGC-1α are used to screen for PARIS inhibitors.

In one embodiment the invention is drawn to a method to identify a small molecule inhibitor of PARIS that leave unaffected other regulatory signaling of PGC-1α that is PARIS independent.

In one embodiment the invention is drawn to an in vitro model of PARIS overexpression that can be used to validate a PARIS inhibitor.

In one embodiment the invention is drawn to an in vitro model of PARIS overexpression that can be used to optimize a PARIS inhibitor.

In one embodiment the invention is drawn to an in vivo model of PARIS overexpression that can be used to validate a PARIS inhibitor.

In one embodiment the invention is drawn to an in vivo model of PARIS overexpression that can be used to optimize a PARIS inhibitor.

In one embodiment the invention is drawn to an in vitro model of Parkin inactivation that can be used to validate a PARIS inhibitor.

In one embodiment the invention is drawn to an in vitro model of Parkin inactivation that can be used to optimize a PARIS inhibitor.

In one embodiment the invention is drawn to an in vivo model of Parkin inactivation that can be used to validate a PARIS inhibitor.

In one embodiment the invention is drawn to an in vivo model of Parkin inactivation that can be used to optimize a PARIS inhibitor.

In one embodiment the invention is drawn to a method to select an inhibitor of PARIS by disrupting a function of PARIS.

In one embodiment the invention is drawn to a method to develop a biologic assay to confirm and/or characterize a PARIS inhibitor.

In one embodiment the invention is drawn to a method to determine the effect of a PARIS inhibitor on neuronal viability in models of Parkinson's disease.

In one embodiment the invention is drawn to an isolated nucleotide of SEQ ID NO. 27.

In one embodiment the invention is drawn to an isolated nucleotide of SEQ ID NO. 28.

In one embodiment the invention is drawn to a method of treating Parkinson's disease by administering a shRNA inhibitor.

In one embodiment the invention is drawn to a method of treating Parkinson's disease by administering an anti-sense microRNA inhibitor.

In one embodiment the invention is drawn to a method of treating Parkinson's disease related disorders by administering a shRNA inhibitor.

In one embodiment the invention is drawn to a method of treating Parkinson's disease related disorders by administering an anti-sense microRNA inhibitor.

In one embodiment the invention is drawn to a method of treating neurodegenerative and related neurologic diseases, such as, Alexander's disease, Alper's disease, Alzheimer's disease, amyotrophic lateral sclerosis, ataxia telangiectasia, Batten disease, bovine spongiform encephalopathy, Canavan disease, Cockayne syndrome, corticobasal degeneration, Creutzfeldt-Jakob disease, Huntington's disease, HIV associated dementia, Kennedy's disease, Krabbe's disease, lewy body dementia, Machado-Joseph disease, multiple sclerosis, multiple system atrophy, narcolepsy, neuroborreliosis, Parkinson's disease, Pelizaeus-Merzbacher Disease, Pick's disease, primary lateral sclerosis, prion diseases, Refsum's disease, Sandhoff's disease, Schilder's disease, subacute combined degeneration of spinal cord secondary to pernicious anemia, schizophrenia, spinocerebellar ataxia, spinal muscular atrophy, Steele-Richardson-Olszewski disease, and tabes dorsalis; by administering an inhibitor of PARIS.

In one embodiment the invention is drawn to a method of treating metabolic disorders such as diabetes mellitus, dyslipidemia, and obesity, by administering am inhibitor of PARIS.

In one embodiment the invention is drawn to a method of treating a circulatory disorder, such as, atherosclerosis, cardiovascular disease, and cardiac ischemia, by administering an inhibitor of PARIS.

In one embodiment the invention is drawn to a method of treating inflammatory conditions such as inflammatory bowel diseases, colitis and psoriasis; by administering an inhibitor of PARIS.

In one embodiment the invention is drawn to a method of treating treatment of cancer by administering an inhibitor of PARIS.

In one embodiment the invention is drawn to a method of treating kidney diseases, including glomerulonephritis, glomerulosclerosis and diabetic nephropathy; by administering an inhibitor of PARIS.

In one embodiment the invention is drawn to a method of treating mitochondrial disorders by administering an inhibitor of PARIS.

In one embodiment the invention is drawn to a method of treating muscle disorders, including muscular dystrophies, by administering an inhibitor of PARIS.

In one embodiment the invention is drawn to a method of treating disorders of circadian rhythms and sleep by administering an inhibitor of PARIS.

In one embodiment the invention is drawn to an isolated polypeptide comprising of any of SEQ ID NO: 1 to SEQ ID NO: 4.

In one embodiment the invention is drawn to an isolated polypeptide consisting of any of SEQ ID NO: 1 to SEQ ID NO: 4.

In one embodiment the invention is drawn to an isolated polypeptide comprising a peptide sequence of any of SEQ ID NO: 1 to SEQ ID NO: 4.

In one embodiment the invention is drawn to an isolated polypeptide comprising the peptide sequence of any of SEQ ID NO: 1 to SEQ ID NO: 4.

In one embodiment the invention is drawn to an isolated polypeptide comprising a polypeptide coded by the nucleotide sequence of any of SEQ ID NO: 5 to SEQ ID NO: 136.

In one embodiment the invention is drawn to an isolated polynucleotide comprising of any of SEQ ID NO: 5 to SEQ ID NO: 136.

In one embodiment the invention is drawn to an isolated polynucleotide consisting of any of SEQ ID NO: 5 to SEQ ID NO: 136.

In one embodiment the invention is drawn to an isolated polynucleotide comprising a nucleotide sequence of any of SEQ ID NO: 5 to SEQ ID NO: 136.

In one embodiment the invention is drawn to an isolated polynucleotide comprising the nucleotide sequence of any of SEQ ID NO: 5 to SEQ ID NO: 136.

In one embodiment the invention is drawn to an isolated polynucleotide comprising a polynucleotide encoding the amino acid sequence of any of SEQ ID NO: 1 to SEQ ID NO: 4.

In one embodiment the invention is drawn to an isolated polynucleotide comprising a polynucleotide which hybridizes under stringent conditions to any of SEQ ID NO: 5 to SEQ ID NO: 136.

In one embodiment the invention is drawn to a composition comprising an isolated polypeptide comprising of any of SEQ ID NO: 1 to SEQ ID NO: 4.

In one embodiment the invention is drawn to a composition comprising an isolated polypeptide consisting of any of SEQ ID NO: 1 to SEQ ID NO: 4.

In one embodiment the invention is drawn to a composition comprising an isolated polypeptide comprising a peptide sequence of any of SEQ ID NO: 1 to SEQ ID NO: 4.

In one embodiment the invention is drawn to a composition comprising an isolated polypeptide comprising the peptide sequence of any of SEQ ID NO: 1 to SEQ ID NO: 4.

In one embodiment the invention is drawn to a composition comprising an isolated polypeptide comprising a polypeptide coded by the nucleotide sequence of any of SEQ ID NO: 5 to SEQ ID NO: 136.

In one embodiment the invention is drawn to a composition comprising an isolated polynucleotide comprising of any of SEQ ID NO: 5 to SEQ ID NO: 136.

In one embodiment the invention is drawn to a composition comprising an isolated polynucleotide consisting of any of SEQ ID NO: 5 to SEQ ID NO: 136.

In one embodiment the invention is drawn to a composition comprising an isolated polynucleotide comprising a nucleotide sequence of any of SEQ ID NO: 5 to SEQ ID NO: 136.

In one embodiment the invention is drawn to a composition comprising an isolated polynucleotide comprising the nucleotide sequence of any of SEQ ID NO: 5 to SEQ ID NO: 136.

In one embodiment the invention is drawn to a composition comprising an isolated polynucleotide comprising a polynucleotide encoding the amino acid sequence of any of SEQ ID NO: 1 to SEQ ID NO: 4.

In one embodiment the invention is drawn to a composition comprising an isolated polynucleotide comprising a polynucleotide which hybridizes under stringent conditions to any of SEQ ID NO: 5 to SEQ ID NO: 136.

In one embodiment the invention is drawn to a composition consisting of an isolated polypeptide comprising of any of SEQ ID NO: 1 to SEQ ID NO: 4.

In one embodiment the invention is drawn to a composition consisting of an isolated polypeptide consisting of any of SEQ ID NO: 1 to SEQ ID NO: 4.

In one embodiment the invention is drawn to a composition consisting of an isolated polypeptide comprising a peptide sequence of any of SEQ ID NO: 1 to SEQ ID NO: 4.

In one embodiment the invention is drawn to a composition consisting of an isolated polypeptide comprising the peptide sequence of any of SEQ ID NO: 1 to SEQ ID NO: 4.

In one embodiment the invention is drawn to a composition consisting of an isolated polypeptide comprising a polypeptide coded by the nucleotide sequence of any of SEQ ID NO: 5 to SEQ ID NO: 136.

In one embodiment the invention is drawn to a composition consisting of an isolated polynucleotide comprising of any of SEQ ID NO: 5 to SEQ ID NO: 136.

In one embodiment the invention is drawn to a composition consisting of an isolated polynucleotide consisting of any of SEQ ID NO: 5 to SEQ ID NO: 136.

In one embodiment the invention is drawn to a composition consisting of an isolated polynucleotide comprising a nucleotide sequence of any of SEQ ID NO: 5 to SEQ ID NO: 136.

In one embodiment the invention is drawn to a composition consisting of an isolated polynucleotide comprising the nucleotide sequence of any of SEQ ID NO: 5 to SEQ ID NO: 136.

In one embodiment the invention is drawn to a composition consisting of an isolated polynucleotide comprising a polynucleotide encoding the amino acid sequence of any of SEQ ID NO: 1 to SEQ ID NO: 4.

In one embodiment the invention is drawn to a composition consisting of an isolated polynucleotide comprising a polynucleotide which hybridizes under stringent conditions to any of SEQ ID NO: 5 to SEQ ID NO: 136.

In one embodiment the invention is drawn to a method of treatment for Parkinson's disease, comprising administering a pharmaceutically effective amount of an isolated polypeptide comprising of any of SEQ ID NO: 1 to SEQ ID NO: 4.

In one embodiment the invention is drawn to a method of treatment for Parkinson's disease, comprising administering a pharmaceutically effective amount of an isolated polypeptide consisting of any of SEQ ID NO: 1 to SEQ ID NO: 4.

In one embodiment the invention is drawn to a method of treatment for Parkinson's disease, comprising administering a pharmaceutically effective amount of an isolated polypeptide comprising a peptide sequence of any of SEQ ID NO: 1 to SEQ ID NO: 4.

In one embodiment the invention is drawn to a method of treatment for Parkinson's disease, comprising administering a pharmaceutically effective amount of an isolated polypeptide comprising the peptide sequence of any of SEQ ID NO: 1 to SEQ ID NO: 4.

In one embodiment the invention is drawn to a method of treatment for Parkinson's disease, comprising administering a pharmaceutically effective amount of an isolated polypeptide comprising a polypeptide coded by the nucleotide sequence of any of SEQ ID NO: 5 to SEQ ID NO: 136.

In one embodiment the invention is drawn to a method of treatment for Parkinson's disease, comprising administering a pharmaceutically effective amount of an isolated polynucleotide comprising of any of SEQ ID NO: 5 to SEQ ID NO: 136.

In one embodiment the invention is drawn to a method of treatment for Parkinson's disease, comprising administering a pharmaceutically effective amount of an isolated polynucleotide consisting of any of SEQ ID NO: 5 to SEQ ID NO: 136.

In one embodiment the invention is drawn to a method of treatment for Parkinson's disease, comprising administering a pharmaceutically effective amount of an isolated polynucleotide comprising a nucleotide sequence of any of SEQ ID NO: 5 to SEQ ID NO: 136.

In one embodiment the invention is drawn to a method of treatment for Parkinson's disease, comprising administering a pharmaceutically effective amount of an isolated polynucleotide comprising the nucleotide sequence of any of SEQ ID NO: 5 to SEQ ID NO: 136.

In one embodiment the invention is drawn to a method of treatment for Parkinson's disease, comprising administering a pharmaceutically effective amount of an isolated polynucleotide comprising a polynucleotide encoding the amino acid sequence of any of SEQ ID NO: 1 to SEQ ID NO: 4.

In one embodiment the invention is drawn to a method of treatment for Parkinson's disease, comprising administering a pharmaceutically effective amount of an isolated polynucleotide comprising a polynucleotide which hybridizes under stringent conditions to any of SEQ ID NO: 5 to SEQ ID NO: 136.

In one embodiment the invention is drawn to a method of treatment for Parkinson's disease, comprising administering a pharmaceutically effective amount of a composition comprising an isolated polypeptide comprising of any of SEQ ID NO: 1 to SEQ ID NO: 4.

In one embodiment the invention is drawn to a method of treatment for Parkinson's disease, comprising administering a pharmaceutically effective amount of a composition comprising an isolated polypeptide consisting of any of SEQ ID NO: 1 to SEQ ID NO: 4.

In one embodiment the invention is drawn to a method of treatment for Parkinson's disease, comprising administering a pharmaceutically effective amount of a composition comprising an isolated polypeptide comprising a peptide sequence of any of SEQ ID NO: 1 to SEQ ID NO: 4.

In one embodiment the invention is drawn to a method of treatment for Parkinson's disease, comprising administering a pharmaceutically effective amount of a composition comprising an isolated polypeptide comprising the peptide sequence of any of SEQ ID NO: 1 to SEQ ID NO: 4.

In one embodiment the invention is drawn to a method of treatment for Parkinson's disease, comprising administering a pharmaceutically effective amount of a composition comprising an isolated polypeptide comprising a polypeptide coded by the nucleotide sequence of any of SEQ ID NO: 5 to SEQ ID NO: 136.

In one embodiment the invention is drawn to a method of treatment for Parkinson's disease, comprising administering a pharmaceutically effective amount of a composition comprising an isolated polynucleotide comprising of any of SEQ ID NO: 5 to SEQ ID NO: 136.

In one embodiment the invention is drawn to a method of treatment for Parkinson's disease, comprising administering a pharmaceutically effective amount of a composition comprising an isolated polynucleotide consisting of any of SEQ ID NO: 5 to SEQ ID NO: 136.

In one embodiment the invention is drawn to a method of treatment for Parkinson's disease, comprising administering a pharmaceutically effective amount of a composition comprising an isolated polynucleotide comprising a nucleotide sequence of any of SEQ ID NO: 5 to SEQ ID NO: 136.

In one embodiment the invention is drawn to a method of treatment for Parkinson's disease, comprising administering a pharmaceutically effective amount of a composition comprising an isolated polynucleotide comprising the nucleotide sequence of any of SEQ ID NO: 5 to SEQ ID NO: 136.

In one embodiment the invention is drawn to a method of treatment for Parkinson's disease, comprising administering a pharmaceutically effective amount of a composition comprising an isolated polynucleotide comprising a polynucleotide encoding the amino acid sequence of any of SEQ ID NO: 1 to SEQ ID NO: 4.

In one embodiment the invention is drawn to a method of treatment for Parkinson's disease, comprising administering a pharmaceutically effective amount of a composition comprising an isolated polynucleotide comprising a polynucleotide which hybridizes under stringent conditions to any of SEQ ID NO: 5 to SEQ ID NO: 136.

In one embodiment the invention is drawn to a method of treatment for Parkinson's disease, comprising administering a pharmaceutically effective amount of a composition consisting of an isolated polypeptide comprising of any of SEQ ID NO: 1 to SEQ ID NO: 4.

In one embodiment the invention is drawn to a method of treatment for Parkinson's disease, comprising administering a pharmaceutically effective amount of a composition consisting of an isolated polypeptide consisting of any of SEQ ID NO: 1 to SEQ ID NO: 4.

In one embodiment the invention is drawn to a method of treatment for Parkinson's disease, comprising administering a pharmaceutically effective amount of a composition consisting of an isolated polypeptide comprising a peptide sequence of any of SEQ ID NO: 1 to SEQ ID NO: 4.

In one embodiment the invention is drawn to a composition consisting of an isolated polypeptide comprising the peptide sequence of any of SEQ ID NO: 1 to SEQ ID NO: 4.

In one embodiment the invention is drawn to a method of treatment for Parkinson's disease, comprising administering a pharmaceutically effective amount of a composition consisting of an isolated polypeptide comprising a polypeptide coded by the nucleotide sequence of any of SEQ ID NO: 5 to SEQ ID NO: 136.

In one embodiment the invention is drawn to a method of treatment for Parkinson's disease, comprising administering a pharmaceutically effective amount of a composition consisting of an isolated polynucleotide comprising of any of SEQ ID NO: 5 to SEQ ID NO: 136.

In one embodiment the invention is drawn to a method of treatment for Parkinson's disease, comprising administering a pharmaceutically effective amount of a composition consisting of an isolated polynucleotide consisting of any of SEQ ID NO: 5 to SEQ ID NO: 136.

In one embodiment the invention is drawn to a method of treatment for Parkinson's disease, comprising administering a pharmaceutically effective amount of a composition consisting of an isolated polynucleotide comprising a nucleotide sequence of any of SEQ ID NO: 5 to SEQ ID NO: 136.

In one embodiment the invention is drawn to a method of treatment for Parkinson's disease, comprising administering a pharmaceutically effective amount of a composition consisting of an isolated polynucleotide comprising the nucleotide sequence of any of SEQ ID NO: 5 to SEQ ID NO: 136.

In one embodiment the invention is drawn to a method of treatment for Parkinson's disease, comprising administering a pharmaceutically effective amount of a composition consisting of an isolated polynucleotide comprising a polynucleotide encoding the amino acid sequence of any of SEQ ID NO: 1 to SEQ ID NO: 4.

In one embodiment the invention is drawn to a method of treatment for Parkinson's disease, comprising administering a pharmaceutically effective amount of a composition consisting of an isolated polynucleotide comprising a polynucleotide which hybridizes under stringent conditions to any of SEQ ID NO: 5 to SEQ ID NO: 136.

In one embodiment the invention is drawn to a kit comprising at least one isolated polynucleotide selected from the group consisting of sequences SEQ ID NO: 5 to SEQ ID NO: 136 and instructions on their use.

In one embodiment the invention is drawn to a kit comprising at least one isolated polypeptide selected from the group consisting of sequences SEQ ID NO: 1 to SEQ ID NO: 4 and instructions on their use.

In one embodiment the invention is drawn to a kit comprising a composition of at least one isolated polypeptide selected from the group consisting of sequences SEQ ID NO: 1 to SEQ ID NO: 4 and instructions on their use.

In one embodiment the invention is drawn to a kit comprising a composition of at least one isolated polynucleotide selected from the group consisting of sequences SEQ ID NO: 5 to SEQ ID NO: 136 and instructions on their use.

Other Embodiments

It is to be understood that while the invention has been described in conjunction with the detailed description thereof, the foregoing description is intended to illustrate and not limit the scope of the invention, which is defined by the scope of the appended claims. For example, although the above description relates to human cells, various aspects of the invention might also be applied to cells from other mammals by making appropriate modifications to the described methods. Other aspects, advantages, and modifications are within the scope of the following claims.

DETAILED DESCRIPTION OF THE INVENTION

PARIS (ZNF746) is a Novel Parkin Substrate

PARIS fulfilled several criteria for a parkin substrate and in the absence of parkin activity in PD it accumulated making it an attractive pathogenic substrate (FIG. 1). In sporadic PD, PARIS only accumulated in the striatum and SN. The selective inactivation of parkin in the striatum and SN in sporadic PD through nitrosative and dopaminergic stress and c-Abl phosphorylation most likely accounted for the accumulation of PARIS. Similarly, in parkin exon 7 KO mice, PARIS was only upregulated in the striatum and SN. However, PARIS accumulated in the cingulate cortex of AR-PD brains, suggesting that parkin regulated the expression of PARIS outside the striatum and SN. The lack of an upregulation in the cortex of parkin exon 7 mice, suggested differential and selective regulatory mechanisms in the cortex versus the striatum and SN.

PARIS is a Novel Transcriptional Repressor of PGC-1α

PARIS is a member of the family of KRAB zinc-finger proteins (KRAB-ZFPs) transcriptional repressors. Homologues of PARIS exist in simpler organisms suggesting that PARIS function may be evolutionarily conserved. PARIS seemed to bind exclusively to IRS/PLM motifs, which provided an important site of regulation of a variety of IRS/PLM responsive proteins. PGC-1α levels were revealed as potently and selectively regulated by PARIS, consistent with the observation that PGC-1α transcription was controlled by IRS/PLM motifs. In PD SN and striatum and conditional parkin KO midbrain, PGC-1α was the only IRS/PLM regulated gene that was downregulated suggesting that PARIS selectively repressed PGC-1α expression in PD.

Notably PARIS was a physiological transcriptional repressor of PGC-1α, which directly and endogenously occupied the cis-regulatory elements of PGC-1α. PGC-1α was a transcriptional co-activator that controlled the transcription of many genes involved in cellular metabolism including mitochondrial biogenesis and respiration and ROS metabolism. The levels of PGC-1α dependent genes were controlled in large part by the nature and composition of the PGC-1α transcriptional co-activator complex. The PGC-1α dependent gene, NRF-1, appeared to be particularly susceptible to the inhibitory effects of PARIS.

It was likely that there was not only a PARIS transcriptional repressor protein complex that played important regulatory roles in PARIS-mediated transcriptional repression and specificity but the repression of PARIS relied on the genomic context rather than simple IRS motif. In addition, under certain contexts it appeared as though PARIS could act a transcriptional activator. Consistent with this notion were observations that PARIS bound the PEPCK or G6Pase endogenous promoters via ChIP and it had no effect on G6Pase promoter-reporter activity, but enhanced PEPCK promoter-reporter activity. DNA response elements could function as allosteric effectors that determined the transcriptional activity of regulators, explaining that regulators may activate transcription in the context of one gene, yet repress transcription in another. Indeed, the IRS motifs in the PGC-1α promoter were organized differently then the IRS motifs of the PEPCK and G6Pase promoters, which may, in part accounted for the ability of PARIS to act as both as a repressor and activator. Other IRS/PLM responsive genes were likely regulated by PARIS.

Dopaminergic Degeneration in Conditional Parkin KO Mice

Germline deletion of parkin using a variety of approaches created parkin KO mice with minimal phenotypes and no loss of DA neurons. A number of reasons have been put forward regarding the lack of overt degeneration of DA neurons in genetic animal models of PD including compensatory mechanisms. Similar compensatory mechanisms likely to occur in PD, and compensation accounts, in part, for the age-dependence of PD. The ultimate failure of these compensatory mechanisms contributes to neurodegeneration.

Since, germline parkin exon 7 KO mice did not have degeneration of DA neurons, conditional parkin exon 7 KO mice were generated and deleted parkin from adult mice to avoid developmental compensation. Similar to germline deletion of parkin, embryonic deletion of glial-cell-line-derived neurotrophic factor (GDNF) had no deleterious effects on DA neurons. However, conditional KO of GDNF in adult animals using a tamoxifen sensitive Cre-Lox recombination unmasked the "true physiologic action of GDNF" and led to mice with profound degeneration of catecholaminergic neurons, indicating that developmental compensation could be overcome by deleting genes in the DA system in adulthood. Similar to the adult GDNF deleted mice; progressive loss of DA neurons was observed when parkin was deleted in adult mice. PARIS levels increased in parkin conditional KO mice similar to levels in AR-PD brain and in sporadic PD SN. Accompanying the upregulation of PARIS was downregulation of PGC-1α and NRF in conditional KO mice similar to the downregulation in sporadic PD striatum and SN. Consistent with the notion that compensation occurred in the germline parkin KO mice was the observation that PARIS was only modestly elevated and there was no alteration in the levels of PGC-1α and NRF and there was no loss of DA neurons.

Parkin, PARIS, PGC-1α and Neurodegeneration

It was not certain that PARIS was the sole substrate or mechanism that contributed to DA neuron degeneration following parkin inactivation. Studies suggested that PINK1 in a mitochondrial membrane potential-dependent manner signaled and recruited parkin from the cytoplasm to the mitochondria to initiate degradation of damaged mitochondria through autophagy (mitophagy). Since PGC-1α and NRF-1 were major transcriptional regulators of mitochondrial biogenesis, it was conceivable that when parkin decreased the number of mitochondria through mitophagy in response to mitochondrial damage, it was counter balanced by downregulation of PARIS levels as a homeostatic mechanism to increase mitochondrial size and number through regulation of PGC-1α and NRF-1 levels. The contribution of other parkin substrates that were regulated by the UPS and accumulate in AR-PD, sporadic PD and models of parkin inactivation, such as the aminoacyl-tRNA synthetase interacting multifunctional protein type 2 (AIMP2) also known as p38/JTV-1 and far upstream element-binding protein 1 (FBP-1), as well as, others were not known. PARIS upregulation was necessary and sufficient to cause DA neuron degeneration in models of parkin inactivation and that maintaining PGC-1α function was beneficial. PGC-1α had been implicated in other models of PD. Moreover, PGC-1α-responsive genes were underexpressed in microdissected dopaminergic neurons of PD suggesting that the alteration of PGC-1α was a cause of PD pathogenesis, not the consequence.

Figure 2:
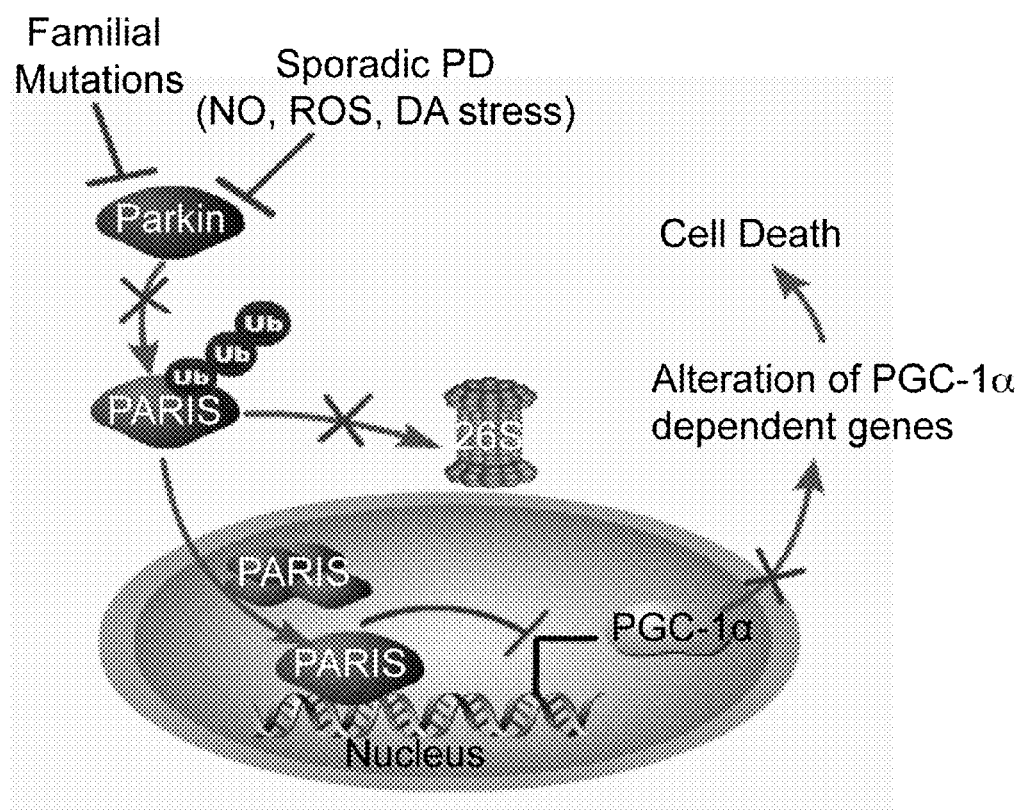
FIG. 2—Parkin-PARIS-PGC-1α pathway as a model in PD. Endogenous PARIS acts to maintain the balance of PGC-1α levels. In PD, parkin is inactivated by diverse insults, such as, familial mutations, reactive oxygen species (ROS), nitrosative (NO) and dopamine (DA) stress and PARIS accumulates. Accumulated PARIS continuously inhibits PGC-1α transcription leading to reduction in PGC-1α dependent genes. Ultimately this situation results in neurodegeneration in PD. [mean±S.E.M. *p<0.05, p<0.01, *p<0.001; ANOVA with the Student-Newman-Keuls post hoc test].

A model was developed that accumulated PARIS in the setting of parkin's inactivation repressed PGC-1α expression leading to neurodegeneration. Consistent with this model were the observations that the reduction in PGC-1α levels and neurodegeneration were substantially reduced by knocking down PARIS levels in the setting of parkin inactivation. Since PARIS was likely regulated other genes, the Parkin-PARIS-PGC-1α was one potential contributory mechanism to PD pathogenesis. This parkin-PARIS-PGC-1α neurodegenerative pathway ultimately resulted in the selective vulnerability of dopamine neurons and accounted, in part, for the neurodegeneration in PD (FIG. 2). The results suggested that parkin inactivation acting through PARIS and downregulation of PGC-1α contributed to the pathogenesis of PD.

EXPERIMENTS

Experiment Methods

Yeast Two-Hybrid Screening

*Saccharomyces cerevisiae* MaV203 was transformed with pDBLeu-R1-parkin, and 3×10$^6$ stable transformants were further transformed with 15 µg of pPC86 human brain cDNA library (Life Tech/Gibco). Transformants were selected and confirmed according to the manufacturer's instructions as previously described (Zhang et al., 2000).

Antibodies

Polyclonal PARIS antibodies were generated. Primary antibodies used include the following: goat anti-PGC-1α (K-15, Santa Cruz Biotechnology), mouse anti-PGC-1α (4C1.3, Calbiochem), goat anti-NRF1 (A-19, Santa Cruz Biotechnology), rabbit anti-NRF1 (ab34682, Abcam), mouse anti-parkin (Park8, Cell Signaling), rabbit anti-TH (Novus Biologicals), rabbit anti-glutamate decarboxylase (GAD) 65&67 (Millipore), rabbit anti-GFP (ab661, Abcam), mouse anti-GFP (ab1218, Abcam); Secondary antibodies used include Biotin-SP-conjugated goat anti-rabbit (Jackson ImmunoResearch lab), donkey anti-goat-Cy3, donkey anti-rabbit-Cy2/Cy3, donkey anti-mouse-Cy2 for immunostaining.

Plasmid Constructions

Full-length parkin, and deletion mutants, Q311X, R42P, R275W, G430D and C431F parkin, HA-ubiquitin, PARIS, PARIS deletion and point mutations, GST-PARIS, ZNF398 vector were constructed. Construct integrity was verified by sequencing. Lentiviral pLV-PGC-1α plasmid was kindly provided by Dr. Dimitri Krainc (Massachusetts General Hospital, Harvard Medical School, Charlestown, USA), MYC-tagged XIAP was generously given from Dr. Kenny K. K. Chung (Hong Kong University of Science and Technology, Clear Water Bay, Hong Kong).

Cell Culture and Transfection

Human neuroblastoma SH-SY5Y cells (ATCC, Manassas, Va.) were grown in DMEM containing 10% FBS and antibiotics in a humidified 5% $CO_2$/95% air atmosphere at 37° C. For transient transfection, cells were transfected with indicated amounts of target vector using Lipofectamine Plus (Invitrogen), according to manufacturer's instructions. For co-immunoprecipitation from cell cultures, SH-SY5Y cells were transfected with 2 µg of each plasmid, unless otherwise indicated. For the ubiquitination assay, SH-SY5Y cells were transiently transfected with 2 µg of pRK5-Myc-tagged parkin, Myc-tagged parkin (C431F, G430D, R275W, and Q311X) pCMV-FLAG-PARIS, and 2 µg of pMT123-HA-ubiquitin plasmids for 48 hours. For the luciferase assay SH-SY5Y cells were transiently transfected with pCMV-empty vector or pCMV-FLAG-PARIS with either wild type or Q311X parkin, or pGL3-Basic, pGL3-PGC-1α promoter-Luciferase, or pGL3-PGC-1α promoter deletion mutant (a gift from Akyoshi Fukamizu, University of Tsukuba, Japan) (Daitoku et al., 2003) for firefly Luciferase assay and 0.1 µg pRL-TK vector (Promega) for *Renilla* luciferase control.

Immunocytochemistry and Immunoblot Analysis

Immunocytochemistry and immunoblot analysis was performed.

In Vitro Interaction and Ubiquitination Assays

GST-PARIS and His-Parkin were used in in vitro interaction and ubiquitination assays.

CAST, EMSA, ChIP, qRT-PCR Assays

A previously published protocol with modification for CAST ((Cyclic Amplification and Selection of Targets) (Voz et al., 2000) was used. GST, GST-PARIS and GST-0571A-PARIS were used for electrophoretic mobility shift assays (EMSA). Chromatin immunoprecipitation was carried out according to the manufacturer's instruction. Primers used for real-time pRT-PCR are listed in Table 4.

Conditional Parkin Knockout

A lentiviral vector expressing GFP fused Cre recombinase (Lenti-GFPCre) was stereotaxically introduced into exon 7 floxed parkin mice (parkin$^{Flx/Flx}$) to generate Cre-flox conditional model of parkin knock out. Furthermore lentiviral shRNA-PARIS was co-administered along with Lenti-GFPCre to demonstrate whether the changes in PGC-1α and NRF-1 are due to PARIS.

Antibodies

A peptide containing amino acids 572 to 590 [GKS-FIRKDHLRKHQRNHAA] (SEQ ID NO. 1) was generated from the C-terminal region and cross-linked to keyhole limpet hemocyanin to generate a peptide antigen of PARIS. The conjugated peptide was used to immunize a New Zealand white rabbit (JH 786-789) (Cocalico Biologicals). Antisera were purified by affinity chromatography using the same peptide immobilized on SulfoLink gel matrix (Pierce), according to manufacturer's protocol. The quality of antibody against PARIS is shown in FIGS. 3-8.

Database Searching

Full-length PARIS sequence of human (Accession: □6NUN9) [SEQ ID NO. 2], mouse (Accession: XP_909399) [SEQ ID NO. 3] and rat (Accession: XP_231752) [SEQ ID NO. 4] were obtained from NCBI (http://www.ncbi.nlm.nih.gov/) and entered as a query for multiple alignment search (ClustalW, http://www.ebi.ac.uk/Tools/clustalw2/). Jalview (http://www.jalview.org/) was used for color-coding editing of multiple alignments. Phylogenetic comparison was performed in ClustalW.

Northern Blot Analysis

A multiple human tissue Northern blot (Clontech) was hybridized using the PARIS cDNA probe (Y2H clone) labeled with DIG-DNA Labeling Mixture (Roche Diagnostics). Hybridization and washing were performed according to manufacturer's instructions, and the PARIS mRNA was detected using a DIG Luminescent Detection Kit (Roche Diagnostics). Levels of PARIS mRNA were normalized to GAPDH.

Plasmid Constructions

Full-length, deletion mutants, Q311X, R42P, R275W, G430D and C431F parkin were cloned into pRK5-MYC vector, and full-length HA-ubiquitin was cloned into pRK5-HA vector as described previously (Chung et al., 2001; Zhang et al., 2000). Full-length parkin and truncations encoding amino acids 1-198 (UBL-SH) and 220-465 (R1-IBR-R2) were cloned into pRK5-HA vector between SalI and NotI sites. Full-length PARIS cDNA (IMAGE: 30347892; Open Biosystems) was cloned into the mammalian expression vector pCMV-Tag2A (Stratagene) between EcoRI and XhoI sites. PARIS cDNA sequences encoding amino acids 1-322, 322-644, and 1-164 were cloned into pCMV-Tag2A vector between EcoRI and XhoI sites to generate PARIS truncations. For the ZNF398 vector, its cDNA was amplified with EcoRI or XhoI site-flanked primers and inserted into pCMV-Tag2A vector. The sequences were confirmed by automated DNA sequencing.

Site-Directed Mutagenesis

The expression plasmid, pEGFP-PARIS mutants was generated using a QuikChange site-directed mutagenesis kit (Stratagene). The sequences were confirmed by automated DNA sequencing. Primers used are listed on Table 6.

Purification of GST-PARIS Recombinant Proteins

Full-length PARIS (a.a. 1-644) and PARIS zinc finger domain (ZFD) (a.a. 453-589) cDNA were PCR-amplified from pCMV-Tag2A-PARIS plasmid and cloned into pGEX-6P-1 vector (GE Healthcare). The sequences were confirmed by automated DNA sequencing. The plasmids were transformed to BL21 pLys, which were then grown in the presence of 0.1 mM IPTG for 4 hours at 30° C. Cells were lysed by sonication in a TNE buffer (10 mM Tris-HCl, pH 7.4, 200 mM NaCl, 1 mM EDTA) containing 0.1% Triton X-100 and protease inhibitors and finally centrifuged at 14,000 rpm for 30 min at 4° C. After centrifugation, the supernatant was recovered, and the GST-PARIS and GST-PARIS-ZFD were purified with glutathione Sepharose 4B (GE Healthcare). The GST protein was also prepared as a control. The purity and quantity of GST-PARIS and GST-PARIS-ZFD were analyzed by SDS-PAGE with a well-defined BSA concentration standard.

In vitro Interaction Assay 0.2 µg of GST or GST-PARIS was incubated for 1 hour at 4° C. with 20 µl of glutathione-sepharose beads, respectively for in vitro protein-protein interaction assays. After washing, GST or GST-PARIS conjugated beads were resuspended in 100 µl binding buffer (20 mM Tris-HCl, pH 8.0, 100 mM NaCl, 1 mM EDTA, 1% NP-40, 0.1% SDS) including the protease inhibitor cocktail (Roche), and incubated for 2 hrs at 4° C. with the His-Parkin (Boston Biochem). After extensive washing, retained proteins were eluted by boiling in SDS protein loading buffer and analyzed by immunoblotting using anti-GST and anti-PARIS antibodies.

In vitro Ubiquitination Assay

GST-PARIS, E1 (50 nM) and different E2s (UbcHs) (50 nM) were incubated with His-tagged parkin (100 nM) in presence or absence of ChIP at 37° C. in reaction buffer containing 50 mM Tris-Cl, pH 7.5, 2.5 mM $MgCl_2$, 2 mM DTT, 2 mM ATP. For reducing conditions, samples were treated with SDS sample buffer and the boiled supernatants were separated by 8-16% gradient SDS-PAGE. Both polymerized ubiquitin chains and ubiquitinated proteins were detected by immunoblot with anti-ubiquitin (DAKO), anti-ubiquitin, K48-specific (Apu2, Millipore), anti-ubiquitin, K63-specific (Apu3, Millipore), anti-ubiquitin, K63-specific (HWA4C4, Millipore), and anti-PARIS antibody. Recombinant E1, UbcHs and ubiquitin were purchased from Calbiochem. GST-PARIS was purified from *Escherichia coli* strain, BL21 pLys (Stratagene).

Co-immunoprecipitation

SH-SY5Y cells were transfected with 2 µg of each plasmid, unless otherwise indicated, for co-immunoprecipitation from cell cultures. After 48 hours, cells were washed with cold PBS and harvested in immunoprecipitation buffer (1% Triton X-100, 2 µg/ml aprotinin, and 100 µg/ml PMSF in PBS). The lysate was then rotated at 4° C. for 1 hour, followed by centrifugation at 14,000 rpm for 20 min. The supernatants were then combined with 50 µl of protein G Sepharose (Amersham Biosciences) preincubated with antibodies against FLAG or MYC (Sigma; Roche, Indianapolis, Ind.), followed by rotating at 4° C. for 2 hours. The protein G Sepharose was pelleted and washed three times using immunoprecipitation buffer or buffer with additional 500 mM NaCl, followed by three washes with PBS. The precipitates were resolved on SDS-PAGE gel and subjected to immunoblot analysis. Immunoblot signals were visualized with chemiluminescence (Pierce, Rockford, Ill.). For co-immunoprecipitation of endogenous proteins from mouse brain, adult human brain was homogenized in lysis buffer [10 mM Tris-HCl, pH 7.4, 150 mM NaCl, 5 mM EDTA, 0.5% Nonidet P-40, 10 mM Na-β-glycerophosphate, Phosphatase Inhibitor Cocktail I and II (Sigma), and Complete Protease Inhibitor Mixture (Roche)], using a Diax 900 homogenizer (Heidolph). The tissue homogenate was incubated on ice for 30 min and mixed twice for complete lysis. The samples were then centrifuged at 52,000 rpm at 4° C. for 20 min. The supernatant was used for immunoprecipitation with one of the following antibodies: mouse or rabbit IgG (mIgG or rIgG), anti-PARIS, or anti-parkin. Immunoprecipitates were separated by SDS-PAGE and subjected to immunoblot analysis with an anti-PARIS or anti-parkin antibody. Immunoblot signals were visualized with chemiluminescence. For mapping of the binding region between parkin and PARIS, MYC- or HA-tagged parkin deletion constructs were transfected with full-length FLAG-PARIS or FLAG-tagged PARIS deletion fragments were co-transfected with full-length parkin. Transfections and co-immunoprecipitation was performed as described above.

Cellular Ubiquitination Assay

SH-SY5Y cells were transiently transfected with 2 µg of pRK5-Myc-tagged parkin or Myc-tagged parkin (C431F, G430D, R275W, and Q311X), pCMV-FLAG-PARIS, and 2 µg of pMT123-HA-ubiquitin plasmids for 48 hours for the ubiquitination assay. Total cell lysates were prepared by harvesting the cells after washing with PBS, followed by solubilizing the pellets in 200 μl of 2% SDS, followed by sonication. The lysates were then rotated at 4° C. for 1 hour, diluted to 1 ml with PBS, and then boiled and sonicated. The samples were used as input and for immunoprecipitation. Immunoprecipitation was performed with an antibody against FLAG. The precipitates were subjected to immunoblotting with anti-HA or anti-FLAG antibodies.

Immunocytochemistry

About 5×10⁴ SH-SY5Y cells or rat cortical neurons were seeded onto polylysine-coated sterile glass cover slips in a 24-well culture plate. After attachment, cells were washed once with PBS and fixed in 3% paraformaldehyde (w/v) for 20 min. The fixed cells were washed three times with PBS before permeabilization in 0.2% (v/v) Triton X-100 in PBS for 5 min. Blocking was then carried out with 5% goat serum in PBS for 1 hour. This was followed by incubation in primary antibodies for 1 hour at 25° C. and secondary antibodies for another hour at 25° C. Immunofluorescent images were acquired on a Carl Zeiss confocal microscope. For immunohistochemistry with mouse brain, animals were perfused with PBS followed by 4% paraformaldehyde. Brains were postfixed with 4% paraformaldehyde, cryoprotected in 30% sucrose. Sagittal or coronal sections were cut throughout the whole brain and sections were reacted with rabbit polyclonal anti-PARIS and visualized with biotinylated goat anti-rabbit IgG, followed by streptavidin-conjugated horseradish peroxidase (HRP) (Vectastain ABC kit, Vector Laboratories). Positive immunostaining was visualized with 3,3'-diaminobenzidine (DAB, Sigma) after reaction with hydrogen peroxide (DAB kit, Vector Laboratories). Stained sections were mounted onto slides and analyzed by Stereo Investigator software (MicroBrightfield).

Preparation of Tissues for Immunoblot

The tissues including nine different organs, eight different brain regions from C57/BL6 mouse, human brain, and mouse brain were homogenized in lysis buffer [10 mM Tris-HCl, pH 7.4, 150 mM NaCl, 5 mM EDTA, 0.5% Nonidet P-40, 10 mM Na-β-glycerophosphate, Phosphate Inhibitor Cocktail I and II (Sigma), and Complete Protease Inhibitor Mixture (Roche)], using a Diax 900 homogenizer. After homogenization, samples were rotated at 4° C. for 30 min for complete lysis, then the homogenate was centrifuged at 52,000 rpm for 20 min, and the resulting fractions were collected. Protein levels were quantified using the BCA kit (Pierce) with BSA standards and analyzed by immunoblot. Immunoblotting was performed with an antibody of interest and was performed with chemiluminescence (Pierce). The densitometric analyses of the bands were performed using ImageJ (NIH, http://rsb.info.nih.gov/ij/). Data are expressed as mean±S.E.M. The results were evaluated for statistical significance by applying the unpaired two-tailed Student's t-test or Student-Newman-Keuls. Differences were considered significant when $p<0.05$.

Luciferase Assay

SH-SY5Y cells were transiently transfected with pCMV-empty vector or pCMV-FLAG-PARIS with either wild type or Q311X parkin. In addition, each well was co-transfected with pGL3-Basic, pGL3-PGC-1α promoter-Luciferase, -pGL3-PGC-1α promoter deletion mutant (a gift from Akyoshi Fukamizu, University of Tsukuba, Japan) (Daitoku et al., 2003), pGL3 Hygro-rat PEPCK, pGL3 MOD-mouse G6Pase (kindly provided by Richard O'Brien, Vanderbilt University, USA) (Boustead et al., 2003) for firefly Luciferase assay and 0.1 μg pRL-TK vector (Promega) for *Renilla* luciferase control. Cells were harvested 48 hours post-transfection and lysates were assayed sequentially for firefly and *Renilla* luciferases, using the Dual-Luciferase Reporter Assay System (Promega) with a Monolight 3010 luminometer (Analytical luminescence Lab), according to the manufacturer's instructions. Firefly luciferase readings were normalized to *Renilla* readings.

CAST (Cyclic Amplification and Selection of Targets)

The published protocol with modification by Voz et al. (2000) was used. Oligonucleotides containing random 26 nucleotides (CAST26-CTGTCGGAATTCGCTGACGT-(N) 26-CGTCTTATCGGATCCTACGT) [SEQ ID NO. 5] were used for generation of random double-strand oligomers for the first round of CAST, 400 pmol of CAST26 were applied into 100 μl of PCR buffer containing 1 μmol of CAST-C (ACGTAGGATCCGATAAGACG) [SEQ ID NO. 6], 200 μM dNTP, and 10 units of Taq (Invitrogen) and incubated as follows: 5 min at 94° C., 20 min at 65° C., and 20 min at 72° C. Fifty μl of random double-strand oligomers were subjected to pull-down with GST-ZF-PARIS (322-644 a.a.) bound to Glutathione Sepharose beads in mixture of 50 μg of BSA and 50 μg of poly polydeoscyinosinic-deoscycytidylic acid (Sigma) in 500 μl of binding buffer containing 10 mM Tris (pH 7.5), 200 mM NaCl, 10% glycerol, 50 mM $ZnCl_2$, 1 mM $MgCl_2$, and 1 mM DTT. The oligonucleotides were extracted from the beads by applying 100 μl of distilled $H_2O$, followed by phenol extraction and ethanol precipitation. An elute was used for the subsequent PCR in the presence of 200 pmol of each primer CAST-N (CTGTCGGAATTCGCTGACG) [SEQ ID NO. 7] and CAST-C with 25 cycles of 1 min at 94° C., 1 min at 65° C., and 1 min at 72° C. After four rounds of selection were done, an additional three rounds of selection were performed by EMSA. An eluate from 4th round CAST was amplified with 1 μl of [α-$^{32}$P]-dCTP (GE Healthcare), incubated with GST-ZF-PARIS, loaded on PAGE. DNA was extracted from the shifted band on EMSA and subsequently used for a second round of selection performed as described above. Following a total of seven selections, oligomers were cloned into the pGEM-T Easy vector according to the manufacturer's protocol (Promega). Twenty-four independent clones were sequenced and 19 clones were identifiable. Among 19 clones, 3 clones were duplicated and the final 16 clones were aligned with MACAW software (NCBI, http://iubio.bio.indiana.edu/soft/molbio/ncbi/old/macaw/).

Cyclic amplification and selection of targets (CASTing) is essentially identical to the selected and amplified (protein) binding site oligonucleotide (SAAB) and target detection assay (TDA) procedures; a procedure for identification of consensus sequences of DNA to which a protein, e.g. a transcription factor, may bind. A random polynucleotide sequence is synthesized flanked by two defined sequences that will serve as templates for PCR primers; the polynucleotides are exposed to the DNA-binding protein, any complex that is formed is separated from the unliganded polynucleotides (e.g. by gel shift assay, affinity chromatography, filter binding) and the polynucleotide of the complex is isolated and amplified by PCR; repeated recycling through the sequence of ligand formation, selection and amplification results in a preparation that is sufficiently pure to be cloned into bacteria for larger-scale production. A variant is systematic evolution of ligands by exponential enrichment (SELEX) for identification of RNA sequences, which begins with a mixture of polyribonucleotides and in each cycle produces DNA from the selected RNA-protein complex using reverse transcriptase, amplifies it by PCR, and then produces new RNA transcripts for the next round of selection.

EMSA

GST, GST-PARIS, and GST-0571A-PARIS were prepared as described above. The different probes for the WT-IRS and Mutant-IRS with mutations in the consensus sequence (underline) were synthesized as followed:

```
IRS1-WT:    986AGTGTGTTGGTATTTTTCCCTCAGTTC960      [SEQ ID NO. 8]

IRS1-MT:    986AGTGTGTTGGTATTGTTCCCTCAGTTC960      [SEQ ID NO. 9]

IRS2-WT:    596ACATACAGGCTATTTTGTTGATTAAAC570      [SEQ ID NO. 10]

IRS2-MT:    596ACATACAGGCTATTGTGTTGATTAAAC570      [SEQ ID NO. 11]

IRS3-WT:    364GCCACTTGCTTGTTTTGGAAGGAAAAT338     [SEQ ID NO. 12]

IRS3-MT:    364GCCACTTGCTTGTTGTGGAAGGAAAAT338     [SEQ ID NO. 13]
```

The complementary probes were annealed in buffer consisting of 100 mM NaCl, 10 mM Tris-Cl (pH 8.0), and 1 mM EDTA, subsequently end-labeled with [γ-$^{32}$P]ATP (GE Healthcare) in present of T4 polynucleotide kinase (Promega), and finally purified with the QIAquick Nucleotide removal kit (Qiagen). Probe-protein binding reactions were performed for 10 min at room temperature in 25 μl of binding buffer consisting of 10 mM Tris (pH 7.9), 4% glycerol, 100 mM KCl, 50 mM $ZnCl_2$, 1 mM DTT, 1 mg polydeoxyadenylic acid-polythymidylic acid (Sigma), and 10 μg of BSA. Probe-protein complexes were analyzed on 5% nondenaturing polyacrylamide gels and electrophoresis was carried out at 4° C.

Chromatin Immunoprecipitation (ChIP)

Chromatin immunoprecipitation was carried out according to manufacturer's instruction (Millipore) with modification. Briefly, powderized brain (mouse and human) was suspended in 1% formaldehyde in PBS for 20 min at room temperature and SH-SY5Y cells were fixed with 1% formaldehyde for 10 min at 37° C. Glycerol quenched samples were lysed in 1 ml of SDS buffer containing protease inhibitors. The lysates were incubated for 10 min on ice and sonicated to shear DNA. The samples were centrifuged at 10,000×g at 4° C. for 10 min and supernatant was taken. Pre-cleared samples were incubated with either PARIS or rabbit IgG (rIgG)-agarose bead followed by a number of washes. Elutes were subjected to reverse cross-linking and DNA was recovered by phenol-chloroform-ethanol purification. PCR was performed using template DNA and the following primers:

```
hPGC-1α promoter
                                                  [SEQ ID NO. 14]
(forward,   5'-ACATACAGGCTATTTTGTTGATTAAAC-3';

[SEQ ID NO. 15])
reverse,    5'-ATTTTCCTTCCAAAACAAGCAAGTGGC-3', hG6Pase promoter
                                                  [SEQ ID NO. 16]
(forward,   5'- GTAGACTCTGTCCTGTGTCTCTGGCCTG-3';

[SEQ ID NO. 17])
reverse,    5'- GGTCAACCCAGCCCTGATCTTTGGACTC-3', hPEPCK promoter
                                                  [SEQ ID NO. 18]
(forward,   5'-GACTGTGACCTTTGACTATGGGGTGACATC-3';

[SEQ ID NO. 19])
reverse,    5'-CTGGATCACGGCCAGGGTCAGTTATGC-3', hGAPDH promoter
                                                  [SEQ ID NO. 20]
(forward,   5'-TACTAGCGGTTTTACGGGCG-3';

[SEQ ID NO. 21])
reverse,    5'-TCGAACAGGAGGAGCAGAGAGCGA-3', mPGC-1α promoter
                                                  [SEQ ID NO. 22]
(forward,   5'-CAAAGCTGGCTTCAGTCACA-3';

[SEQ ID NO. 23])
reverse,    5'-TTGCTGCACAAACTCCTGAC-3',
and mGAPDH promoter
                                                  [SEQ ID NO. 24]
(forward,   5'-TGGGTGGAGTGTCCTTTATCC-3';

[SEQ ID NO. 25])
reverse     5'-TATGCCCGAGGACAATAAGG-3'.
```

Real-Time Quantitative RT-PCR (qRT-PCR)

Total RNA was extracted with Trizol reagent (Invitrogen), and cDNA was synthesized from total RNA (1.5 μg) using a First-strand cDNA synthesis kit (Invitrogen). Aliquots of cDNA were used as templates for real-time qRT-PCR procedure. Relative quantities of mRNA expression were analyzed using real-time PCR (Applied Biosystems ABI Prism 7700 Sequence Detection System, Applied Biosystems). The SYBR greenER reagent (Invitrogen) was used according to the manufacturer's instruction. For microdissected specimens, RNA was extracted with proteinase K/acid phenol method (Khodosevich et al., 2007). To eliminate DNA, dissolved RNA was treated with DNase I (RNase free, Stratagene) for 15 min at 37° C. and purified by RNeasy kit (Qiagen). RNA was directly used for qRT-PCR according to the manufacturer's instruction (QuantiTect SYBR Green RT-PCR kit, Qiagen). The primer sequences are listed in Table 4.

AAV1-Plasmid Construction and Generation of AAV1 Virus cDNAs for PARIS and parkin were sub-cloned into an AAV1 expression plasmid (AAV/CBA-WPRE-bGHpA) under the control of a CBA (chicken beta-actin) promoter and containing WPRE (woodchuck hepatitis virus post-transcriptional-regulatory element), and bovine growth hormone polyadenylation signal flanked by AAV2 inverted terminal repeats (ITRs). dGFP (destabilized GFP) was cloned into the same AAV expression vector backbone and was used as control vector. High-titer AAV virus generation and purification were performed as described in detail elsewhere (During et al., 2003).

Lentiviral shRNA Constructs

MISSION short hairpin RNA (shRNA) plasmids encoding small interfering RNAs (siRNAs) targeting parkin or PARIS were purchased from Sigma (St Louis, Mo.). TRCN0000000285 and TRCN0000000283 vectors successfully knockdown human parkin. Three plasmids (TRCN0000156627 TRCN0000157534 and TRCN0000157931) were effective in knocking down PARIS expression. As a control, shRNA-dsRed co-expressing GFP and short hairpin sequence (AGTTCCAGTACGGCTCCAA) [SEQ ID NO. 26] under the control of the EF1α and human U6 promoter was used. For knockdown human parkin or PARIS in SH-SY5Y cells, two lentiviral vectors were combined and the TRCN0000157931 lentiviral vector was used to knockdown mouse PARIS in vivo.

Stereological Assessment

Experimental procedures were followed for stereotaxic injection of AAV1 overexpressing GFP, PARIS or parkin and lentivirus overexpressing PGC-1α, GFP or GFPCre. Six-week-old male C57BL mice (Charles River Laboratories, Inc) or 6~8 week old parkin$^{flx/flx}$ mice were anesthetized with pentobarbital (60 mg/kg). An injection cannula (26.5 gauge) was applied stereotaxically into the substantia nigra (anteroposterior, −3.0 mm from bregma; mediolateral, 1.2 mm; dorsoventral, 4.3 mm). The infusion was performed at a rate of 0.2 μl/min and wound healing and recovery were monitored after the injection was done. Four weeks, 3 months and 10 months after injection, animals were anesthetized and perfused with PBS followed by 4% paraformaldehyde. Brains were post-fixed with 4% paraformaldehyde, cryoprotected in 30% sucrose, and processed for immunohistochemistry. Forty-μm coronal sections were cut throughout the brain including substantia nigra and every 4$^{th}$ section was utilized for analysis. For tyrosine hydroxylase (TH) or glutamate decarboxylase 65/67 (GAD 65/67), sections were reacted with a 1:1000 dilution of rabbit polyclonal anti-TH (Novus) or anti-GAD65/67 (Chemicon) and visualized with biotinylated goat anti-rabbit IgG, followed by streptavidin-conjugated horseradish peroxidase (HRP) (Vectastain ABC kit, Vector Laboratories, Burlingame, Calif.). Positive immunostaining was visualized with 3,3'-diaminobenzidine (DAB, Sigma) after reaction with hydrogen peroxide (DAB kit, Vector Laboratories). Stained sections were mounted onto slides and counterstained with thionin for Nissl substance. Total numbers of TH-, and Nissl-stained neurons in substantia nigra pars compacta were counted using the Optical Fractionator probe of Stereo Investigator software (MicroBrightfield, Williston, Vt.). For Nissl counting, a cell was defined as a bright blue-stained neuronal perikarya with a nucleolus. Nissl positive counts were restricted to Nissl+/TH+ neurons along with large Nissl+ neurons with dopaminergic-like morphology, that contain little or no TH immunostaining.

Laser Capture Microdissection (LCM)

Approximately 6 week old parkin$^{flx/flx}$ mice injected with either lentiviral GFP (n=3) or lentiviral GFPCre (n=3) were transcardially perfused by autoclaved 1×PBS for 3 min (10 ml/min), 2% paraformaldehyde (resolved in autoclaved PBS) for 5 min (10 ml/min), and 20% sucrose for 5 min (10 ml/min). The brains were rapidly removed and frozen on dry ice. In order to preserve fluorescence and RNA integrity, an RNase inhibitor and autoclaved PBS were used during all staining procedures. Fifteen micron-thick coronal sections of the midbrain on superfrost glass slide were incubated with blocking solution for 30 min and rinsed with 1×PBS followed by incubation with rabbit anti-TH (1:50) and mouse anti-GFP (1:50) for 3-4 hours. Rinsed sections were incubated with Cy3-conjugated anti-rabbit (1:25) and Cy2-conjugated anti-mouse (1:25) for 1 hour. Sections were rinsed with 1×PBS three times and were washed once again with DEPC-treated water. Double, TH and GFP, positive neurons were obtained by LCM (P.A.L.M., Microlaser Technologies). Microdissected cells were directly used for RNA extraction.

Statistics

Quantitative data is presented as the mean±S.E.M. Statistical significance was either assessed via an unpaired two-tailed Student's t-test or an ANOVA test with Student-Newman-Keuls post-hoc analysis. Assessments were considered significant with a $p<0.05$.

Experiment 1

PARIS was a KRAB and C2H2 Zinc Finger Protein

Figure 3:
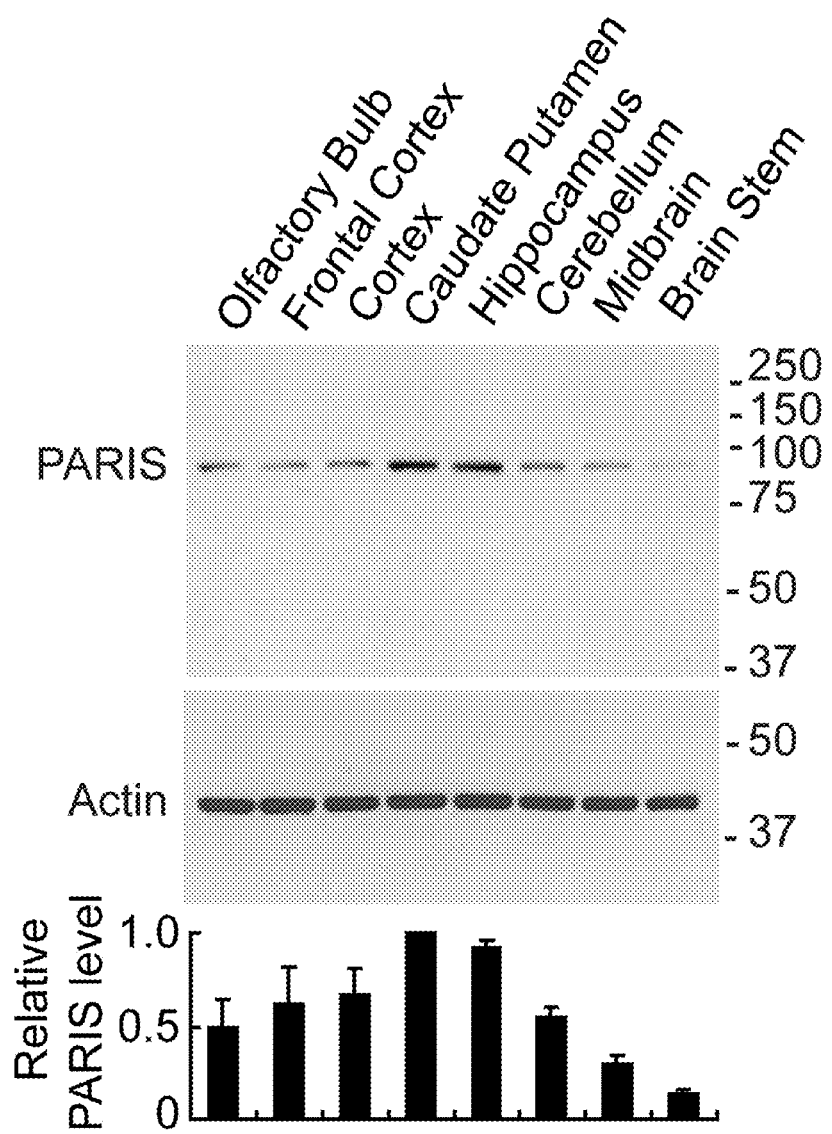
FIG. 3—A regional analysis and levels of PARIS protein expression via immunoblot in various brain regions. [mean±S.E.M., n=3].
Figure 4:
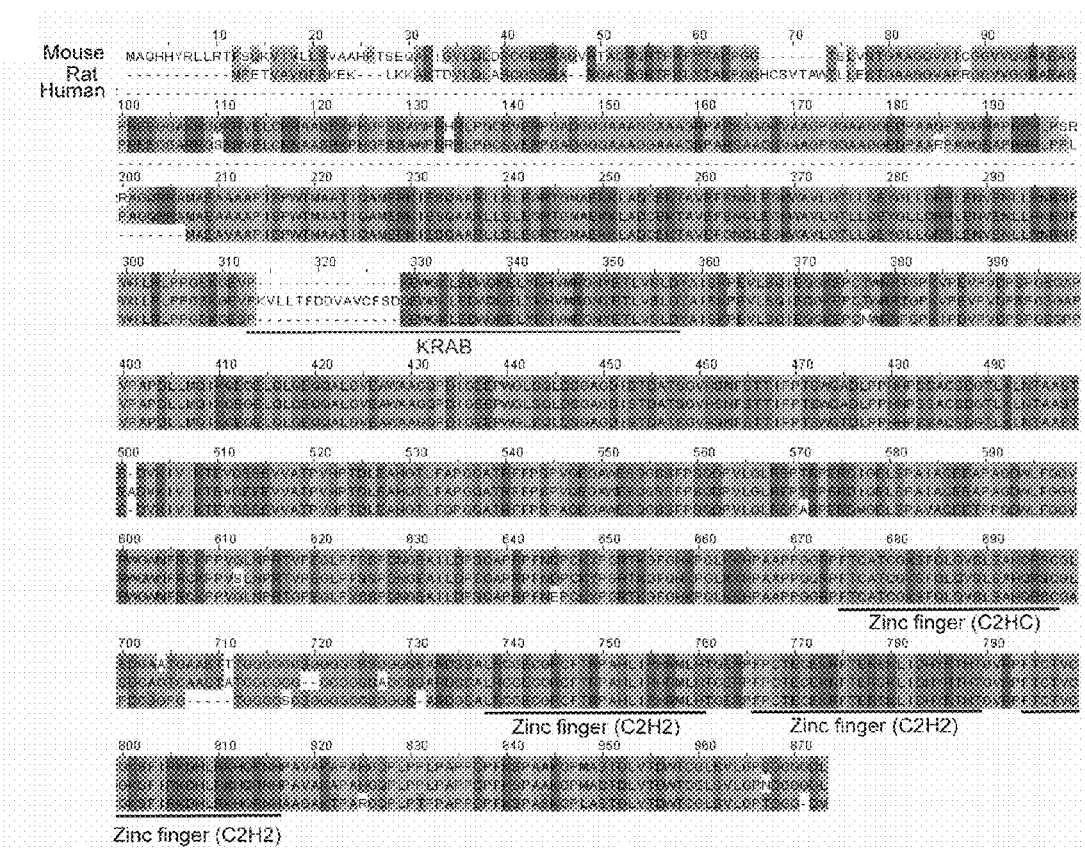
FIG. 4—Multiple sequence alignment of human (SEQ ID NO. 2), mouse (SEQ ID NO. 155) and rat (SEQ ID NO. 156) PARIS reveals highly conserved amino acid sequence among the different species. The KRAB domain (blue bar) and zinc finger domains (black bars) are indicated.
Figure 5:
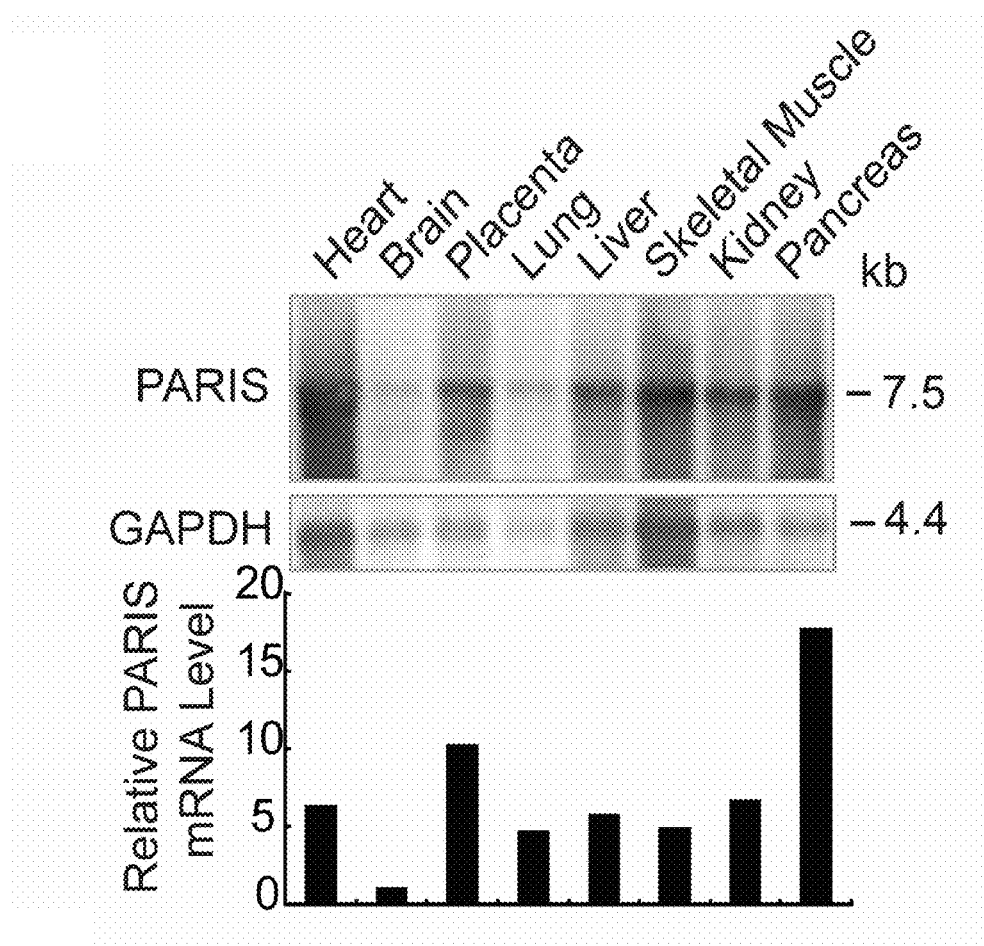
FIG. 5—Northern blot analysis of PARIS gene expression in different tissues. Relative levels of PARIS normalized to GAPDH control is indicated in bottom panel.
Figure 6:
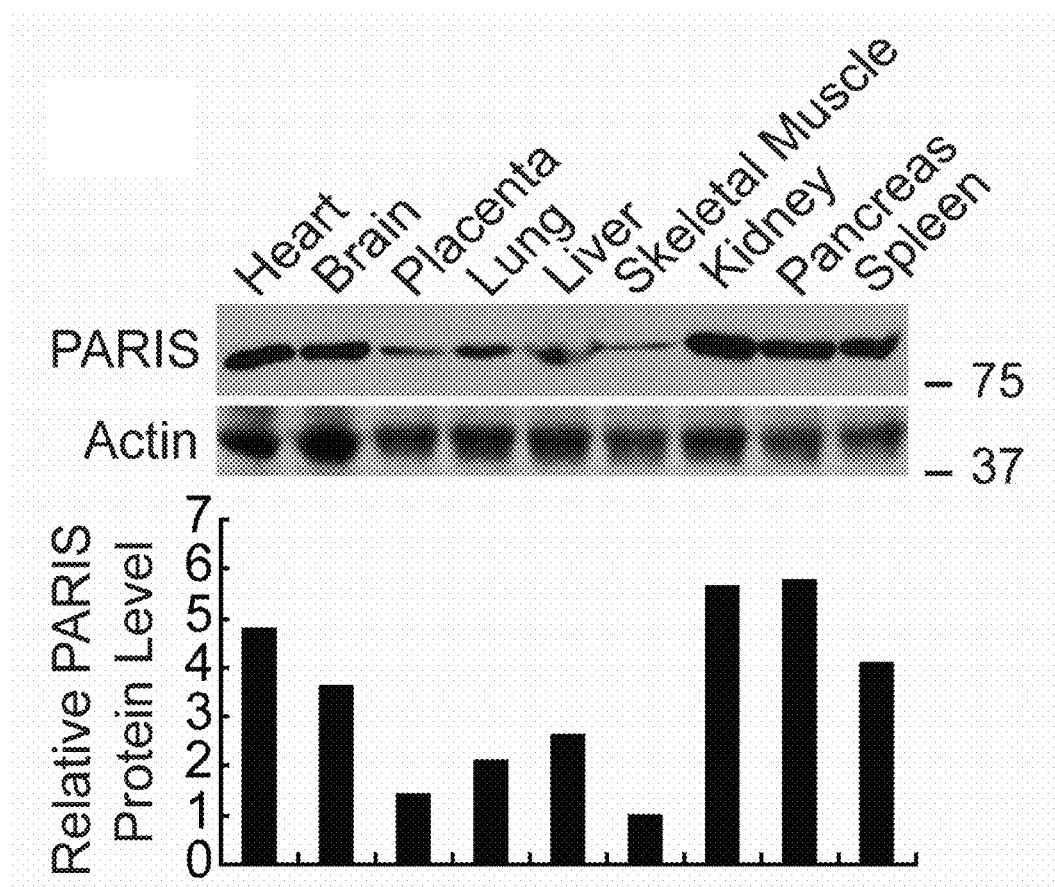
FIG. 6—Regional analysis of PARIS protein expression in various mouse tissues. Relative levels of PARIS normalized to β-actin control is indicated in bottom panel. Repeated three times with similar results.
Figure 7:
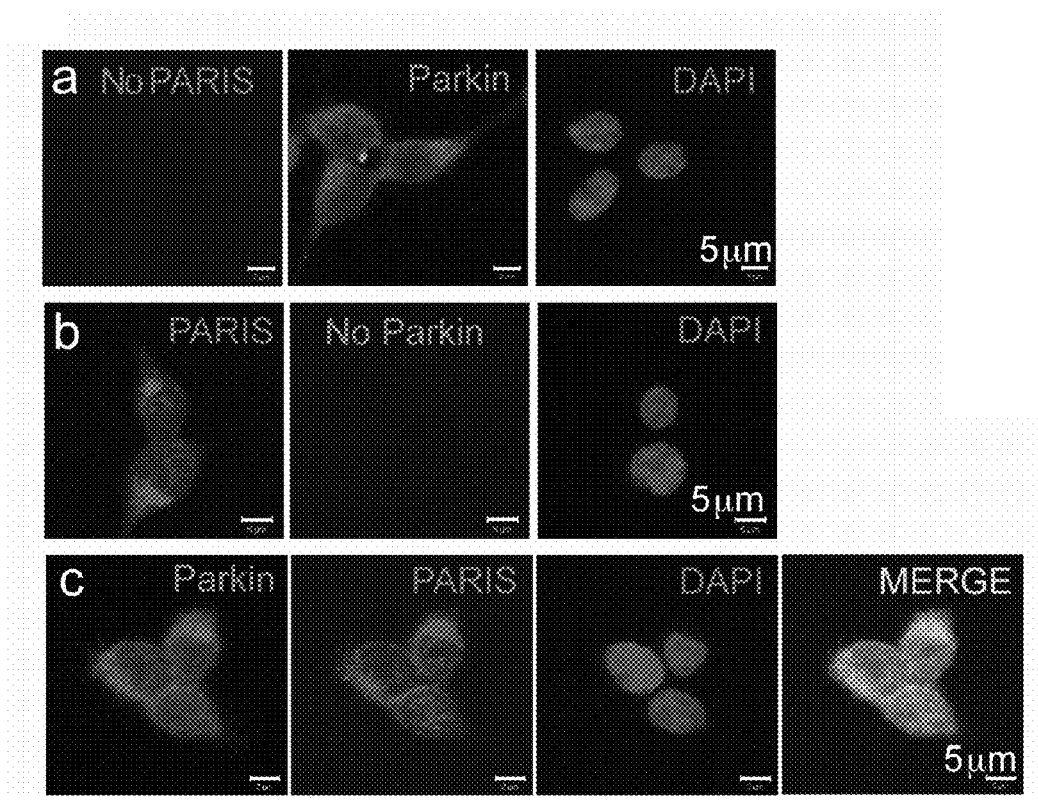
FIG. 7—Representative confocal images with (a) anti-parkin antibody alone, (b) anti-PARIS antibody alone, or (c) anti-parkin along with anti-PARIS antibodies reveal that there is no channel crosstalk and that endogenous PARIS and parkin are co-localized mostly in the cytoplasm of SH-SY5Y dopaminergic-like cells. Parkin (green); PARIS (red); Nucleus (DAPI, blue), n=4.
Figure 8:
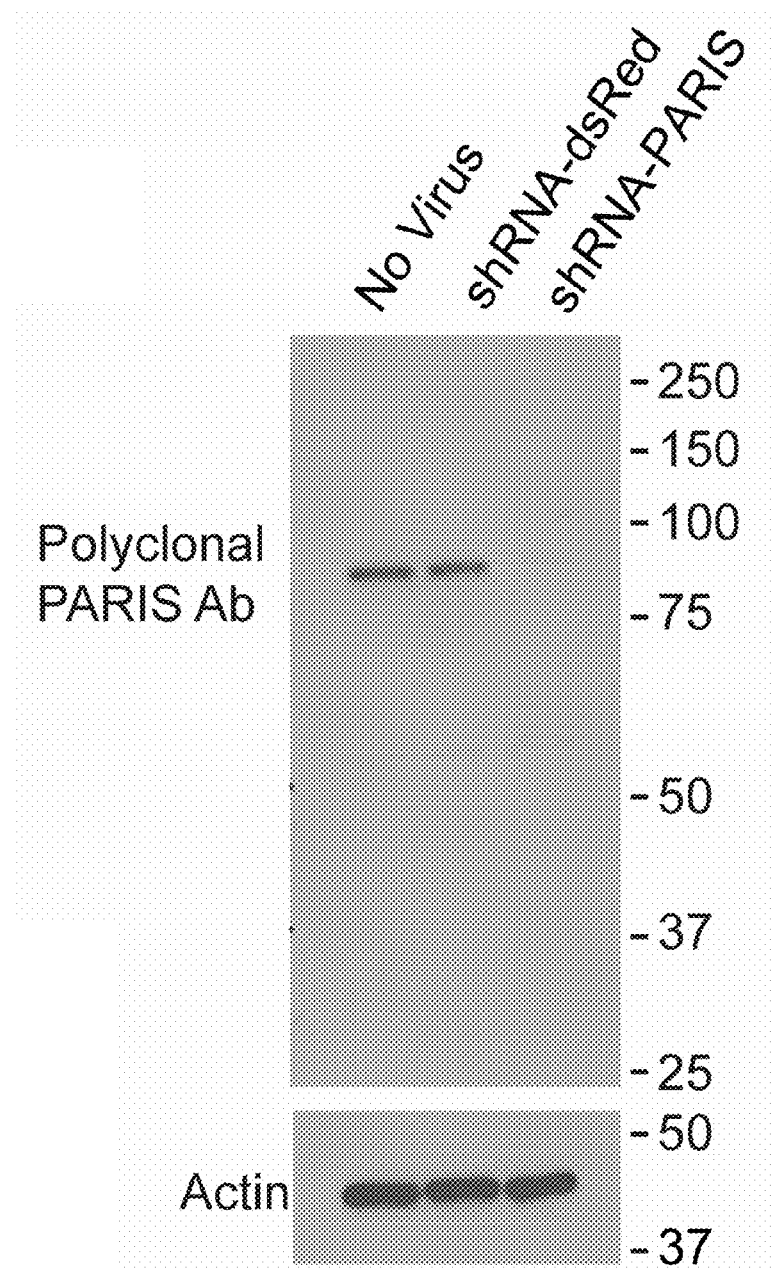
FIG. 8—Immunoblot analysis using a polyclonal PARIS antibody in SH-SY5Y cells transduced with lentiviral shRNA-dsRed or shRNA-PARIS. The polyclonal PARIS antibody used in these studies is specific for PARIS since it recognizes a single band on immunoblot from mouse brain. β-actin was used as a loading control, n=3.
Figure 9:
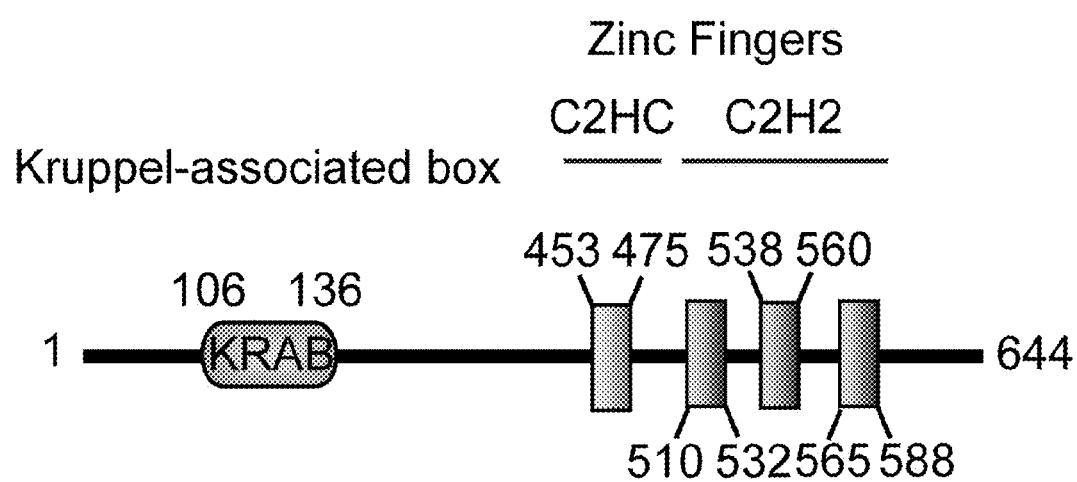
FIG. 9—A schematic representation of PARIS. The conserved Kruppel associated Box (KRAB) and Zinc Finger motifs and their location are indicated.
Figure 10:
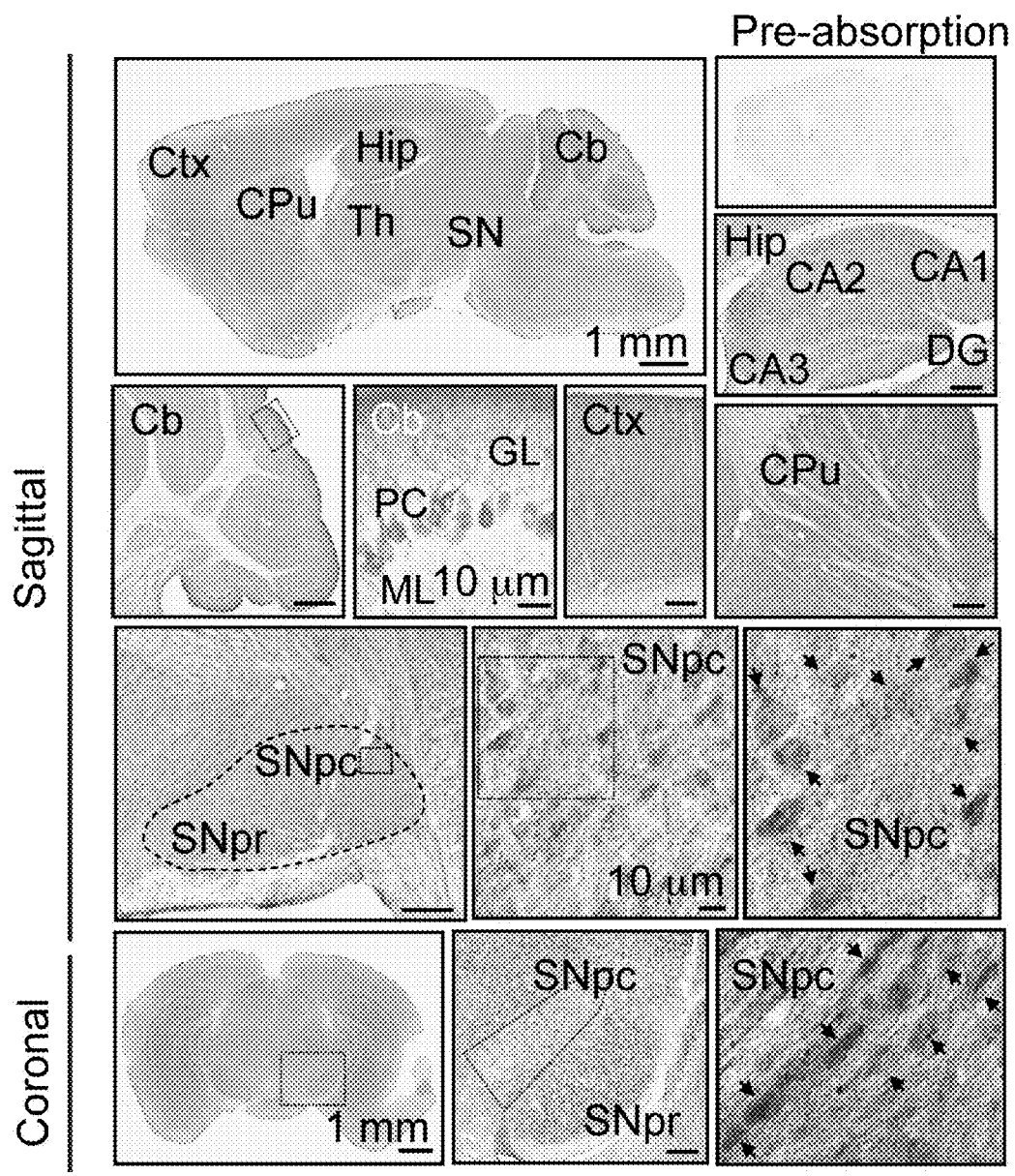
FIG. 10—Immunohistochemical distribution of PARIS in sagittal and coronal sections of six-week-old male C57BL mouse brain. Right upper panel shows an antigen preabsorption control. Ctx, cerebral cortex; Hip, hippocampus; CPu, caudate putamen; SNpr, SN pars reticulata; SNpc, SN pars compacta; Th, thalamus; Cb, cerebellum; (Cb); PC, Purkinje cells; ML, molecular cell layer; GL, granule cell layer; DG, dentate gyrus. Dashed (-) line outlines SN. High power view of SNpc (rectangles in third row) is shown in the third row middle and right panels and lower middle and right panel. Scale bars, 200 µm unless indicated, n=3.
Figure 11:
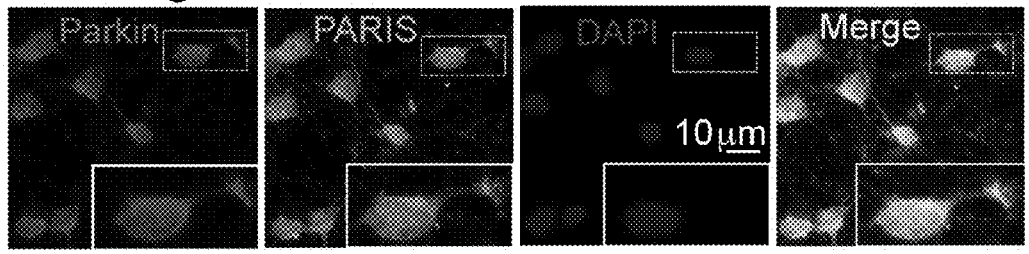
FIG. 11—Confocal microscopy of endogenous PARIS and parkin in the cytoplasm of rat cortical neurons. Top Panel, Left—Parkin; Middle Left—PARIS, Middle Right—DAPI, Right—merge of Parkin and Paris images. Inset—high power view of an individual neuron. Bottom panel, Left—Parkin; Middle Left—PARIS, Middle Right—Nucleus-DAPI, Right—merge, n=4.
Figure 11:
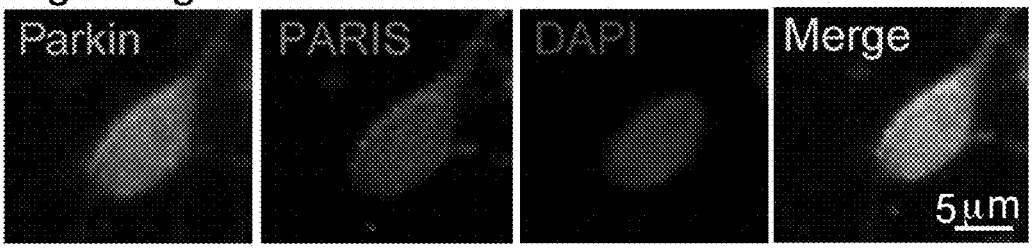

PARIS was identified by yeast two-hybrid screening using parkin as bait. Human PARIS (ZNF746) was a 644 amino acid protein that contained a Kruppel-associated box (KRAB) at its N-terminus and a C2HC/C2H2 type zinc finger at its C-terminus (FIG. 9). There was a high degree of homology among human, mouse and rat PARIS proteins (FIG. 4) (see Table 1). Northern blot and immunoblot analysis revealed that PARIS was expressed in all organs examined (FIGS. 5 and 6). PARIS was differentially expressed in the brain with low levels in cerebellum and midbrain (FIG. 3). Immunohistochemistry revealed that PARIS was heterogeneously distributed throughout the brain and that it was localized to neurons, including substantia nigra (SN) pars compacta DA containing neurons (FIG. 10). Confocal imaging indicated that PARIS was co-localized with parkin in primary cortical neuron cultures (FIG. 11) and in SH-SY5Y dopaminergic-like cells (FIG. 7). The polyclonal PARIS antibody used in these studies was specific for PARIS since it recognized a single band on immunoblot from mouse brain (see FIG. 8).

TABLE 1

Comparison of full-length PARIS sequence of human [SEQ ID NO. 2], mouse [SEQ ID NO. 3] and rat [SEQ ID NO. 4]

```
Mouse  MAEAAAAPISPWTMAATIQAMERKIESQAARLLSLEGRTGMAEKKLADCEKTAVEFSNQL    60

Rat    MAEAAAAPISPWTMAATIQAMERKIESQAARLLSLEGRTGMAEKKLADCEKTAVEFSNQL    60

Human  MAEAVAAPISPWTMAATIQAMERKIESQAARLLSLEGRTGMAEKKLADCEKTAVEFGNQL    60
       ****.*******************************************************.***

Mouse  EGKWAVLGTLLQEYGLLQRRLENVENLLRNRNFWILRLPPGSKGEVPKEWGKLEDWQKEL   120

Rat    EGKWAVLGTLLQEYGLLQRRLENVENLLRNRNFWILRLPPGSKGEVPKEWGKLEDWQKEL   120

Human  EGKWAVLGTLLQEYGLLQRRLENVENLLRNRNFWILRLPPGSKGESPKEWGKLEDWQKEL   120
       ********************************************* *************

Mouse  YKHVMRGNYETLVSLDYAISKPEVLSQIEQGKEPCTWRRTGPKVPEVPVDPSPGSGAPVP   180

Rat    YKHVMRGNYETLVSLDYAISKPEVLSQIEQGKEPCTWRRTGPKVPEVPVDPSPGSGAPVP   180

Human  YKHVMRGNYETLVSLDYAISKPEVLSQIEQGKEPCNWRRPGPKIPDVPVDPSPGSGPPVP   180
       ***********************************.***.***:*:**********.***

Mouse  APDLLMQIKQEGELQLQEQQALGVEAWAAGQPDIGEEPWGLSQLDSGAGDISTDATSGVH   240

Rat    APDLLMQIKQEGELQLQEQQALGVEAWAAGQPDIGEEPWGLSQLDSGAGDISTDATSGVH   240
```

TABLE 1-continued

Comparison of full-length PARIS sequence of human [SEQ ID NO. 2], mouse [SEQ ID NO. 3] and rat [SEQ ID NO. 4]

```
Human APDLLMQIKQEGELQLQEQQALGVEAWAAGQPDIGEEPWGLSQLDSGAGDISTDATSGVH            240
      ************************************************************

Mouse SNFSTTIPPTSWQADLPPHHPSSACSDGTLKLNTAASTEADVKIVIKTEVQEEEVVATPV            300

Rat   SNFSTTIPPTSWQADLPPHHPSSACSDGTLKLNTAASTEADVKIVIKTEVQEEEVVATPV            300

Human SNFSTTIPPTSWQTDLPPHHPSSACSDGTLKLNTAASTE-DVKIVIKTEVQEEEVVATPV            299
      *************:******************************* *********************

Mouse HPTDLEAHGTLFAPGQATRFFPSPVQEGAWESQGSSFPSQDPVLGLREPTRPERDIGELS            360

Rat   HPTDLEAHGTLFAPGQATRFFPSPVQEGAWESQGSSFPSQDPVLGLREPTRPERDIGELS            360

Human HPTDLEAHGTLFGPGQATRFFPSPAQEGAWESQGSSFPSQDPVLGLREPARPERDMGELS            359
      ************.***********.*************************:*****:****

Mouse PAIAQEEAPAGDWLFGGVRWGWNFRCKPPVGLNPRTVPEGLPFSSPDNGEAILDPSQAPR            420

Rat   PAIAQEEAPAGDWLFGGVRWGWNFRCKPPVSLNPRTVPEGLPFSSPDNGEAILDPSQAPR            420

Human PAVAQEETPPGDWLFGGVRWGWNFRCKPPVGLNPRTGPEGLPYSSPDNGEAILDPSQAPR            419
      **:****.*.********************.***** *****:****************

Mouse PFNDPCKYPGRTKGFGHKPGLKKHPAAPPGGRPFTCATCGKSFQLQVSLSAHQRSCGLSD            480

Rat   PFNDPCKYPGRTKGFGHKPGLKKHPAAPPGGRPFTCATCGKSFQLQVSLSAHQRSCGLSD            480

Human PFNEPCKYPGRTKGFGHKPGLKKHPAAPPGGRPFTCATCGKSFQLQVSLSAHQRSCGAPD            479
      ***:********************************************************  .*

Mouse GAATGAASTTTGGGGGGSGGGGGSSGGGSSARDSSALRCGECGRCFTRPAHLIRHRMLHT            540

Rat   GAGTGAASTATGGGGGG--GGGGSSAGGSSARDSSALRCGECGRCFTRPAHLIRHRMLHT            538

Human GSGPG-----TGGGGSGSGGGGGSGGGS-ARDSGALRCGECGRCFTRPAHLIRHRMLHT             533
      *:..*      *****.*  ****.*.***  ***.**********************

Mouse GERPFPCTECEKRFTERSKLIDHYRTHTGVRPFTCTVCGKSFIRKDHLRKHQRNHPAVAK            600

Rat   GERPFPCTECEKRFTERSKLIDHYRTHTGVRPFTCTVCGKSFIRKDHLRKHQRNHPAVAK            598

Human GERPFPCTECEKRFTERSKLIDHYRTHTGVRPFTCTVCGKSFIRKDHLRKHQRNHAAGAK            593
      ******************************************************.* **

Mouse APAHGQPLPPLPAPPDPFKSPAAKGPMASTDLVTDWTCGLSVLGPSDGGGDL                     652

Rat   APAHGQPLPPLPAPPDPFKSPAAKGPMASTDLVTDWTCGLSVLGPNDGGGDL                     650

Human TPARGQPLPTPPAPPDPFKSPASKGPLASTDLVTDWTCGLSVLGPTDGG-DM                     644
      :**:*****. ***********:***.****************.*** *:
```

Experiment 2

Parkin Interacted with PARIS

Figure 12:
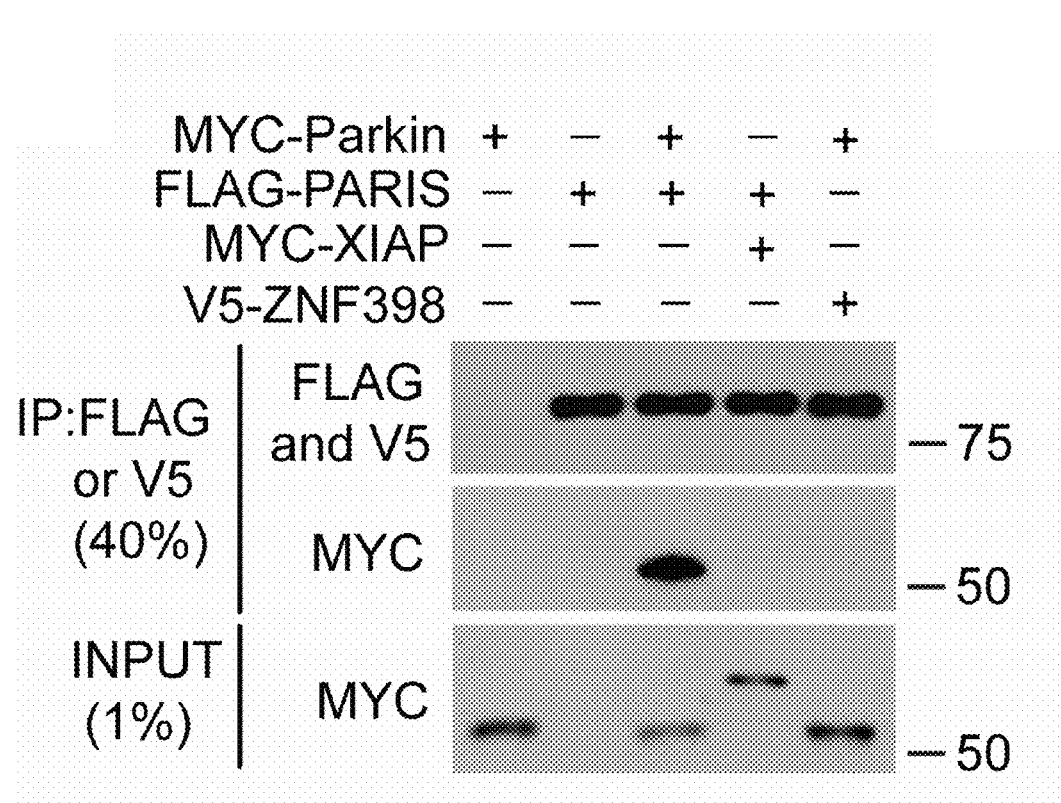
FIG. 12—Immunoprecipitated (IP) FLAG-PARIS interacts with MYC-Parkin, but not MYC-XIAP or the PARIS homologue, V5-ZNF398 (lane 6), n=3.
Figure 13:
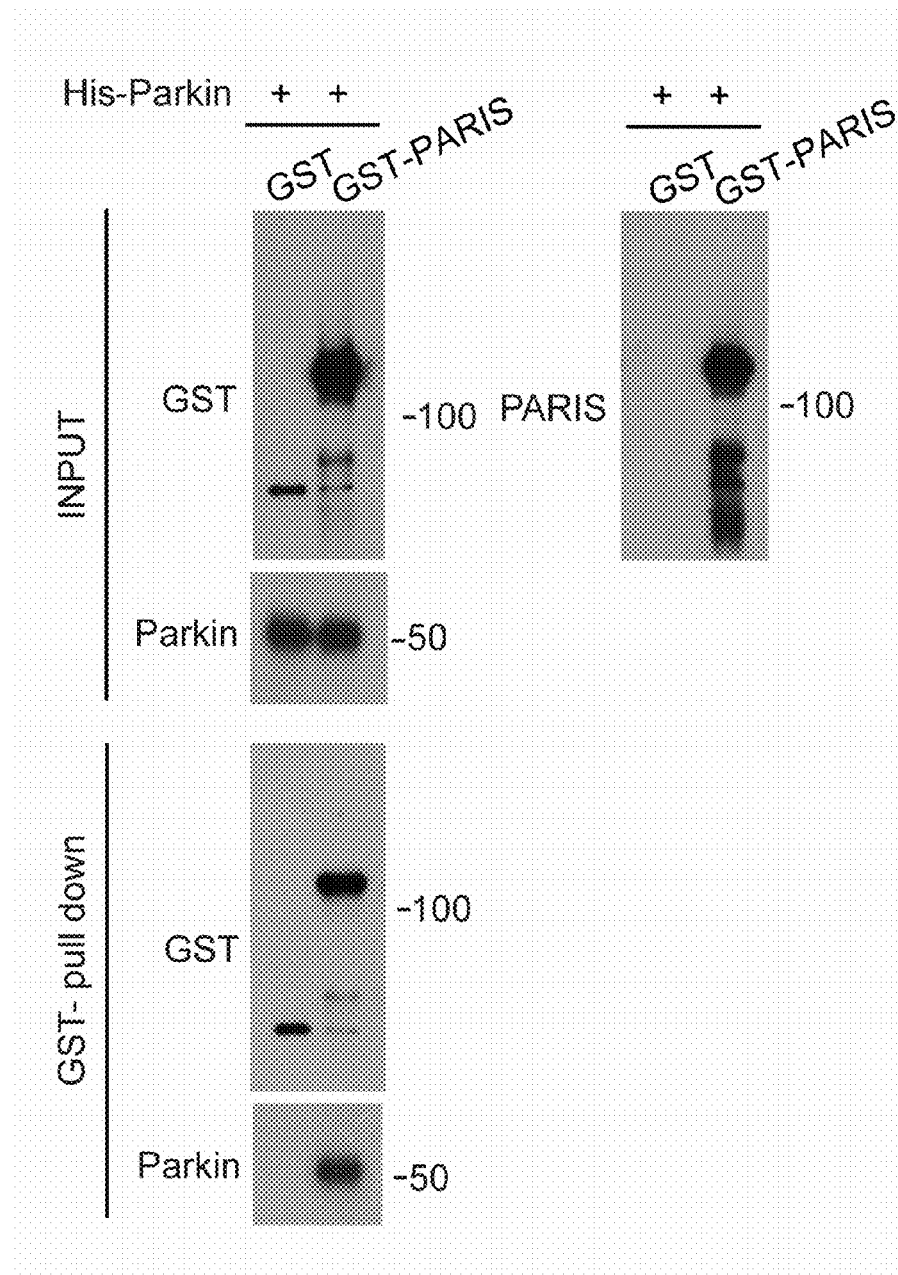
FIG. 13—GST-pull down assay between parkin and PARIS indicates a robust interaction between parkin and PARIS, n=4.
Figure 14:
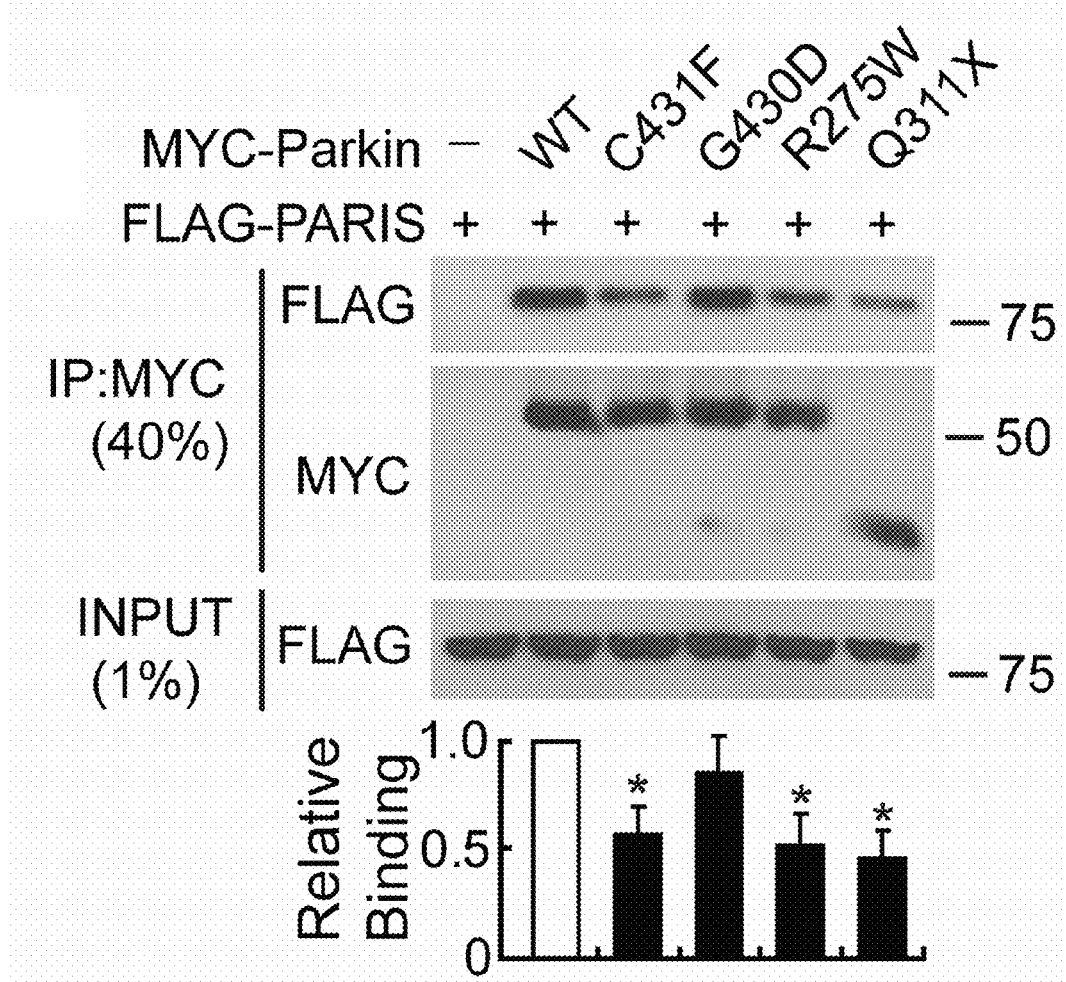
FIG. 14—Immunoprecipitated FLAG-PARIS interacts with WT Parkin and Parkin mutants (C431F, G430D, R275W, Q311X) in SH-SY5Y cells. Lower panel, relative binding [mean±S.E.M., n=3, *p<0.05, Student's t-test].
Figure 15:
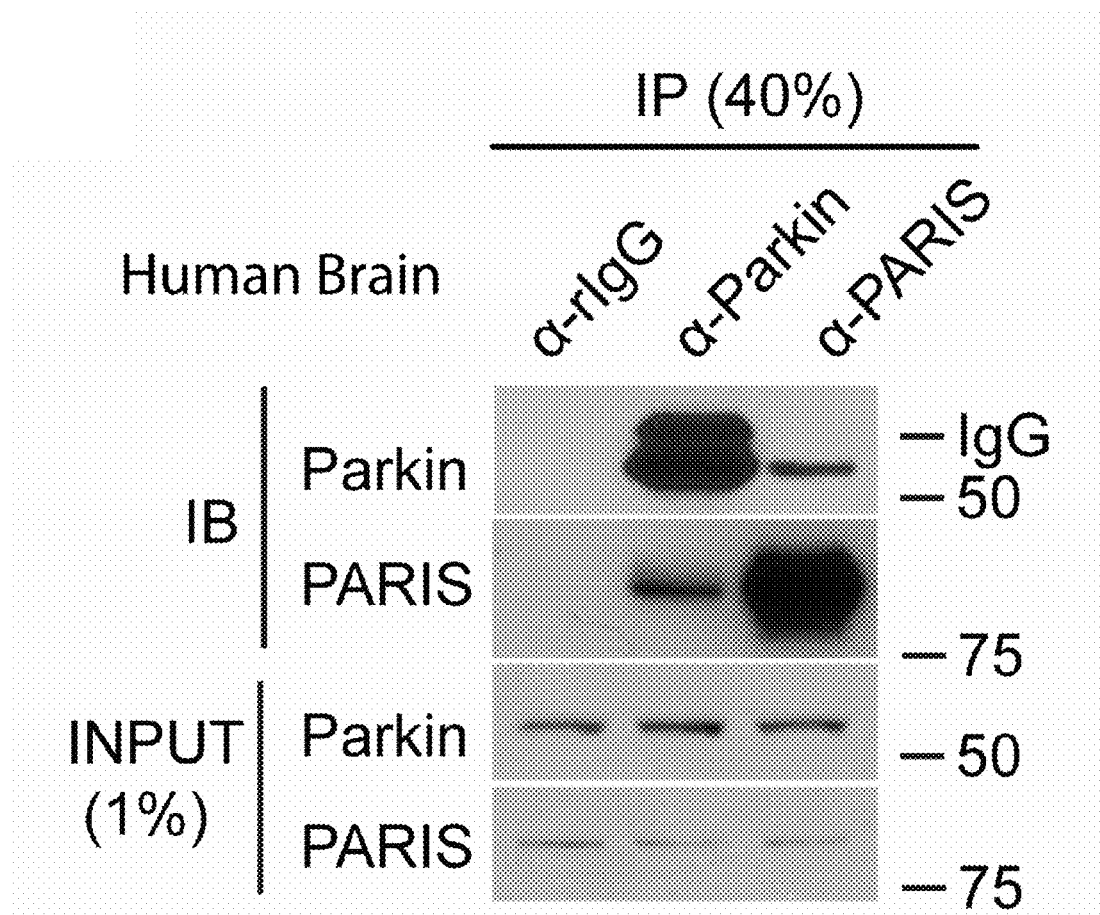
FIG. 15—Immunoblot (IB) shows that Parkin and PARIS co-immunoprecipitate in human striatum, n=3.
Figure 16:
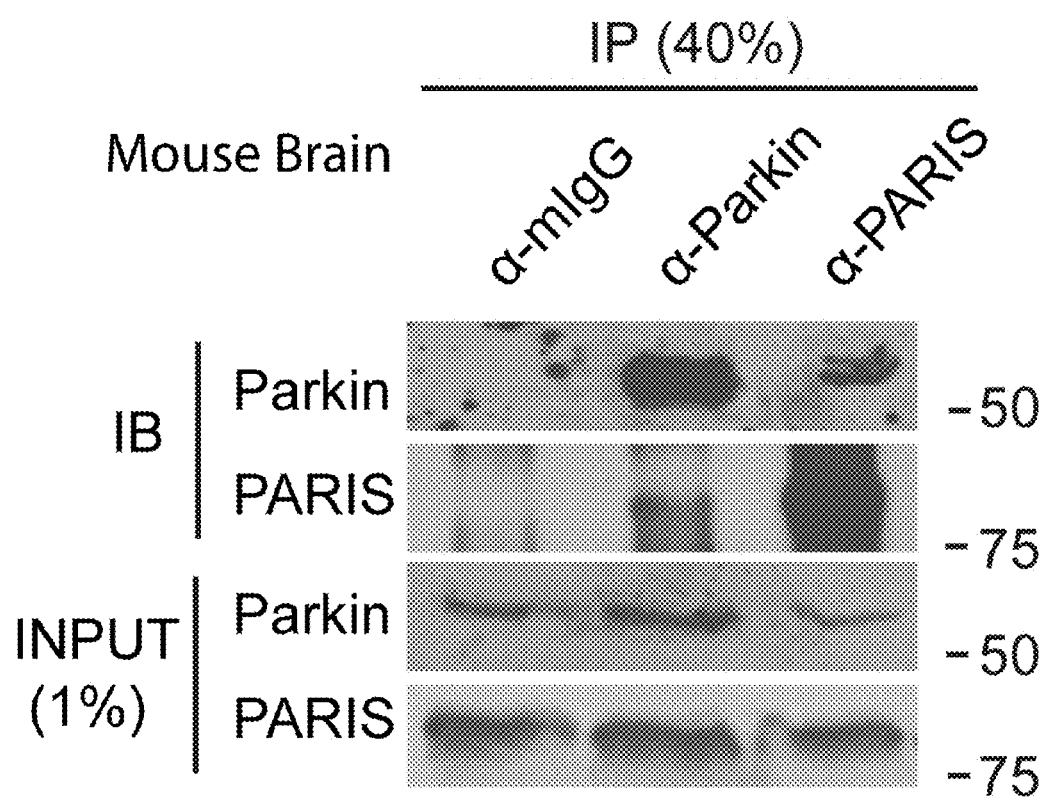
FIG. 16—Co-immunoprecipitation between parkin and PARIS in mouse brain using antibodies to parkin, PARIS. Mouse IgG was used as a control.
Figure 17:
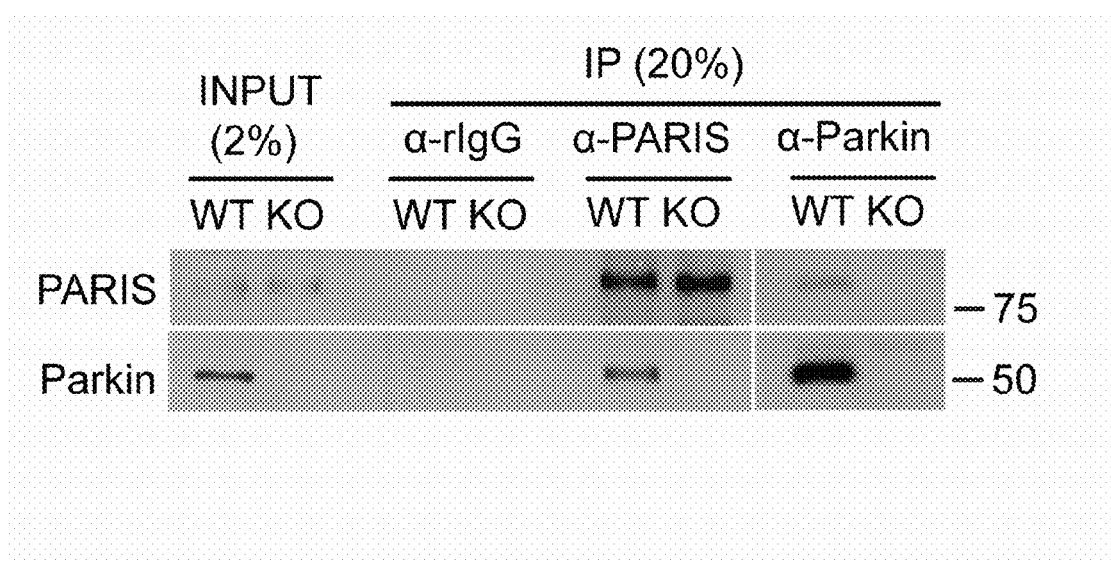
FIG. 17—Parkin and PARIS co-immunoprecipitate from WT mouse ventral midbrain, but not parkin KO ventral midbrain, n=3.

MYC-tagged parkin and FLAG-tagged PARIS co-immunoprecipitated in SH-SY5Y cells, whereas XIAP, a RING finger ubiquitin E3 ligase and ZNF398, a highly conserved homologue of PARIS did not interact with PARIS and parkin, respectively (FIG. 12). Recombinant GST-PARIS pulled down recombinant His-Parkin indicating that PARIS and parkin directly interacted (FIG. 13). The familial PD-associated mutations in parkin, C431F, R275W and Q311X bound to PARIS less avidly than WT parkin, whereas G430D mutant parkin bound to PARIS in a manner similar to WT parkin (FIG. 14). PARIS co-immunoprecipitated with parkin and parkin co-immunoprecipitated with PARIS from whole human striatum (FIG. 15) or mouse brain (FIG. 16). This endogenous interaction between parkin and PARIS was not observed in parkin exon 7 KO brain (FIG. 17) confirming the specificity of the interaction.

Figure 18:
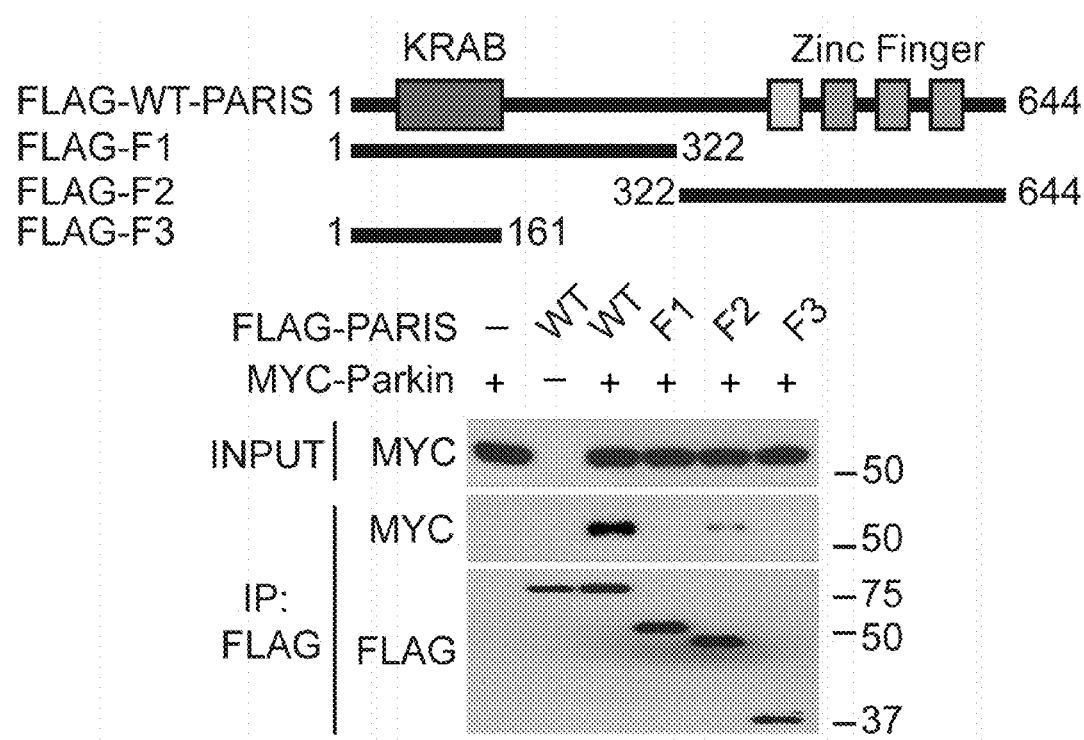
FIG. 18—Full-length WT PARIS and the F2 fragment of PARIS interact with parkin.
Figure 19:
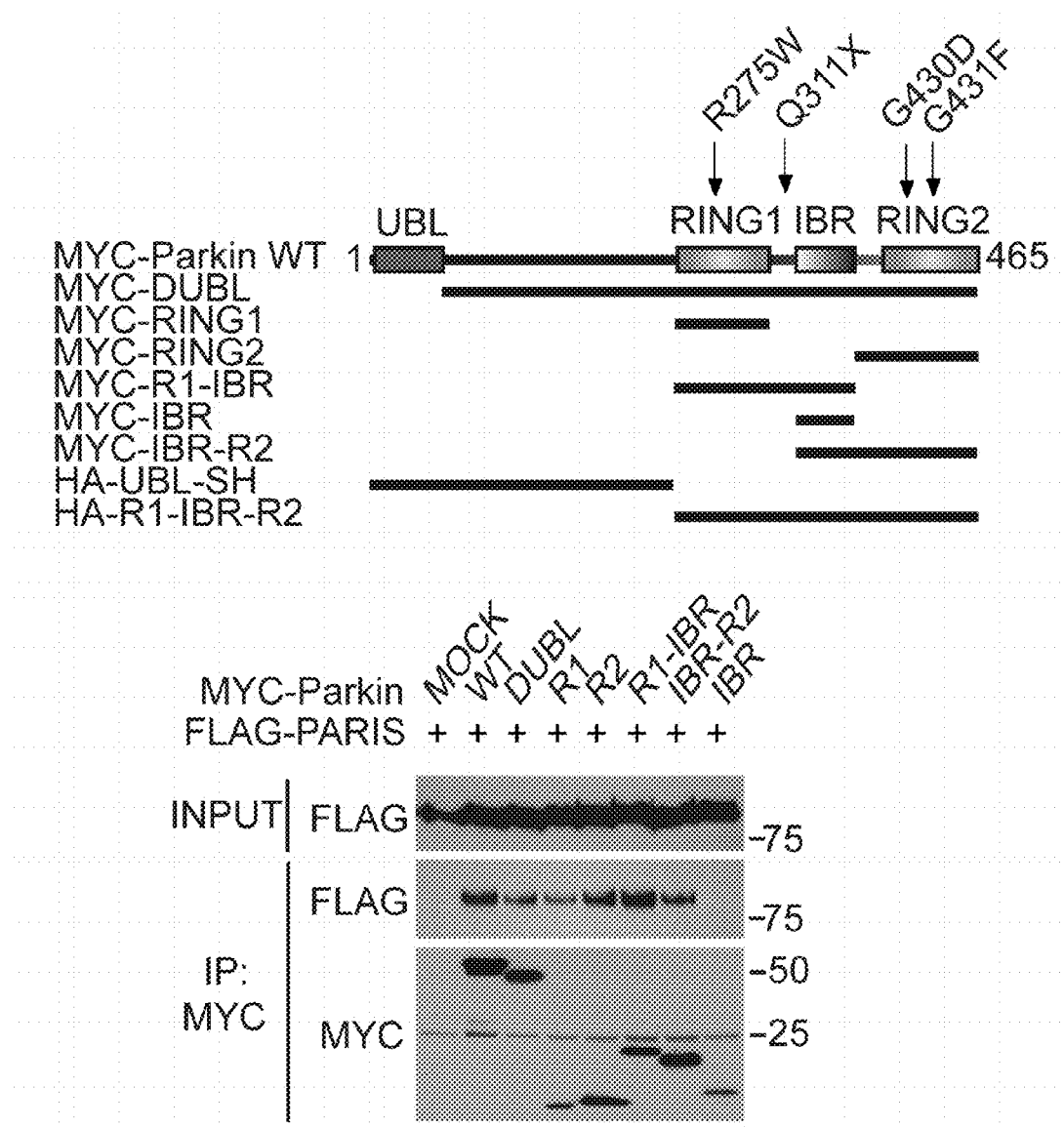
FIG. 19—PARIS interacts with parkin's RING1 and RING2 domains. Immunoprecipitated MYC-parkin deletions bind FLAG-PARIS except for the IBR domain (lane 8 on left bottom panel).
Figure 20:
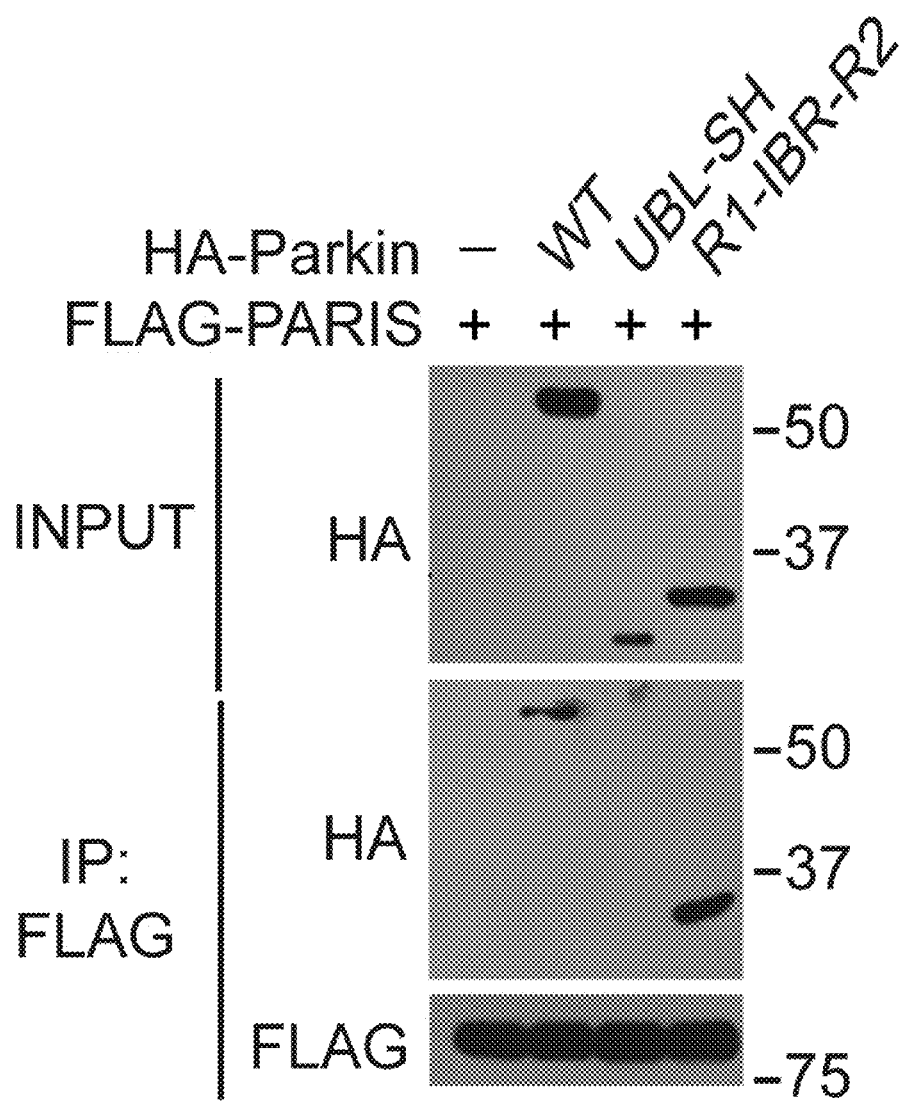
FIG. 20—Immunoprecipitated FLAG-PARIS interacts with WT and the C-terminal RING domains of parkin, but not the N-terminal UBL-SH domain (bottom right panel).

Domain mapping indicated that parkin bound to the C-terminal domain, but not to the N-terminal domain of PARIS (FIG. 18). To ascertain which domain of parkin bound to PARIS, various deletion constructs of MYC-tagged parkin were utilized. Co-immunoprecipitation experiments showed that both the RING 1 or RING2 domains were required for parkin binding to PARIS (FIGS. 19 and 20). Taken together these results indicated that parkin interacted with the zinc finger domain of PARIS and PARIS bound to either the RING1 or RING2 domain of parkin.

Experiment 3

Parkin Ubiquitinated PARIS and Regulated PARIS Levels

Figure 21:
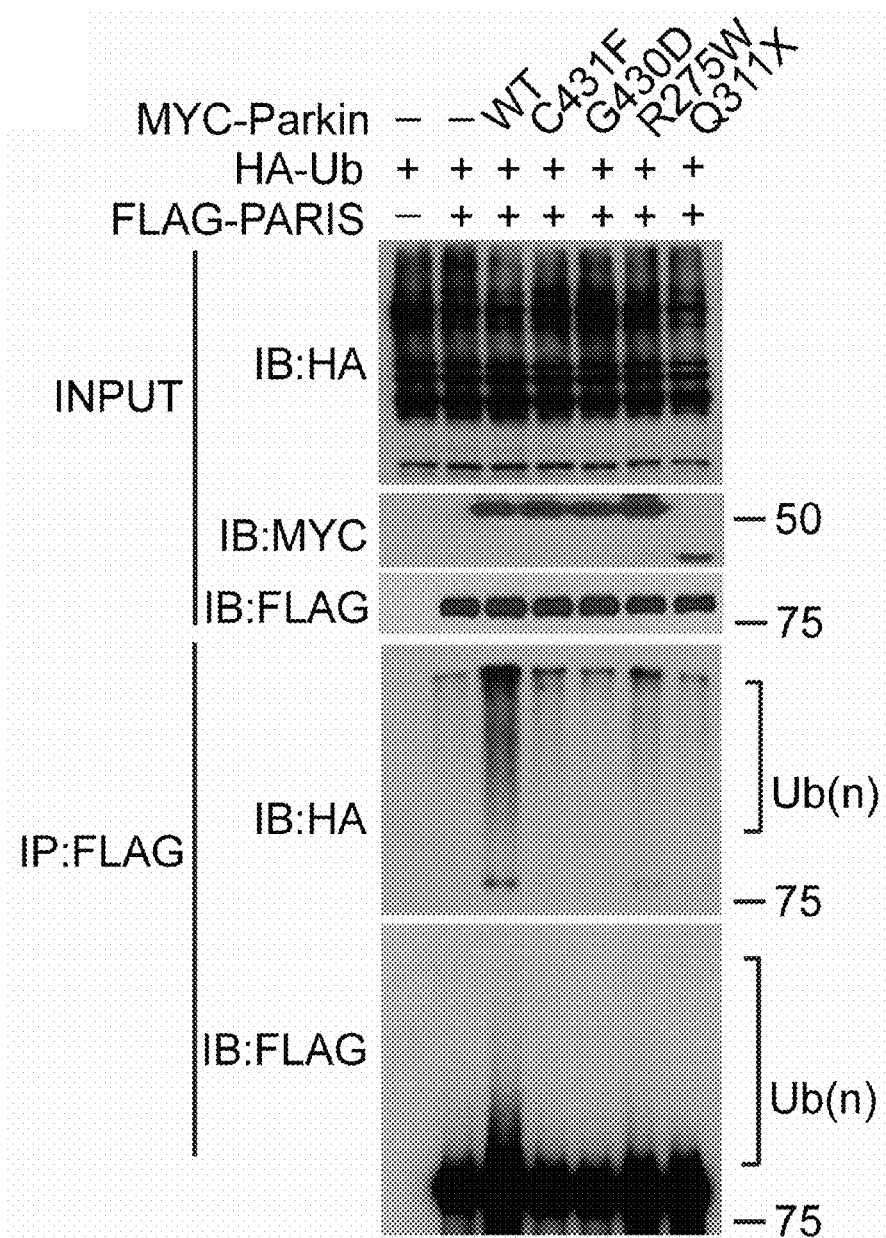
FIG. 21—WT MYC-Parkin ubiquitinates FLAG-PARIS (lane 3). Parkin mutants (C431F, G430D, and Q311X) are unable to efficiently ubiquitinate FLAG-PARIS (lanes 4-7). Ubiquitination (Ub(n)) is indicated on right with brackets, n=3.

FLAG-tagged PARIS was ubiquitinated by MYC-tagged parkin in SH-SY5Y cells as shown by the substantial HA immunoreactivity in the form of a smear, which was characteristic of polyubiquitinated proteins (lane 3, FIG. 21). Familial linked parkin mutations C431F, G430D and Q311X have substantially reduced ubiqutination activity against PARIS, whereas R275W had modest activity (FIG. 21). The reduction in ubiquitination of PARIS by these mutants was due, in part, to their reduced binding (see FIG. 14), as well as, reduced E3 ligase activity of these parkin mutants.

Figure 22:
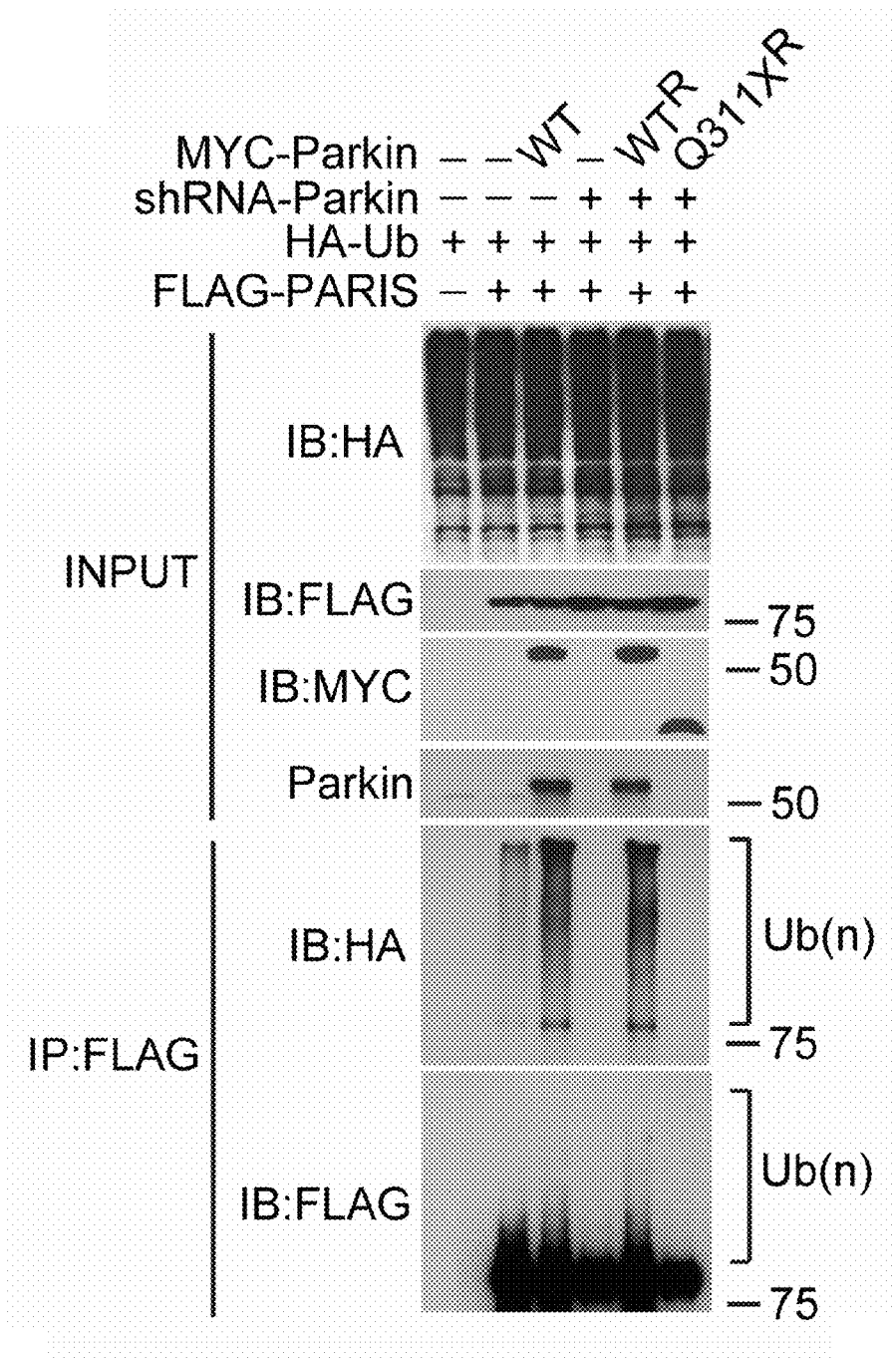
FIG. 22—Endogenous ubiquitination of PARIS (lane 2) is enhanced with exogenous WT Parkin (lane 3) and it is eliminated with shRNA-Parkin (lane 4). In the presence of shRNA-Parkin, robust ubiquitination of PARIS is observed via co-expression of shRNA-resistant WT parkin (WT$^R$) but not shRNA-resistant Q311X mutant parkin (Q311X$^R$), n=3.

FLAG-PARIS was ubiquitinated in the absence of exogenous parkin (lane 2, FIG. 21 and lane 2, FIG. 22). This endogenous ubiquitination was enhanced with co-expression of WT parkin (lane 3, FIG. 21 and lane 3, FIG. 22). ShRNA-Parkin eliminated the endogenous ubiquitination (lane 4, FIG. 22). To control for potential off-targets effects of shRNA-parkin, a shRNA-resistant WT parkin, but not a shRNA-resistant Q311X parkin mutant restored the ubiquitination of PARIS in the presence of shRNA-parkin (FIG. 22).

Target sequences for shRNA to PARIS were identified and isolated. One target sequence was the 3'UTR region of PARIS (GCCTCAAAGGAACTTCTGCTT) [SEQ ID NO. 27]. Another target sequence was the coding region of PARIS (GCCATTCAACGAACCCTGTAA) [SEQ ID NO. 28].

Figure 23:
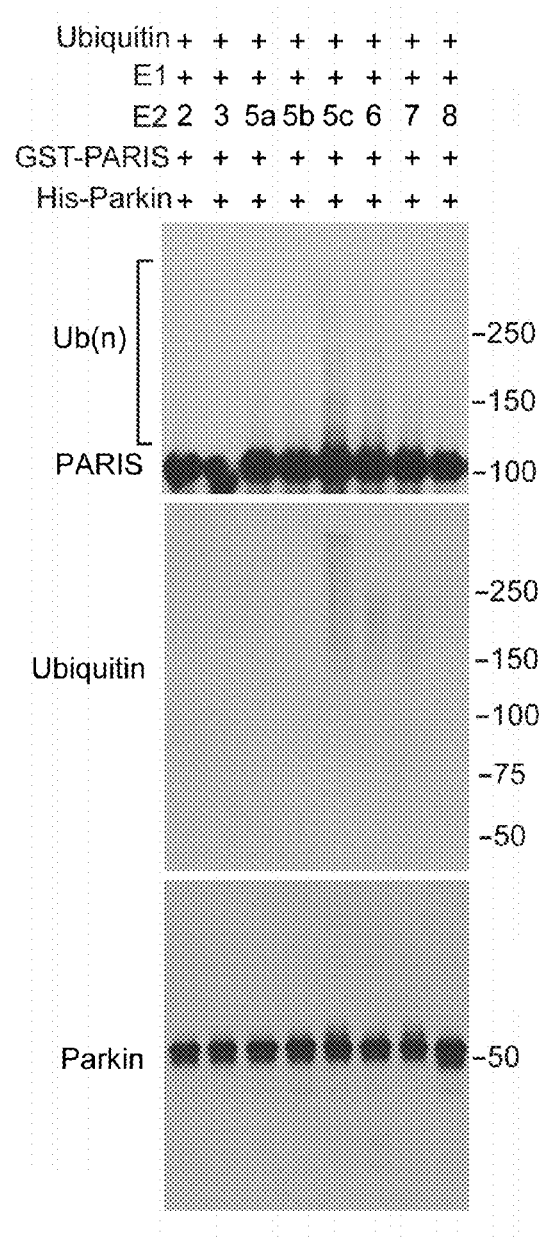
FIG. 23—In vitro ubiquitination reactions with GST-PARIS, E1, E2s UbcH2 (2), UbcH3 (3), UbcH5a (5a), UbcH5b (5b), UbcH5c (5c), UbcH6 (6), UbcH7 (7), UbcH8 (8), and His-tagged parkin were performed at pH=7.5 showing that parkin ubiquitinates PARIS in the presence of various E2 enzyme including UbcH5c, n=3.
Figure 24:
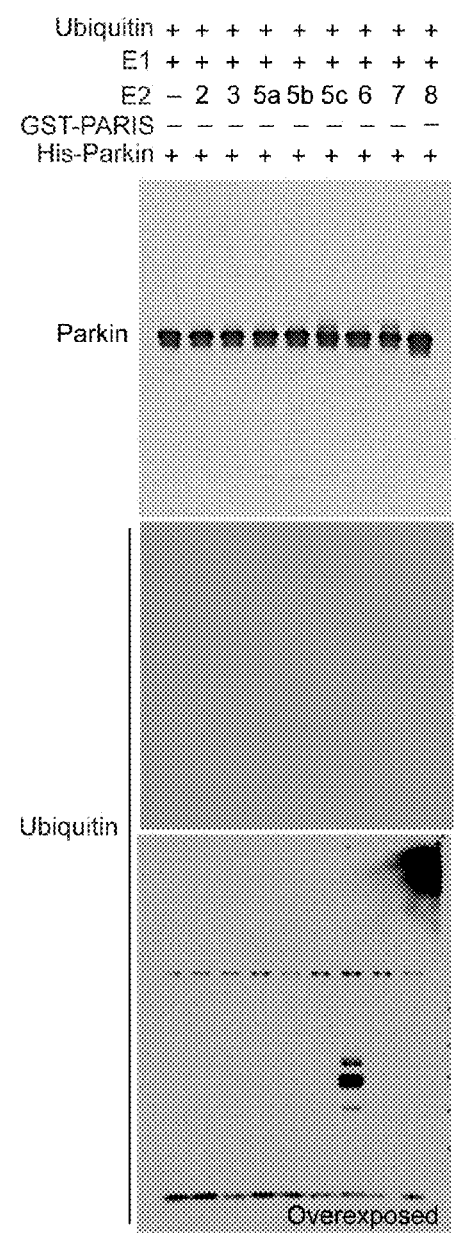
FIG. 24—In vitro ubiquitination reactions with His-tagged parkin, E1, E2s UbcH2 (2), UbcH3 (3), UbcH5a (5a), UbcH5b (5b), UbcH5c (5c), UbcH6 (6), UbcH7 (7), UbcH8 (8), in the absence of GST-PARIS were performed at pH=7.5 showing that the ubiquitin signal (FIG. 23) was derived from PARIS and not parkin, n=3.
Figure 25:
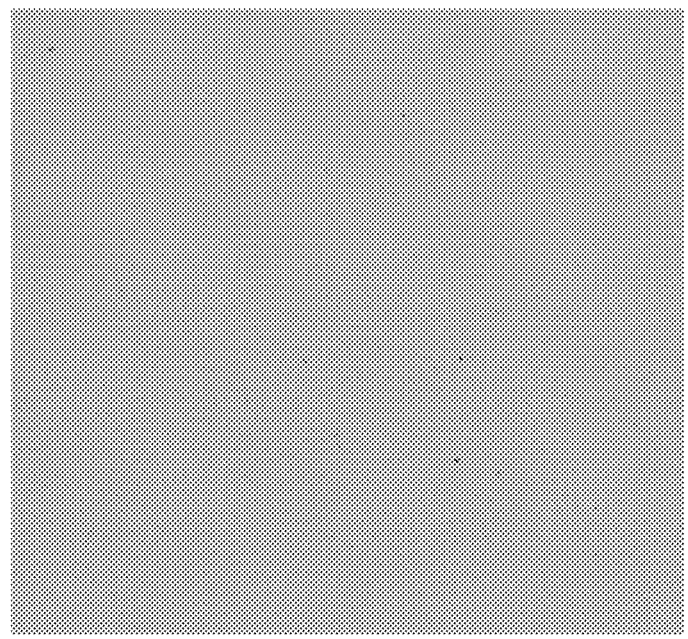
FIG. 25—In vitro ubiquitination reactions with E1, E2s UbcH2 (2), UbcH3 (3), UbcH5a (5a), UbcH5b (5b), UbcH5c (5c), UbcH6 (6), UbcH7 (7), UbcH8 (8), in the absence of GST-PARIS and His-tagged parkin were performed at pH=7.5 showing that there is no ubiquitin signal in the absence of parkin and PARIS, n=3.
Figure 26:
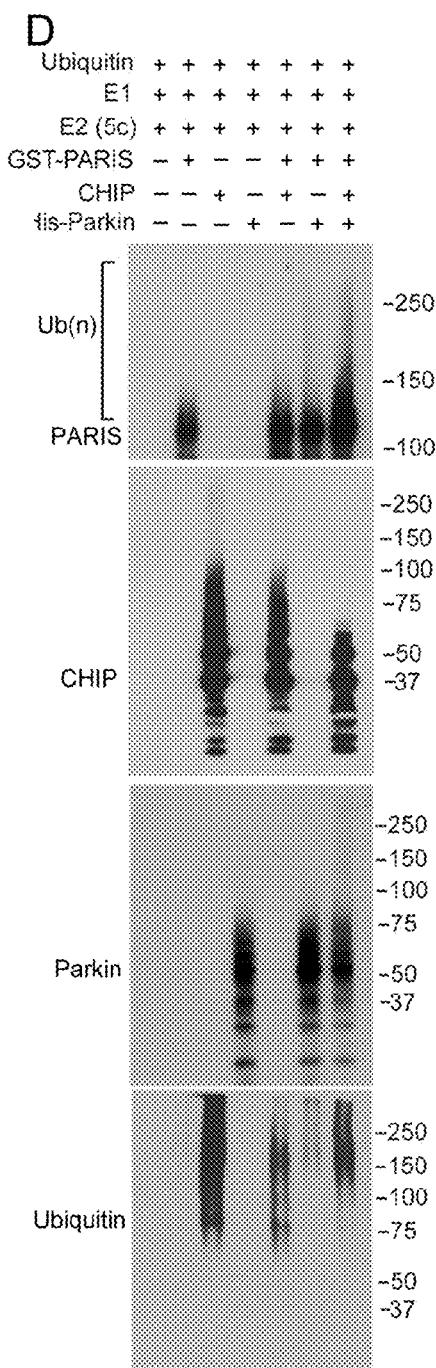
FIG. 26—ChIP, which acts as an E4 for parkin (Imai et al., 2002), enhances the ubiquitination of PARIS by parkin, but it has no affect in the absence of parkin, n=3.
Figure 27:
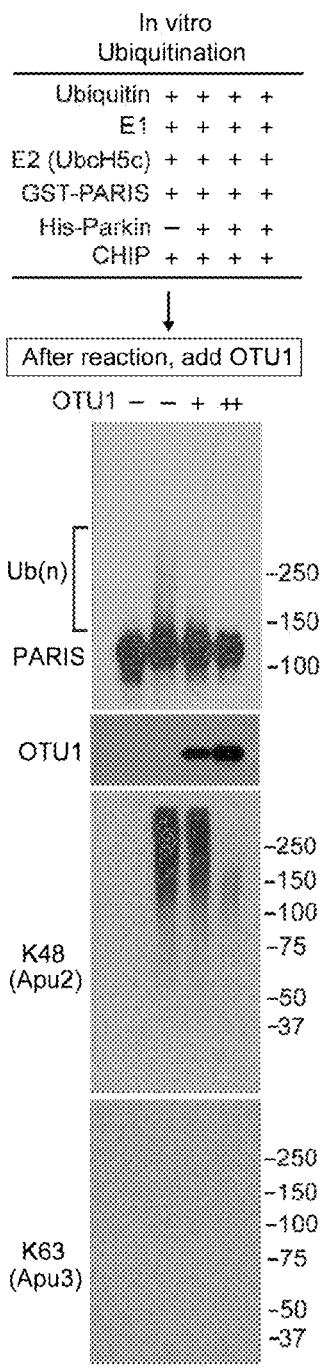
FIG. 27—OTU1, a K48-linkage specific deubiquitinating enzyme eliminates the ubiquitination of PARIS by parkin and ChIP indicating that parkin ubiquitinates PARIS via K48 linkages. K48 ubiquitin linkages were confirmed by immunoreactivity with a K48-specific anti-ubiquitin antibody (Apu2) and no immunoreactivity with a K63-specific anti-ubiquitin antibody (Apu3), n=3.
Figure 28:
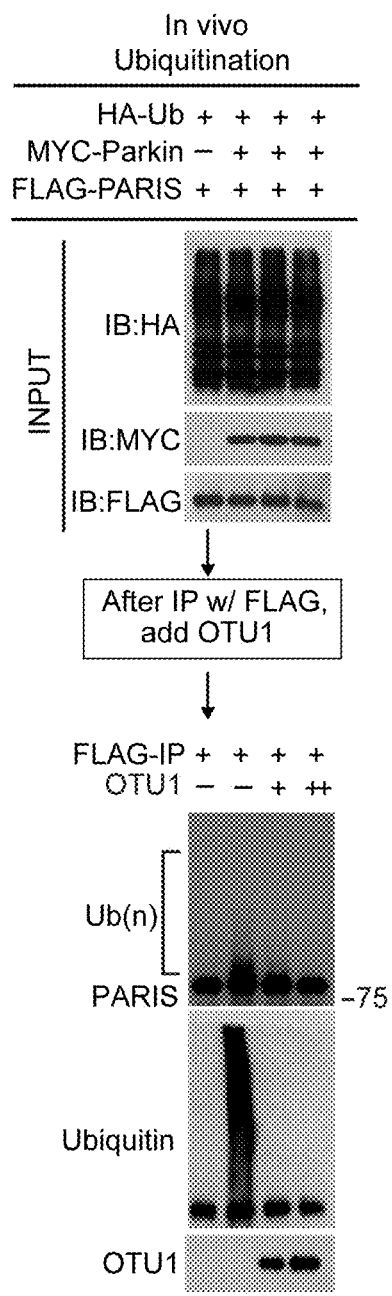
FIG. 28—Parkin mediated ubiquitination of FLAG-PARIS in SH-SY5Y cells is via K48 linkages as co-expression of OTU1 eliminates the ubiquitination, n=3.

In vitro ubiquitin assays showed that parkin ubiquitinates PARIS in the presence of various E2 enzymes including UbcH5c (FIG. 23). There was no ubiquitination signal in the absence of PARIS (FIG. 24) and in the absence of parkin (FIG. 25) indicating that the ubiquitination signal was specific for PARIS ubiqutination. ChIP, which acted as an E4 for parkin, enhanced the ubiquitination of PARIS by parkin, but it had no affect in the absence of parkin indicating that ChIP did not ubiquitinate PARIS directly (FIG. 26). OTU1, a K48-linkage specific deubiquitinating enzyme, successfully hydrolyzed the poly-ubiquitin chain on PARIS (FIGS. 27 and 28) and a K48-specific anti-ubiquitin antibody, but a K63 antibody did not detect the poly-ubiquitin chain on PARIS (FIG. 27), suggesting that endogenous and exogenous parkin ubiquitinated PARIS via K48 linkages.

Figure 29:
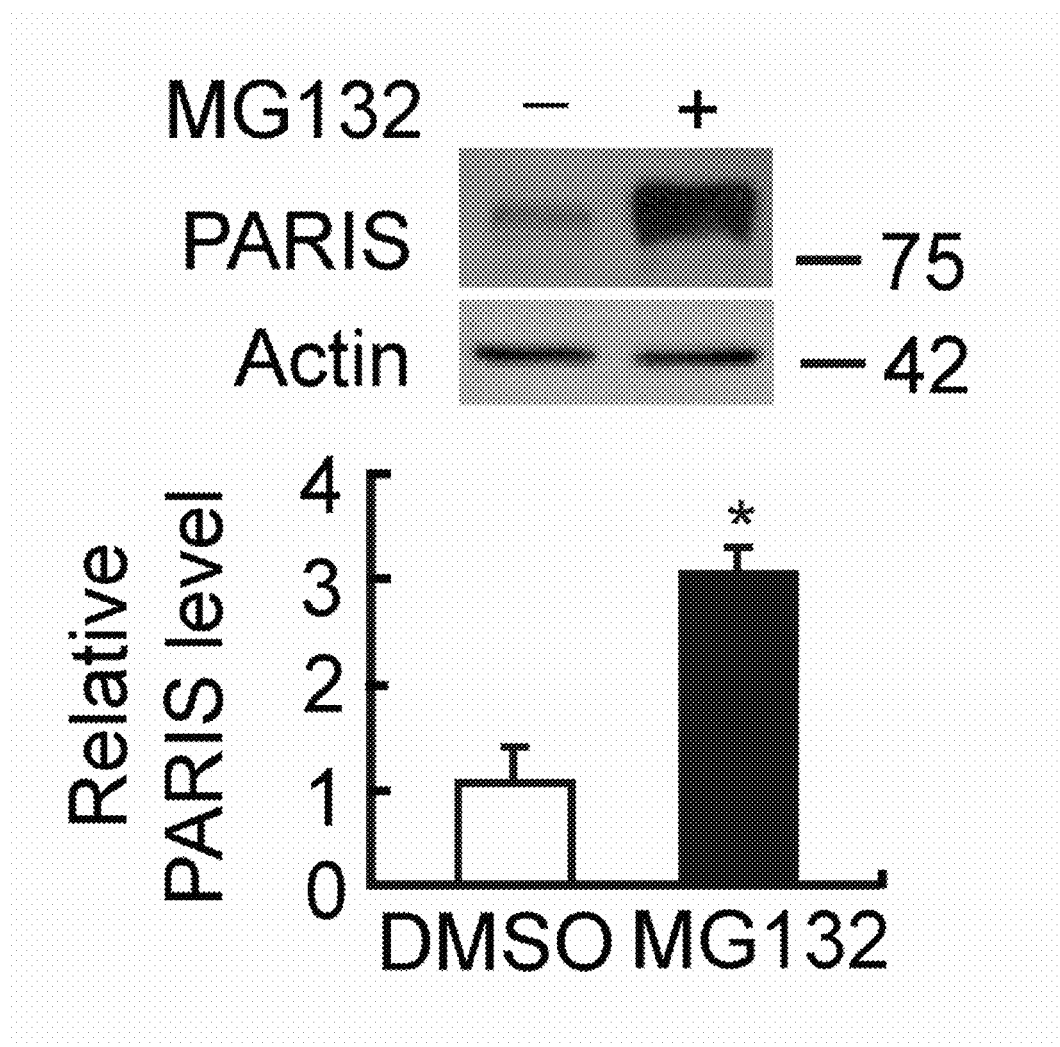
Figure 30:
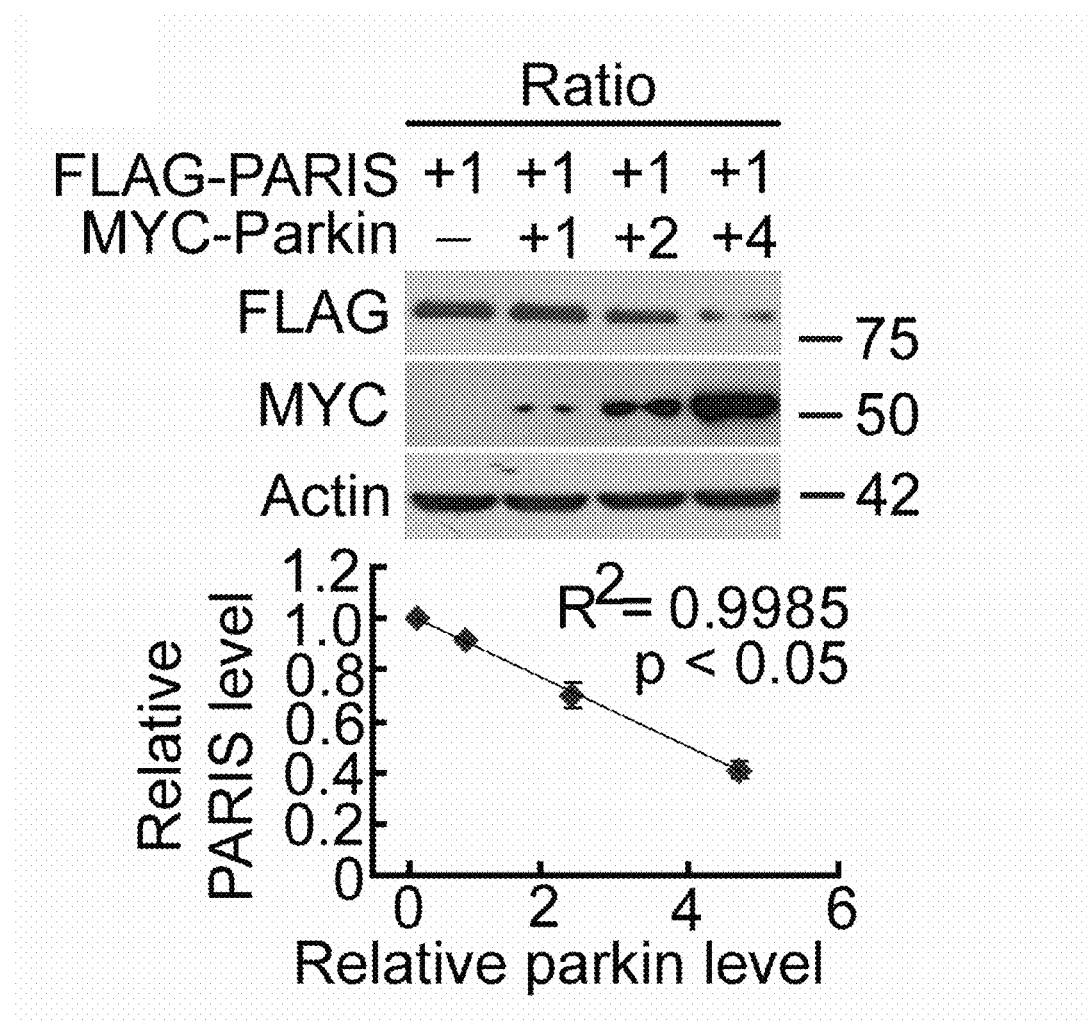
FIG. 30—Increasing ratio (1:1 to 4:1) of MYC-Parkin results in decreased steady-state levels of FLAG-PARIS (lanes 1-4). Bottom panel, relative PARIS and parkin levels normalized to β-actin, n=3; regression analysis, $R^2=0.9985$, $p<0.05$).
Figure 31:
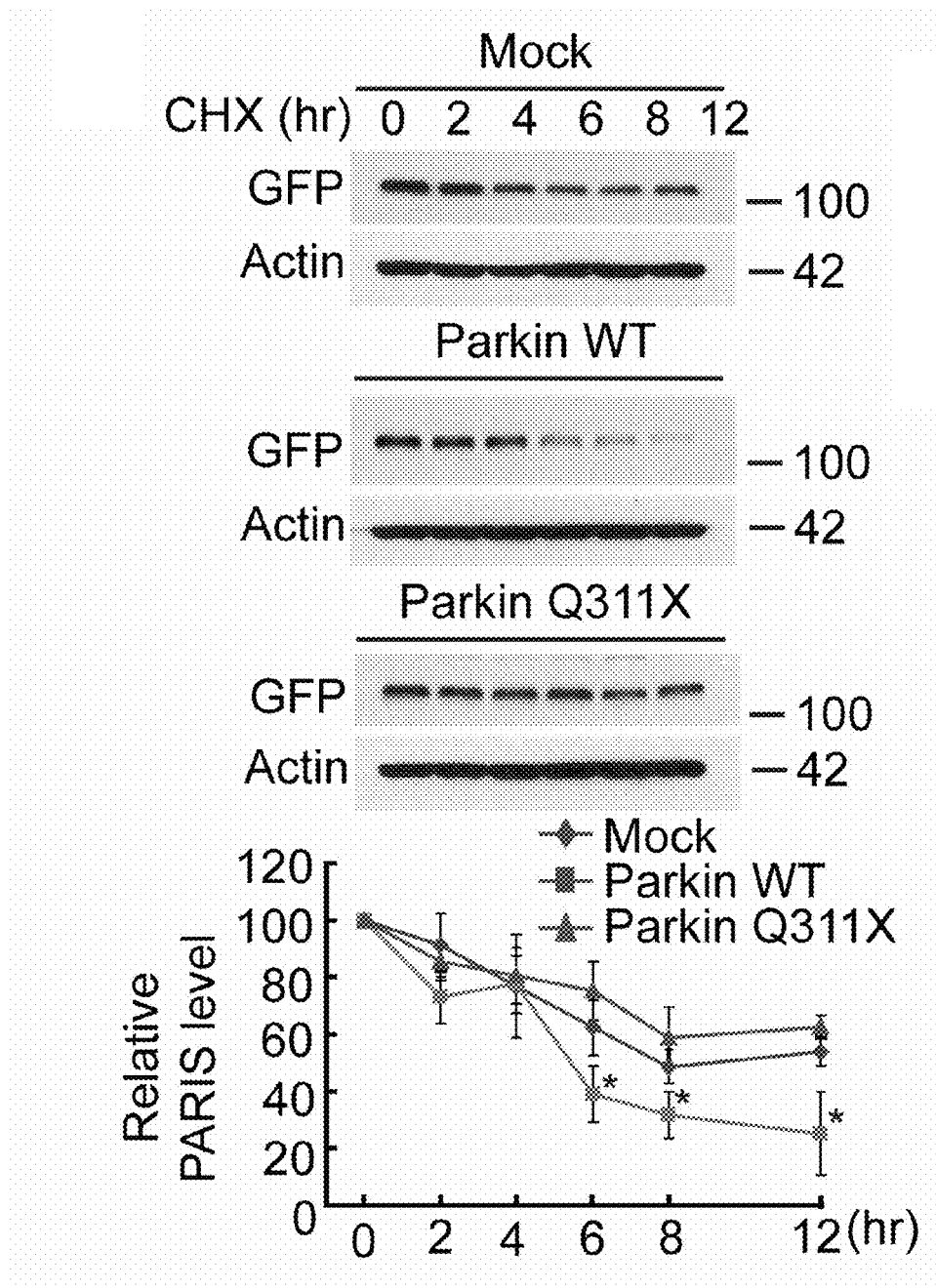
FIG. 31—WT Parkin decreases the steady-state levels of PARIS compared to mutant Q311X parkin or GFP transfected control cells in cyclohexamide (CHX)-chase experiments in SH-SY5Y cells transiently expressing FLAG-PARIS. Bottom panel, relative PARIS levels normalized to β-actin, n=3. [mean±S.E.M., $*p<0.05$, $p<0.01$ and $*p<0.001$, ANOVA with Student-Newman-Keuls post-hoc analysis].
Figure 32:
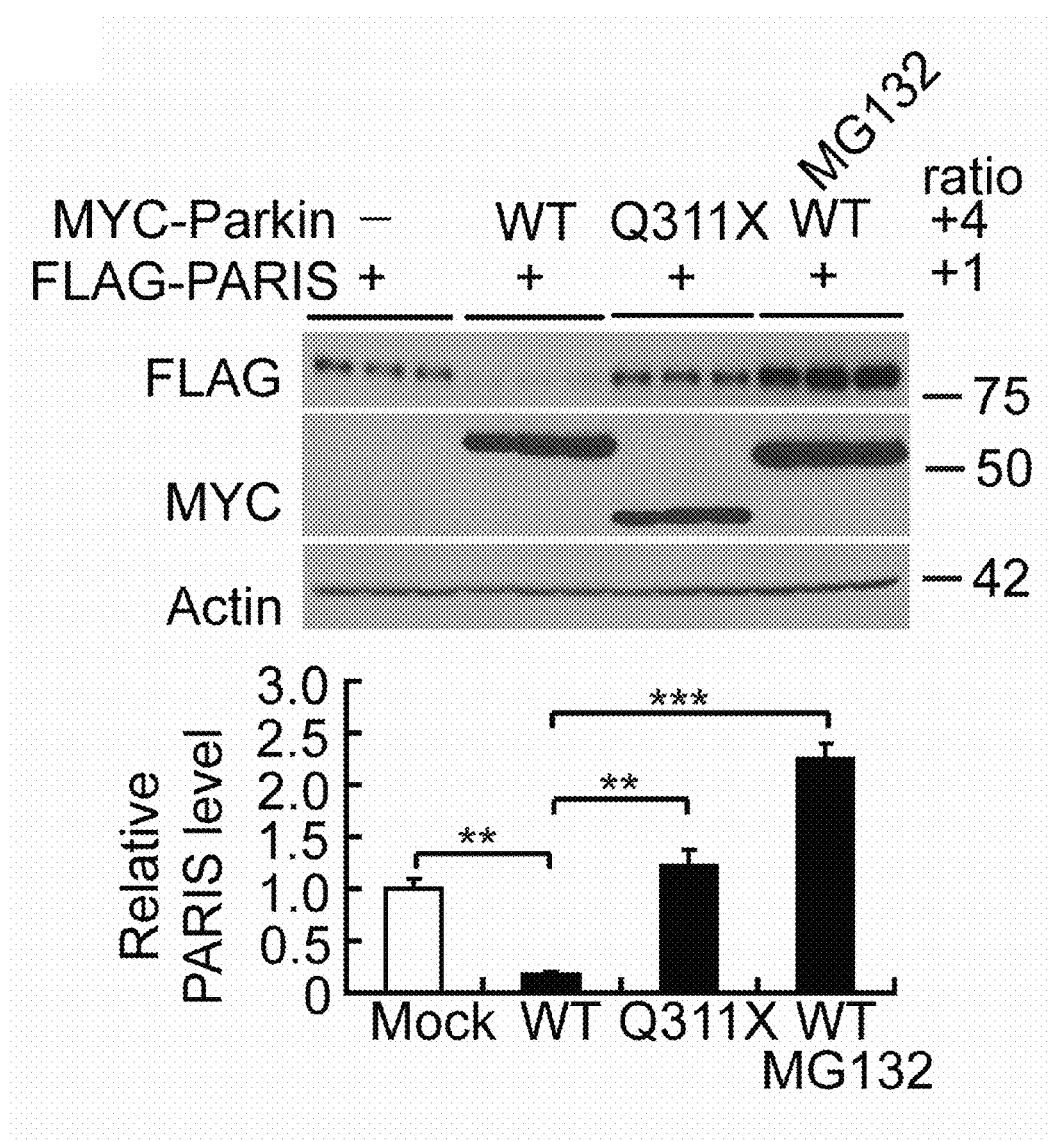
FIG. 32—MYC-parkin leads to degradation of FLAG-PARIS at a 4 to 1 ratio, respectively. 10 μM MG-132 prevents the degradation of FLAG-PARIS and MYC-Q311X parkin has no effect, n=3). [mean±S.E.M., $*p<0.05$, $p<0.01$ and $*p<0.001$, ANOVA with Student-Newman-Keuls post-hoc analysis].
Figure 33:
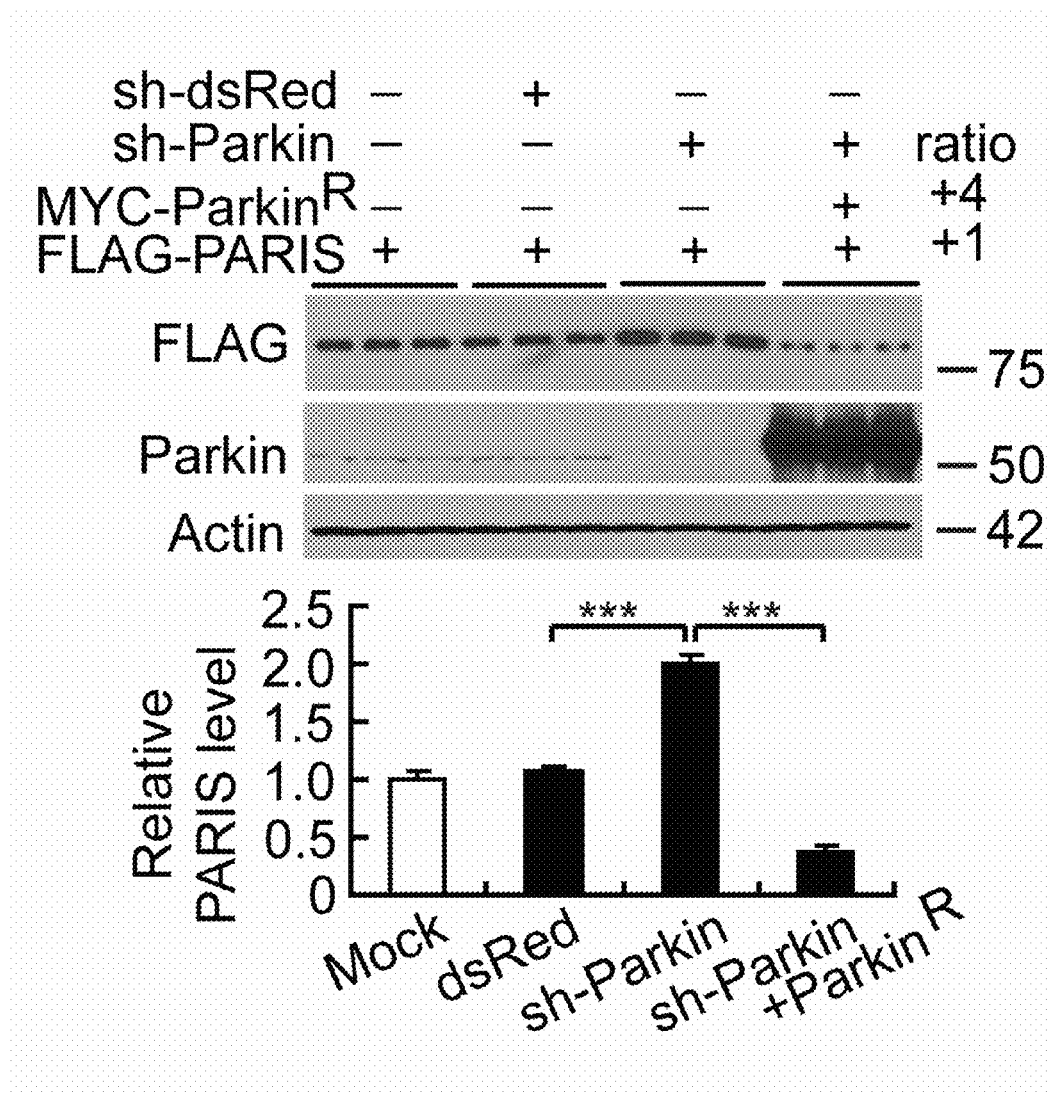
FIG. 33—PARIS accumulates after shRNA-Parkin and co-expression of shRNA resistant parkin (MYC-Parkin$^R$) leads to robust degradation of PARIS, n=3. [Data=mean±S.E.M., $*p<0.05$, $p<0.01$ and $*p<0.001$, ANOVA with Student-Newman-Keuls post-hoc analysis].

The steady state level of PARIS was regulated by the ubiquitin proteasome system since the level of PARIS increased approximately two to three fold when SH-SY5Y cells were treated with the proteasome inhibitor, MG132 (FIG. 29). The levels of PARIS and parkin were tightly and significantly correlated ($R^2=0.9985$) in co-expression experiments in SH-SY5Y cells in which increased levels of parkin led to decreased levels of PARIS (FIG. 30). Cyclohexamide (100 µg/ml) chase experiments in SH-SY5Y cells transiently expressing GFP-tagged PARIS with or without WT parkin or Q311X parkin demonstrated that the decrease in the steady state levels of PARIS was accelerated in the presence of WT parkin compared with cells transfected with GFP-vector or familial linked parkin Q311X mutant (FIG. 31). Parkin at a 4 to 1 ratio with PARIS led to a statistically significant reduction in PARIS that was blocked by MG132, whereas the catalytically inactive Q311X parkin failed to reduce PARIS levels (FIG. 32). ShRNA-Parkin led to a significant increase in the level of PARIS, which was reduced by expression of a shRNA-resistant WT parkin (FIG. 33). These results taken together suggested that parkin controls the levels of PARIS via the ubiquitin proteasome system.

Experiment 4

PARIS Accumulated in the Absence of Parkin Activity

PARIS levels were increased two fold in the cingulate cortex of AR-PD patients, which lacked functional parkin, versus age-matched controls (FIGS. 34 and 35) (See Table 2). Due to the lack of tissue availability, it was not possible to assess the levels of PARIS in other brain regions of AR-PD patients. PARIS levels were also increased by more than two fold in both the striatum and the SN of sporadic PD compared to controls (FIGS. 36 and 37) (See Table 3). No alteration in the levels of PARIS mRNA was found in PD striatum or PD SN versus control striatum and SN indicating that the increased level of PARIS was not due to a transcriptional effect (see FIGS. 38 and 39) (See Table 4 for qRT-PCR primers and Table 5 for details on human brain samples). PARIS levels were not increased in regions of the brain that were relatively unaffected in PD including the cerebellum and the frontal cortex of sporadic PD patients compared to controls (FIGS. 36 and 37) suggesting that the upregulation was primarily within the nigrostriatal pathway.

TABLE 2

|  | Final Diagnosis | Age | PMD |
| --- | --- | --- | --- |
| Control | Control | 61 | 15 |
|  | Control | 67 | 6 |
|  | Control | 68 | 10 |
|  | Control | 49 | 15 |
| AR-PD | PD | 62 | 15 |
|  | PD | 65 | 4 |
|  | PD | 52 | 18 |
|  | PD | 68 | 10 |

Figure 34:
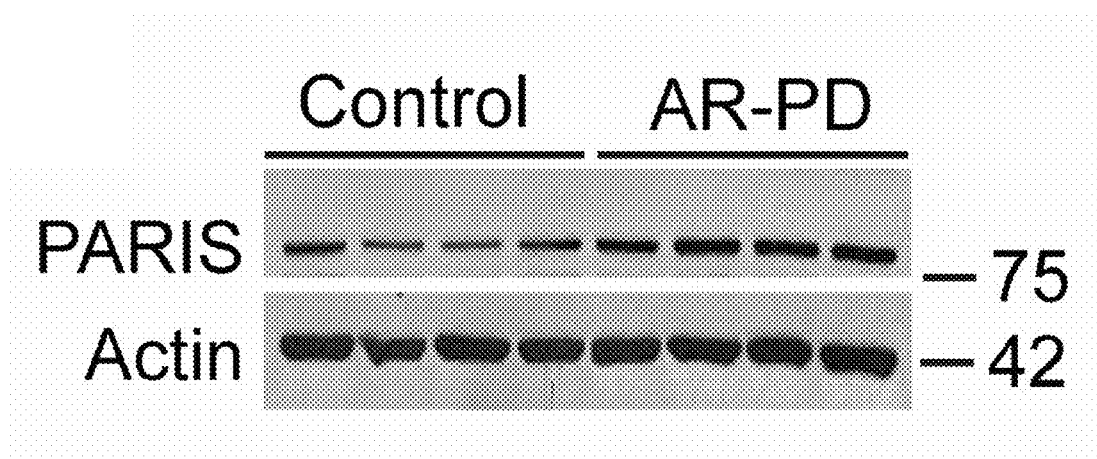
FIG. 34—Immunoblot analysis of PARIS and β-actin in cingulate cortex from age-matched controls and AR-PD patient brains with parkin mutations.
Figure 35:
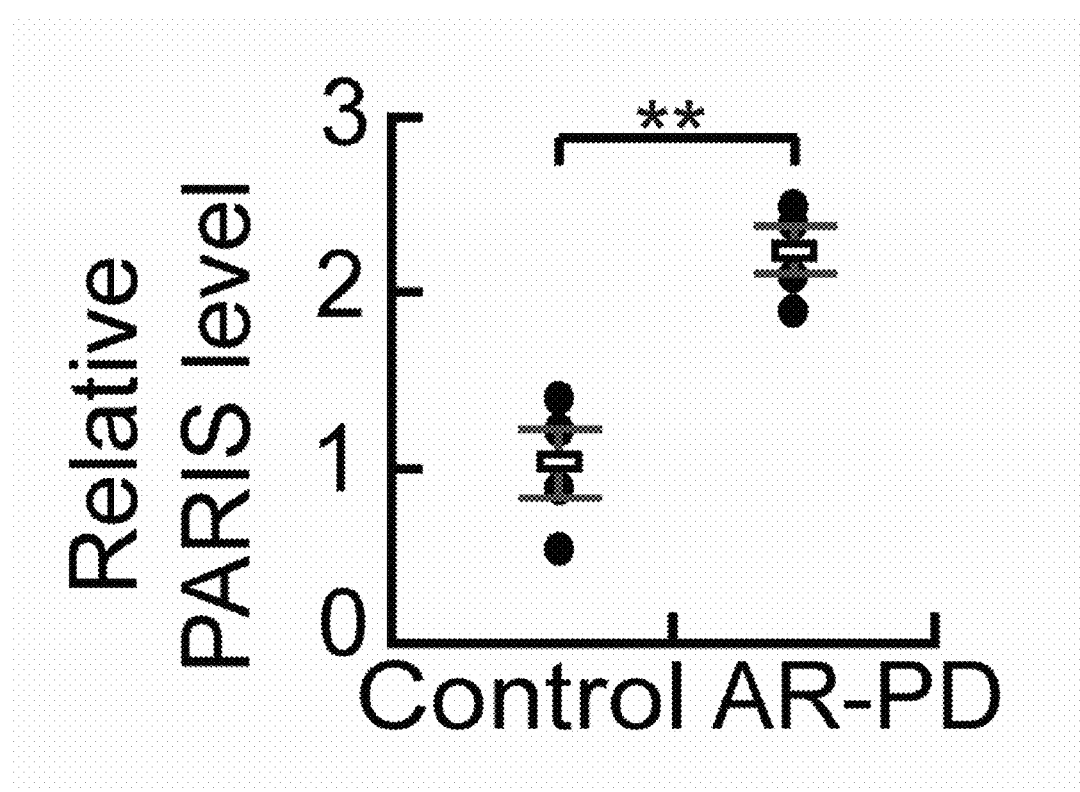
FIG. 35—Quantitation of the immunoblots in FIG. 34 normalized to β-actin, n=4. [Data=mean±S.E.M., $*p<0.05$, $p<0.01$ and $*p<0.001$, unpaired two-tailed Student's t-test].

AR-PD cingulate cortex used for immunoblot in FIGS. 34 and 35. Abbreviations: PD, Parkinson's disease; PMD, postmortem delay.

TABLE 3

|  | Final Diagnosis | Age | Sex | Race | PMD |
| --- | --- | --- | --- | --- | --- |
| Control | Control | 87 | F | W | 7 |
|  | Control | 89 | M | W | 8.5 |
|  | Control | 71 | M | W | 16 |
|  | Control | 79 | M | W | 16 |
| PD | PD w/dementia | 76 | M | W | 17 |
|  | PD w/dementia, neurodegeneration, occipital infarct | 83 | M | W | 5 |
|  | PD, multiple infarcts/contusions | 80 | F | W | 6 |
|  | PD, Neocortical | 71 | M | W | 8 |
|  | PD w/dementia | 73 | M | W | 6.5 |

Figure 36:
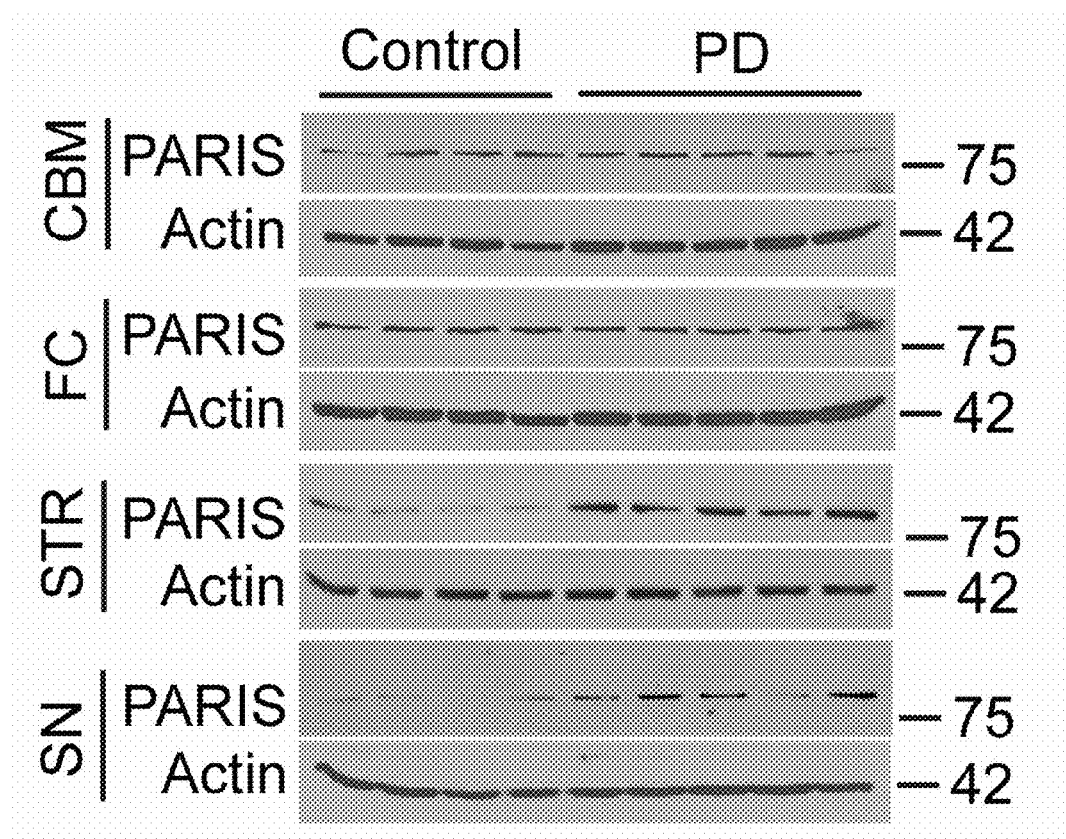
FIG. 36—PARIS levels in cerebellum (CBM), frontal cortex (FC), striatum (STR) and SN of sporadic PD patient brains compared to age-matched controls.
Figure 37:
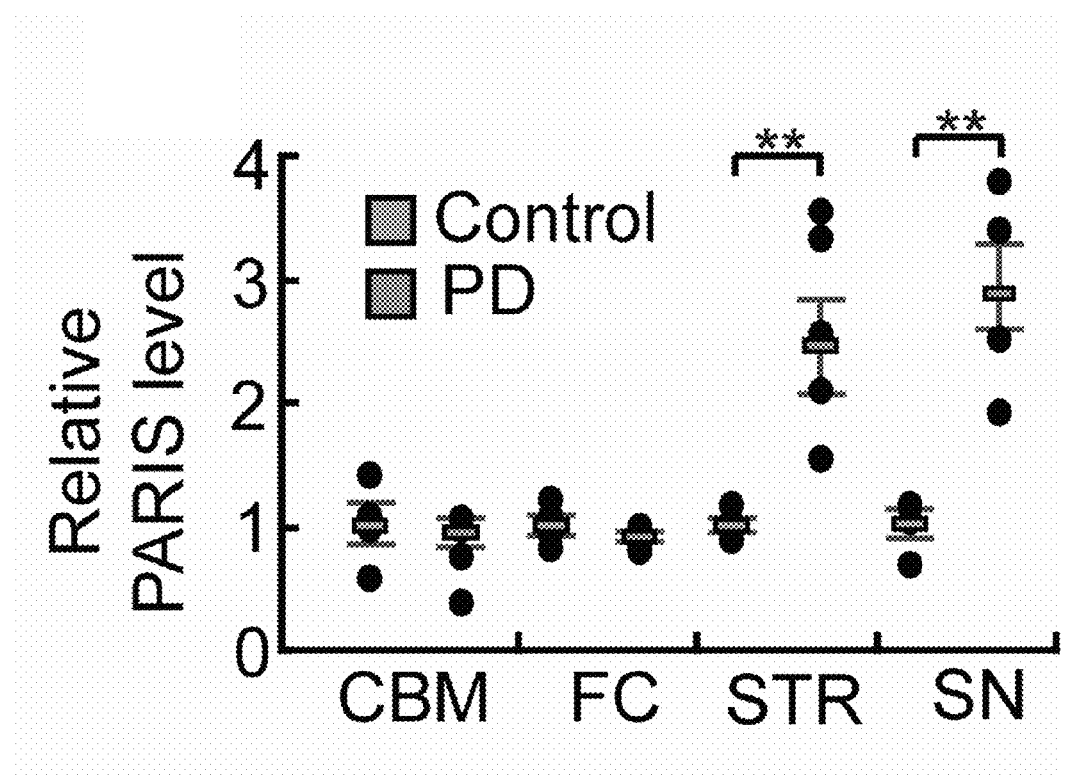
FIG. 37—Relative PARIS levels normalized to β-actin in FIG. 35, Controls n=4; PD n=5. [Data=mean±S.E.M., $*p<0.05$, $p<0.01$ and $*p<0.001$, ANOVA test with Student-Newman-Keuls post-hoc analysis].
Figure 40:
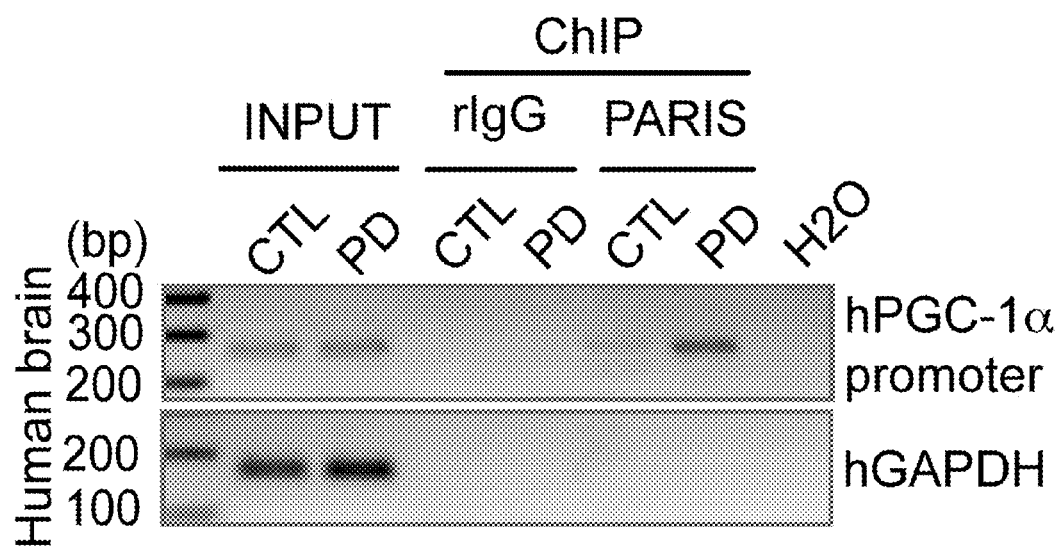
FIG. 40—ChIP assay of endogenous PARIS binding to the IRS region of the human PGC-1α promoter in human PD and aged-matched control (CTL) striatum, control n=3; PD n=4.
Figure 41:
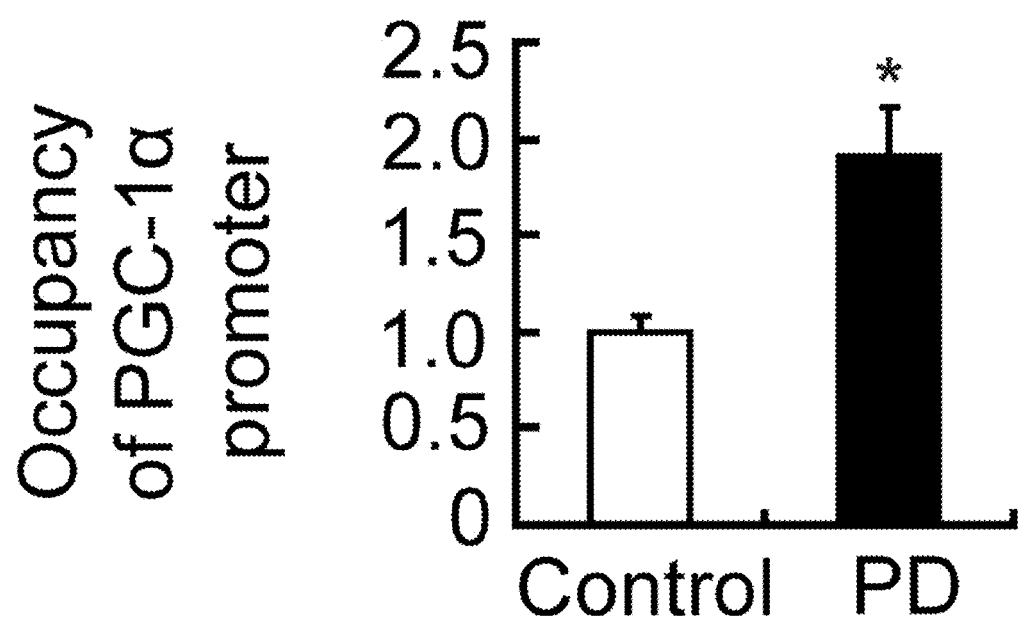
FIG. 41—Quantitation of ChIP in FIG. 40. Human specific IRS primers for FIG. 67 and FIG. 40 are indicated in FIG. 57. [mean±S.E.M., $*p<0.05$, $p<0.01$, $*p<0.001$, unpaired two-tailed Student's t-test].

Human postmortem tissues used for immunoblot in FIGS. 36 and 37, and ChIP in FIGS. 40 and 41. Abbreviations: PD, Parkinson's disease; W, white; B, black; PMD, postmortem delay.

TABLE 4

| Target genes | Mouse primers (5'-3') | Human primers (5'-3') |
| --- | --- | --- |
| PGC-1α | F AGCCGTGACCACTGACAACGAG (SEQ ID NO. 29) | TCCTCACAGAGACACTAGACA (SEQ ID NO. 31) |
|  | R GCTGCATGGTTCTGAGTGCTAAG (SEQ ID NO. 30) | CTGGTGCCAGTAAGAGCTTCT (SEQ ID NO. 32) |

TABLE 4-continued

| Target genes | Mouse primers (5'-3') | Human primers (5'-3') |
|---|---|---|
| PEPCK | F CTGCATAACGGTCTGGACTTC (SEQ ID NO. 33) | CAAGACGGTTATCGTCACCCA (SEQ ID NO. 35) |
| | R CAGCAACTGCCCGTACTCC (SEQ ID NO. 34) | GAACCTGGCATTGAACGCTT (SEQ ID NO. 36) |
| G6Pase | F CGACTCGCTATCTCCAAGTGA (SEQ ID NO. 37) | GTGTCCGTGATCGCAGACC (SEQ ID NO. 39) |
| | R GTTGAACCAGTCTCCGACCA (SEQ ID NO. 38) | GACGAGGTTGAGCCAGTCTC (SEQ ID NO. 40) |
| IGFBP-1 | F ATCAGCCCATCCTGTGGAAC (SEQ ID NO. 41) | GAGCACGGAGATAACTGAGGA (SEQ ID NO. 43) |
| | R TGCAGCTAATCTCTCTAGCACTT (SEQ ID NO. 42) | GCCTTCGAGCCATCATAGGTA (SEQ ID NO. 44) |
| APOC3 | F TACAGGGCTACATGGAACAAGC (SEQ ID NO. 45) | CTCCCTTCTCAGCTTCATGC (SEQ ID NO. 47) or TGCAGGGTTACATGAAGCACG (SEQ ID NO. 48) |
| | R CAGGGATCTGAAGTGATTGTCC (SEQ ID NO. 46) | GTCTGACCTCAGGGTCCAAA (SEQ ID NO. 49) or CTCCAGTAGTCTTTCAGGGAACT (SEQ ID NO. 50) |
| TAT | F TGCTGGATGTTCGCGTCAATA (SEQ ID NO. 51) | TGTGTCCCCATCTTAGCTGAT (SEQ ID NO. 53) or TACAGACCCTGAAGTTACCCAG (SEQ ID NO. 54) |
| | R CGGCTTCACCTTCATGTTGTC (SEQ ID NO. 52) | AATGGTACAGGGTCCCAAAATG (SEQ ID NO. 55) or TAAGAAGCAATCTCCTCCCGA (SEQ ID NO. 56) |
| SOD1 | F CCAGTGCAGGACCTCATTTT (SEQ ID NO. 57) | AGGGCATCATCAATTTCGAGC (SEQ ID NO. 59 |
| | R TTGTTTCTCATGGACCACCA (SEQ ID NO. 58) | GCCCACCGTGTTTTCTGGA (SEQ ID NO. 60) |
| SOD2 | F CCGAGGAGAAGTACCACGAG (SEQ ID NO. 61) | TTGGCCAAGGGAGATGTTAC (SEQ ID NO. 63) |
| | R GCTTGATAGCCTCCAGCAAC (SEQ ID NO. 62) | AGTCACGTTTGATGGCTTCC (SEQ ID NO. 64) |
| GPX1 | F CCGTGCAATCAGTTCGGACA (SEQ ID NO. 65) | GCACCCTCTCTTCGCCTTC (SEQ ID NO. 67) |
| | R TCACTTCGCACTTCTCAAACAAT (SEQ ID NO. 66) | TCAGGCTCGATGTCAATGGTC (SEQ ID NO. 68) |
| CAT | F AGCGACCAGATGAAGCAGTG (SEQ ID NO. 69) | CGCAGAAAGCTGATGTCCTGA (SEQ ID NO. 71) |
| | R TCCGCTCTCTGTCAAAGTGTG (SEQ ID NO. 70) | TCATGTGTGACCTCAAAGTAGC (SEQ ID NO. 72) |
| NRF1 | F GTTGGTACAGGGGCAACAGT (SEQ ID NO. 73) | CTTACAAGGTGGGGGACAGA (SEQ ID NO. 75) |

TABLE 4-continued

| Target genes | | Mouse primers (5'-3') | Human primers (5'-3') |
|---|---|---|---|
| | R | TCGTCTGGATGGTCATTTCA (SEQ ID NO. 74) | GGTGACTGCGCTGTCTGATA (SEQ ID NO. 76) |
| TFAM | F | CCAAAAAGACCTCGTTCAGC (SEQ ID NO. 77) | CCGAGGTGGTTTTCATCTGT (SEQ ID NO. 79) |
| | R | CTTCAGCCATCTGCTCTTCC (SEQ ID NO. 78) | TCCGCCTATAAGCATCTTG (SEQ ID NO. 80) |
| UCP2 | F | ACTTTCCCTCTGGATACCGC (SEQ ID NO. 81) | GCATCGGCCTGTATGATTCT (SEQ ID NO. 83) |
| | R | ACGGAGGCAAAGCTCATCTG (SEQ ID NO. 82) | TTGGTATCTCCGACCACCTC (SEQ ID NO. 84) |
| UCP3 | F | CTGCACCGCCAGATGAGTTT (SEQ ID NO. 85) | AGCCTCACTACCCGGATTTT (SEQ ID NO. 87) |
| | R | ATCATGGCTTGAAATCGGACC (SEQ ID NO. 86) | CGTCCATAGTCCCGCTGTAT (SEQ ID NO. 88) |
| ANT1 | F | GTCTCTGTCCAGGGCATCAT (SEQ ID NO. 89) | ATGGTCTGGGCGACTGTATC (SEQ ID NO. 91) |
| | R | ACGACGAACAGTCTCAAACG (SEQ ID NO. 90) | TCAAAGGGGTAGGACACCAG (SEQ ID NO. 92) |
| ATP5B | F | GAGGGATTACCACCCATCCT (SEQ ID NO. 93) | GCACGGAAAATACAGCGTTT (SEQ ID NO. 95) |
| | R | CATGATTCTGCCCAAGGTCT (SEQ ID NO. 94) | GCCAGCTTATCAGCTTTTGC (SEQ ID NO. 96) |
| CYTC | F | CCAAATCTCCACGGTCTGTTC (SEQ ID NO. 97) | GGTGATGTTGAGAAAAGGCAAG (SEQ ID NO. 99) |
| | R | ATCAGGGTACCTCTCCCCAG (SEQ ID NO. 98) | GTTCTTATTGGCGGCTGTGT (SEQ ID NO. 100) |
| COX II | F | ACGAAATCAACAACCCCGTA (SEQ ID NO. 101) | TTCATGATCACGCCCTCATA (SEQ ID NO. 103) |
| | R | GGCAGAACGACTCGGTTATC (SEQ ID NO. 102) | TAAAGGATGCGTAGGGATGG (SEQ ID NO. 104) |
| COX IV | F | ACCAAGCGAATGCTGGACAT (SEQ ID NO. 105) | CCGCGCTCGTTATCATGTG (SEQ ID NO. 107) |
| | R | GGCGGAGAAGCCCTGAA (SEQ ID NO. 106) | CGTTCTTTTCGTAGTCCCACTTG (SEQ ID NO. 108) |
| GAPDH | F | AAACCCATCACCATCTTCCAG (SEQ ID NO. 109) | AAACCCATCACCATCTTCCAG (SEQ ID NO. 111) |
| | R | AGGGGCCATCCACAGTCTTCT (SEQ ID NO. 110) | AGGGGCCATCCACAGTCTTCT (SEQ ID NO. 112) |
| Parkin | F | TGGAAAGCTCCGAGTTCAGT (SEQ ID NO. 113) | CAGCAGTATGGTGCAGCGGA (SEQ ID NO. 115) |
| | R | CCTTGTCTGAGGTTGGGTGT (SEQ ID NO. 114) | TCAAATACGGCACTGCACTC (SEQ ID NO. 116) |
| PARIS | F | AGTTGGACTCTGGAGCAGGA (SEQ ID NO. 117) | GCTGGAATTTCCGGTGTAAACC (SEQ ID NO. 119) |
| | R | GCTGCTGTGTTGAGCTTCAG (SEQ ID NO. 118) | GGGGTCCAAGATGGCCTCT (SEQ ID NO. 120) |

Figure 38:
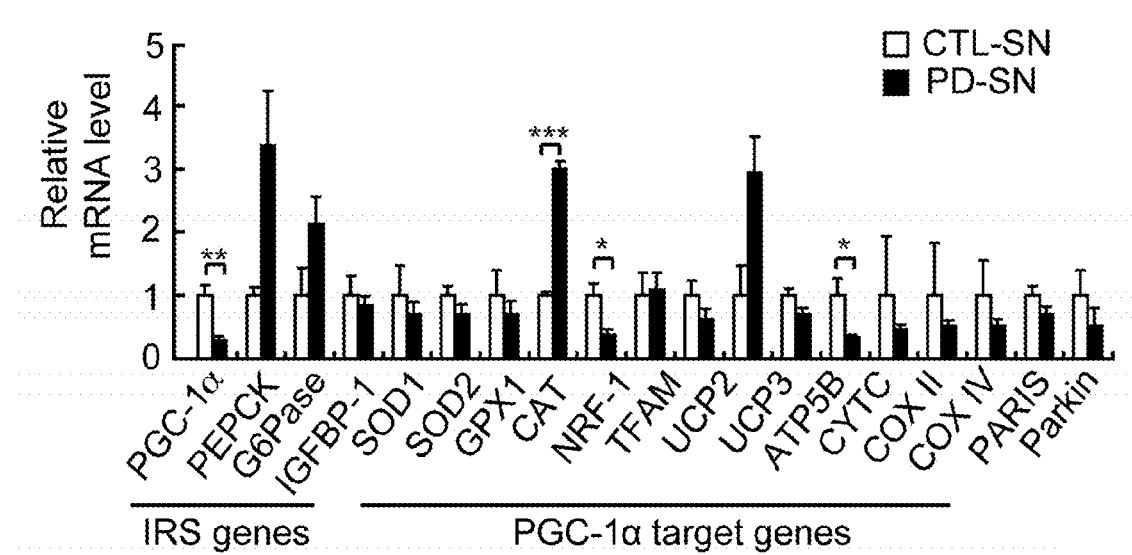
FIG. 38—Real-time qRT-PCR of IRS (PEPCK-like motif)-containing genes and PGC-1α dependent genes in PD SN compared to age-matched CTL-SN normalized to GAPDH, n =3-4 per group. [mean±S.E.M., $*p<0.05$, $p<0.01$ and $*p<0.001$, unpaired two-tailed Student's t-test].
Figure 39:
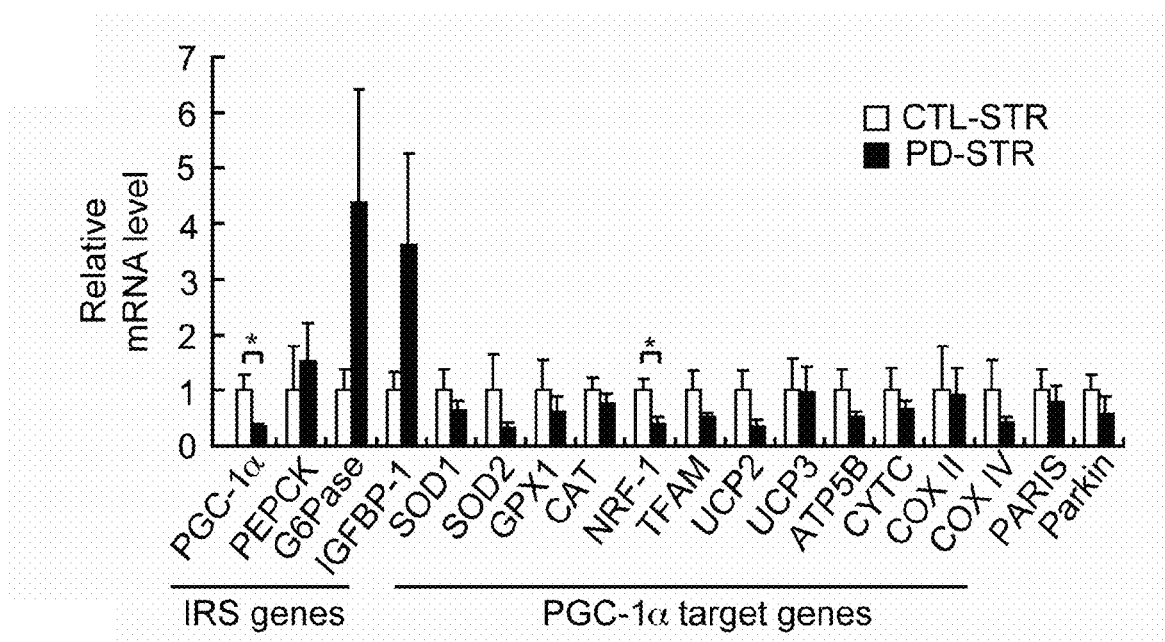
FIG. 39—Real-time qRT-PCR of qRT-PCR of IRS (PEPCK-like motif)-containing genes and PGC-1α dependent genes reveals that PGC-1α and NRF-1 are reduced in PD striatum compared to age-matched controls (n=4 per group). Relative mRNA levels of PGC-1α, parkin, PARIS and PGC-1α dependent genes normalized to GAPDH are indicated. No mRNA for APOC3 and TAT was detected with 2 different pairs of primers.
Figure 42:
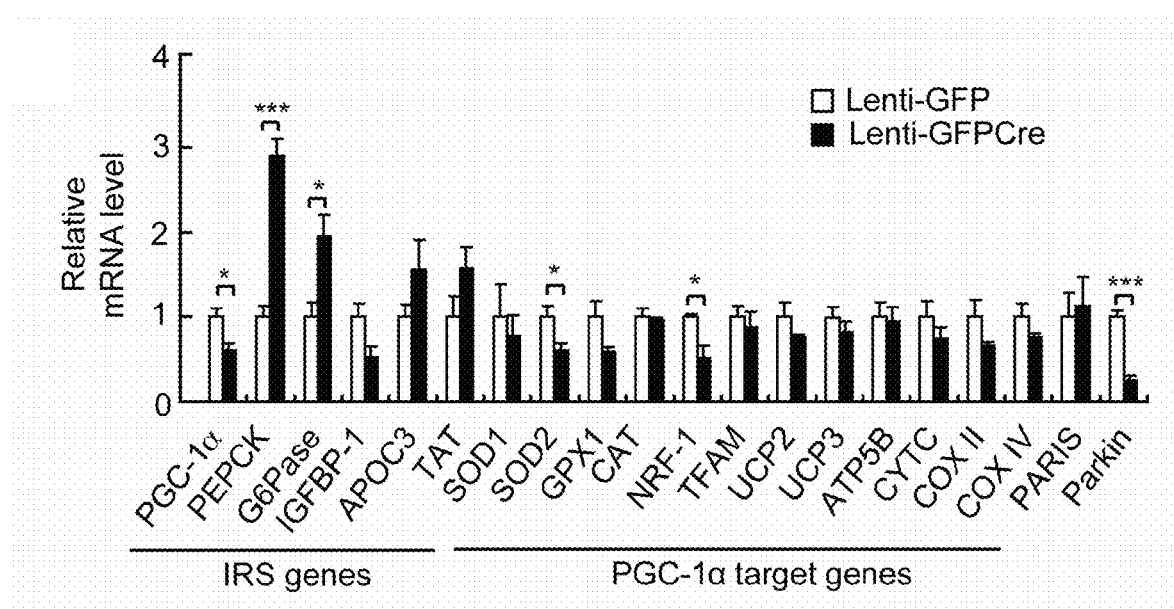
FIG. 42—Relative mRNA levels as determined by real-time qRT-PCR of IRS (PEPCK-like motif)-containing genes, PGC-1α, PARIS, parkin and PGC-1α dependent genes normalized to GAPDH in the SN of the lentiviral-mediated conditional parkin knockout model, n=4 per group. See Table 4 for qRT-PCR primers.
Figure 43:
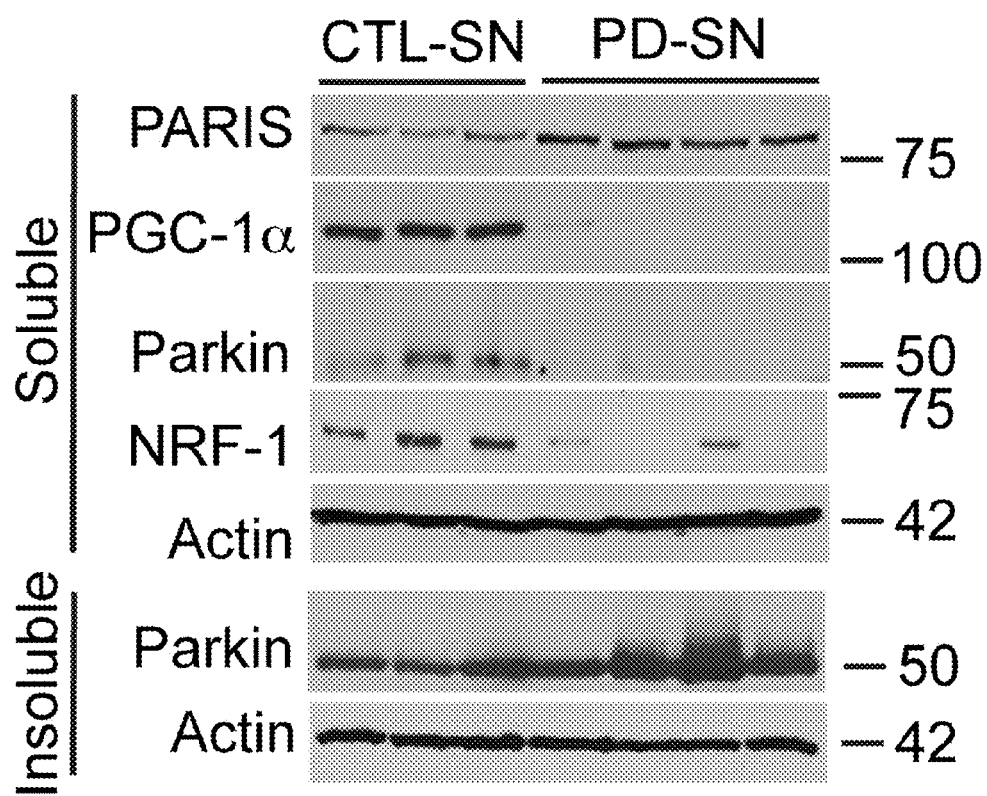
FIG. 43—Immunoblots of PARIS, PGC-1α, parkin and NRF-1 in soluble and insoluble fractions of PD SN compared to age-matched CTL-SN.
Figure 44:
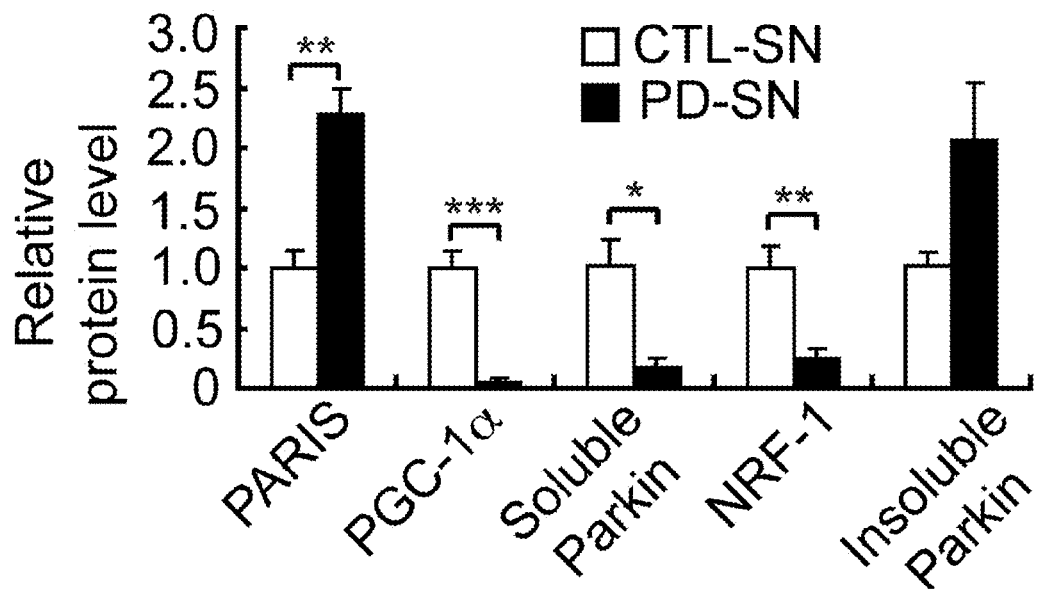
FIG. 44—Quantitation of the immunoblots in FIG. 43 normalized to β-actin, PD, n=4; Control, n=3. [mean±S.E.M., $*p<0.05$, $p<0.01$ and $*p<0.001$, unpaired two-tailed Student's t-test].

Primers used for real-time qRT-PCR in FIGS. 38, 39 and 42. Abbreviations: PGC-1α, peroxisome proliferators-activated receptor γ coactivator-1α; PEPCK, phosphoenolpyruvate carboxylase; G6Pase, glucose-6-phosphatase; IGFBP-1, insulin-like growth factor binding protein 1; APOC3, apolipoprotein C-III; TAT, tyrosine aminotransferase; SOD, superoxide dismutase-1; GPX1, Glutathione Peroxidase 1; CAT, Catalase; NRF1, nuclear respiratory factor 1; TFAM, mitochondrial transcription factor A; UCP, uncoupling protein; ANTI, adenine nucleotide translocator; ATP5B, ATP synthase, H+ transporting, mitochondrial F1 complex; CYTC, cytochrome c; COX, cytochrome C oxidase; F, forward primer; R, reverse primer (5'-3'); N/A, not applicable.

TABLE 5

|  | Final Diagnosis | Age | Sex | Race | PMD | Tissue |
|---|---|---|---|---|---|---|
| Control | Control | 62 | M | W | 14 | Str |
|  | Control | 59 | M | W | 12 | Str |
|  | Control | 79 | M | W | 16 | Str, SN |
|  | Control | 53 | M | W | N/A | Str |
|  | Control | 73 | F | W | 9 | SN |
|  | Control | 85 | M | B | 6 | SN |
| PD | PD, CVD | 85 | F | W | 9 | Str, SN |
|  | PD, W/D | 60 | M | W | 16 | Str |
|  | PD, W/D, ND, OI | 83 | M | W | 5 | Str, SN |
|  | PD, W/D | 84 | F | W | 11 | Str, SN |
|  | PD, W/D | 71 | M | W | 24 | SN |

Figure 46:
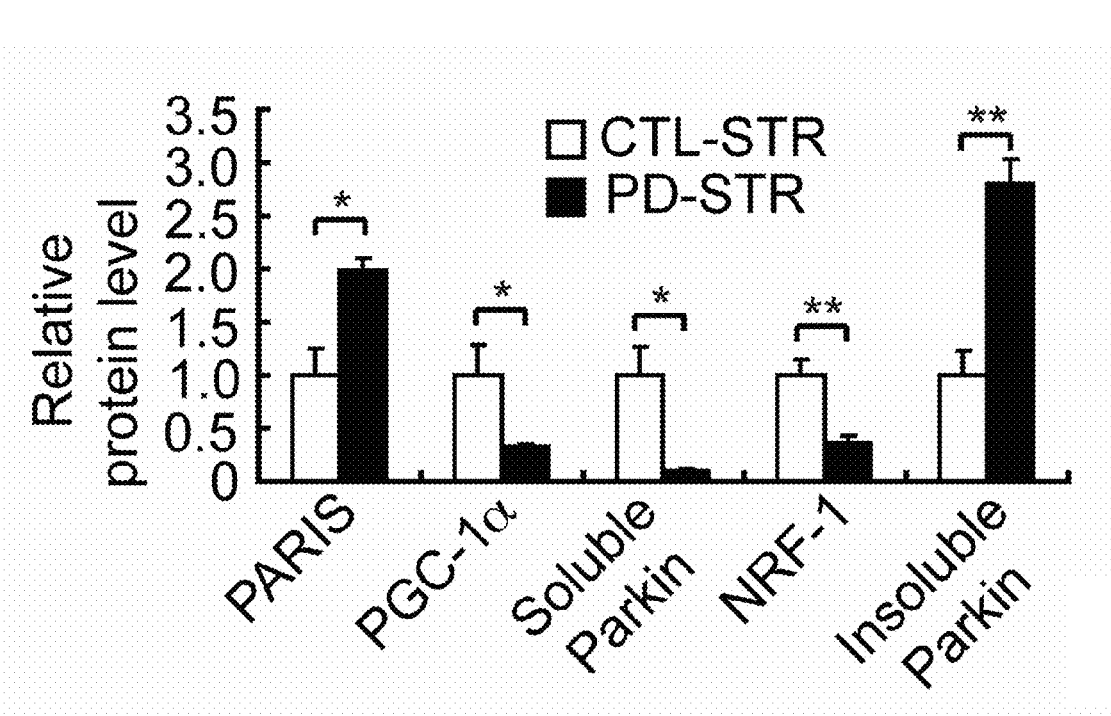
FIG. 46—Quantitation of the immunoblots in FIG. 45 normalized to β-actin, n=4 per group. (See Table 5 for details on human brain samples).
Figure 47:
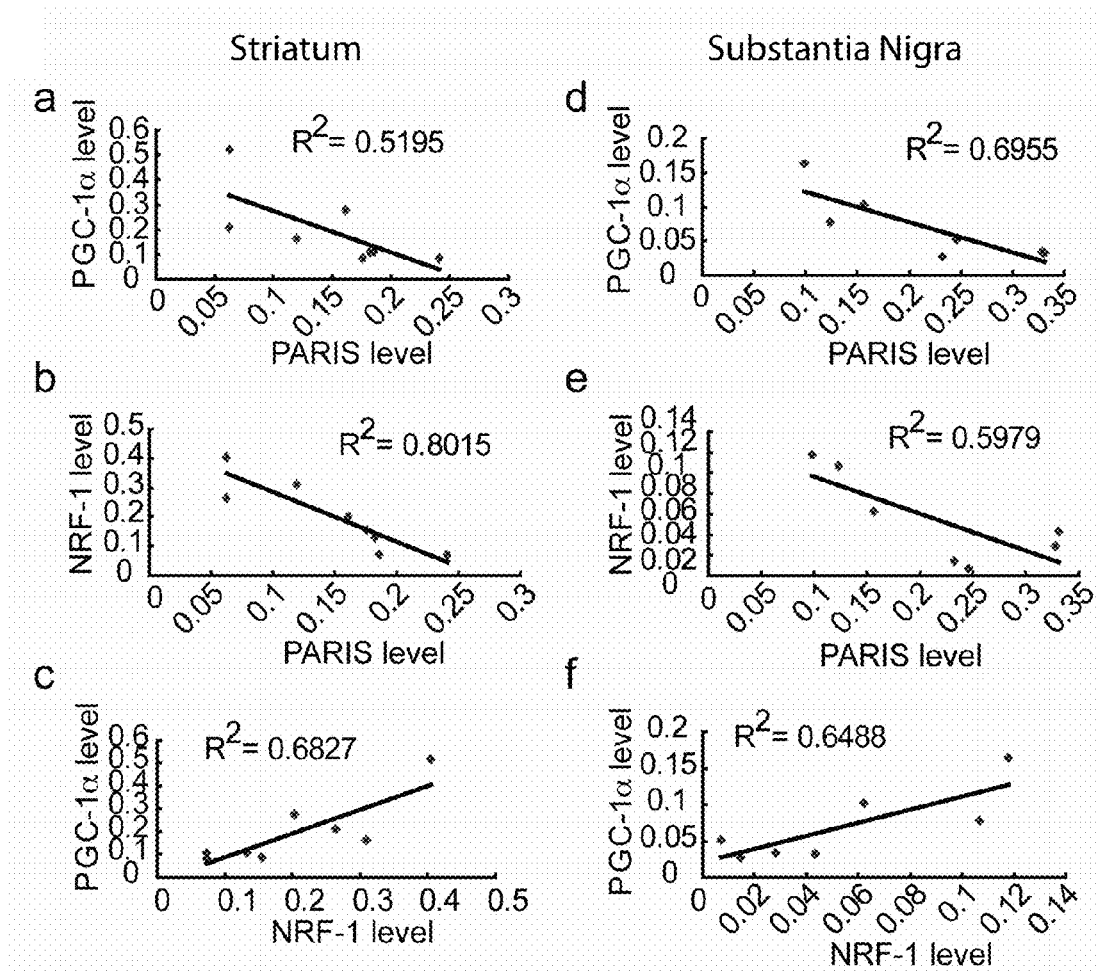
FIG. 47—a-f, Regression analysis of the quantified level of PARIS, PGC-1α, and NRF-1 shows there is a strong negative correlation between the protein levels of PARIS and PGC-1α ($R^2=0.5195$, $p<0.05$) and NRF-1 ($R^2=0.8015$, $p<0.01$) in the striatum and between PARIS and PGC-1α ($R^2=0.6955$, $p<0.05$) and NRF-1 ($R^2=0.5979$, $p<0.05$) in the SN and a positive correlation between PGC-1α and NRF-1 in the striatum ($R^2=0.6827$, $p<0.05$) and in the SN ($R^2=0.6488$, $p<0.05$), n=4 per group. See Table 5 for details on human brain samples.
Figure 48:
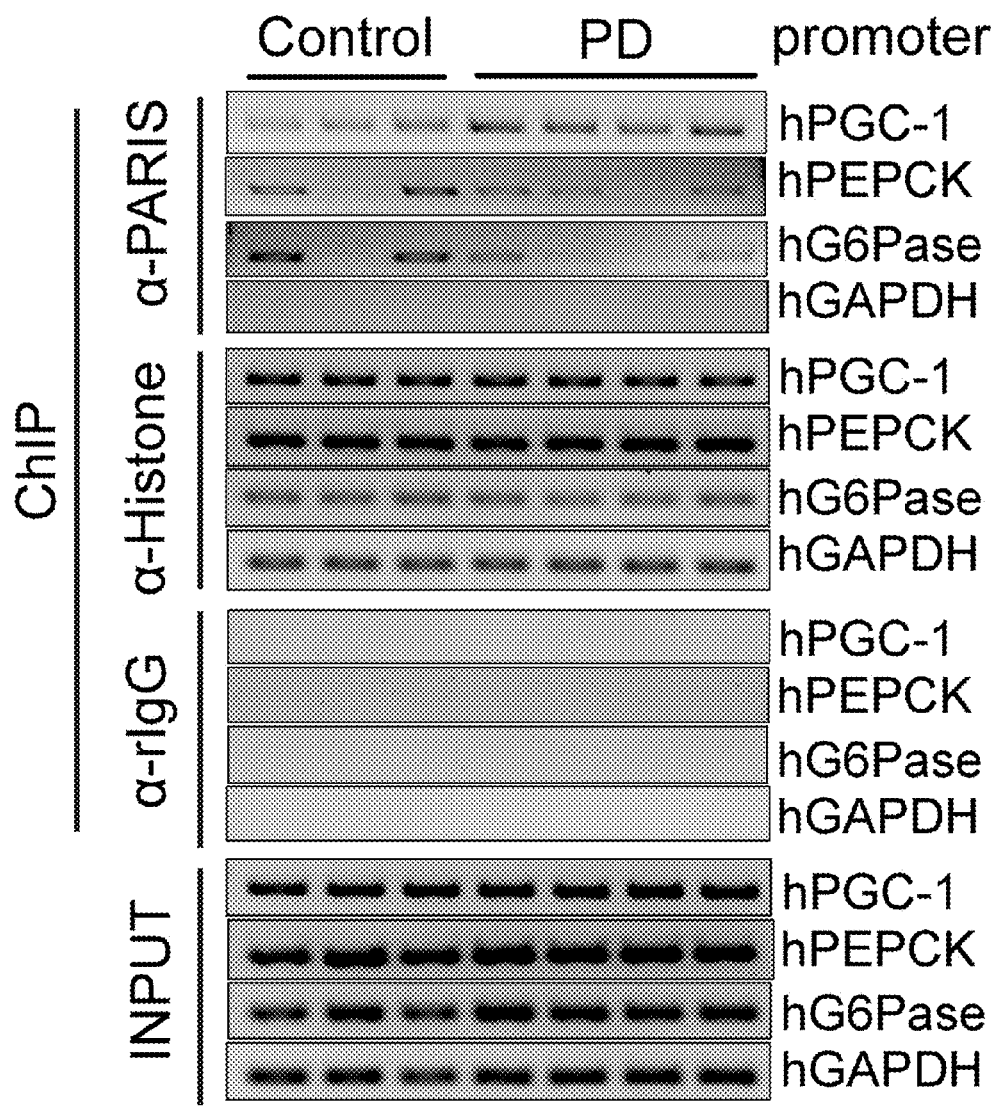
FIG. 48—PARIS occupies the endogenous PEPCK and G6Pase promoter. ChIP assay shows increased endogenous binding of PARIS in human PD and aged-matched control striatum to the IRS region of the human PGC-1α promoter and occupies the PEPCK and G6Pase promoter (CTL n=3; PD n=4; see Table 5 for details on human brain samples).

Human postmortem tissues used for immunoblot and real time qRT-PCR analysis in FIGS. 38, 39 and 43-47 and ChIP analysis in FIG. 48. Abbreviations: CVD, cerebrovascular disease; W/D, with dementia; ND, neurodegeneration; OI, occipital infarction; W, white; B, black; PMD, post-mortem delay; N/A, not available; Str, striatum; SN, substantial nigra.

Figure 49:
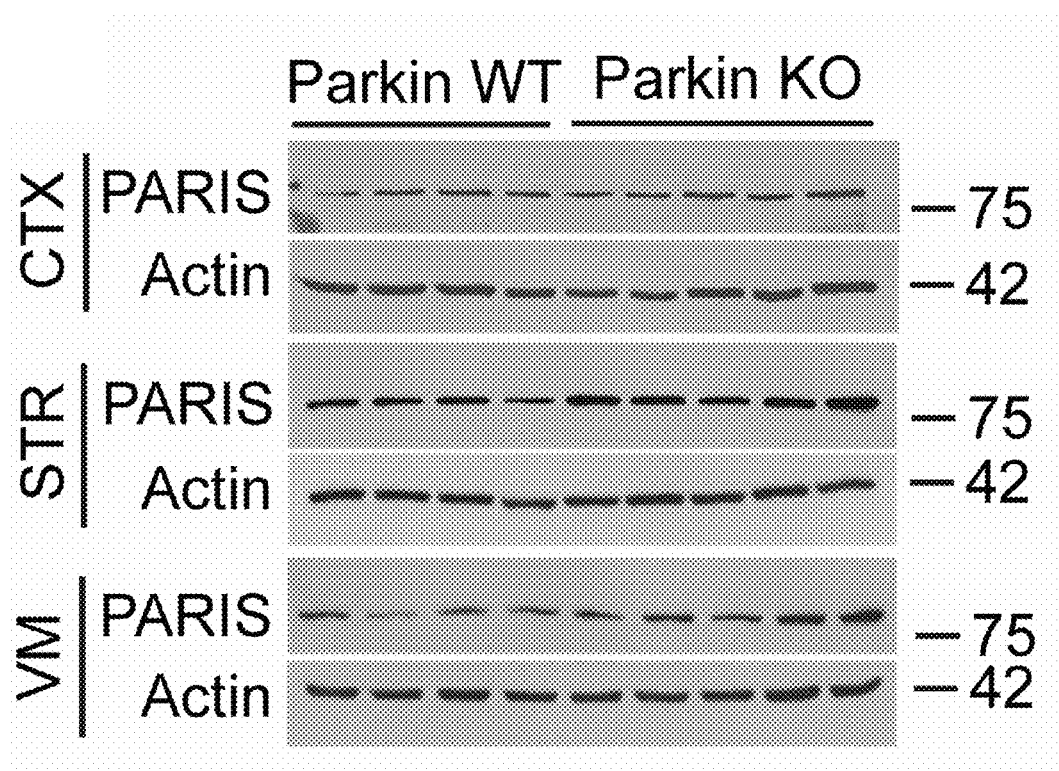
FIG. 49—Immunoblot analysis of PARIS in cortex (CTX), STR and ventral midbrain (VM) from WT and parkin exon 7 KO 18-24 month old mice.
Figure 50:
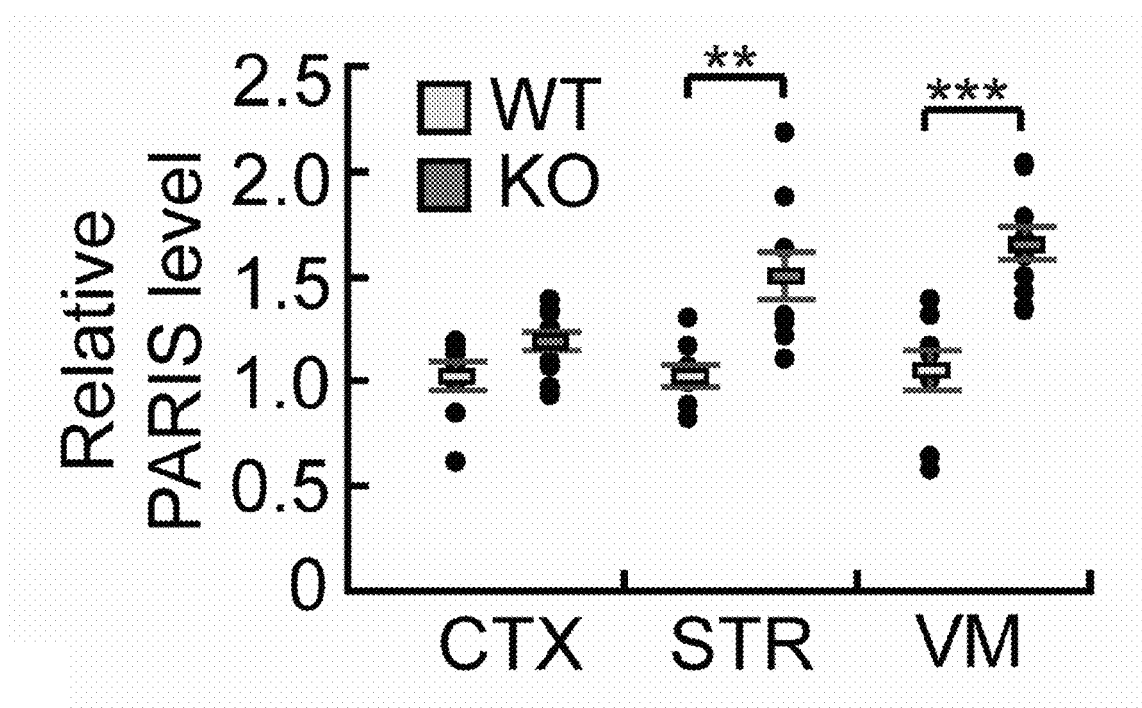
FIG. 50—Relative protein levels of PARIS normalized to β-actin for FIG. 49, WT n=9; parkin KO n=10. [Data=mean±S.E.M., *p<0.05, p<0.01 and *p<0.001, ANOVA test with Student-Newman-Keuls post-hoc analysis].
Figure 51:
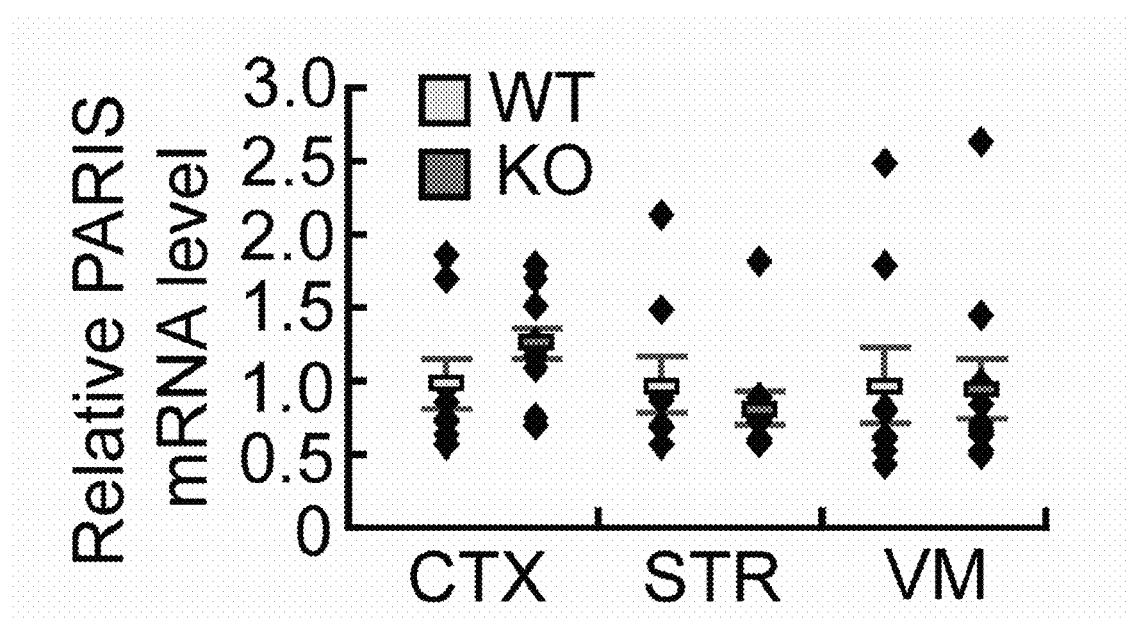
FIG. 51—PARIS mRNA levels in indicated brain regions from WT and parkin exon 7 KO 18-24 month old mice. [Data=mean±S.E.M., *p<0.05, p<0.01 and *p<0.001, ANOVA test with Student-Newman-Keuls post-hoc analysis].

Next, PARIS was evaluated to determine if it was increased in germline parkin exon 7 KO mice. PARIS was modestly upregulated by approximately 48% in the striatum and by 63% in ventral midbrain of germline parkin exon 7 KO mice compared to age matched WT controls, whereas the levels of PARIS in the cortex was not changed (FIGS. 49 and 50). The upregulation of PARIS was not due to a transcriptional effect since there was no difference in the level of PARIS mRNA in germline parkin KO ventral midbrain and striatum versus WT ventral midbrain and striatum (FIG. 51).

Figure 52:
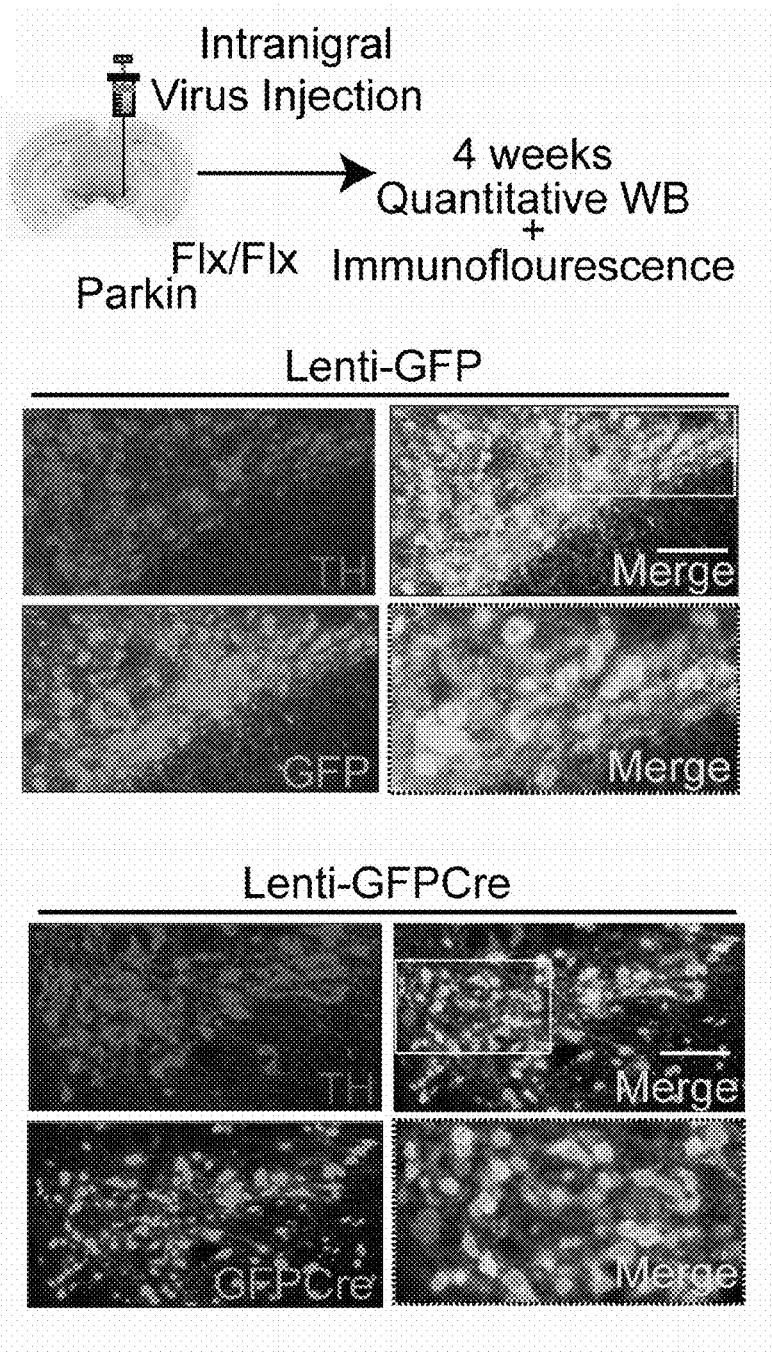
FIG. 52—Top panel, experimental illustration of stereotaxic intranigral virus injection. Bottom panels, immunofluorescent images of TH, GFP and merged in exon 7 floxed parkin mice (parkin$^{Flx/Flx}$) after stereotactic delivery of Lenti-GFP or Lenti-GFPCre into the SNpc. 84.9±1.9% and 78.1±2.6% of TH neurons express GFP and GFPCre, respectively, n=3 per group. Enlarged images in the right bottom panels were taken from the white rectangle region from the merged images of Lenti-GFPCre and Lenti-GFP, bar=100 μm.
Figure 53:
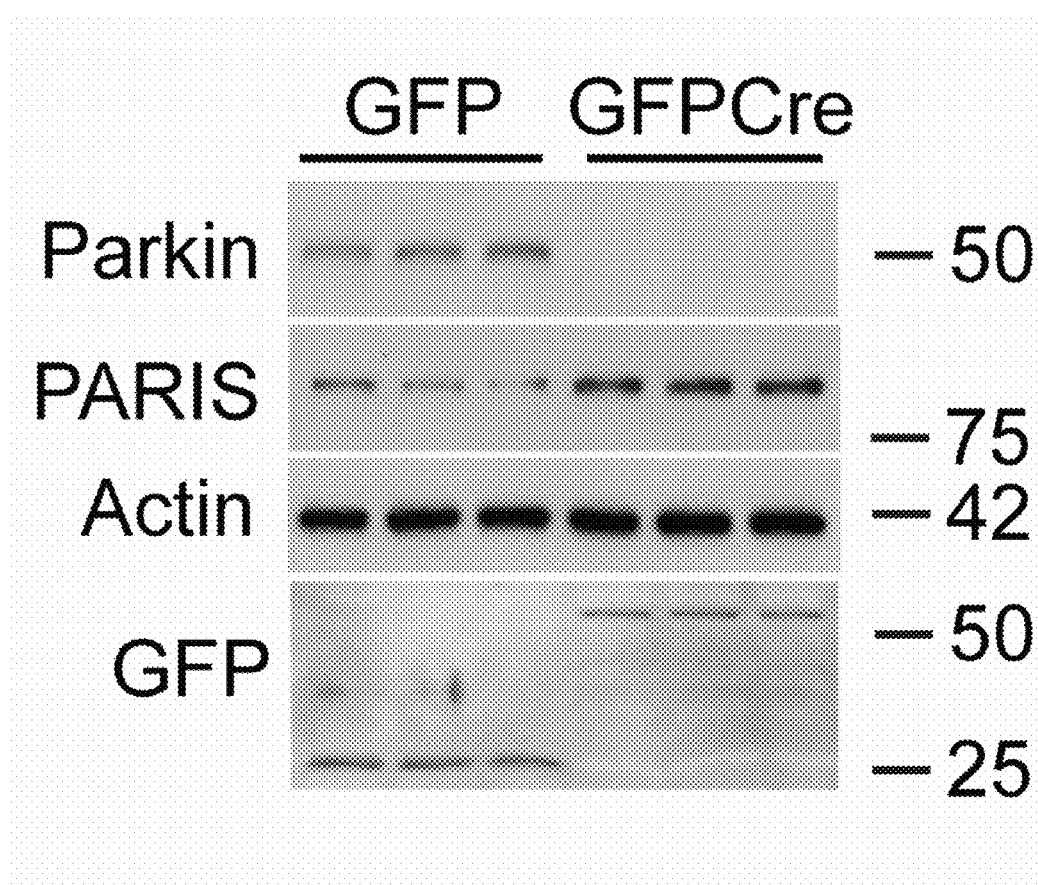
FIG. 53—Immunoblot analysis of parkin, PARIS, actin and GFP 4 weeks after intranigral Lenti-GFPCre or Lenti-GFP injection into parkin$^{Flx/Flx}$ mice.
Figure 54:
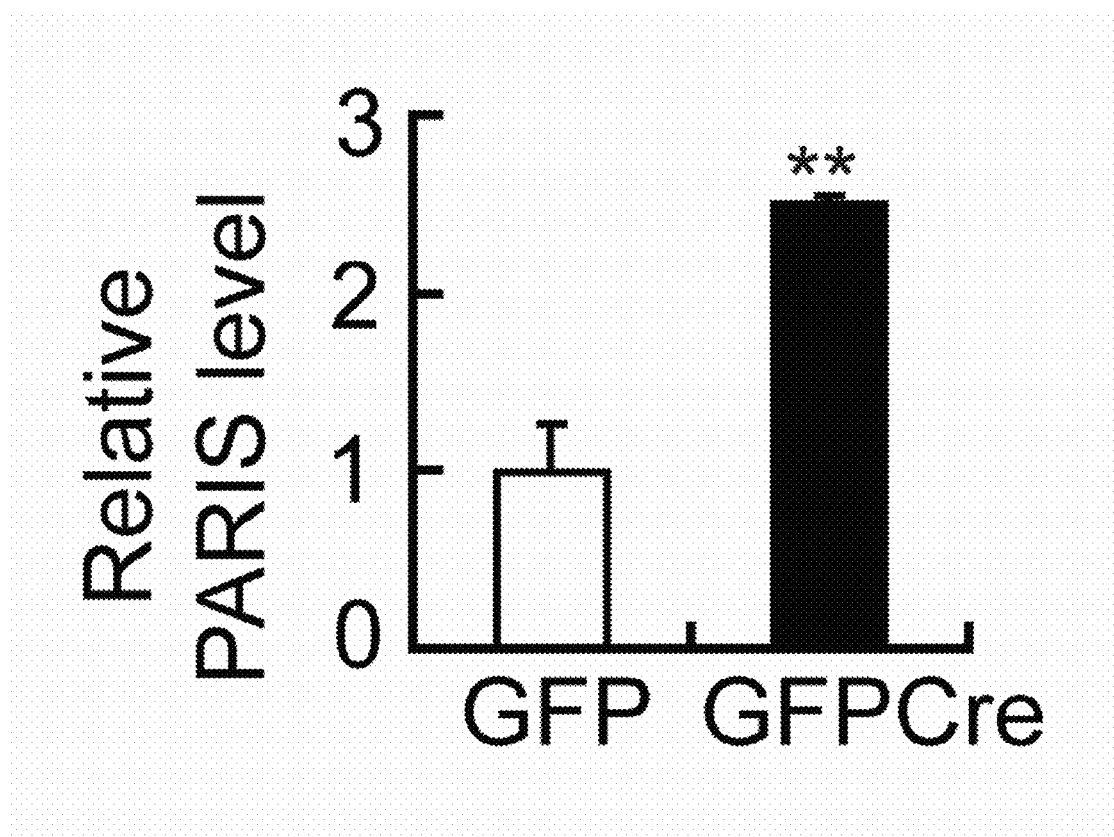
FIG. 54—Relative protein levels of PARIS normalized to β-actin for FIG. 53. [Data=mean±S.E.M., *p<0.05, p<0.01 and *p<0.001, unpaired two-tailed Student's t-test].

Since germline parkin exon 7 KO mice lack parkin from the point of conception, it was possible that compensatory mechanisms account for the lack of a more substantial upregulation of PARIS. To avoid potential developmental compensation, exon 7 was deleted in 6-8 week old conditional parkin KO mice in which exon 7 was flanked by loxP sites (parkin$^{Flx/Flx}$) by SN stereotactic injection of a GFP-fused Cre recombinase lentivirus (Lenti-GFPCre) and compared to control SN injections of lentivirus expressing GFP (Lenti-GFP) in parkin$^{Flx/Flx}$ mice (FIGS. 52 and 53). Four weeks after injection of the lentiviruses, Lenti-GFP and Lenti-GFPCre effectively transduced neurons in the SN including DA neurons (FIG. 52). Lenti-GFPCre led to almost a complete loss of parkin from the ventral midbrain of parkin$^{Flx/Flx}$ mice compared to Lenti-GFP mice (FIGS. 53 and 54). Accompanying the loss of parkin was greater than a two-fold upregulation of PARIS. The upregulation of PARIS in the conditional parkin exon 7 KO model was not due to a transcriptional effect since there was no alteration in PARIS mRNA in the conditional parkin KO ventral midbrain versus WT ventral midbrain (FIG. 42). Thus, the levels of PARIS were increased in conjunction with parkin inactivation and impairment of ubiquitin-mediated proteasomal degradation in sporadic PD, AR-PD and in an animal model of parkin inactivation.

Experiment 5

PARIS was a Transcriptional Repressor of PGC-1α

Figure 55:
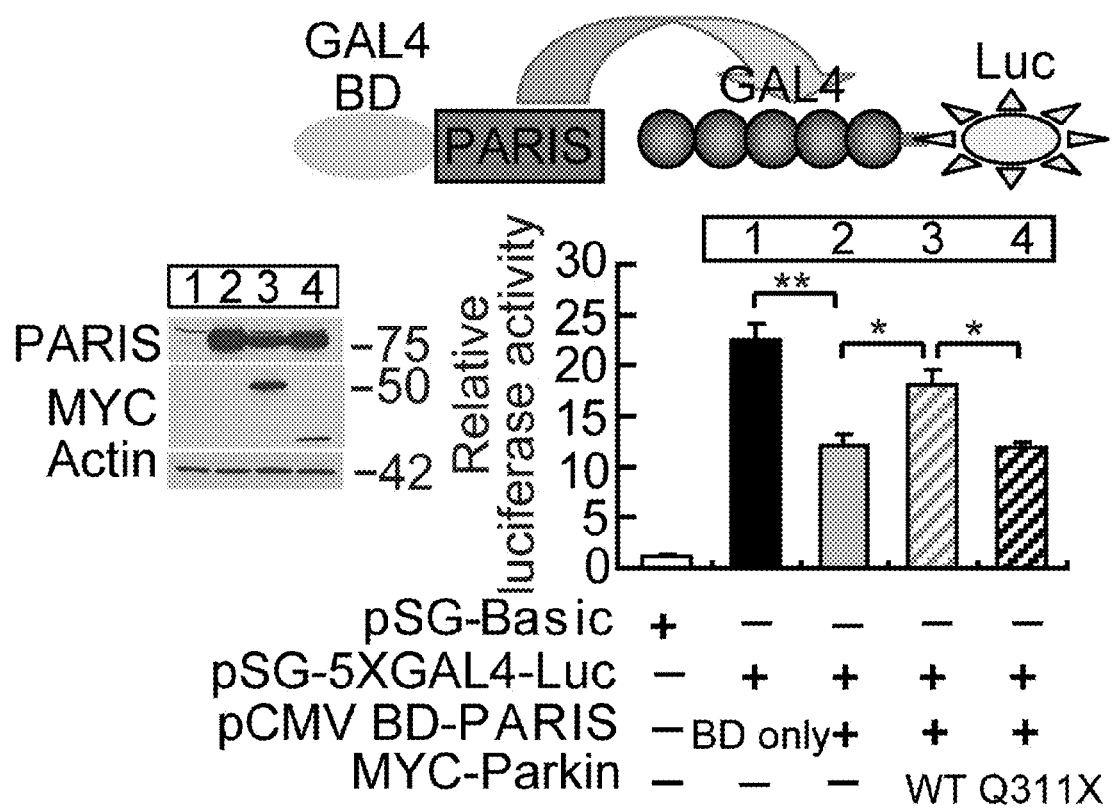
FIG. 55—GAL4-luciferase assay demonstrates that PARIS decreases promoter activity, which is recovered by co-expression of WT parkin, but not Q311X mutant. Relative luciferase activity compared to *Renilla* luciferase control is indicated in the histogram (n=3). Immunoblot analysis confirms the expression of FLAG-PARIS, MYC-Parkin, and MYC-Q311X parkin. β-Actin was used as a loading control (bottom of panel). *p<0.05, **p<0.01 in an ANOVA test followed by Student-Newman-Keuls post-hoc analysis. Schematic representation of the promoter construct is indicated at the top of the panel.
Figure 56:
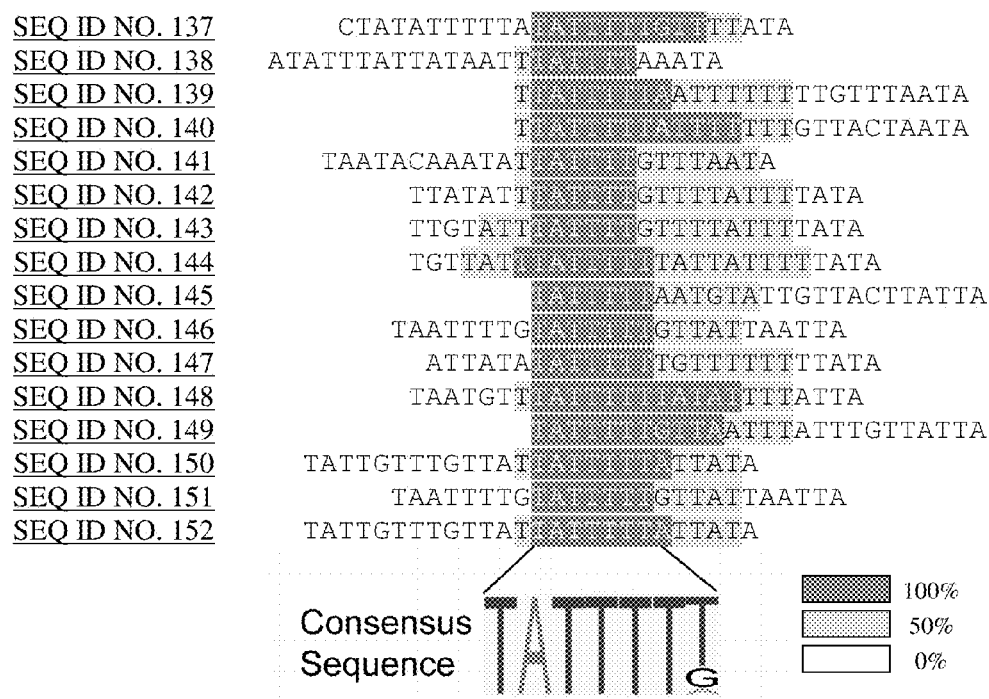
FIG. 56—Identification and MACAW alignment of the PARIS DNA-binding sequence as determined by CASTing. Darker shades represent a greater degree of overlap of the segment pairs (bottom right–% overlap). *Duplicate sequence tags.

Proteins with KRAB domains can function as transcriptional repressors. GAL4-BD fused PARIS led to decreased luciferase activity from a 5×GAL4-luciferase reporter construct, which was restored by co-expression of WT parkin, but not Q311X mutant parkin (FIG. 55). To identify the PARIS DNA binding consensus sequence, a chimeric protein containing the zinc finger domain (ZF) of PARIS (amino acids, 453-589) fused in frame to glutathione-S-tranferase (GST), GST-ZF-PARIS, was used in a Cyclic Amplification and Selection of Targets (CAST) assay (FIG. 56). Immobilized GST-ZF-PARIS was incubated with a pool of oligonucleotides containing 26 random nucleotides. The final pool of oligonucleotides remaining after four rounds of CASTing followed by three rounds of electrophoretic mobility shift assays (EMSA) was cloned, sequenced and analyzed. Alignment of all the sequences using the program MACAW (National Center for Biotechnology Information) revealed a consensus sequence with a core sequence composed of TATTTT (T/G) (FIG. 56). 19 out of 24 sequences contained the core sequence and 3 out of 19 sequence tags were identified as duplicates indicating this was the primary DNA binding sequence for PARIS. The TATTTT (T/G) consensus sequence was an insulin response sequence (IRS) designated the phosphoenolpyruvate carboxykinase (PEPCK)-like motif (PLM), which was involved in the regulation of transcripts involved in energy metabolism and insulin responsiveness.

Figure 57:
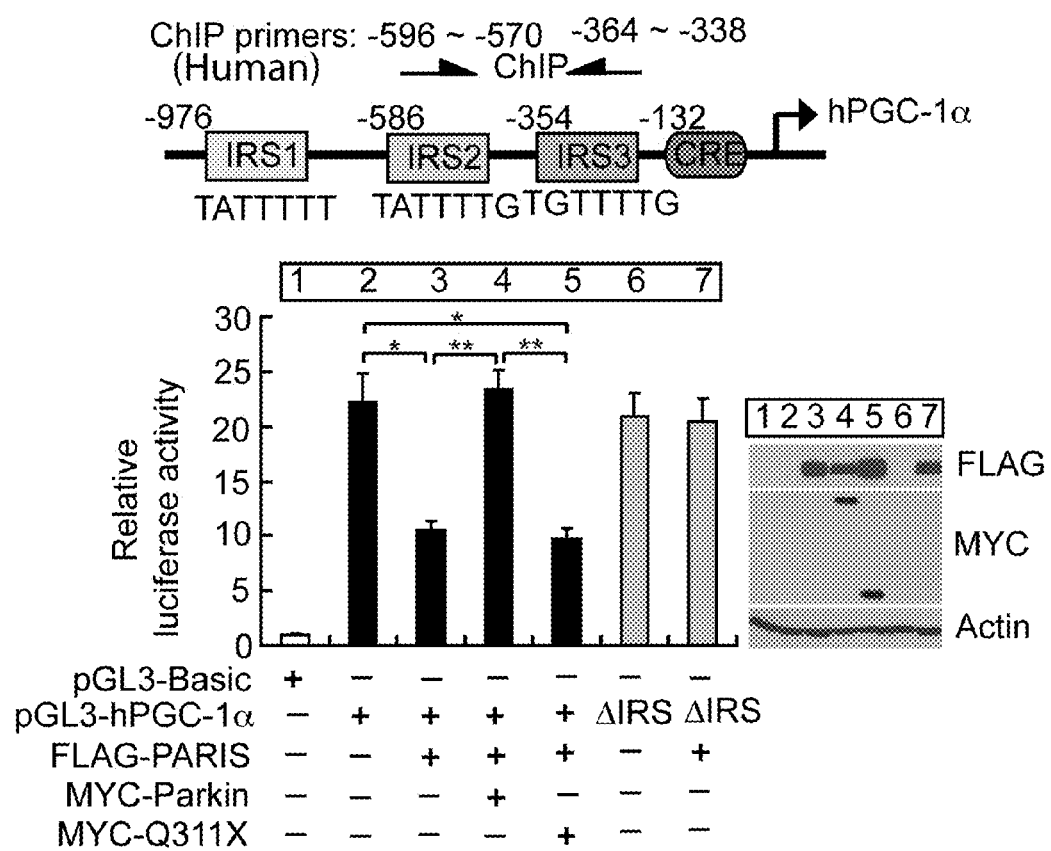
FIG. 57—Relative luciferase activity of the 1-kilobase human PGC-1α (−992 to +90) compared to *Renilla* luciferase±PARIS or ±parkin or ±familial mutant Q311X parkin, n=3. Location of IRS, CRE motifs and oligos for human ChIP (arrows) in the PGC-1α promoter construct (top of panel). Immunoblot analysis confirms the expression of FLAG-PARIS, MYC-Parkin and MYC-Q311X parkin (right panel). [mean±S.E.M., *p<0.05, p<0.01, *p<0.001, ANOVA with Student-Newman-Keuls post-hoc analysis].
Figure 58:
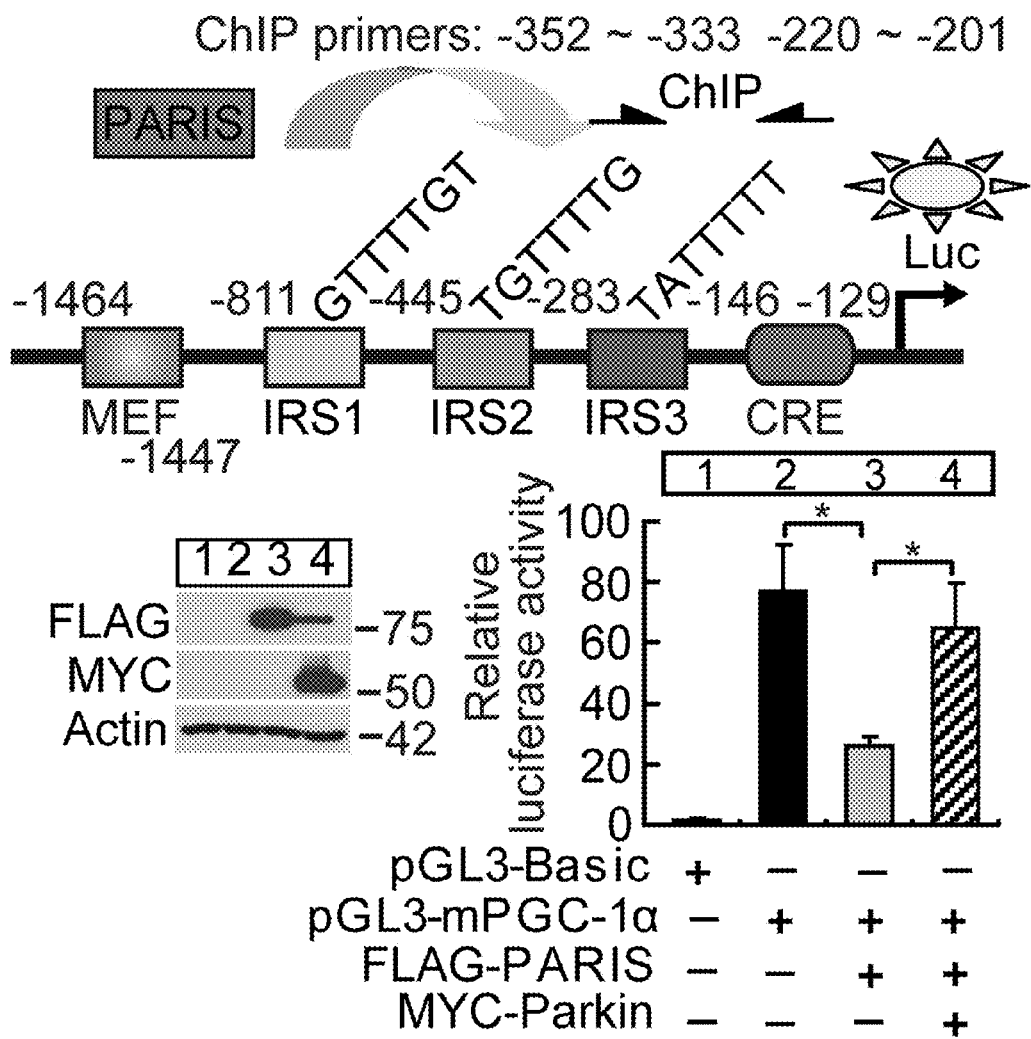
FIG. 58—PARIS represses the mouse PGC-1α promoter luciferase reporter activity. Co-transfection of SH-SY5Y cells with PARIS and the mouse PGC-1α promoter (−2533 to +78), results in decreased activity of PGC-1α promoter. Introduction of WT parkin rescues PARIS suppression of the mouse PGC-1α promoter. Relative luciferase activity compared to *Renilla* luciferase control is indicated in histogram (n=4). Immunoblot analysis confirms the expression of FLAG-PARIS, MYC-Parkin and β-actin was used as a loading control (bottom of panel). *p<0.05 in an ANOVA test followed by Student-Newman-Keuls post-hoc analysis. Schematic representation of the promoter construct is indicated at the top of the panel.

A NCBI survey of IRS/PLM responsive transcripts revealed that members of the PPARγ coactivator-1 (PGC-1) family of transcriptional co-activators were regulated by IRS sites. PGC-1α contained three IRS/PLM elements within its 5'-promoter region (FIG. 57). The activity of the 1 kb human PGC-1α promoter was decreased approximately 40% in the presence of PARIS, which was rescued by parkin overexpression (FIG. 57). Similar results were observed with the 2 kb mouse PGC-1α promoter (FIG. 58). The familial parkin mutant, Q311X, had minimal effects on the PGC-1α promoter (FIG. 57). PARIS repressed PGC-1α promoter activity by binding to the IRS sites, since it failed to inhibit the reporter in which the three IRS sites were deleted in the context of the PGC-1α promoter-reporter construct (FIG. 57). Reporter constructs for PGC-1α (pGL3-h PGC-1α) were repressed by PARIS.

Figure 59:
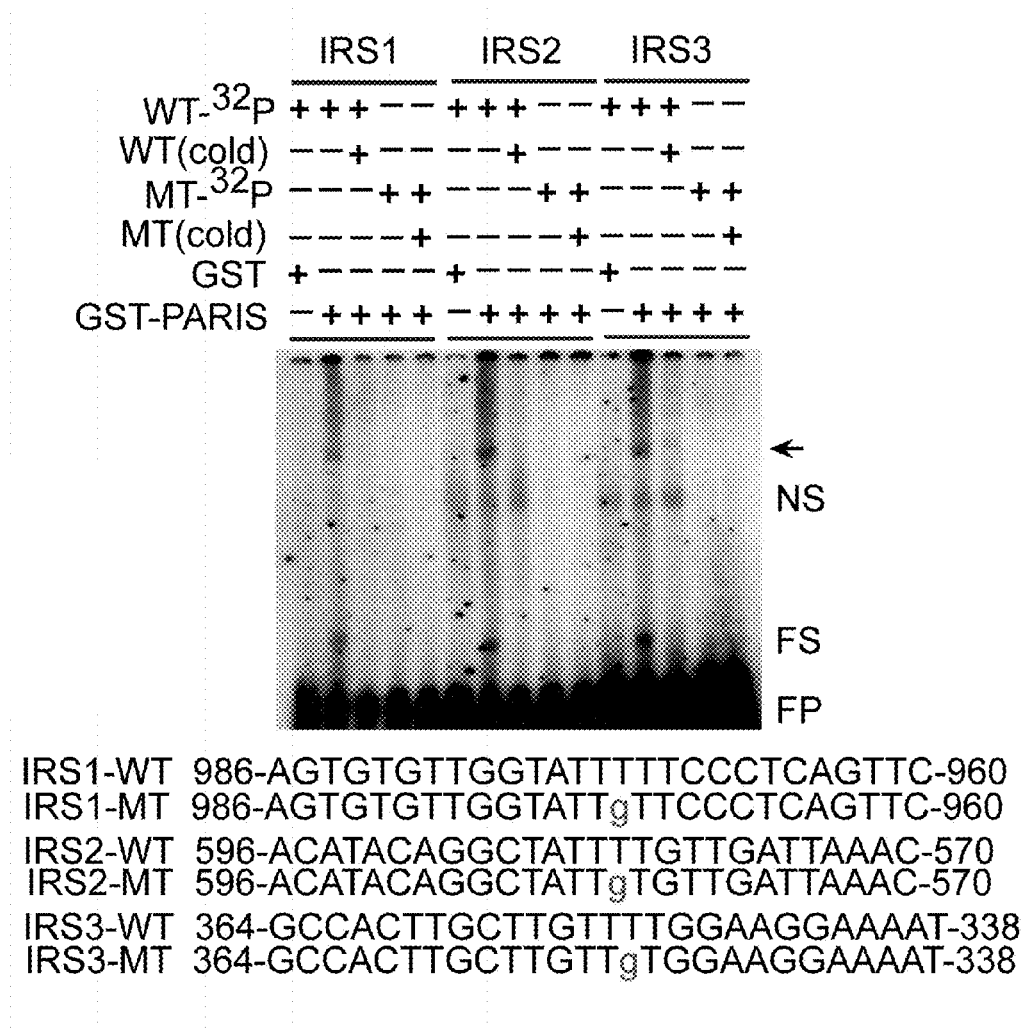
FIG. 59—EMSA of GST-PARIS of $^{32}$P-labeled WT (WT-$^{32}$P) IRS oligonucleotides (IRS1-WT (SEQ ID NO. 8), IRS2-WT (SEQ ID NO. 10) and IRS3-WT (SEQ ID NO. 12)) of the human PGC-1α promoter and $^{32}$P-labeled mutant (T→g) (MT-$^{32}$P) IRS oligonucleotides (IRS1-MT (SEQ ID NO. 9), IRS2-MT (SEQ ID NO. 11) and IRS3-MT (SEQ ID NO. 13)). Unlabeled WT (WT cold) IRS oligonucleotides disrupt the GST-PARIS-DNA protein complexes with the WT-$^{32}$P IRS oligonucleotides, n=3. Unlabeled mutant probe (MT cold) has no effect on mutant (MT-$^{32}$P). Arrow indicates specific PARIS-shifted probe; NS, nonspecific; FS, fragmented PARIS-shifted probe; FP, free probe.
Figure 60:
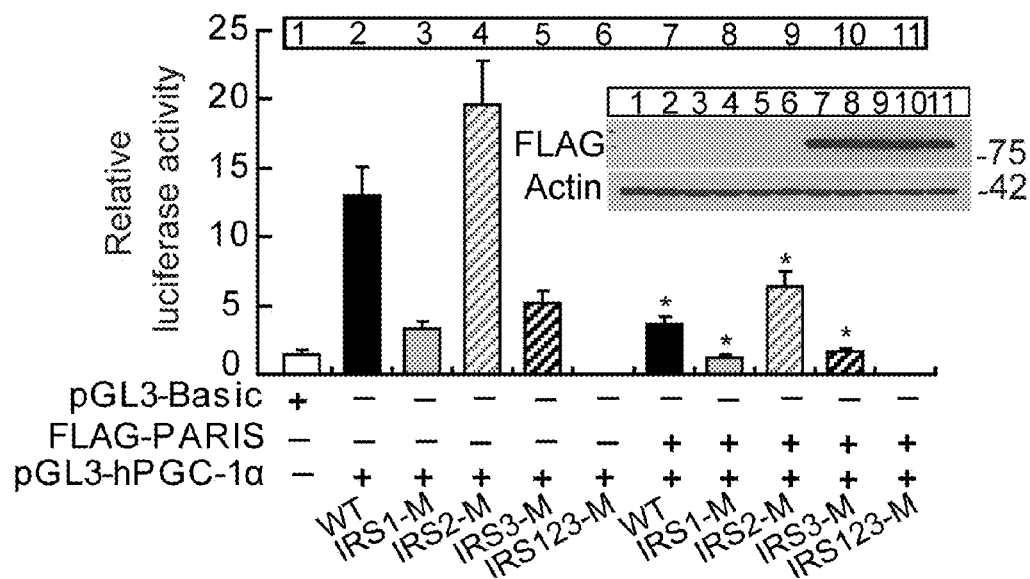
FIG. 60—Schematic representation of the PGC-1α WT, IRS1-M, IRS2-M, IRS3-M and IRS123-M promoter reporter constructs harboring the T→G point mutation on the IRS elements is indicated at the top of the panel. The basal promoter activities of PGC-1α WT, IRS1-M, IRS2-M, IRS3-M and IRS123-M promoter reporter constructs were monitored in the presence and absence of PARIS. Relative luciferase activity compared to *Renilla* luciferase control is indicated in histogram (n=3). *p<0.05 in an ANOVA test followed by Student-Newman-Keuls post-hoc analysis. Immunoblot analysis confirms the expression of FLAG-PARIS. β-actin was used as a loading control.

Individual IRS site mutants (IRS1-M, IRS2-M, IRS3-M) within the PGC-1α reporter that disrupted PARIS binding to the PGC-1α promoter as determined by EMSA (see FIG. 59) and a promoter construct, IRS123-M, containing all three mutations were evaluated in the promoter reporter assay (FIG. 60). IRS1-M and IRS3-M substantially reduced PGC-1α reporter promoter activity, whereas IRS2-M increased the activity (FIG. 60). PARIS overexpression inhibited IRS1-M, IRS2-M, IRS3-M PGC-1α reporter promoter activity suggesting that PARIS bound to and regulated all three sites (FIG. 60) as indicated from the EMSA assays (FIG. 59).

Figure 61:
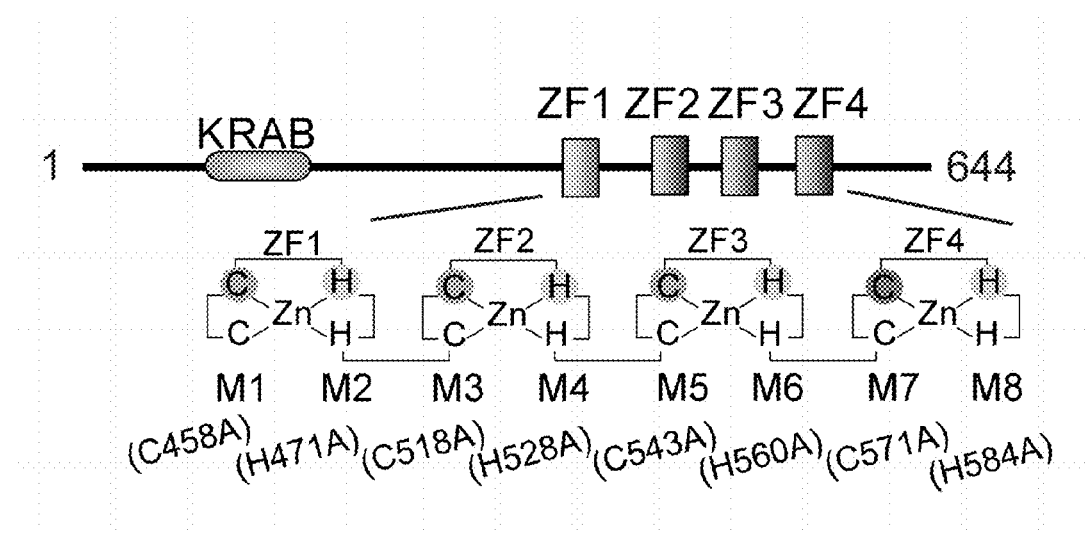
FIG. 61—Schematic representation of PARIS zinc finger mutants.
Figure 62:
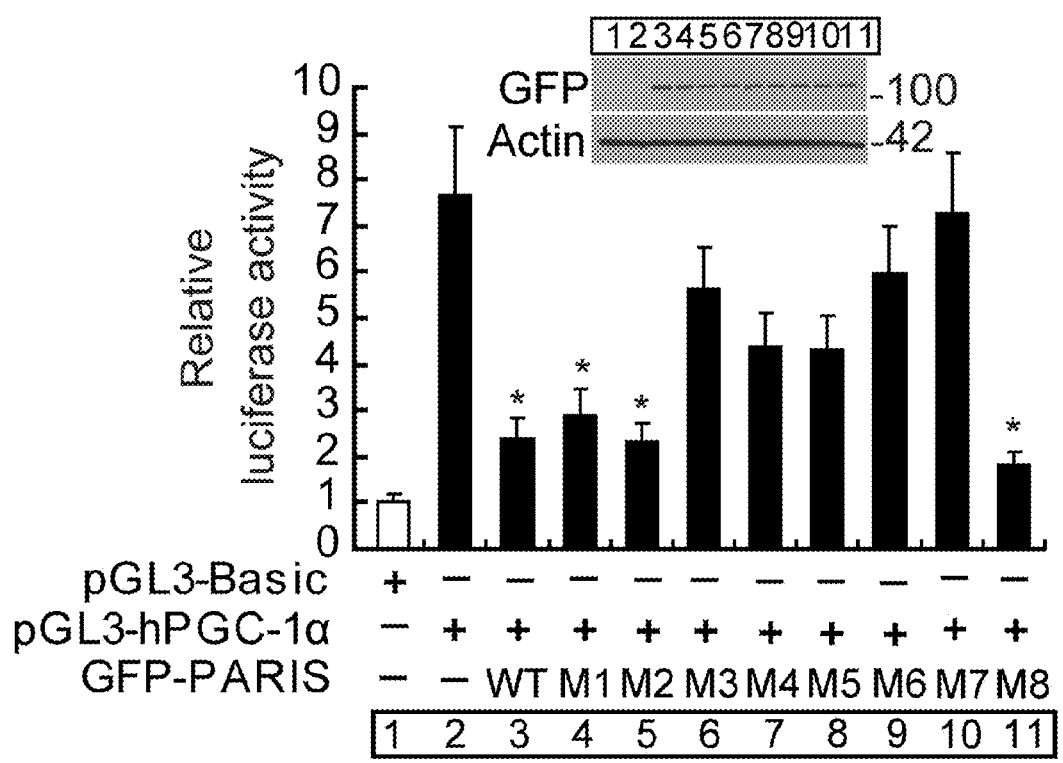
FIG. 62—The basal promoter activity of the human PGC-1α promoter reporter construct in SH-SY5Y cells was monitored in the presence and absence of WT PARIS and the 8 zinc finger PARIS mutants depicted in FIG. 55. Relative luciferase activity compared to *Renilla* luciferase control is indicated in the histogram, n=3. Immunoblot analysis confirms the expression of GFP-PARIS, and PARIS zinc finger mutants. β-actin was used as a loading control (Top Panel). *p<0.05 in an ANOVA test followed by Student-Newman-Keuls post-hoc analysis.
Figure 63:
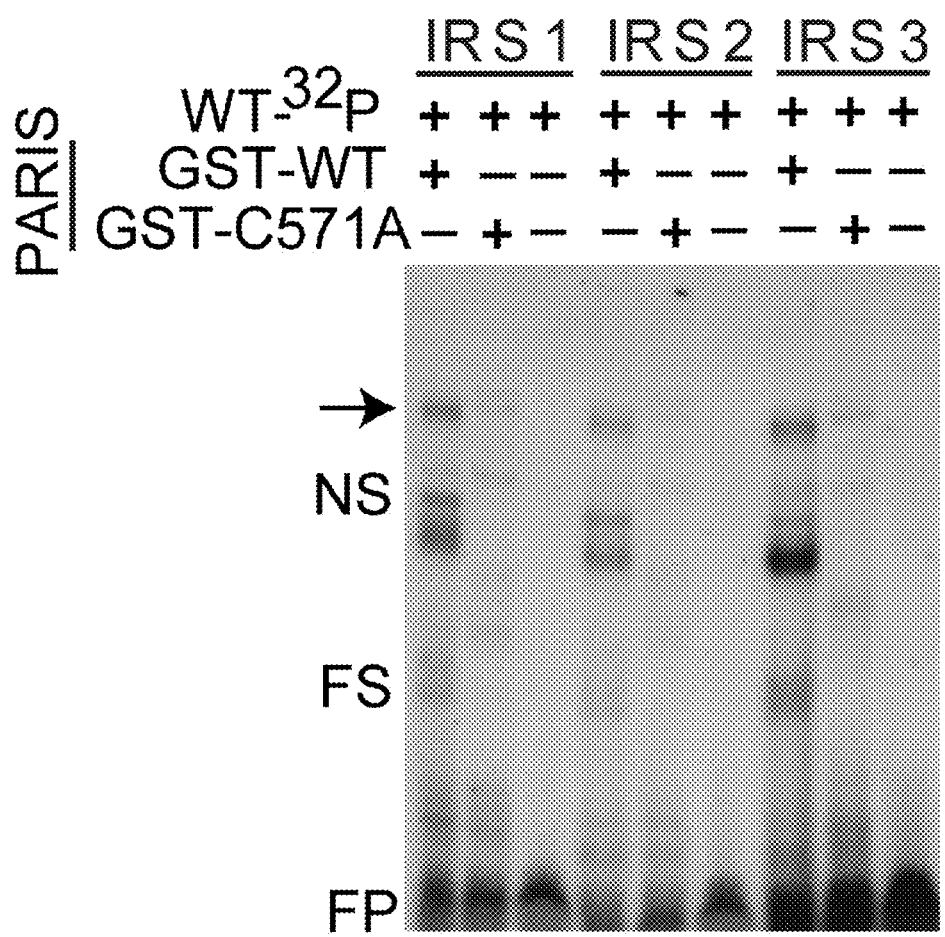
FIG. 63—EMSA reveals that GST-PARIS binds to $^{32}$P-labeled WT (WT-$^{32}$P) IRS oligonucleotides (IRS1-WT, IRS2-WT, IRS3-WT) of the human PGC-1α promoter, whereas the PARIS C571A mutant has substantially reduced binding (n=3). The arrow indicates the specific PARIS-shifted probe. NS, nonspecific; FS, fragmented PARIS-shifted probe; FP, free probe.

EMSA showed that PARIS bound to the PGC-1α IRS elements since GST-PARIS (full length) elicited a shift of [$^{32}$P]-labeled oligonucleotides containing the IRS1, IRS2, and IRS3 sequences of the PGC-1α promoter, whereas it failed to cause a shift of IRS1, IRS2 and IRS3 containing a single base substitution within the IRS sequence (FIG. 59). Additionally eight zinc finger mutants of PARIS were assessed for their ability to repress the PGC-1α reporter promoter construct (FIGS. 61 and 62) (see Table 6). M1, M2, M8 PARIS mutants repressed PGC-1α reporter promoter activity, similar to WT PARIS. M3, M4, M5, M6 PARIS mutants partially repressed PGC-1α reporter promoter activity, whereas the M7 (C571A) PARIS mutant had no affect on PGC-1α reporter promoter activity. The M7 GST-C571A-PARIS mutant had substantially reduced IRS-binding capacity as determined by EMSA (FIG. 63).

TABLE 6

| Target genes | | Primers (5'-3') | |
|---|---|---|---|
| M1 | PARIS C458A | F ACC TGC GCC ACG GCT GGG AAG AGC TTC<br>R GAA GCT CTT CCC AGC CGT GGC GCA GGT | (SEQ ID NO. 121)<br>(SEQ ID NO. 122) |
| M2 | PARIS H471A | F AGC CTG AGC GCG GCC CAG CGC AGC TGT<br>R ACA GCT GCG CTG GGC CGC GCT CAG GCT | (SEQ ID NO. 123)<br>(SEQ ID NO. 124) |
| M3 | PARIS C518A | F GAG TGC GGC CGT GCC TTC ACG CGC CCC<br>R GGG GCG CGT GAA GGC ACG GCC GCA CTC | (SEQ ID NO. 125)<br>(SEQ ID NO. 126) |
| M4 | PARIS H528A | F CAC CTC ATC CGC GCT CGC ATG CTG CAC<br>R GTG CAG CAT GCG AGC GCG GAT GAG GTG | (SEQ ID NO. 127)<br>(SEQ ID NO. 128) |
| M5 | PARIS C543A | F TTC CCC TGC ACC GAG GCT GAG AAG CGC TTC<br>R GAA GCG CTT CTC AGC CTC GGT GCA GGG GAA | (SEQ ID NO. 129)<br>(SEQ ID NO. 130) |
| M6 | PARIS H560A | F CAC TAC CGA ACG GCC ACG GGC GTG CGG<br>R CCG CAC GCC CGT GGC CGT TCG GTA GTG | (SEQ ID NO. 131)<br>(SEQ ID NO. 132) |
| M7 | PARIS C571A | F ACC TGC ACC GTC GCC GGC AAA AGC TTC<br>R GAA GCT TTT GCC GGC GAC GGT GCA GGT | (SEQ ID NO. 133)<br>(SEQ ID NO. 134) |
| M8 | PARIS H584A | F CAC CTC CGC AAG GCC CAG CGC AAC CAT<br>R ATG GTT GCG CTG GGC CTT GCG GAG GTG | (SEQ ID NO. 135)<br>(SEQ ID NO. 136) |

List of primers used for site-directed mutagenesis for PARIS used in FIGS. 61-66. Abbreviations: F, forward; R, reverse.

Figure 67:
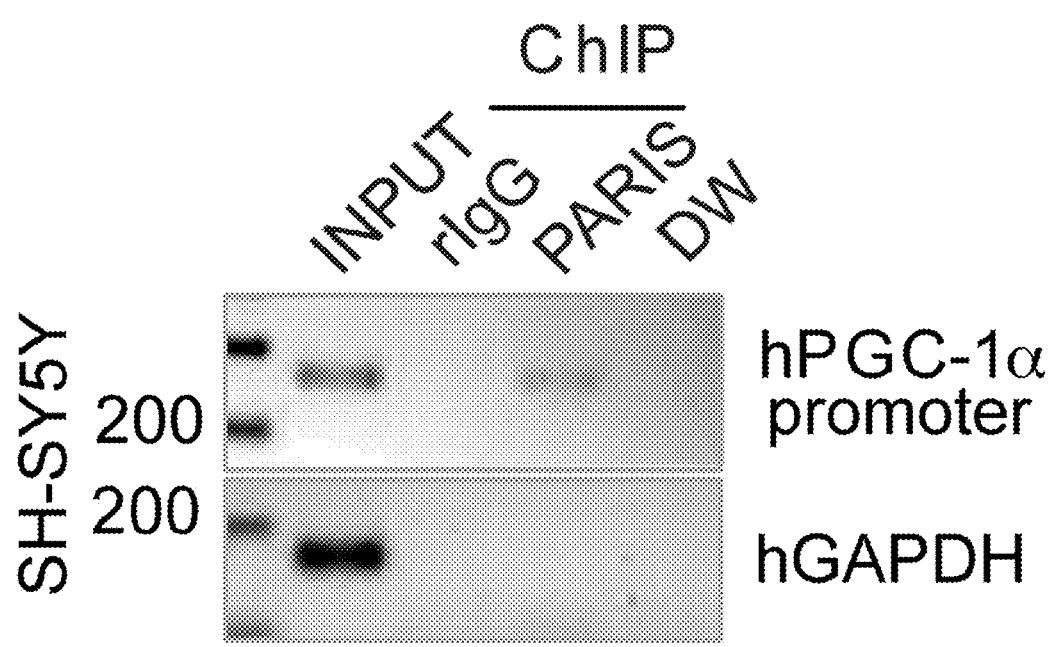
FIG. 67—PARIS occupies the endogenous PGC-1α promoter as determined by ChIP assay with anti-PARIS polyclonal antibodies in SH-SY5Y cells, n=3.
Figure 68:
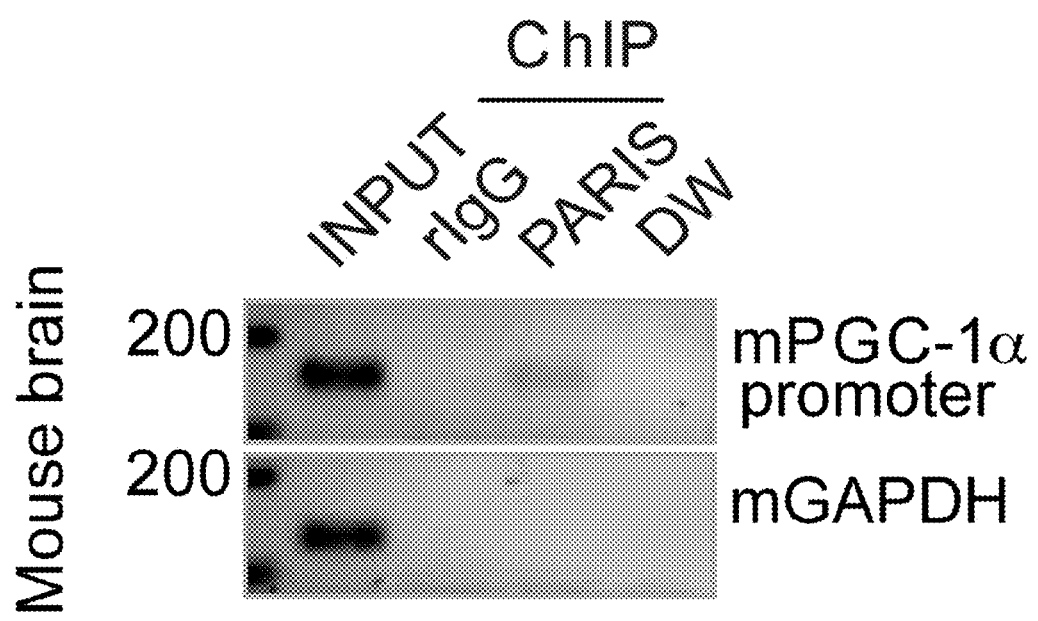
FIG. 68—PARIS occupies the endogenous mouse PGC-1α promoter as determined by ChIP in mouse whole brain, n=3. Mouse specific IRS primers are indicated in FIG. 58.
Figure 69:
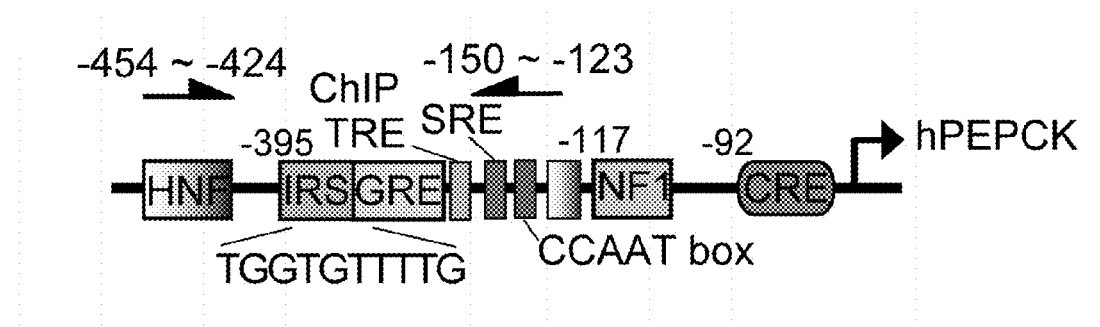
FIG. 69—Schematic representation of the promoter construct of human PEPCK (SEQ ID NO: 153).
Figure 70:
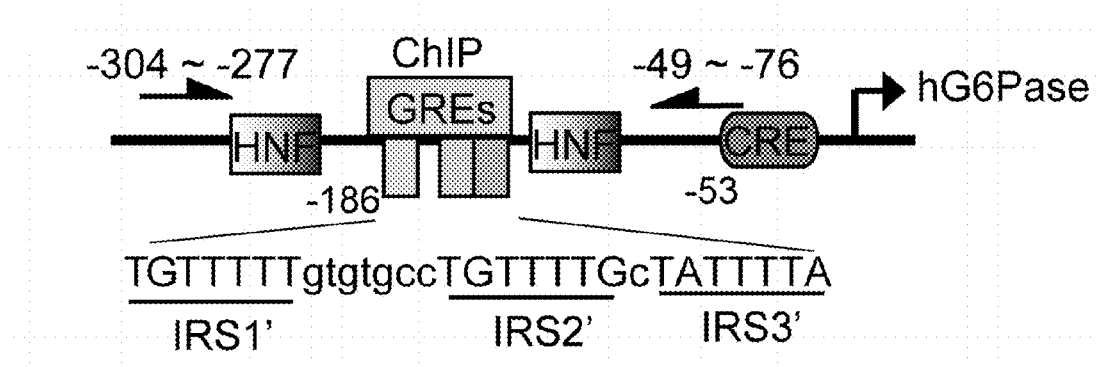
FIG. 70—Schematic representation of the promoter construct of human G6Pase, including a representation of IRS1' IRS2', and IRS3'.
Figure 71:
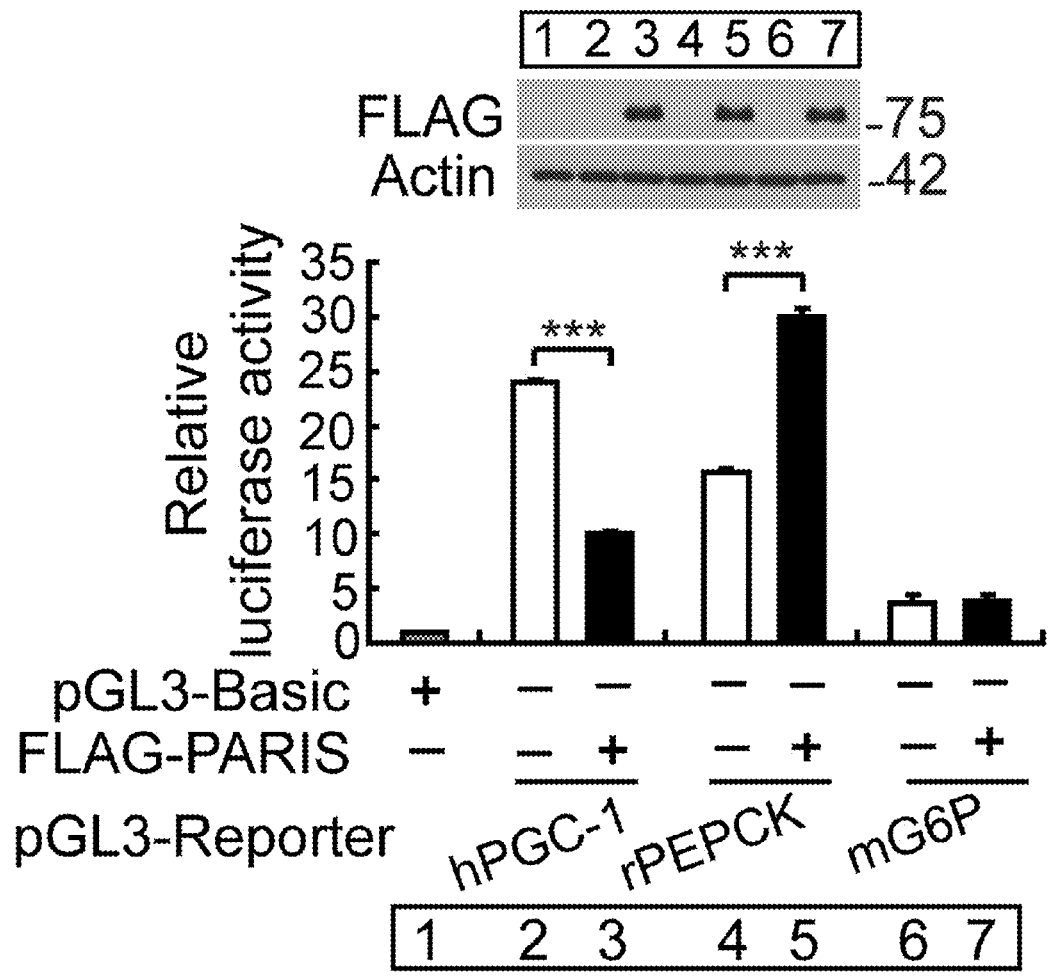
FIG. 71—PARIS does not repress the IRS-containing genes, PEPCK and G6Pase. Co-transfection of SH-SY5Y cells with PARIS and the rat PEPCK (rPEPCK) promoter-luciferase reporter (−2100 to +68), results in increased promoter activity of rPEPCK. While overexpression of PARIS does not alter mouse G6Pase (mG6Pase) promoter (−484 to +66) activity. Relative luciferase activity compared to *Renilla* luciferase control is indicated in histogram, n=J. Immunoblot analysis confirms the expression of FLAG-PARIS and β-actin was used as a loading control (top of panel). ***p<0.001 in an unpaired two-tailed Student's t-test.
Figure 72:
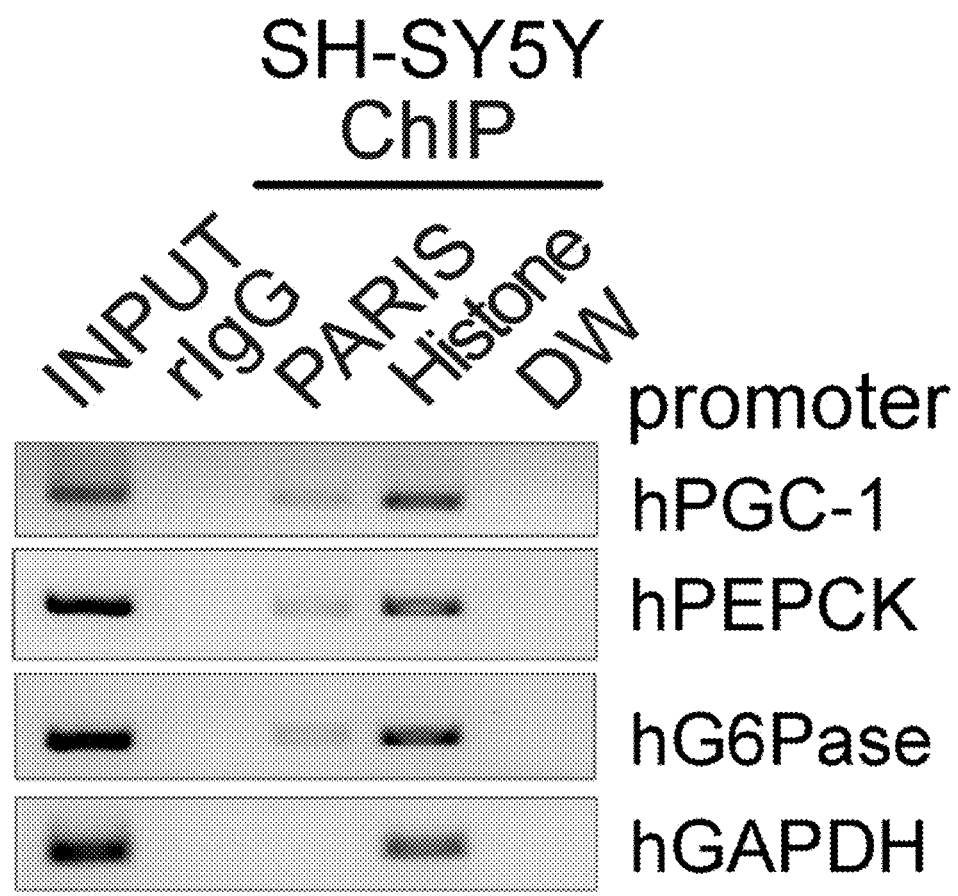
FIG. 72—PARIS occupies the endogenous PEPCK and G6Pase promoter. ChIP assay monitoring the occupancy of the endogenous PEPCK and G6Pase promoter by PARIS in SH-SY5Y, n=3.

Chromatin immunoprecipitation (ChIP) indicated that PARIS bound to the endogenous PGC-1α promoter in SH-SY5Y cells (FIG. 67) and mouse brain (FIG. 68). PARIS also bound to the endogenous PGC-1α promoter in human brain (FIG. 40) and consistent with its upregulation in PD striatum (see FIGS. 36 and 37) there was enhanced PARIS occupancy of endogenous PGC-1α in PD striatum compared to control (FIG. 41). Luciferase reporter assay was performed in SH-SY5Y cells and ChIP assays in PD versus control striatum and SH-SY5Y cells with phosphoenolpyruvate carboxykinase (PEPCK) (FIG. 69) and glucose-6-phosphatase (G6Pase) (FIG. 70). The luciferase reporter assay showed that overexpression of PARIS enhanced the promoter activity of rat PEPCK, but not mouse G6Pase promoter activity (FIG. 71). The ChIP assay demonstrated that PARIS bound to the endogenous promoter of human PEPCK and G6Pase in SH-SY5Y cells and in control and PD postmortem striatum (FIG. 72). In contrast to PGC-1α, there was not enhanced occupancy of the PEPCK and G6Pase promoter by PARIS. These data suggested that PARIS can bind to the promoter of PEPCK and G6Pase, but in contrast to PGC-1α it positively regulated PEPCK and it had no appreciable effect on G6Pase. Thus, the transcriptional repressive effects of PARIS were relatively specific to PGC-1α.

Figure 64:
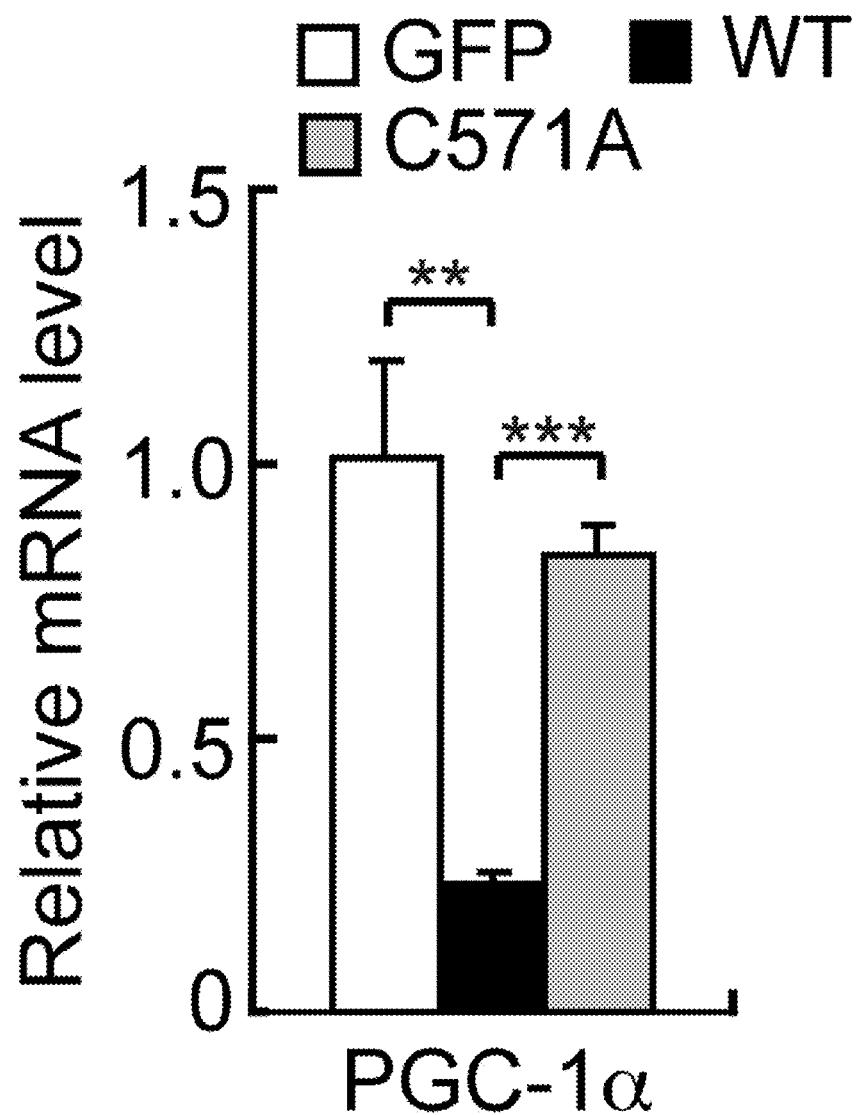
FIG. 64—Real-time qRT-PCR of PGC-1α, GFP and β-actin following transient transfection of GFP, GFP-PARIS or GFP-0571A PARIS mutant, n=4. [mean±S.E.M., *p<0.05, p<0.01, *p<0.001, ANOVA with Student-Newman-Keuls post-hoc analysis].
Figure 65:
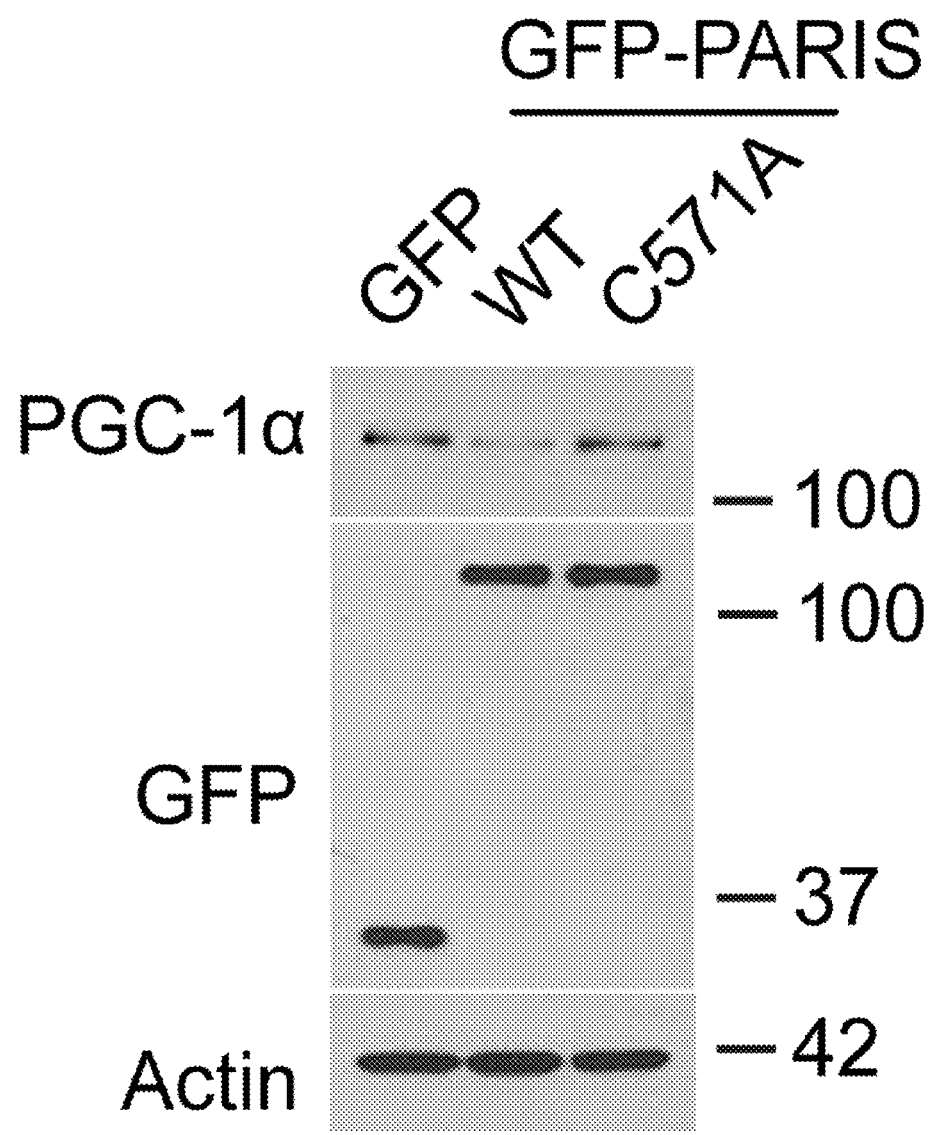
FIG. 65—Immunoblot analysis of PGC-1α, GFP and β-actin following transient transfection of GFP, GFP-PARIS or GFP-0571A PARIS mutant, n=4.
Figure 66:
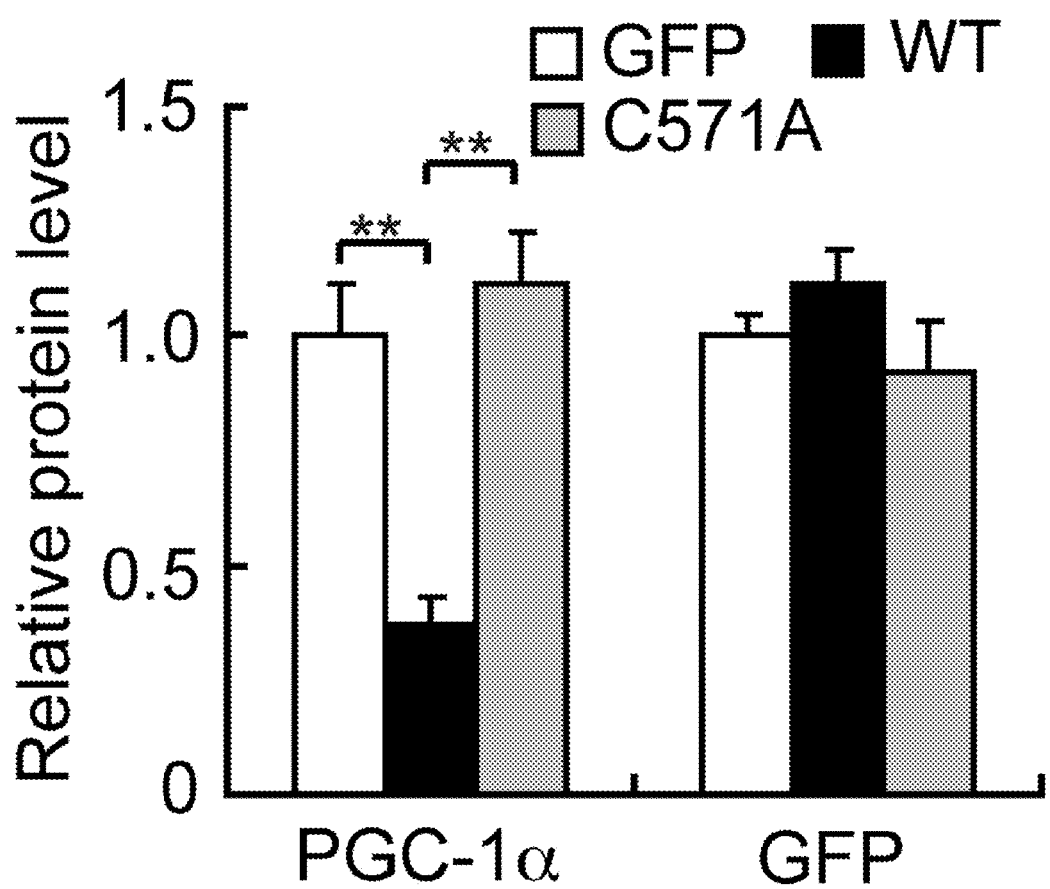
FIG. 66—Quantitation of the immunoblots in FIG. 65 normalized to β-actin, n=4. [mean±S.E.M., *p<0.05, p<0.01, *p<0.001, ANOVA with Student-Newman-Keuls post-hoc analysis].
Figure 73:
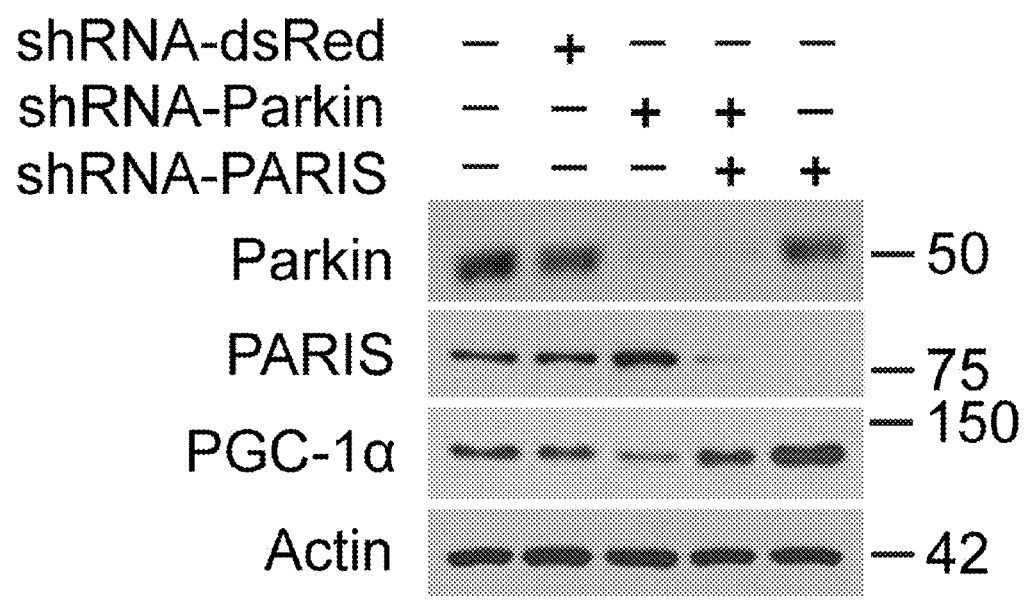
FIG. 73—Immunoblot analysis of parkin, PARIS, PGC-1α and β-actin in double knockdown experiments via lentiviral transduction of shRNA-parkin and/or shRNA-PARIS in SH-SY5Y cells, n=3.
Figure 74:
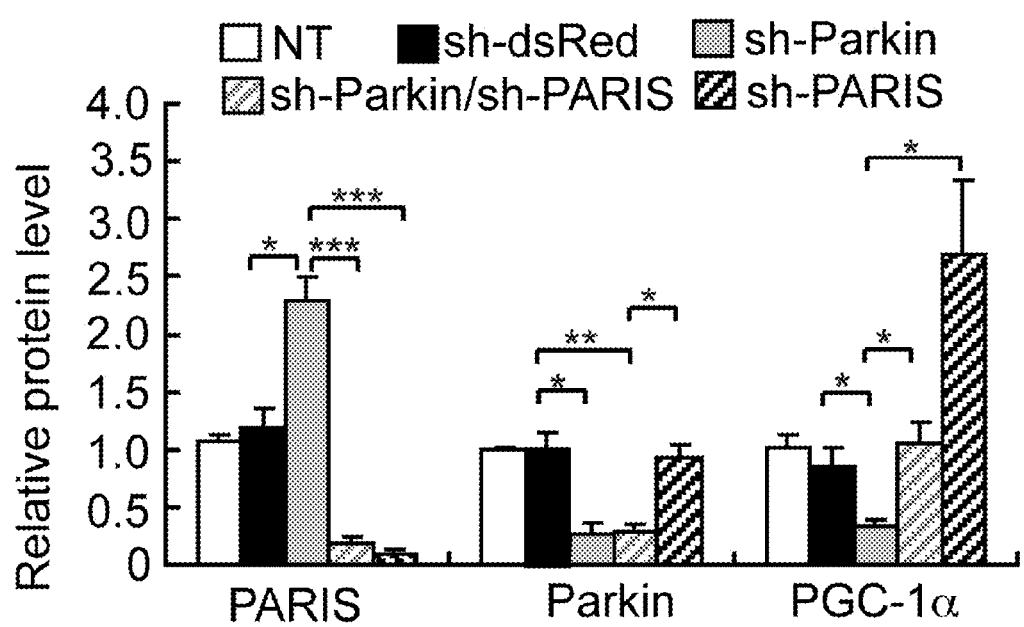
FIG. 74—Quantitation of the immunoblots in FIG. 73 normalized to β-actin, n=3, sh=shRNA. [mean±S.E.M., *p<0.05, p<0.01, *p<0.001, ANOVA with Student-Newman-Keuls post-hoc analysis].
Figure 75:
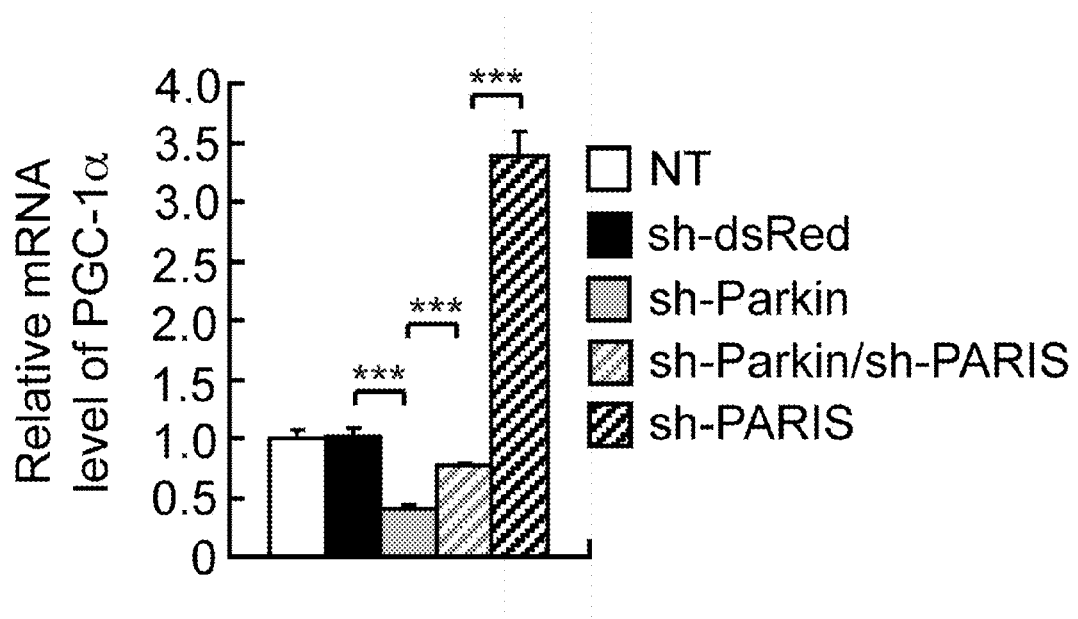
FIG. 75—Relative mRNA levels of PGC-1α normalized to GAPDH, n=3. [mean±S.E.M., *p<0.05, p<0.01, *p<0.001, ANOVA with Student-Newman-Keuls post-hoc analysis].

GFP-WT-PARIS overexpression led to approximately a 75% reduction in PGC-1α mRNA (FIG. 64) and approximately a 60% reduction in protein levels of PGC-1α (FIGS. 65 and 66), whereas the GFP-0571A-PARIS mutant had no effect on PGC-1α protein or message levels (FIGS. 64-66). Lentiviral shRNA-parkin led to a two fold increase in the level of PARIS followed by a 66% reduction of PGC-1α (FIGS. 73 and 74). To determine whether the reduction in PGC-1α levels induced by the absence of parkin was dependent on the presence of PARIS, a double knockdown experiment was performed by lentiviral shRNA-parkin and/or shRNA-PARIS in SH-SY5Y cells. Knockdown of PARIS prevented the downregulation of PGC-1α levels induced by parkin knockdown (FIGS. 73 and 74). Knockdown of PARIS resulted in a 3 fold increase in PGC-1α protein levels (FIGS. 73 and 74) and a 3.5 fold increase in PGC-1α mRNA (FIG. 75). Knockdown of PARIS in the setting of parkin knockdown also prevented the down regulation of PGC-1α mRNA (FIG. 75). These results taken together indicated that PARIS was a transcriptional repressor that negatively regulated the levels of endogenous PGC-1α and that the downregulation of PGC-1α in the absence of parkin was due to the upregulation of PARIS.

Experiment 6

Identification of NRF-1 as a Potential In Vivo PGC-1α Target Gene in PD

PGC-1α is a transcriptional coactivator that regulates a variety of genes. Real-time quantitative RT-PCR (qRT-PCR) was performed on a variety of PGC-1α target genes in PD SN and striatum to determine which PGC-1α target genes are co-regulated by PARIS in PD.

The levels of PGC-1α co-regulated genes; which play important roles in mitochondrial function and oxidant metabolism, were measured. The PGC-1α co-regulated genes included nuclear respiratory factor-1 (NRF-1), copper/zinc superoxide dismutase (SOD 1), manganese SOD (SOD2), glutathione peroxidase (GPx1), catalase (CAT), mitochondrial uncoupling proteins (UCP2 and UCP3), mitochondrial transcription factor A (Tfam) and the oxidative phosphorylation regulators, ATP5b, cytochrome C (CytC) and cytochrome C oxidase (COX II and IV) (FIGS. 38 and 39). In addition, the levels of other genes containing IRS/PLM in their promoter including PEPCK, G6Pase, insulin-like-growth-factor binding protein 1 (IGFBP-1), tyrosine aminotransferase (TAT), and apolipoprotein C III (APOC3) were monitored along with PGC-1α to assess whether PGC-1α is selectively affected in PD (FIGS. 38 and 39). The levels of PARIS and parkin were also assessed as controls.

It was found that PGC-1α and NRF-1 mRNA were downregulated in PD SN and striatum compared to control SN and striatum (FIGS. 38 and 39). In PD SN ATP5B was also significantly downregulated and CAT was significantly upregulated (FIG. 38). All other PGC-1α dependent genes were not significantly altered (FIGS. 38 and 39). In addition there was no significant change in the levels of the IRS/PLM responsive transcripts PEPCK, G6Pase and IGFBP-1 (FIGS. 38 and 39). TAT and APOC3 were not detectable. No significant alteration in the mRNA level of PARIS and parkin was observed between PD and control SN and striatum (FIGS. 38 and 39) indicating that the upregulation in PARIS protein levels (see FIGS. 36 and 37) were most likely due to impairment of parkin E3 ubiquitin ligase activity. Moreover, the absence of an alteration in the mRNA levels of PARIS and parkin suggested that the changes in the mRNA levels of PGC-1α and NRF-1 were specific and not due to the degenerative process that occurred in PD.

Figure 45:
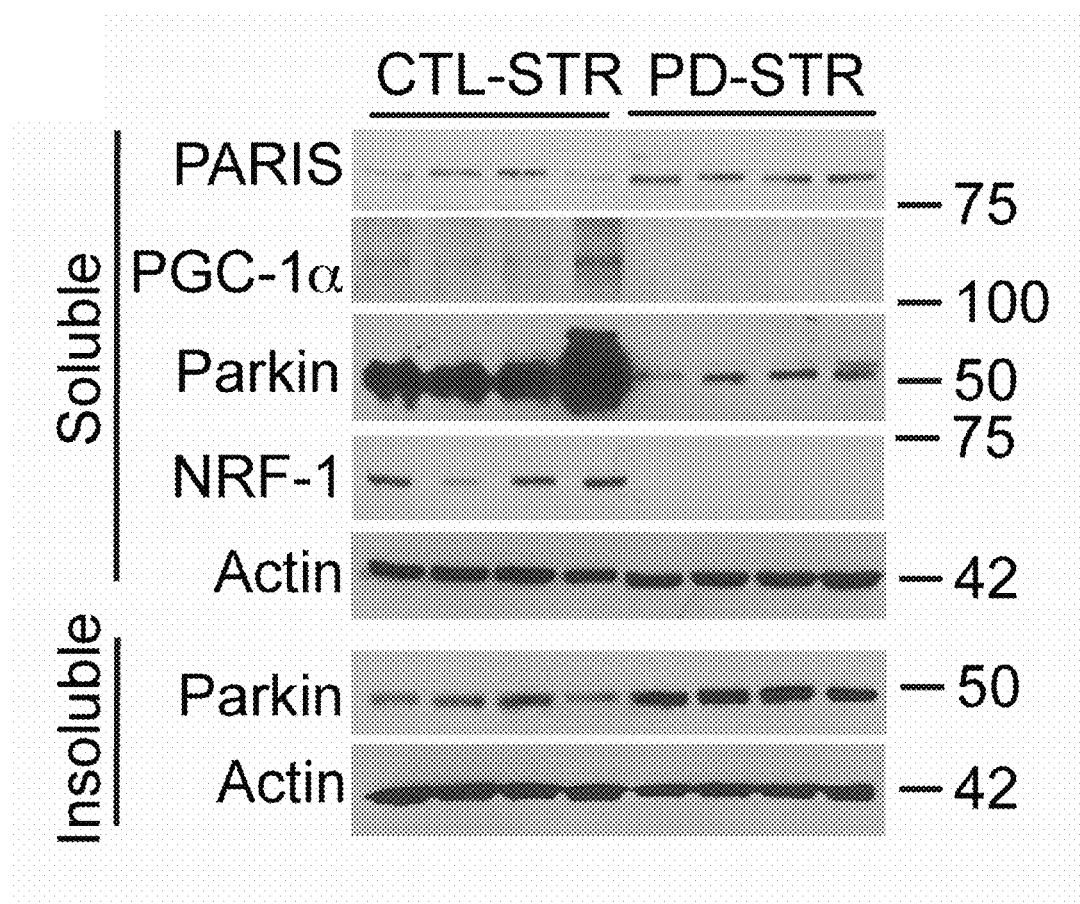
FIG. 45—Immunoblot analysis shows that PGC-1α and NRF-1 protein levels are reduced in PD striatum compared to age-matched controls, n=4 per group. Parkin redistributes to the insoluble fraction consistent with its inactivation in PD.

As shown above (see FIGS. 36 and 37) PARIS protein was upregulated almost 3 fold in PD SN (FIGS. 43 and 44) and greater than two-fold in PD striatum (FIGS. 45 and 46) compared to control SN and striatum respectively. Accompanying the upregulation of PARIS was the down regulation of PGC-1α and NRF-1 in SN (FIGS. 43 and 44) and striatum (FIGS. 45 and 46). There was a trend towards redistribution of parkin from the soluble to insoluble fraction in SN (FIGS. 43 and 44) and parkin shifted from the soluble to insoluble fraction in PD striatum (FIGS. 45 and 46). There was a strong negative correlation between the protein levels of PARIS and PGC-1α ($R^2=0.5195$, $p<0.05$) and NRF-1 ($R^2=0.8015$, $p<0.01$) in the striatum and between PARIS and PGC-1α ($R^2=0.6955$, $p<0.05$) and NRF-1 ($R^2=0.5979$, $p<0.05$) in the SN and a positive correlation between PGC-1α and NRF-1 striatum ($R^2=0.6827$, $p<0.05$) and SN ($R^2=0.6488$, $p<0.05$) (FIG. 47). These results taken together indicated that PARIS accumulated in the nigrostriatal pathway in PD leading to the down regulation of PGC-1α and the PGC-1α dependent gene, NRF-1.

Experiment 7

Figure 76:
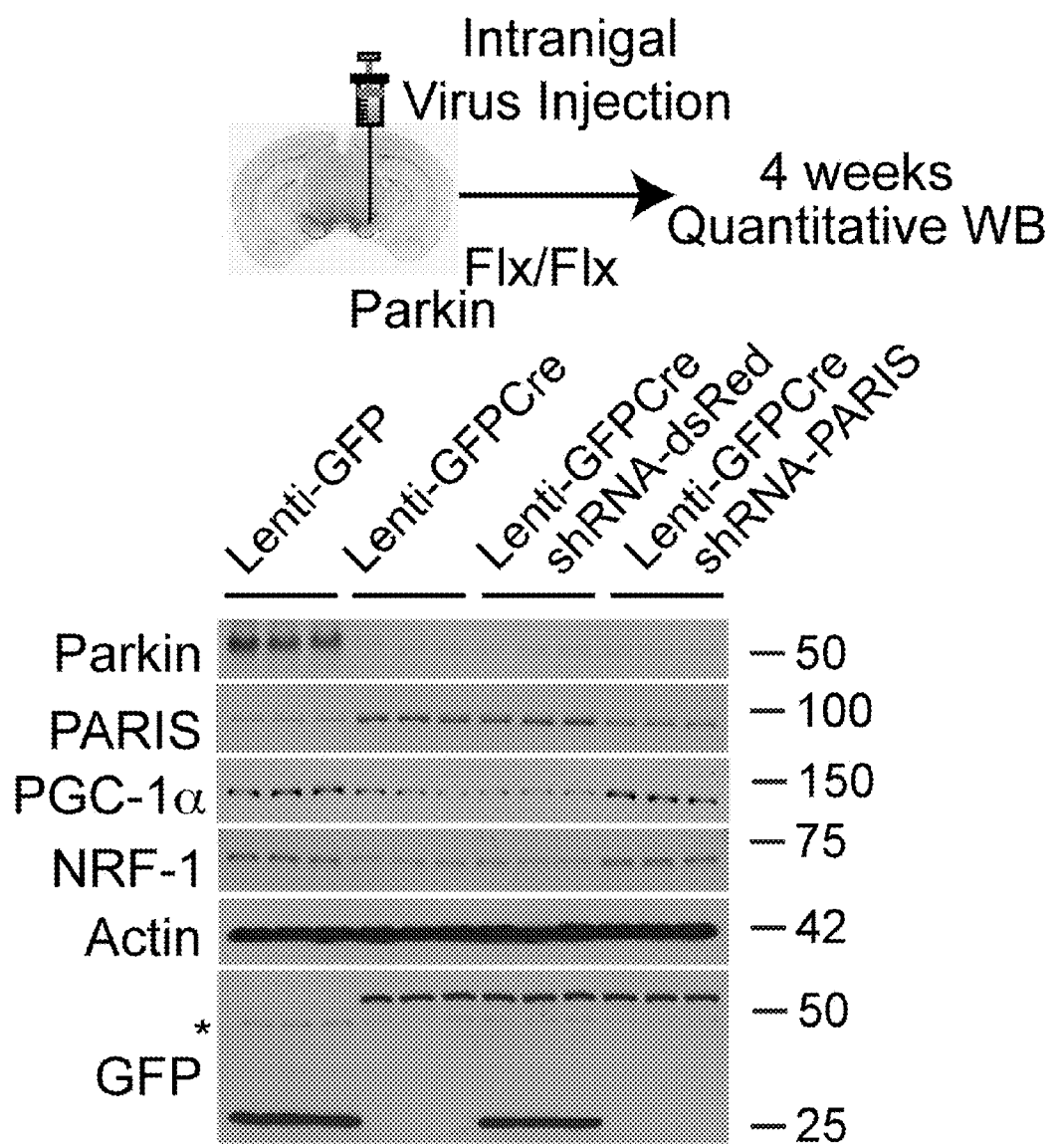
FIG. 76—Top panel, experimental illustration of stereotaxic intranigral virus injection. Below are immunoblots of parkin, PARIS, PGC-1α, NRF-1, β-actin and GFP, 4 weeks after stereotactic delivery of Lenti-GFP, Lenti-GFPCre, Lenti-GFPCre+shRNA-dsRed, or Lenti-GFPCre+shRNA-PARIS into exon 7 floxed parkin mice (parkin$^{Flx/Flx}$), n=3 per group. *nonspecific band.
Figure 77:
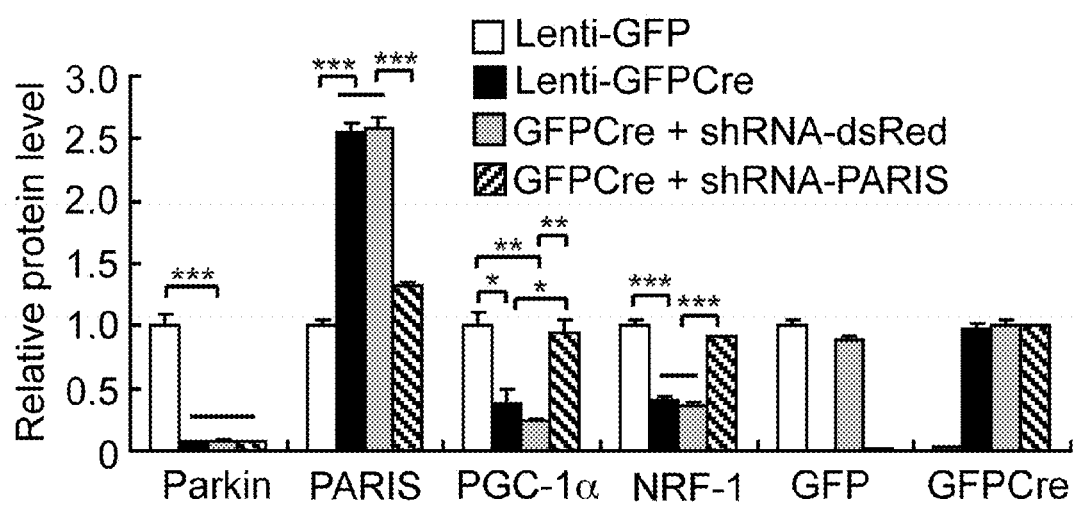
FIG. 77—Quantitation of the immunoblots in FIG. 76 normalized to β-actin, n=3 per group. [mean±S.E.M., *p<0.05, p<0.01 and *p<0.001, ANOVA with Student-Newman-Keuls post-hoc analysis].
Figure 78:
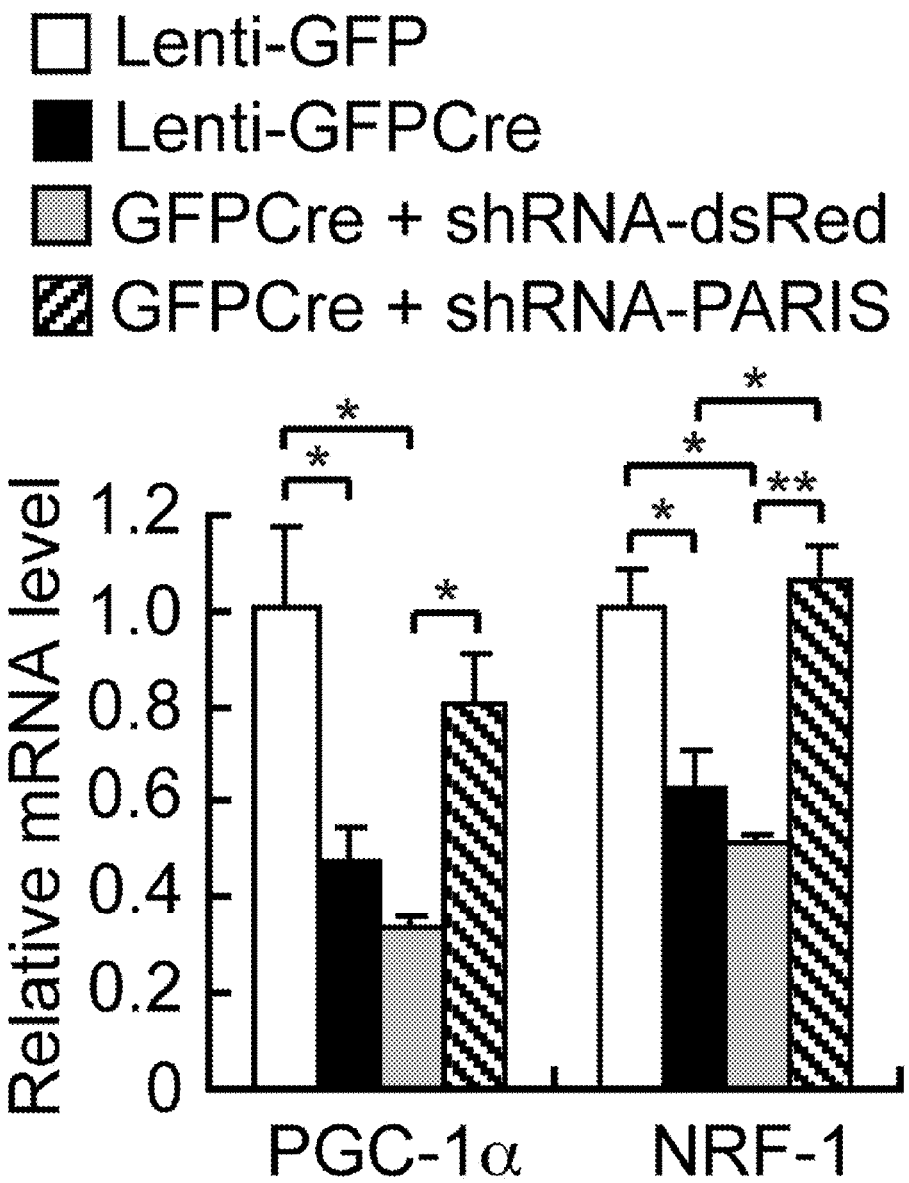
FIG. 78—The alteration of PGC-1α and NRF1 shown in FIG. 76 and FIG. 77 results from transcriptional changes as determined by real-time qRT-PCR, n=3 per group. [mean±S.E.M., *p<0.05, p<0.01 and *p<0.001, ANOVA with Student-Newman-Keuls post-hoc analysis].
Figure 80:
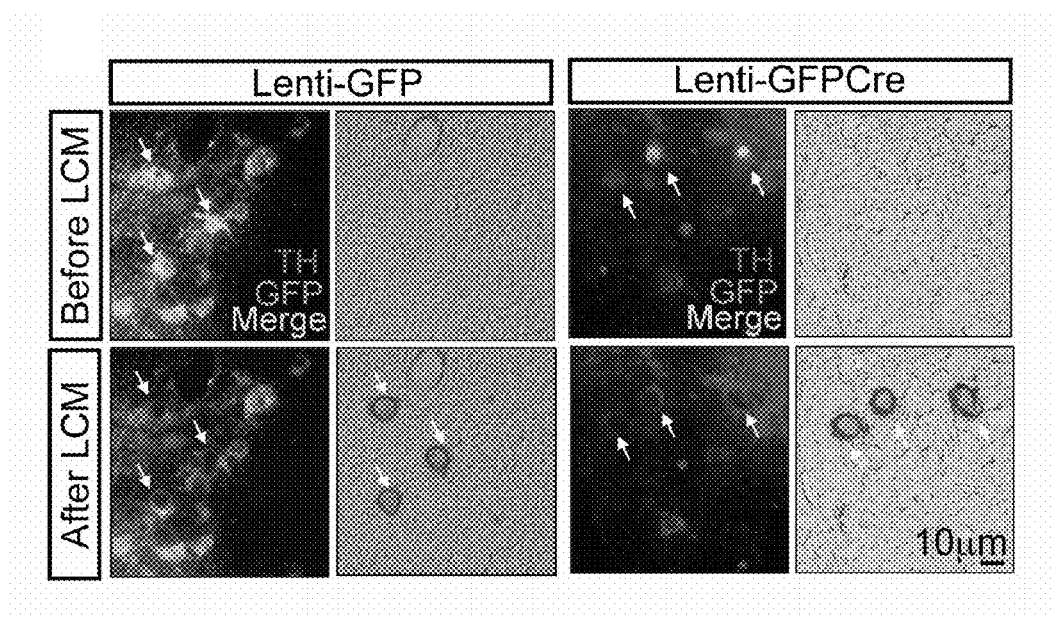
FIG. 80—Representative photomicrographs of laser capture microdissection (LCM) of dopaminergic neurons from conditional parkin KO mice. Upper panels are immunofluorescent images of TH and either GFP (left panel) or GFPCre (right panel) in conditional parkin KO mice before LCM. Lower panels are after LCM.
Figure 81:
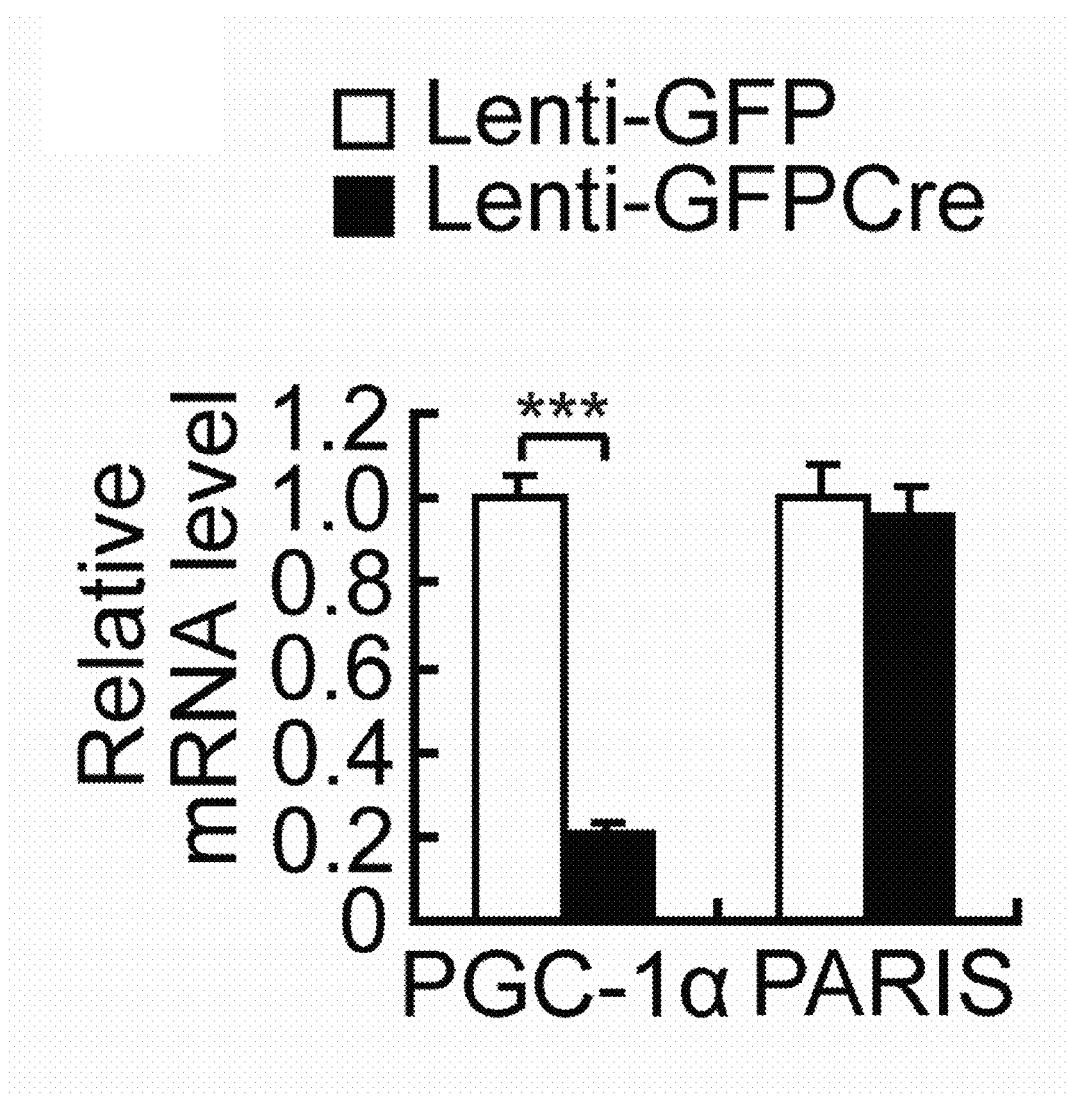
FIG. 81—Robust reduction of PGC-1α mRNA in microdissected parkin KO dopaminergic neurons. PARIS level was assessed to monitor RNA quality (negative control). Values were normalized to GAPDH, n=3 per group. ***p<0.001 in an unpaired two-tailed Student's t-test.
Figure 82:
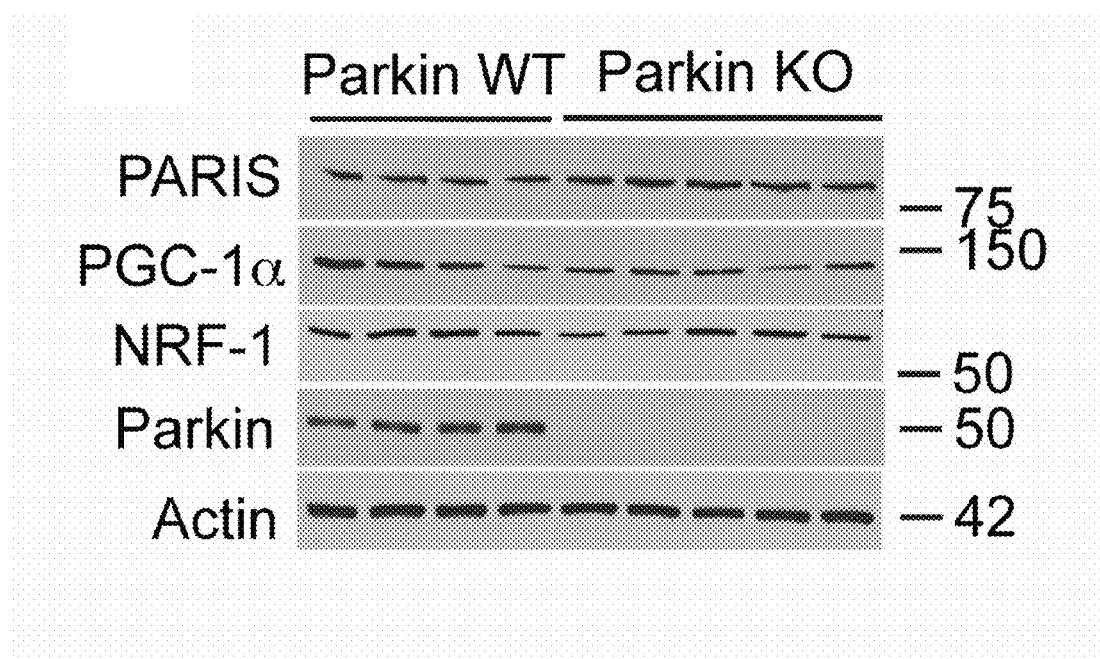
FIG. 82—PGC-1α and NRF-1 levels are not altered in the ventral midbrain (VM) of 18-24 month old germline parkin exon 7 KO mice compared to age-matched WT controls mice where is PARIS is modestly upregulated, WT, n=4; KO, n=5.
Figure 83:
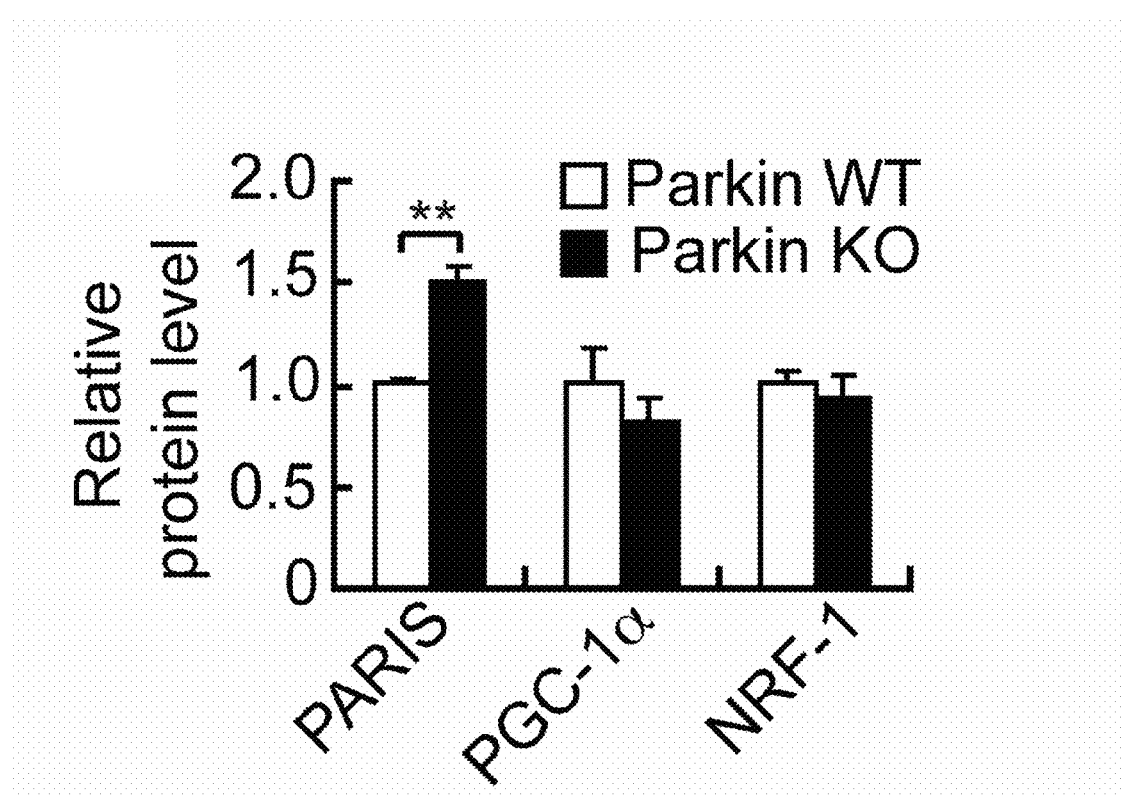
FIG. 83—Quantitation of the immunoblots in FIG. 82 normalized to β-actin, WT, n=4; KO, n=5. All data are expressed as mean±S.E.M. Asterisk indicates statistical significance (*p<0.05, p<0.01 and *p<0.001) in an unpaired two-tailed Student's t-test.

Down Regulation of PGC-1α and NRF-1 in Conditional Parkin KO Mice Required PARIS In adult conditional parkin KO mice (see FIGS. 52-54) four weeks after Lenti-GFPCre mediated parkin deletion there was a greater than two fold upregulation of PARIS (FIGS. 52-54, 76 and 77), comparable to that which occurred in sporadic PD SN (see FIGS. 36 and 37) and a concomitant down regulation of PGC-1α and NRF-1 (FIGS. 76 and 77). The alteration of PGC-1α and NRF1 resulted from the reduction of their mRNA levels (FIG. 78). Moreover, the mRNA levels of PGC-1α target genes in the ventral midbrain of the Lenti-GFPCre-mediated conditional parkin KO were analyzed and showed a significant reduction of PGC-1α, SOD2, and NRF-1 and no significant alteration in other sampled PGC-1α regulated transcripts (FIG. 42) similar to what occurred in sporadic PD brain. In addition, the levels of other genes containing IRS/PLM in their promoter including PEPCK, G6Pase, IGFBP-1, TAT, and APOC were monitored. Of the genes containing IRS/PLM in their promoters, only PGC-1α was significantly down regulated (FIG. 42). The upregulation of PARIS and subsequent downregulation of PGC-1α and NRF-1 occurred prior to the loss of DA neurons since there was no appreciable loss of DA neurons at 3 months after the Lenti-GFPCre injection (see FIG. 79). Moreover, laser capture microdissection (LCM) was performed prior to the loss of DA neurons to obtain mRNA from TH positive neurons transduced with GFP-Cre from conditional parkin KO mice 4 weeks after the Lenti-GFPCre injection to ascertain whether the reduction of PGC-1α was cell autonomous in DA neurons (FIGS. 80 and 81). There was a robust reduction of PGC-1α mRNA in TH-positive DA neurons of conditional parkin KO mice, whereas the levels of PARIS mRNA were unchanged (FIGS. 80 and 81). PARIS was only modestly upregulated in germline parkin exon 7 KO mice (also see FIGS. 49 and 50). PGC-1α and NRF-1 protein levels in germline parkin exon 7 KO mice were comparable to those of WT mice (FIGS. 82 and 83). Thus, germline deletion of parkin apparently led to compensatory changes that prevented substantial alterations in the levels of PGC-1α and NRF-1.

The Cre-flox conditional parkin exon 7 KO model was developed by introducing lentiviral shRNA-PARIS along with lenti-GFPCre into parkin$^{Flx/Flx}$ mice to address whether the changes in PGC-1α and NRF-1 were due to PARIS (FIGS. 76-80). Co-administration of lentiviral shRNA-PARIS along with Lenti-GFPCre prevented the changes in PGC-1α and NRF-1 protein and mRNA as compared to control lentiviral shRNA-dsRed plus Lenti-GFPCre (FIGS. 76-80). These results taken together indicated that PARIS accumulated in the nigrostriatal pathway in PD and in models of parkin inactivation led to the down regulation of PGC-1α and the PGC-1α dependent gene, NRF-1. These changes in PGC-1α and NRF-1 due to the loss of parkin were cell autonomous and preceded the loss of DA neurons and were due to the upregulation of PARIS, since knockdown of PARIS prevented these changes. Moreover, since deletion of parkin from adult mice led to similar events that occurred in sporadic PD, it was likely that the absence and/or inactivation of parkin in PD led to PARIS upregulation and impairment of PGC-1α signaling.

Experiment 8

Neurodegeneration in Conditional Parkin KO Mice Required PARIS

Figure 79:
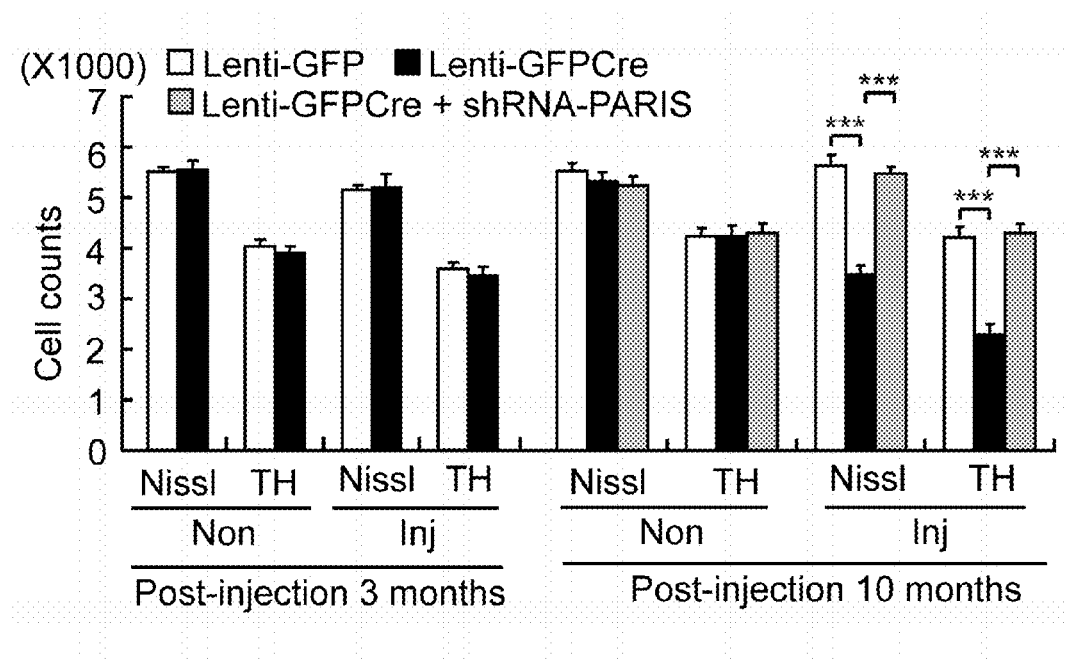
FIG. 79—Stereological assessment of TH and Nissl positive neurons in the SN of parkin$^{Flx/Flx}$ mice injected with Lenti-GFP, and Lenti-GFPCre±Lenti-shRNA-PARIS 3 (n=3 per group) and 10 months (n=7 per group) after injection of virus. [mean±S.E.M., *p<0.05, p<0.01 and *p<0.001, ANOVA with Student-Newman-Keuls post-hoc analysis].
Figure 84:
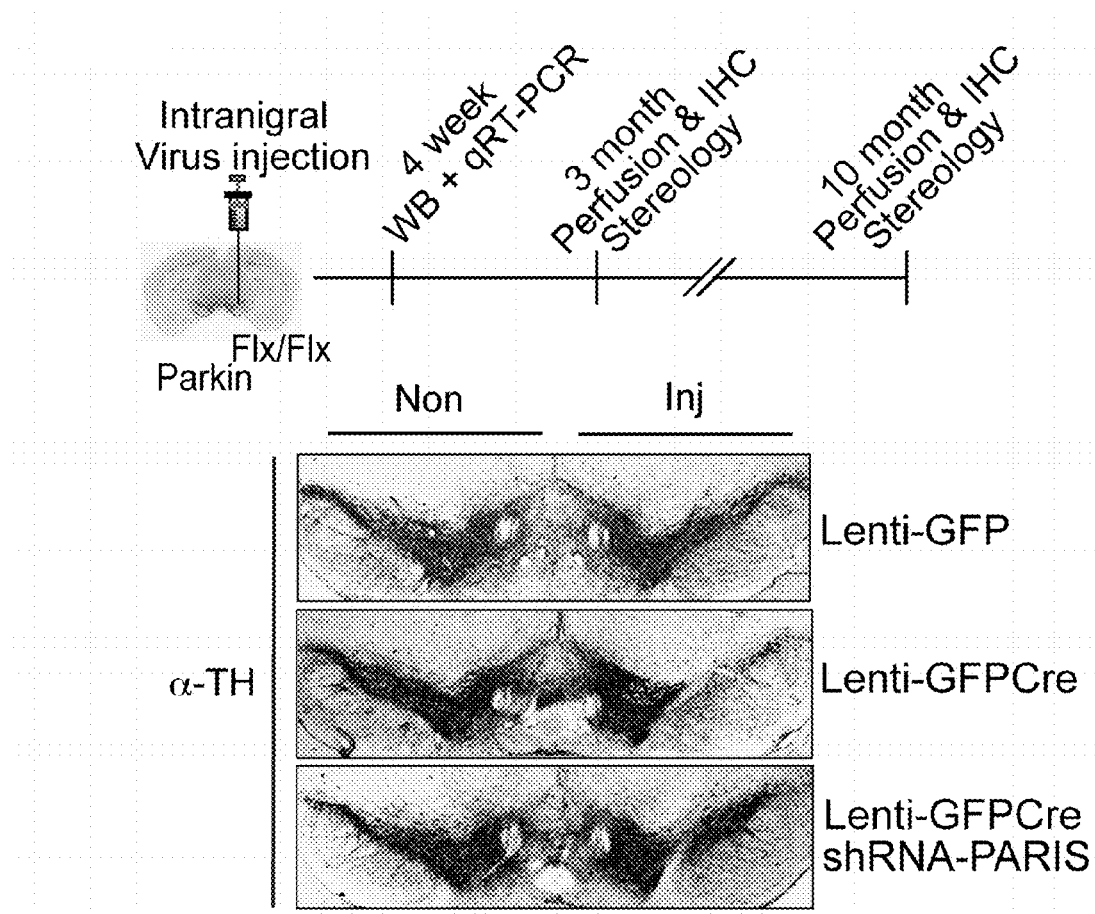
FIG. 84—Top panel, experimental illustration of stereotaxic intranigral virus injection. Below is TH immunostaining of representative mice midbrain sections from SN of parkin-$^{Flx/Flx}$ mice injected with Lenti-GFP, and Lenti-GFPCre±Lenti-shRNA-PARIS 10 months post-injection of virus.

Conditional KO of parkin led to a significant reduction in tyrosine hydroxylase (TH) positive and Nissl stained DA neurons 10 months after stereotaxic injection of Lenti-GPFCre into the SN of 6-8 week old parkin$^{Flx/Flx}$ mice compared to parkin$^{Flx/Flx}$ mice injected with control Lenti-GFP (FIGS. 79 and 84). The loss of DA neurons was progressive; since there was no substantial loss of DA neurons after 3 months (FIG. 79). PARIS was required for the loss of DA neurons in conditional parkin KO mice, since co-administration of lentiviral shRNA-PARIS along with Lenti-GFPCre significantly reduced the loss of DA neurons due to conditional KO of parkin (FIGS. 79 and 84). Taken together these results indicated that conditional KO of parkin in adult mice led to degeneration of DA neurons and the upregulation of PARIS was necessary to contribute to the demise of DA neurons.

Experiment 9

Overexpression of PARIS Killed Dopamine Neurons In Vivo: Restoration by Parkin and PGC-1α

Figure 85:
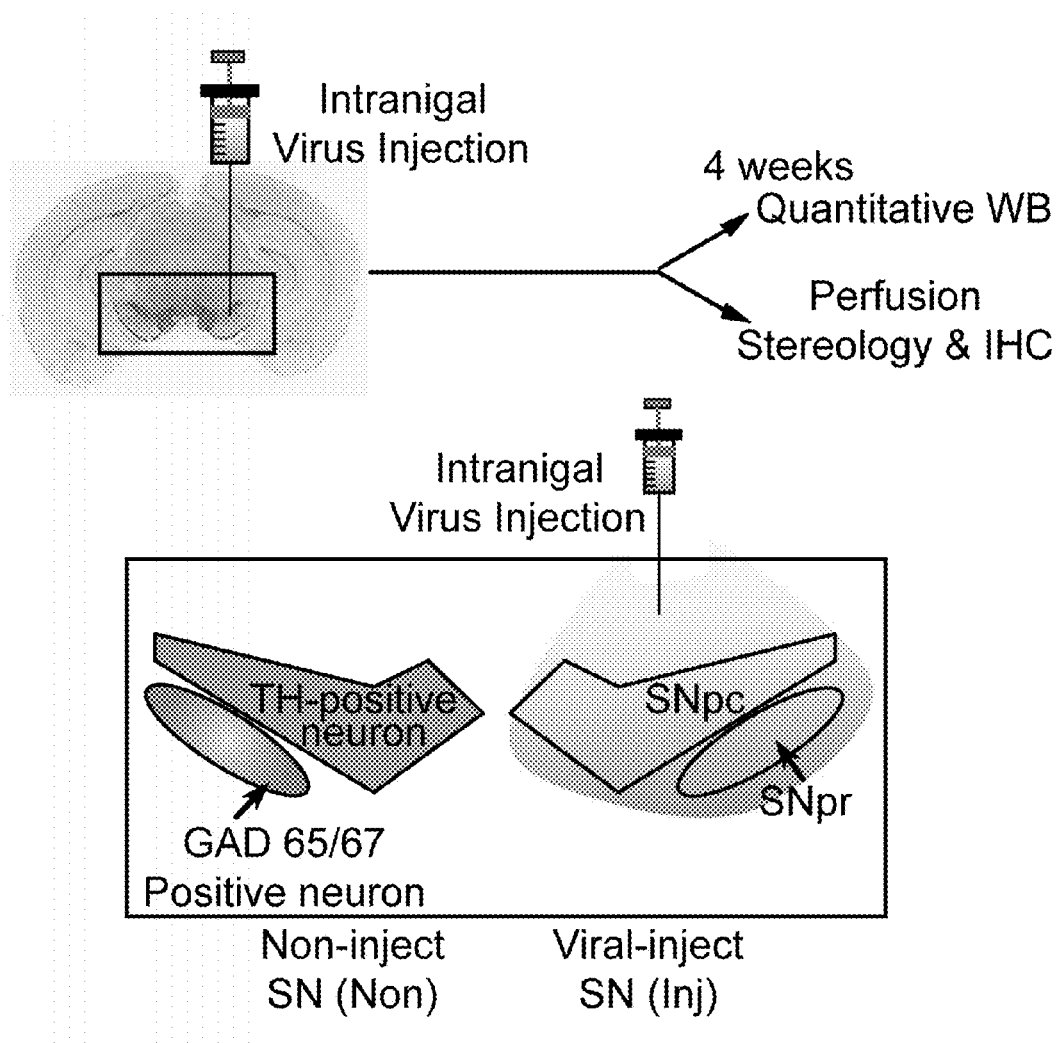
FIG. 85—Schematic illustration of intranigral viral injection and transduced brain regions.
Figure 86:
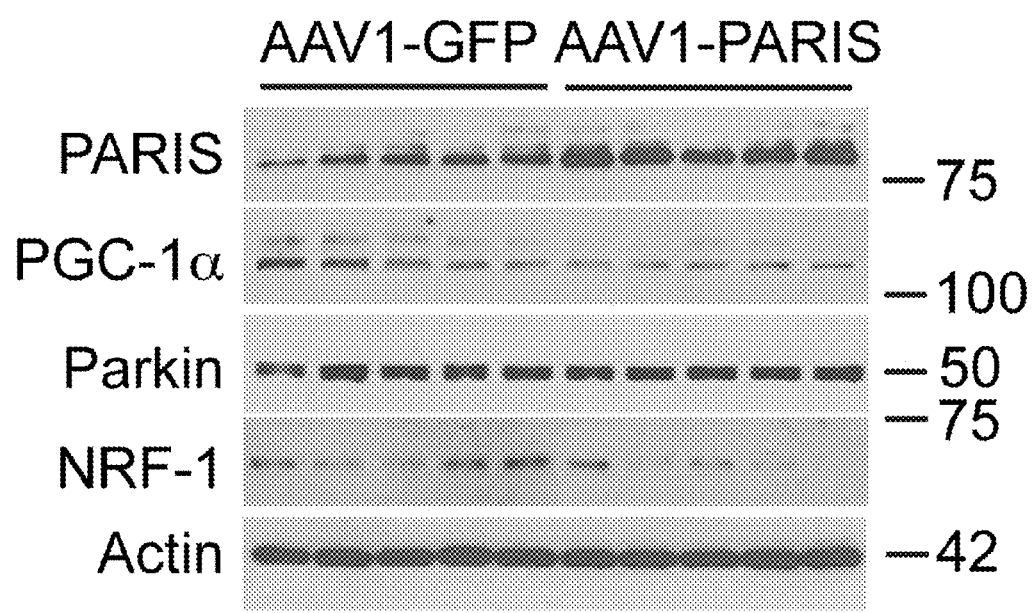
FIG. 86—Immunoblot analysis of PARIS, PGC-1α, parkin and NRF-1 four-weeks post intranigral injection of AAV1-PARIS, n=5 per group.
Figure 87:
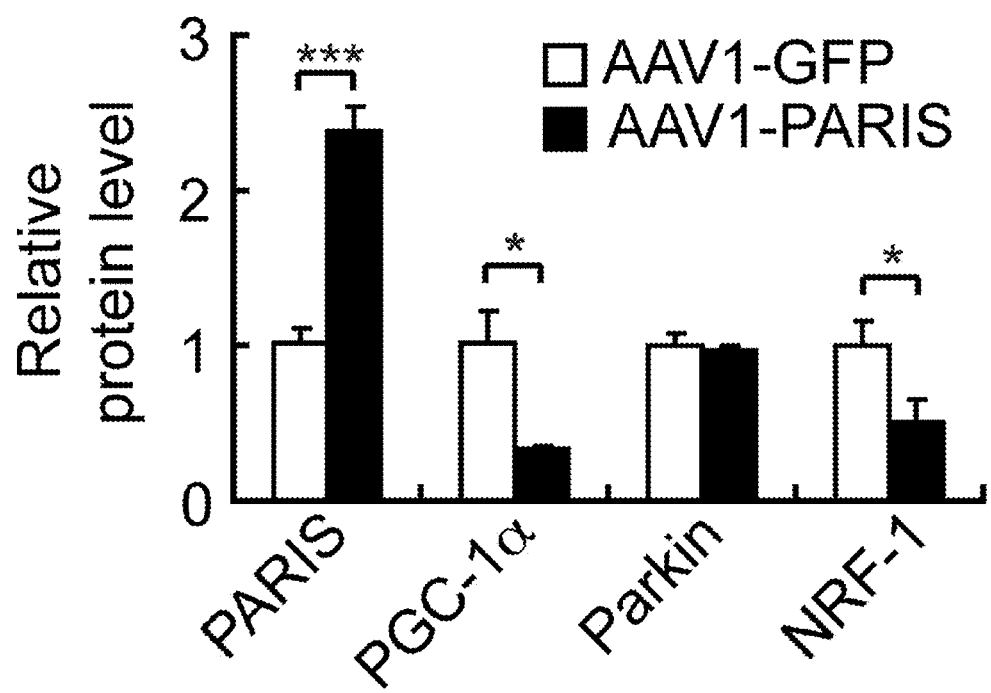
FIG. 87—Quantitation of the immunoblots in FIG. 22 normalized to β-actin.

A PARIS overexpression model was developed in which AAV1-PARIS was stereotactically injected into the SN of C57Bl/6 mice and compared to mice injected with control AAV1-GFP virus. Stereotactic intranigral injection of AAV1 effectively transduced the entire SN (FIG. 85). One month after stereotactic injection of the viruses, AAV1 mediated overexpression of PARIS led to a greater than two-fold upregulation of PARIS levels in the SN of mice (FIGS. 86 and 87) and it had no affect on parkin levels (FIGS. 86 and 87). Accompanying the increase in PARIS levels was a concomitant downregulation of PGC-1α and NRF-1 protein levels (FIGS. 86 and 87).

Figure 88:
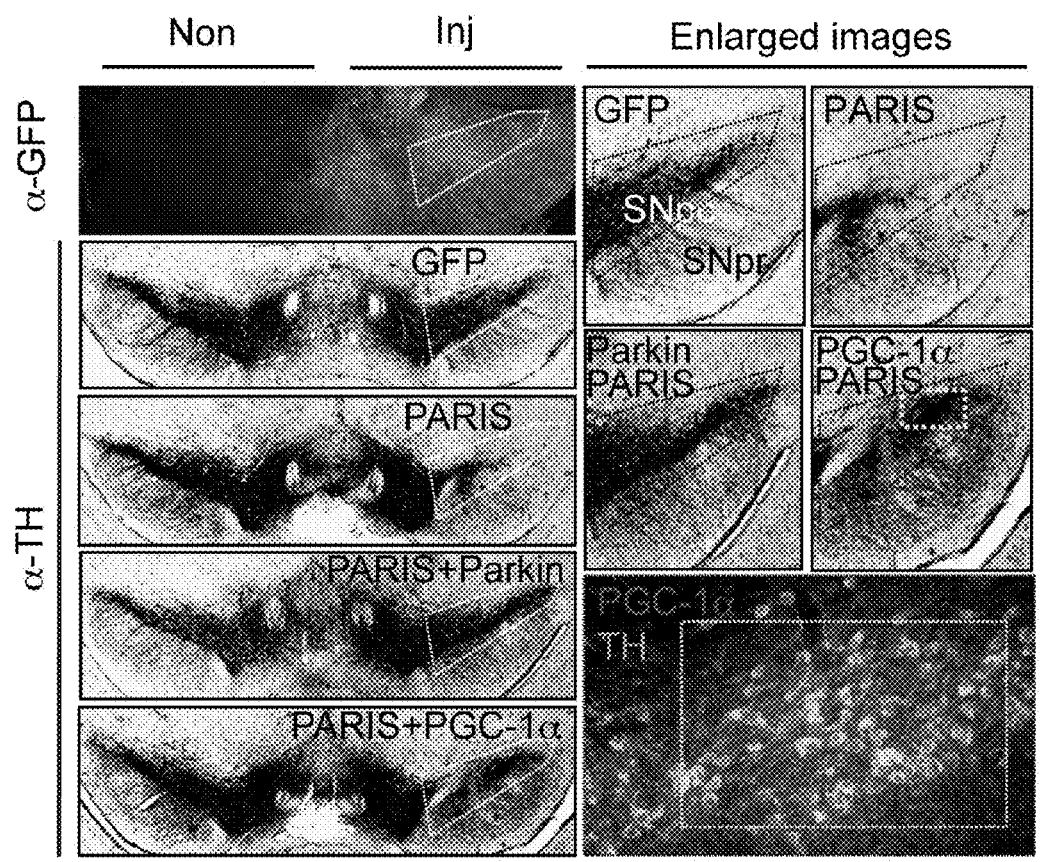
FIG. 88—TH staining of a representative section of mice injected with AAV1-GFP, AAV1-PARIS±AAV1-parkin or AAV1-PARIS±Lenti-PGC-1α. Each panel shows the noninjected side (Non) and contralateral injected side (Inj) and white pentagonal box indicates the SNpc. Enlarged images containing SNpc and SNpr are shown on the right panels. AAV1 encoding GFP was used as transduction control in all injection procedures. Broad regions including SNpc and SNpr were successfully transduced (left top panel). In right bottom panel, yellow rectangle indicates the region that PARIS and lenti-PGC-1α co-transduced. Approximately 30% of the SNpc was transduced with lenti-PGC-1α and this is the region, which is protected from PARIS toxicity, n=6 per group.
Figure 89:
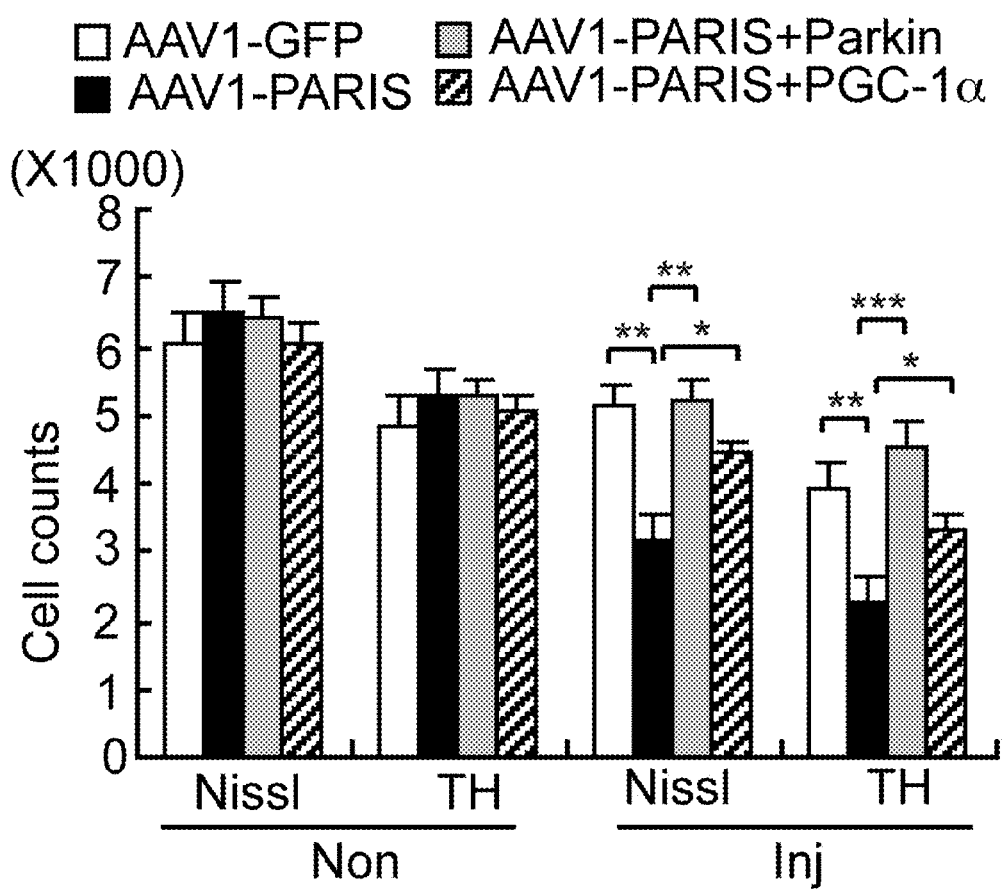
FIG. 89—Stereological TH, Nissl-positive neuronal counting, n=6 per group.
Figure 90:
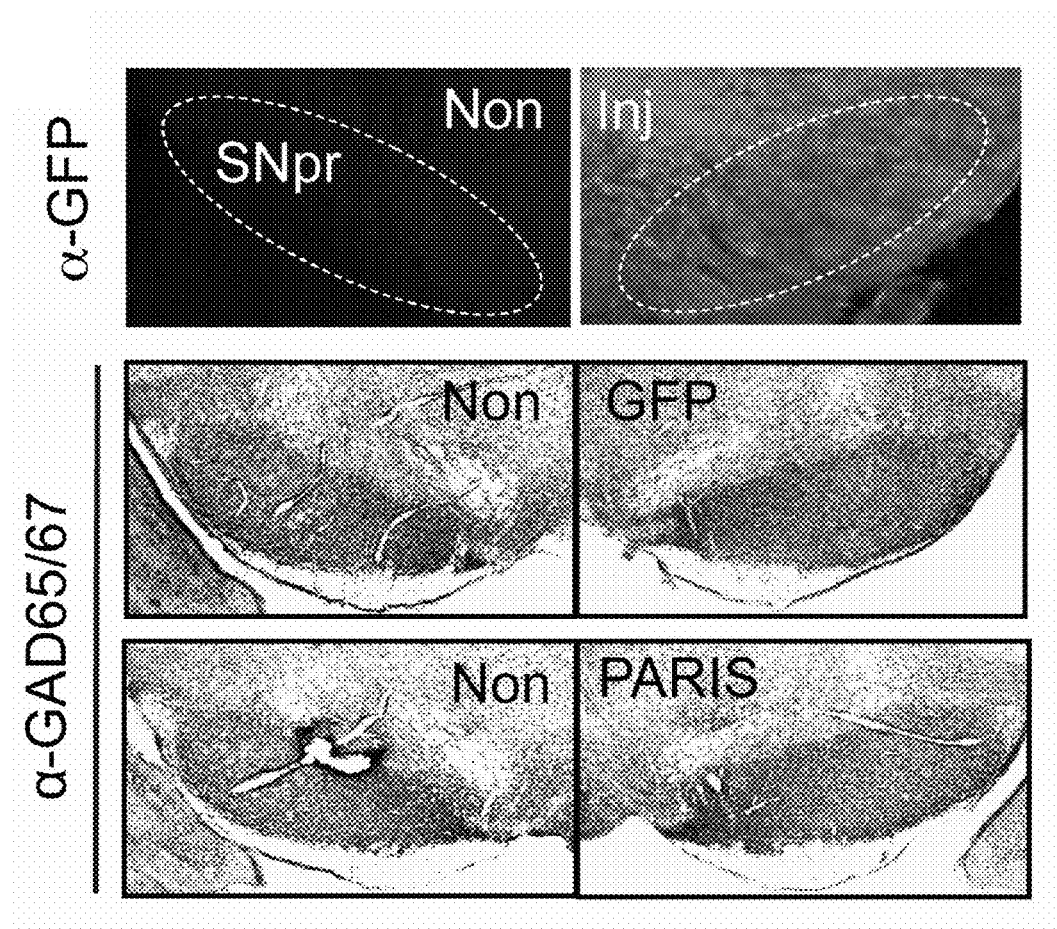
FIG. 90—Representative SN sections stained with α-GAD 65/67, Robust viral expression was evaluated by GFP immunofluoresence in SNpr (top panel). The GABAergic neuronal marker shows no difference between AAV1-GFP and AAV1-PARIS between noninjected side and injected side, n=6 per group.
Figure 91:
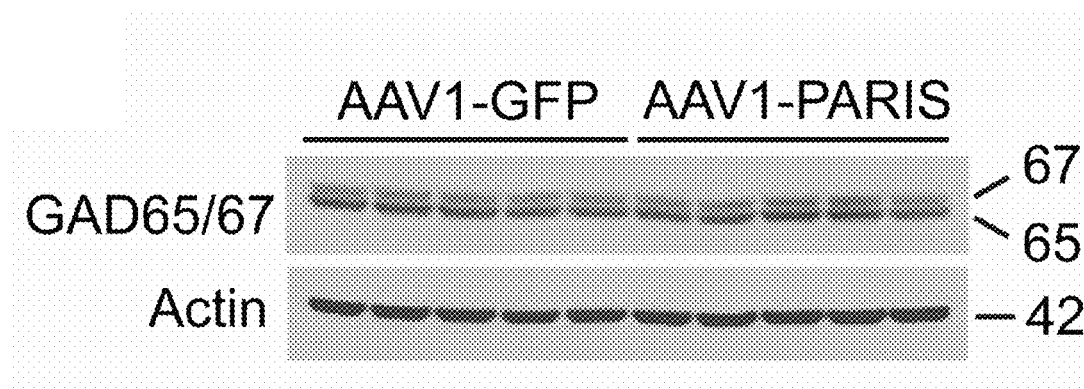
FIG. 91—Equivalent protein levels of GAD 65/67 were confirmed by immunoblot analysis, n=5 per group.
Figure 92:
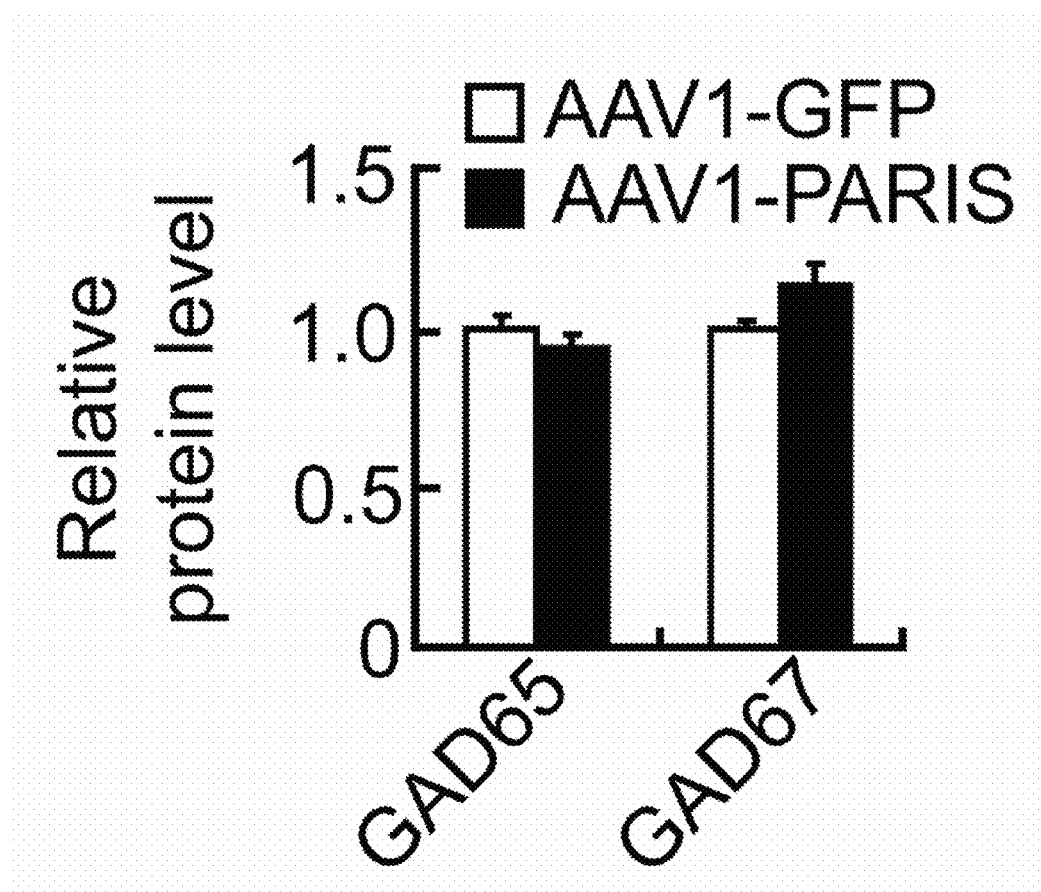
FIG. 92—Quantitation of the immunoblots in FIG. 91 normalized to β-actin, n=5. Data are expressed as mean±S.E.M. Statistical significance was evaluated ANOVA with the Student-Newman-Keuls post hoc test.
Figure 93:
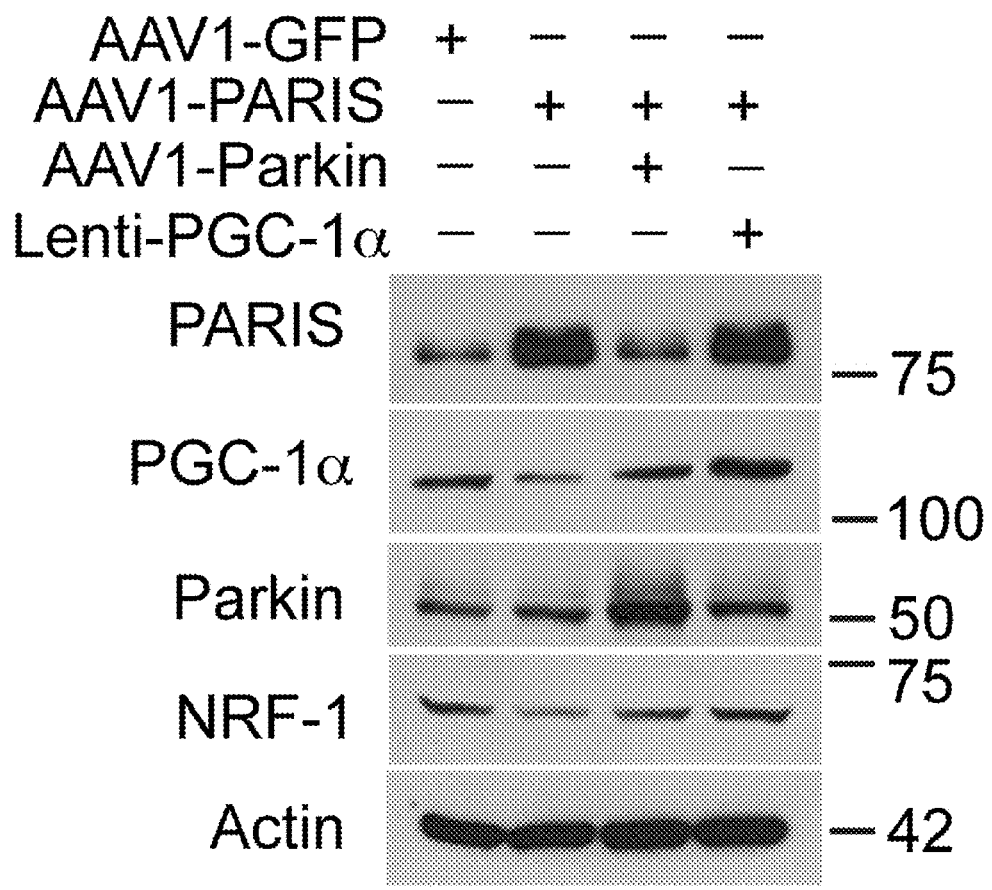
FIG. 93—Immunoblot analysis of PARIS, PGC-1α, parkin and NRF-1, n=3.
Figure 94:
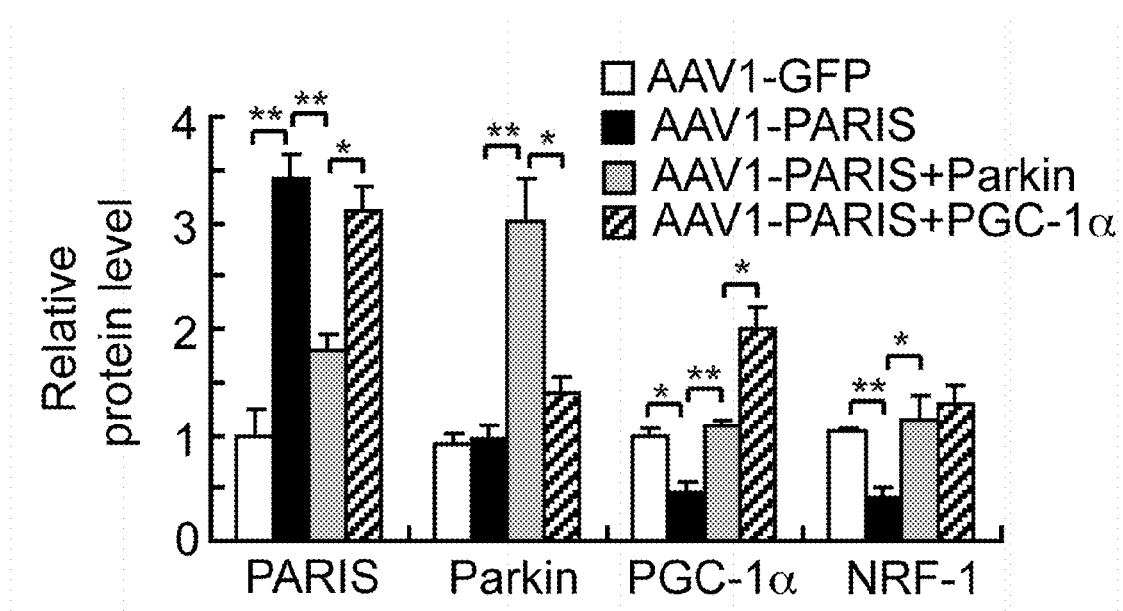
FIG. 94—Quantitation of the immunoblots in FIG. 32 normalized to β-actin.

PARIS overexpression led to a greater than 40% reduction in TH positive and Nissl stained DA neurons positive neurons (FIGS. 88 and 89). No substantial decrement in GABAergic neurons as assessed by GAD65/67 immunoreactivity via immunohistochemistry was observed (FIG. 90) or via immunoblot (FIGS. 91 and 92) in AAV1-PARIS versus AAV1-GFP transduced SN, indicating that PARIS overexpression was selectively detrimental to DA neurons. Co-administration of AAV1-Parkin with AAV1-PARIS prevented the loss of dopamine neurons induced by PARIS overexpression (FIGS. 88 and 89). Lentiviral PGC-1α also prevented the loss of DA neurons induced by PARIS overexpression (FIGS. 88 and 89). AAV1-mediated overexpression of PARIS was confirmed by immunoblot analysis and reduced PGC-1α and NRF-1 levels by 52% and 60%, respectively. These reductions were restored by co-overexpression of parkin or PGC-1α (FIGS. 93 and 94). These results indicated that PARIS overexpression was sufficient to downregulate PGC-1α, NRF-1 and selectively killed DA kills neurons through a PGC-1α dependent mechanism.

EXAMPLES

Additional embodiments are described in the following paragraphs.

Paragraph 1. A method to diagnose Parkinson's disease by testing for an elevated level of PARIS.

Paragraph 2. A method to diagnose Parkinson's disease by testing for an elevated level of PARIS in urine.

Paragraph 3. A method to diagnose Parkinson's disease by testing for an elevated level of PARIS in blood.

Paragraph 4. A method to diagnose Parkinson's disease by testing for an elevated level of PARIS in cerebra-spinal fluid.

Paragraph 5. A method to diagnose Parkinson's disease by testing for an elevated level of PARIS in the brain.

Paragraph 6. A method to diagnose Parkinson's disease by testing for an elevated level of PARIS in a bodily fluid.

Paragraph 7. A method to diagnose Parkinson's disease by measuring a protein level of PARIS.

Paragraph 8. A method to diagnose Parkinson's disease by measuring a protein level of PARIS in urine.

Paragraph 9. A method to diagnose Parkinson's disease by measuring a protein level of PARIS in blood.

Paragraph 10. A method to diagnose Parkinson's disease by measuring a protein level of PARIS in cerebra-spinal fluid.

Paragraph 11. A method to diagnose Parkinson's disease by measuring a protein level of PARIS in the brain.

Paragraph 12. A method to diagnose Parkinson's disease by measuring a protein level of PARIS in a bodily fluid.

Paragraph 13. A method to diagnose Parkinson's disease by testing for an elevated level of a metabolite of PARIS.

Paragraph 14. A method to diagnose Parkinson's disease by testing for an elevated level of a metabolite of PARIS in urine.

Paragraph 15. A method to diagnose Parkinson's disease by testing for an elevated level of a metabolite of PARIS in blood.

Paragraph 16. A method to diagnose Parkinson's disease by testing for an elevated level of a metabolite of PARIS in cerebra-spinal fluid.

Paragraph 17. A method to diagnose Parkinson's disease by testing for an elevated level of a metabolite of PARIS in the brain.

Paragraph 18. A method to diagnose Parkinson's disease by testing for an elevated level of a metabolite of PARIS in a bodily fluid.

Paragraph 19. A method to diagnose Parkinson's disease by measuring a protein level of a metabolite of PARIS.

Paragraph 20. A method to diagnose Parkinson's disease by measuring a protein level of a metabolite of PARIS in urine.

Paragraph 21. A method to diagnose Parkinson's disease by measuring a protein level of a metabolite of PARIS in blood.

Paragraph 22. A method to diagnose Parkinson's disease by measuring a protein level of a metabolite of PARIS in cerebra-spinal fluid.

Paragraph 23. A method to diagnose Parkinson's disease by measuring a protein level of a metabolite of PARIS in the brain.

Paragraph 24. A method to diagnose Parkinson's disease by measuring a protein level of a metabolite of PARIS in a bodily fluid.

Paragraph 25. A method to diagnose Parkinson's disease by measuring level of an mRNA coding for PARIS.

Paragraph 26. A method to diagnose Parkinson's disease by measuring level of an mRNA coding for PARIS in urine.

Paragraph 27. A method to diagnose Parkinson's disease by measuring level of an mRNA coding for PARIS in blood.

Paragraph 28. A method to diagnose Parkinson's disease by measuring level of an mRNA coding for PARIS in cerebra-spinal fluid.

Paragraph 29. A method to diagnose Parkinson's disease by measuring level of an mRNA coding for PARIS in blood the brain.

Paragraph 30. A method to diagnose Parkinson's disease by measuring level of a mRNA coding for PARIS in a bodily fluid.

Paragraph 31. A method to diagnose Parkinson's disease by testing for a reduced level of PGC-1α.

Paragraph 32. A method to diagnose Parkinson's disease by testing for a reduced level of PGC-1α in urine.

Paragraph 33. A method to diagnose Parkinson's disease by testing for a reduced level of PGC-1α in blood.

Paragraph 34. A method to diagnose Parkinson's disease by testing for a reduced level of PGC-1α in cerebra-spinal fluid.

Paragraph 35. A method to diagnose Parkinson's disease by testing for a reduced level of PGC-1α in the brain.

Paragraph 36. A method to diagnose Parkinson's disease by testing for a reduced level of PGC-1α in a bodily fluid.

Paragraph 37. A method to diagnose Parkinson's disease by measuring protein level of PGC-1α.

Paragraph 38. A method to diagnose Parkinson's disease by measuring protein level of PGC-1α in urine.

Paragraph 39. A method to diagnose Parkinson's disease by measuring protein level of PGC-1α in blood.

Paragraph 40. A method to diagnose Parkinson's disease by measuring protein level of PGC-1α in cerebra-spinal fluid.

Paragraph 41. A method to diagnose Parkinson's disease by measuring protein level of PGC-1α in the brain.

Paragraph 42. A method to diagnose Parkinson's disease by measuring protein level of PGC-1α in a bodily fluid.

Paragraph 43. A method to diagnose Parkinson's disease by measuring level of an mRNA coding for PGC-1α.

Paragraph 44. A method to diagnose Parkinson's disease by measuring level of an mRNA coding for PGC-1α in urine.

Paragraph 45. A method to diagnose Parkinson's disease by measuring level of an mRNA coding for PGC-1α in blood.

Paragraph 46. A method to diagnose Parkinson's disease by measuring level of an mRNA coding for PGC-1α in cerebra-spinal fluid.

Paragraph 47. A method to diagnose Parkinson's disease by measuring level of an mRNA coding for PGC-1α in the brain.

Paragraph 48. A method to diagnose Parkinson's disease by measuring level of an mRNA coding for PGC-1α in a bodily fluid.

Paragraph 49. A method to identify small molecular compound that can be used to treat Parkinson's disease.

Paragraph 50. A method to identify small molecular compound that can be used to treat Parkinson's disease related disorders.

Paragraph 51. A reporter construct for PGC-1α (pGL3-h PGC-1α) that is repressed by PARIS.

Paragraph 52. A SK-SHSY cell line to stably express PARIS and pGL3-h PGC-1α, and GL3-h PGC-1α alone, wherein PARIS and pGL3-h PGC-1α are used to screen for PARIS inhibitors.

Paragraph 53. A method to identify small molecule compounds of PARIS that leave unaffected other regulatory signaling of PGC-1α that is PARIS independent.

Paragraph 54. An in vitro model of PARIS overexpression that can be used to validate a PARIS inhibitor.

Paragraph 55. An in vitro model of PARIS overexpression that can be used to optimize a PARIS inhibitor.

Paragraph 56. An in vivo model of PARIS overexpression that can be used to validate a PARIS inhibitor.

Paragraph 57. An in vivo model of PARIS overexpression that can be used to optimize a PARIS inhibitor.

Paragraph 58. An in vitro model of Parkin inactivation that can be used to validate a PARIS inhibitor.

Paragraph 59. An in vitro model of Parkin inactivation that can be used to optimize a PARIS inhibitor.

Paragraph 60. An in vivo model of Parkin inactivation that can be used to validate a PARIS inhibitor.

Paragraph 61. An in vivo model of Parkin inactivation that can be used to optimize a PARIS inhibitor.

Paragraph 62. A method to select inhibitors of PARIS by disrupting a function of PARIS.

Paragraph 63. A method to develop biologic assays to confirm and/or characterize a PARIS inhibitor.

Paragraph 64. A method to determine the effect of an inhibitor of PARIS on neuronal viability in model of Parkinson's disease.

Paragraph 65. An isolated nucleotide of SEQ ID NO. 27.

Paragraph 66. An isolated nucleotide of SEQ ID NO. 28.

Paragraph 67. A method of treating Parkinson's disease by administering a shRNA inhibitor.

Paragraph 68. A method of treating Parkinson's disease by administering an anti-sense microRNA inhibitor.

Paragraph 69. A method of treating Parkinson's disease related disorders by administering a shRNA inhibitor.

Paragraph 70. A method of treating Parkinson's disease related disorders by administering an anti-sense microRNA inhibitor.

Paragraph 71. A method of treating neurodegenerative and related neurologic diseases, such as, Alexander's disease, Alper's disease, Alzheimer's disease, amyotrophic lateral sclerosis, ataxia telangiectasia, Batten disease, bovine spongiform encephalopathy, Canavan disease, Cockayne syndrome, corticobasal degeneration, Creutzfeldt-Jakob disease, Huntington's disease, HIV associated dementia, Kennedy's disease, Krabbe's disease, lewy body dementia, Machado-Joseph disease, multiple sclerosis, multiple system atrophy, narcolepsy, neuroborreliosis, Parkinson's disease, Pelizaeus-Merzbacher Disease, Pick's disease, primary lateral sclerosis, prion diseases, Refsum's disease, Sandhoff's disease, Schilder's disease, subacute combined degeneration of spinal cord secondary to pernicious anemia, schizophrenia, spinocerebellar ataxia, spinal muscular atrophy, Steele-Richardson-Olszewski disease, and tabes dorsalis; by administering inhibitors of PARIS.

Paragraph 72. A method of treating a metabolic disorder, such as, diabetes mellitus, dyslipidemia, and obesity, by administering an inhibitor of PARIS.

Paragraph 73. A method of treating a circulatory disorder, such as, atherosclerosis, cardiovascular disease, and cardiac ischemia, by administering an inhibitor of PARIS.

Paragraph 74. A method of treating an inflammatory condition such as inflammatory bowel diseases, colitis and psoriasis; by administering an inhibitor of PARIS.

Paragraph 75. A method of treating a cancer by administering an inhibitor of PARIS.

Paragraph 76. A method of treating a kidney disease including glomerulonephritis, glomerulosclerosis and diabetic nephropathy by administering an inhibitor of PARIS.

Paragraph 77. A method of treating a mitochondrial disorder by administering an inhibitor of PARIS.

Paragraph 78. A method of treating a muscle disorder including muscular dystrophies by administering an inhibitor of PARIS.

Paragraph 79. A method of treating a disorder of circadian rhythms and sleep by administering an inhibitor of PARIS.

Paragraph 80. An isolated polypeptide comprising of any of SEQ ID NO: 1 to SEQ ID NO: 4.

Paragraph 81. An isolated polypeptide consisting of any of SEQ ID NO: 1 to SEQ ID NO: 4.

Paragraph 82. An isolated polypeptide comprising a peptide sequence of any of SEQ ID NO: 1 to SEQ ID NO: 4.

Paragraph 83. An isolated polypeptide comprising the peptide sequence of any of SEQ ID NO: 1 to SEQ ID NO: 4.

Paragraph 84. An isolated polypeptide comprising a polypeptide coded by the nucleotide sequence of any of SEQ ID NO: 5 to SEQ ID NO: 136.

Paragraph 85. An isolated polynucleotide comprising of any of SEQ ID NO: 5 to SEQ ID NO: 136.

Paragraph 86. An isolated polynucleotide consisting of any of SEQ ID NO: 5 to SEQ ID NO: 136.

Paragraph 87. An isolated polynucleotide comprising a nucleotide sequence of any of SEQ ID NO: 5 to SEQ ID NO: 136.

Paragraph 88. An isolated polynucleotide comprising the nucleotide sequence of any of SEQ ID NO: 5 to SEQ ID NO: 136.

Paragraph 89. An isolated polynucleotide comprising a polynucleotide encoding the amino acid sequence of any of SEQ ID NO: 1 to SEQ ID NO: 4.

Paragraph 90. An isolated polynucleotide comprising a polynucleotide which hybridizes under stringent conditions to any of SEQ ID NO: 5 to SEQ ID NO: 136.

Paragraph 91. A composition comprising an isolated polypeptide comprising of any of SEQ ID NO: 1 to SEQ ID NO: 4.

Paragraph 92. A composition comprising an isolated polypeptide consisting of any of SEQ ID NO: 1 to SEQ ID NO: 4.

Paragraph 93. A composition comprising an isolated polypeptide comprising a peptide sequence of any of SEQ ID NO: 1 to SEQ ID NO: 4.

Paragraph 94. A composition comprising an isolated polypeptide comprising the peptide sequence of any of SEQ ID NO: 1 to SEQ ID NO: 4.

Paragraph 95. A composition comprising an isolated polypeptide comprising a polypeptide coded by the nucleotide sequence of any of SEQ ID NO: 5 to SEQ ID NO: 136.

Paragraph 96. A composition comprising an isolated polynucleotide comprising of any of SEQ ID NO: 5 to SEQ ID NO: 136.

Paragraph 97. A composition comprising an isolated polynucleotide consisting of any of SEQ ID NO: 5 to SEQ ID NO: 136.

Paragraph 98. A composition comprising an isolated polynucleotide comprising a nucleotide sequence of any of SEQ ID NO: 5 to SEQ ID NO: 136.

Paragraph 99. A composition comprising an isolated polynucleotide comprising the nucleotide sequence of any of SEQ ID NO: 5 to SEQ ID NO: 136.

Paragraph 100. A composition comprising an isolated polynucleotide comprising a polynucleotide encoding the amino acid sequence of any of SEQ ID NO: 1 to SEQ ID NO: 4.

Paragraph 101. A composition comprising an isolated polynucleotide comprising a polynucleotide which hybridizes under stringent conditions to any of SEQ ID NO: 5 to SEQ ID NO: 136.

Paragraph 102. A composition consisting of an isolated polypeptide comprising of any of SEQ ID NO: 1 to SEQ ID NO: 4.

Paragraph 103. A composition consisting of an isolated polypeptide consisting of any of SEQ ID NO: 1 to SEQ ID NO: 4.

Paragraph 104. A composition consisting of an isolated polypeptide comprising a peptide sequence of any of SEQ ID NO: 1 to SEQ ID NO: 4.

Paragraph 105. A composition consisting of an isolated polypeptide comprising the peptide sequence of any of SEQ ID NO: 1 to SEQ ID NO: 4.

Paragraph 106. A composition consisting of an isolated polypeptide comprising a polypeptide coded by the nucleotide sequence of any of SEQ ID NO: 5 to SEQ ID NO: 136.

Paragraph 107. A composition consisting of an isolated polynucleotide comprising of any of SEQ ID NO: 5 to SEQ ID NO: 136.

Paragraph 108. A composition consisting of an isolated polynucleotide consisting of any of SEQ ID NO: 5 to SEQ ID NO: 136.

Paragraph 109. A composition consisting of an isolated polynucleotide comprising a nucleotide sequence of any of SEQ ID NO: 5 to SEQ ID NO: 136.

Paragraph 110. A composition consisting of an isolated polynucleotide comprising the nucleotide sequence of any of SEQ ID NO: 5 to SEQ ID NO: 136.

Paragraph 111. A composition consisting of an isolated polynucleotide comprising a polynucleotide encoding the amino acid sequence of any of SEQ ID NO: 1 to SEQ ID NO: 4.

Paragraph 112. A composition consisting of an isolated polynucleotide comprising a polynucleotide which hybridizes under stringent conditions to any of SEQ ID NO: 5 to SEQ ID NO: 136.

Paragraph 113. A method of treatment for Parkinson's disease, comprising administering a pharmaceutically effective amount of an isolated polypeptide comprising of any of SEQ ID NO: 1 to SEQ ID NO: 4.

Paragraph 114. A method of treatment for Parkinson's disease, comprising administering a pharmaceutically effective amount of an isolated polypeptide consisting of any of SEQ ID NO: 1 to SEQ ID NO: 4.

Paragraph 115. A method of treatment for Parkinson's disease, comprising administering a pharmaceutically effective amount of an isolated polypeptide comprising a peptide sequence of any of SEQ ID NO: 1 to SEQ ID NO: 4.

Paragraph 116. A method of treatment for Parkinson's disease, comprising administering a pharmaceutically effective amount of an isolated polypeptide comprising the peptide sequence of any of SEQ ID NO: 1 to SEQ ID NO: 4.

Paragraph 117. A method of treatment for Parkinson's disease, comprising administering a pharmaceutically effective amount of an isolated polypeptide comprising a polypeptide coded by the nucleotide sequence of any of SEQ ID NO: 5 to SEQ ID NO: 136.

Paragraph 118. A method of treatment for Parkinson's disease, comprising administering a pharmaceutically effective amount of an isolated polynucleotide comprising of any of SEQ ID NO: 5 to SEQ ID NO: 136.

Paragraph 119. A method of treatment for Parkinson's disease, comprising administering a pharmaceutically effective amount of an isolated polynucleotide consisting of any of SEQ ID NO: 5 to SEQ ID NO: 136.

Paragraph 120. A method of treatment for Parkinson's disease, comprising administering a pharmaceutically effective amount of an isolated polynucleotide comprising a nucleotide sequence of any of SEQ ID NO: 5 to SEQ ID NO: 136.

Paragraph 121. A method of treatment for Parkinson's disease, comprising administering a pharmaceutically effective amount of an isolated polynucleotide comprising the nucleotide sequence of any of SEQ ID NO: 5 to SEQ ID NO: 136.

Paragraph 122. A method of treatment for Parkinson's disease, comprising administering a pharmaceutically effective amount of an isolated polynucleotide comprising a polynucleotide encoding the amino acid sequence of any of SEQ ID NO: 1 to SEQ ID NO: 4.

Paragraph 123. A method of treatment for Parkinson's disease, comprising administering a pharmaceutically effective amount of an isolated polynucleotide comprising a polynucleotide which hybridizes under stringent conditions to any of SEQ ID NO: 5 to SEQ ID NO: 136.

Paragraph 124. A method of treatment for Parkinson's disease, comprising administering a pharmaceutically effective amount of a composition comprising an isolated polypeptide comprising of any of SEQ ID NO: 1 to SEQ ID NO: 4.

Paragraph 125. A method of treatment for Parkinson's disease, comprising administering a pharmaceutically effective amount of a composition comprising an isolated polypeptide consisting of any of SEQ ID NO: 1 to SEQ ID NO: 4.

Paragraph 126. A method of treatment for Parkinson's disease, comprising administering a pharmaceutically effective amount of a composition comprising an isolated polypeptide comprising a peptide sequence of any of SEQ ID NO: 1 to SEQ ID NO: 4.

Paragraph 127. A method of treatment for Parkinson's disease, comprising administering a pharmaceutically effective amount of a composition comprising an isolated polypeptide comprising the peptide sequence of any of SEQ ID NO: 1 to SEQ ID NO: 4.

Paragraph 128. A method of treatment for Parkinson's disease, comprising administering a pharmaceutically effective amount of a composition comprising an isolated polypeptide comprising a polypeptide coded by the nucleotide sequence of any of SEQ ID NO: 5 to SEQ ID NO: 136.

Paragraph 129. A method of treatment for Parkinson's disease, comprising administering a pharmaceutically effective amount of a composition comprising an isolated polynucleotide comprising of any of SEQ ID NO: 5 to SEQ ID NO: 136.

Paragraph 130. A method of treatment for Parkinson's disease, comprising administering a pharmaceutically effective amount of a composition comprising an isolated polynucleotide consisting of any of SEQ ID NO: 5 to SEQ ID NO: 136.

Paragraph 131. A method of treatment for Parkinson's disease, comprising administering a pharmaceutically effective amount of a composition comprising an isolated polynucleotide comprising a nucleotide sequence of any of SEQ ID NO: 5 to SEQ ID NO: 136.

Paragraph 132. A method of treatment for Parkinson's disease, comprising administering a pharmaceutically effective amount of a composition comprising an isolated polynucleotide comprising the nucleotide sequence of any of SEQ ID NO: 5 to SEQ ID NO: 136.

Paragraph 133. A method of treatment for Parkinson's disease, comprising administering a pharmaceutically effective amount of a composition comprising an isolated polynucleotide comprising a polynucleotide encoding the amino acid sequence of any of SEQ ID NO: 1 to SEQ ID NO: 4.

Paragraph 134. A method of treatment for Parkinson's disease, comprising administering a pharmaceutically effective amount of a composition comprising an isolated polynucleotide comprising a polynucleotide which hybridizes under stringent conditions to any of SEQ ID NO: 5 to SEQ ID NO: 136.

Paragraph 135. A method of treatment for Parkinson's disease, comprising administering a pharmaceutically effective amount of a composition consisting of an isolated polypeptide comprising of any of SEQ ID NO: 1 to SEQ ID NO: 4.

Paragraph 136. A method of treatment for Parkinson's disease, comprising administering a pharmaceutically effective amount of a composition consisting of an isolated polypeptide consisting of any of SEQ ID NO: 1 to SEQ ID NO: 4.

Paragraph 137. A method of treatment for Parkinson's disease, comprising administering a pharmaceutically effective amount of a composition consisting of an isolated polypeptide comprising a peptide sequence of any of SEQ ID NO: 1 to SEQ ID NO: 4.

Paragraph 138. A composition consisting of an isolated polypeptide comprising the peptide sequence of any of SEQ ID NO: 1 to SEQ ID NO: 4.

Paragraph 139. A method of treatment for Parkinson's disease, comprising administering a pharmaceutically effective amount of a composition consisting of an isolated polypeptide comprising a polypeptide coded by the nucleotide sequence of any of SEQ ID NO: 5 to SEQ ID NO: 136.

Paragraph 140. A method of treatment for Parkinson's disease, comprising administering a pharmaceutically effective amount of a composition consisting of an isolated polynucleotide comprising of any of SEQ ID NO: 5 to SEQ ID NO: 136.

Paragraph 141. A method of treatment for Parkinson's disease, comprising administering a pharmaceutically effective amount of a composition consisting of an isolated polynucleotide consisting of any of SEQ ID NO: 5 to SEQ ID NO: 136.

Paragraph 142. A method of treatment for Parkinson's disease, comprising administering a pharmaceutically effective amount of a composition consisting of an isolated polynucleotide comprising a nucleotide sequence of any of SEQ ID NO: 5 to SEQ ID NO: 136.

Paragraph 143. A method of treatment for Parkinson's disease, comprising administering a pharmaceutically effective amount of a composition consisting of an isolated polynucleotide comprising the nucleotide sequence of any of SEQ ID NO: 5 to SEQ ID NO: 136.

Paragraph 144. A method of treatment for Parkinson's disease, comprising administering a pharmaceutically effective amount of a composition consisting of an isolated polynucleotide comprising a polynucleotide encoding the amino acid sequence of any of SEQ ID NO: 1 to SEQ ID NO: 4.

Paragraph 145. A method of treatment for Parkinson's disease, comprising administering a pharmaceutically effective amount of a composition consisting of an isolated polynucleotide comprising a polynucleotide which hybridizes under stringent conditions to any of SEQ ID NO: 5 to SEQ ID NO: 136.

Paragraph 145. A kit comprising an isolated polynucleotide selected from the group consisting of sequences SEQ ID NO: 5 to SEQ ID NO: 136 and instructions on their use.

Paragraph 145. A kit comprising an isolated polypeptide selected from the group consisting of sequences SEQ ID NO: 1 to SEQ ID NO: 4 and instructions on their use.

Paragraph 145. A kit comprising the composition of any of Paragraphs 91 to 112 and instructions on their use.

References

Bezard, E., Gross, C. E., and Brotchie, J. M. (2003). Presymptomatic compensation in Parkinson's disease is not dopamine-mediated. Trends Neurosci 26, 215-221.

Boustead, J. N., Stadelmaier, B. T., Eeds, A. M., Wiebe, P. O., Svitek, C. A., Oeser, J. K., and O'Brien, R. M. (2003). Hepatocyte nuclear factor-4 alpha mediates the stimulatory effect of peroxisome proliferator-activated receptor gamma co-activator-1 alpha (PGC-1 alpha) on glucose-6-phosphatase catalytic subunit gene transcription in H4IIE cells. Biochem J 369, 17-22.

Chung, K. K., Thomas, B., Li, X., Pletnikova, O., Troncoso, J. C., Marsh, L., Dawson, V. L., and Dawson, T. M. (2004). S-nitrosylation of parkin regulates ubiquitination and compromises parkin's protective function. Science 304, 1328-1331.

Chung, K. K., Zhang, Y., Lim, K. L., Tanaka, Y., Huang, H., Gao, J., Ross, C. A., Dawson, V. L., and Dawson, T. M. (2001). Parkin ubiquitinates the alpha-synuclein-interacting protein, synphilin-1: implications for Lewy-body formation in Parkinson disease. Nat Med 7, 1144-1150.

Corti, O., Hampe, C., Koutnikova, H., Darios, F., Jacquier, S., Prigent, A., Robinson, J. C., Pradier, L., Ruberg, M., Mirande, M., et al. (2003). The p38 subunit of the aminoacyltRNA synthetase complex is a Parkin substrate: linking protein biosynthesis and neurodegeneration. Hum Mol Genet. 12, 1427-1437.

Daitoku, H., Yamagata, K., Matsuzaki, H., Hatta, M., and Fukamizu, A. (2003). Regulation of PGC-1 promoter activity by protein kinase B and the forkhead transcription factor FKHR. Diabetes 52, 642-649.

Dawson, T. M., and Dawson, V. L. (2010). The role of parkin in familial and sporadic Parkinson's disease. Mov Disord 25 Suppl 1, S32-39.

Dawson, T. M., Ko, H. S., and Dawson, V. L. (2010). Genetic animal models of Parkinson's disease. Neuron 66, 646-661.

During, M. J., Young, D., Baer, K., Lawlor, P., and Klugmann, M. (2003). Development and optimization of adeno-associated virus vector transfer into the central nervous system. Methods Mol Med 76, 221-236.

Finck, B. N., and Kelly, D. P. (2006). PGC-1 coactivators: inducible regulators of energy metabolism in health and disease. J Clin Invest 116, 615-622.

Funk, W. D., and Wright, W. E. (1992). Cyclic amplification and selection of targets for multicomponent complexes: myogenin interacts with factors recognizing binding sites for basic helix-loop-helix, nuclear factor 1, myocyte-specific enhancer-binding factor 2, and COMP1 factor. Proc Natl Acad Sci USA 89, 9484-9488.

Gasser, T. (2007). Update on the genetics of Parkinson's disease. Mov Disord 22, S343-S350.

Goldberg, M. S., Fleming, S. M., Palacino, J. J., Cepeda, C., Lam, H. A., Bhatnagar, A., Meloni, E. G., Wu, N., Ackerson, L. C., Klapstein, G. J., et al. (2003). Parkin-deficient mice exhibit nigrostriatal deficits but not loss of dopaminergic neurons. J Biol Chem 278, 43628-43635.

Imai, Y., Soda, M., Hatakeyama, S., Akagi, T., Hashikawa, T., Nakayama, K. I., and Takahashi, R. (2002). CHIP is associated with Parkin, a gene responsible for familial Parkinson's disease, and enhances its ubiquitin ligase activity. Mol Cell 10, 55-67.

Khodosevich, K., Inta, D., Seeburg, P. H., and Monyer, H. (2007). Gene expression analysis of in vivo fluorescent cells. PLoS One 2, e1151.

Ko, H. S., Kim, S. W., Sriram, S. R., Dawson, V. L., and Dawson, T. M. (2006). Identification of far upstream element-binding protein-1 as an authentic Parkin substrate. J Biol Chem 281, 16193-16196.

Ko, H. S., Lee, Y., Shin, J. H., Karuppagounder, S. S., Gadad, B. S., Koleske, A. J., Pletnikova, O., Troncoso, J. C., Dawson, V. L., and Dawson, T. M. (2010). Phosphorylation by the c-Abl protein tyrosine kinase inhibits parkin'subiquitination and protective function. Proc Natl Acad Sci USA 107, 16691-16696.

Ko, H. S., von Coelln, R., Sriram, S. R., Kim, S. W., Chung, K. K., Pletnikova, O., Troncoso, J., Johnson, B., Saffary, R., Goh, E. L., et al. (2005). Accumulation of the authentic parkin substrate aminoacyl-tRNA synthetase cofactor, p38/JTV-1, leads to catecholaminergic cell death. J Neurosci 25, 7968-7978.

LaVoie, M. J., Ostaszewski, B. L., Weihofen, A., Schlossmacher, M. G., and Selkoe, D. J. (2005). Dopamine covalently modifies and functionally inactivates parkin. Nat Med 11, 1214-1221.

Lefstin, J. A., and Yamamoto, K. R. (1998). Allosteric effects of DNA on transcriptional regulators. Nature 392, 885-888.

Lin, J., Handschin, C., and Spiegelman, B. M. (2005). Metabolic control through the PGC-1 family of transcription coactivators. Cell Metab 1, 361-370.

Looman, C., Abrink, M., Mark, C., and Hellman, L. (2002). KRAB zinc finger proteins: an analysis of the molecular mechanisms governing their increase in numbers and complexity during evolution. Mol Biol Evol 19, 2118-2130.

Messick, T. E., Russell, N. S., Iwata, A. J., Sarachan, K. L., Shiekhattar, R., Shanks, J. R., Reyes-Turcu, F. E., Wilkinson, K. D., and Marmorstein, R. (2008). Structural basis for ubiquitin recognition by the Otu1 ovarian tumor domain protein. J Biol Chem 283, 11038-11049.

Mounier, C., and Posner, B. I. (2006). Transcriptional regulation by insulin: from the receptor to the gene. Can J Physiol Pharmacol 84, 713-724.

O'Brien, R. M., Streeper, R. S., Ayala, J. E., Stadelmaier, B. T., and Hornbuckle, L. A. (2001). Insulin-regulated gene expression. Biochem Soc Trans 29, 552-558.

Palop, J. J., Chin, J., and Mucke, L. (2006). A network dysfunction perspective on neurodegenerative diseases. Nature 443, 768-773.

Pascual, A., Hidalgo-Figueroa, M., Piruat, J. I., Pintado, C. O., Gomez-Diaz, R., and Lopez-Barneo, J. (2008). Absolute requirement of GDNF for adult catecholaminergic neuron survival. Nat Neurosci 11, 755-761.

Savitt, J. M., Dawson, V. L., and Dawson, T. M. (2006). Diagnosis and treatment of Parkinson disease: molecules to medicine. J Clin Invest 116, 1744-1754.

Shields, J. M., and Yang, V. W. (1998). Identification of the DNA sequence that interacts with the gut-enriched Kruppel-like factor. Nucleic Acids Res 26, 796-802.

Shimura, H., Hattori, N., Kubo, S., Mizuno, Y., Asakawa, S., Minoshima, S., Shimizu, N., Iwai, K., Chiba, T., Tanaka, K., et al. (2000). Familial Parkinson disease gene product, parkin, is a ubiquitin-protein ligase. Nat Genet. 25, 302-305.

Sriram, S. R., Li, X., Ko, H. S., Chung, K. K., Wong, E., Lim, K. L., Dawson, V. L., and Dawson, T. M. (2005). Familial-associated mutations differentially disrupt the solubility, localization, binding and ubiquitination properties of parkin. Hum Mol Genet. 14, 2571-2586.

St-Pierre, J., Drori, S., Uldry, M., Silvaggi, J. M., Rhee, J., Jager, S., Handschin, C., Zheng, K., Lin, J., Yang, W., et al. (2006). Suppression of reactive oxygen species and neurodegeneration by the PGC-1 transcriptional coactivators. Cell 127, 397-408.

Tanaka, K., Suzuki, T., Hattori, N., and Mizuno, Y. (2004). Ubiquitin, proteasome and parkin. Biochim Biophys Acta 1695, 235-247.

Ventura-Clapier, R., Garnier, A., and Veksler, V. (2008). Transcriptional control of mitochondrial biogenesis: the central role of PGC-1alpha. Cardiovasc Res 79, 208-217.

Vives-Bauza, C., and Przedborski, S. (2010). PINK1 points Parkin to mitochondria. Autophagy 6.

Von Coelln, R., Thomas, B., Savitt, J. M., Lim, K. L., Sasaki, M., Hess, E. J., Dawson, V. L., and Dawson, T. M. (2004). Loss of locus coeruleus neurons and reduced startle in parkin null mice. Proc Natl Acad Sci USA 101, 10744-10749.

Voz, M. L., Agten, N. S., Van de Ven, W. J., and Kas, K. (2000). PLAG1, the main translocation target in pleomorphic adenoma of the salivary glands, is a positive regulator of IGF-II. Cancer Res 60, 106-113.

Winklhofer, K. F., Henn, I. H., Kay-Jackson, P. C., Heller, U., and Tatzelt, J. (2003). Inactivation of parkin by oxidative stress and C-terminal truncations: a protective role of molecular chaperones. J Biol Chem 278, 47199-47208.

Witzgall, R., O'Leary, E., Leaf, A., Onaldi, D., and Bonventre, J. V. (1994). The Kruppel-associated box-A (KRAB-A) domain of zinc finger proteins mediates transcriptional repression. Proc Natl Acad Sci USA 91, 4514-4518.

Wu, Z., Puigserver, P., Andersson, U., Zhang, C., Adelmant, G., Mootha, V., Troy, A., Cinti, S., Lowell, B., Scarpulla, R. C., et al. (1999). Mechanisms controlling mitochondrial biogenesis and respiration through the thermogenic coactivator PGC-1. Cell 98, 115-124.

Zhang, Y., Gao, J., Chung, K. K., Huang, H., Dawson, V. L., and Dawson, T. M. (2000). Parkin functions as an E2-dependent ubiquitin-protein ligase and promotes the degradation of the synaptic vesicle-associated protein, CDCrel-1. Proc Natl Acad Sci USA 97, 13354-13359.

Zheng, B., Liao, Z., Locascio, J. J., Lesniak, K. A., Roderick, S. S., Watt, M. L., Eklund, A. C., Zhang-James, Y., Kim, P. D., Hauser, M. A., et al. (2010). PGC-1alpha, a potential therapeutic target for early intervention in Parkinson's disease. Sci Transl Med 2, 52ra73.

---

The invention claimed is:

1. A method of identifying a compound as an inhibitor of Parkin Interacting Substrate (PARIS) from screening compounds, the method comprising:
   a) exposing a cell line containing a reporter construct to the compounds to identify an inducer of peroxisome profilerator-activated receptor gamma coactivator -1α(PGC-1α);
      wherein the reporter construct comprises a cell line that stably expresses pGL3-h PGC-1α wherein a PGC-1α promoter is operably linked to a reporter gene; and
      wherein the inducer of PGC-1α stimulates the PGC-1α promoter to express the reporter gene;
   b) exposing the cell line to the inducer of PGC-1α identified in step a) in the presence of PARIS to identify a compound that maintains its ability to stimulate the PGC-1αpromoter to express the reporter gene in the presence of PARIS,
      wherein the compound thereby inhibits the ability of PARIS to inhibit the PGC-1α promoter activity to identify an inhibitor of PARIS.

2. The method of claim 1 wherein the cell line is SK-SH5Y.

3. The method of claim 1 wherein the compounds comprise small molecules.

\* \* \* \* \*

SEQUENCE LISTING

```
<160> NUMBER OF SEQ ID NOS: 152

<210> SEQ ID NO 1
<211> LENGTH: 19
<212> TYPE: PRT
<213> ORGANISM: Artificial Sequence
<220> FEATURE:
<223> OTHER INFORMATION: amino acids 572 to 590  of PARIS

<400> SEQUENCE: 1

Gly Lys Ser Phe Ile Arg Lys Asp His Leu Arg Lys His Gln Arg Asn
1               5                   10                  15

His Ala Ala

<210> SEQ ID NO 2
<211> LENGTH: 644
<212> TYPE: PRT
<213> ORGANISM: Homo sapiens

<400> SEQUENCE: 2

Met Ala Glu Ala Val Ala Ala Pro Ile Ser Pro Trp Thr Met Ala Ala
1               5                   10                  15

Thr Ile Gln Ala Met Glu Arg Lys Ile Glu Ser Gln Ala Ala Arg Leu
            20                  25                  30

Leu Ser Leu Glu Gly Arg Thr Gly Met Ala Glu Lys Lys Leu Ala Asp
        35                  40                  45

Cys Glu Lys Thr Ala Val Glu Phe Gly Asn Gln Leu Glu Gly Lys Trp
    50                  55                  60

Ala Val Leu Gly Thr Leu Leu Gln Glu Tyr Gly Leu Leu Gln Arg Arg
65                  70                  75                  80

Leu Glu Asn Val Glu Asn Leu Leu Arg Asn Arg Asn Phe Trp Ile Leu
                85                  90                  95

Arg Leu Pro Pro Gly Ser Lys Gly Glu Ser Pro Lys Glu Trp Gly Lys
            100                 105                 110

Leu Glu Asp Trp Gln Lys Glu Leu Tyr Lys His Val Met Arg Gly Asn
        115                 120                 125

Tyr Glu Thr Leu Val Ser Leu Asp Tyr Ala Ile Ser Lys Pro Glu Val
    130                 135                 140

Leu Ser Gln Ile Glu Gln Gly Lys Glu Pro Cys Asn Trp Arg Arg Pro
145                 150                 155                 160

Gly Pro Lys Ile Pro Asp Val Pro Val Asp Pro Ser Pro Gly Ser Gly
                165                 170                 175

Pro Pro Val Pro Ala Pro Asp Leu Leu Met Gln Ile Lys Gln Glu Gly
            180                 185                 190

Glu Leu Gln Leu Gln Glu Gln Ala Leu Gly Val Glu Ala Trp Ala
        195                 200                 205

Ala Gly Gln Pro Asp Ile Gly Glu Glu Pro Trp Gly Leu Ser Gln Leu
    210                 215                 220

Asp Ser Gly Ala Gly Asp Ile Ser Thr Asp Ala Thr Ser Gly Val His
```

```
            225                 230                 235                 240
        Ser Asn Phe Ser Thr Thr Ile Pro Pro Thr Ser Trp Gln Thr Asp Leu
                        245                 250                 255
        Pro Pro His His Pro Ser Ser Ala Cys Ser Asp Gly Thr Leu Lys Leu
                        260                 265                 270
        Asn Thr Ala Ala Ser Thr Glu Asp Val Lys Ile Val Ile Lys Thr Glu
                        275                 280                 285
        Val Gln Glu Glu Glu Val Val Ala Thr Pro Val His Pro Thr Asp Leu
                290                 295                 300
        Glu Ala His Gly Thr Leu Phe Gly Pro Gly Gln Ala Thr Arg Phe Phe
        305                 310                 315                 320
        Pro Ser Pro Ala Gln Glu Gly Ala Trp Glu Ser Gln Gly Ser Ser Phe
                        325                 330                 335
        Pro Ser Gln Asp Pro Val Leu Gly Leu Arg Glu Pro Ala Arg Pro Glu
                        340                 345                 350
        Arg Asp Met Gly Glu Leu Ser Pro Ala Val Ala Gln Glu Glu Thr Pro
                        355                 360                 365
        Pro Gly Asp Trp Leu Phe Gly Gly Val Arg Trp Gly Trp Asn Phe Arg
                        370                 375                 380
        Cys Lys Pro Pro Val Gly Leu Asn Pro Arg Thr Gly Pro Glu Gly Leu
        385                 390                 395                 400
        Pro Tyr Ser Ser Pro Asp Asn Gly Glu Ala Ile Leu Asp Pro Ser Gln
                        405                 410                 415
        Ala Pro Arg Pro Phe Asn Glu Pro Cys Lys Tyr Pro Gly Arg Thr Lys
                        420                 425                 430
        Gly Phe Gly His Lys Pro Gly Leu Lys Lys His Pro Ala Ala Pro Pro
                        435                 440                 445
        Gly Gly Arg Pro Phe Thr Cys Ala Thr Cys Gly Lys Ser Phe Gln Leu
                        450                 455                 460
        Gln Val Ser Leu Ser Ala His Gln Arg Ser Cys Gly Ala Pro Asp Gly
        465                 470                 475                 480
        Ser Gly Pro Gly Thr Gly Gly Gly Ser Gly Ser Gly Gly Gly Gly Gly
                        485                 490                 495
        Gly Gly Ser Gly Gly Gly Ser Ala Arg Asp Gly Ser Ala Leu Arg Cys
                        500                 505                 510
        Gly Glu Cys Gly Arg Cys Phe Thr Arg Pro Ala His Leu Ile Arg His
                        515                 520                 525
        Arg Met Leu His Thr Gly Glu Arg Pro Phe Pro Cys Thr Glu Cys Glu
                        530                 535                 540
        Lys Arg Phe Thr Glu Arg Ser Lys Leu Ile Asp His Tyr Arg Thr His
        545                 550                 555                 560
        Thr Gly Val Arg Pro Phe Thr Cys Thr Val Cys Gly Lys Ser Phe Ile
                        565                 570                 575
        Arg Lys Asp His Leu Arg Lys His Gln Arg Asn His Ala Ala Gly Ala
                        580                 585                 590
        Lys Thr Pro Ala Arg Gly Gln Pro Leu Pro Thr Pro Pro Ala Pro Pro
                        595                 600                 605
        Asp Pro Phe Lys Ser Pro Ala Ser Lys Gly Pro Leu Ala Ser Thr Asp
                        610                 615                 620
        Leu Val Thr Asp Trp Thr Cys Gly Leu Ser Val Leu Gly Pro Thr Asp
        625                 630                 635                 640
        Gly Gly Asp Met
```

<210> SEQ ID NO 3
<211> LENGTH: 652
<212> TYPE: PRT
<213> ORGANISM: Mus musculus

<400> SEQUENCE: 3

```
Met Ala Glu Ala Ala Ala Pro Ile Ser Pro Trp Thr Met Ala Ala
1               5                   10                  15

Thr Ile Gln Ala Met Glu Arg Lys Ile Glu Ser Gln Ala Ala Arg Leu
            20                  25                  30

Leu Ser Leu Glu Gly Arg Thr Gly Met Ala Glu Lys Lys Leu Ala Asp
            35                  40                  45

Cys Glu Lys Thr Ala Val Glu Phe Ser Asn Gln Leu Glu Gly Lys Trp
    50                  55                  60

Ala Val Leu Gly Thr Leu Leu Gln Glu Tyr Gly Leu Leu Gln Arg Arg
65                  70                  75                  80

Leu Glu Asn Val Glu Asn Leu Arg Asn Arg Asn Phe Trp Ile Leu
                85                  90                  95

Arg Leu Pro Pro Gly Ser Lys Gly Glu Val Pro Lys Glu Trp Gly Lys
            100                 105                 110

Leu Glu Asp Trp Gln Lys Glu Leu Tyr Lys His Val Met Arg Gly Asn
            115                 120                 125

Tyr Glu Thr Leu Val Ser Leu Asp Tyr Ala Ile Ser Lys Pro Glu Val
    130                 135                 140

Leu Ser Gln Ile Glu Gln Gly Lys Glu Pro Cys Thr Trp Arg Arg Thr
145                 150                 155                 160

Gly Pro Lys Val Pro Glu Val Pro Val Asp Pro Ser Pro Gly Ser Gly
                165                 170                 175

Ala Pro Val Pro Ala Pro Asp Leu Leu Met Gln Ile Lys Gln Glu Gly
            180                 185                 190

Glu Leu Gln Leu Gln Glu Gln Gln Ala Leu Gly Val Glu Ala Trp Ala
            195                 200                 205

Ala Gly Gln Pro Asp Ile Gly Glu Pro Trp Gly Leu Ser Gln Leu
    210                 215                 220

Asp Ser Gly Ala Gly Asp Ile Ser Thr Asp Ala Thr Ser Gly Val His
225                 230                 235                 240

Ser Asn Phe Ser Thr Thr Ile Pro Pro Thr Ser Trp Gln Ala Asp Leu
                245                 250                 255

Pro Pro His His Pro Ser Ser Ala Cys Ser Asp Gly Thr Leu Lys Leu
            260                 265                 270

Asn Thr Ala Ala Ser Thr Glu Ala Asp Val Lys Ile Val Lys Thr
            275                 280                 285

Glu Val Gln Glu Glu Val Val Ala Thr Pro Val His Pro Thr Asp
    290                 295                 300

Leu Glu Ala His Gly Thr Leu Phe Ala Pro Gly Gln Ala Thr Arg Phe
305                 310                 315                 320

Phe Pro Ser Pro Val Gln Glu Gly Ala Trp Glu Ser Gln Gly Ser Ser
                325                 330                 335

Phe Pro Ser Gln Asp Pro Val Leu Gly Leu Arg Glu Pro Thr Arg Pro
            340                 345                 350

Glu Arg Asp Ile Gly Glu Leu Ser Pro Ala Ile Ala Gln Glu Glu Ala
            355                 360                 365

Pro Ala Gly Asp Trp Leu Phe Gly Gly Val Arg Trp Gly Trp Asn Phe
    370                 375                 380
```

```
Arg Cys Lys Pro Pro Val Gly Leu Asn Pro Arg Thr Val Pro Glu Gly
385                 390                 395                 400

Leu Pro Phe Ser Ser Pro Asp Asn Gly Glu Ala Ile Leu Asp Pro Ser
            405                 410                 415

Gln Ala Pro Arg Pro Phe Asn Asp Pro Cys Lys Tyr Pro Gly Arg Thr
        420                 425                 430

Lys Gly Phe Gly His Lys Pro Gly Leu Lys Lys His Pro Ala Ala Pro
            435                 440                 445

Pro Gly Arg Pro Phe Thr Cys Ala Thr Cys Gly Lys Ser Phe Gln
        450                 455                 460

Leu Gln Val Ser Leu Ser Ala His Gln Arg Ser Cys Gly Leu Ser Asp
465                 470                 475                 480

Gly Ala Ala Thr Gly Ala Ala Ser Thr Thr Gly Gly Gly Gly
            485                 490                 495

Gly Ser Gly Gly Gly Gly Ser Ser Gly Gly Ser Ser Ala Arg
        500                 505                 510

Asp Ser Ser Ala Leu Arg Cys Gly Cys Gly Arg Cys Phe Thr Arg
            515                 520                 525

Pro Ala His Leu Ile Arg His Arg Met Leu His Thr Gly Glu Arg Pro
        530                 535                 540

Phe Pro Cys Thr Glu Cys Glu Lys Arg Phe Thr Glu Arg Ser Lys Leu
545                 550                 555                 560

Ile Asp His Tyr Arg Thr His Thr Gly Val Arg Pro Phe Thr Cys Thr
            565                 570                 575

Val Cys Gly Lys Ser Phe Ile Arg Lys Asp His Leu Arg Lys His Gln
            580                 585                 590

Arg Asn His Pro Ala Val Ala Lys Ala Pro Ala His Gly Gln Pro Leu
        595                 600                 605

Pro Pro Leu Pro Ala Pro Pro Asp Pro Phe Lys Ser Pro Ala Ala Lys
        610                 615                 620

Gly Pro Met Ala Ser Thr Asp Leu Val Thr Asp Trp Thr Cys Gly Leu
625                 630                 635                 640

Ser Val Leu Gly Pro Ser Asp Gly Gly Asp Leu
                645                 650

<210> SEQ ID NO 4
<211> LENGTH: 650
<212> TYPE: PRT
<213> ORGANISM: Rattus norvegicus

<400> SEQUENCE: 4

Met Ala Glu Ala Ala Ala Pro Ile Ser Pro Trp Thr Met Ala Ala
1               5                   10                  15

Thr Ile Gln Ala Met Glu Arg Lys Ile Glu Ser Gln Ala Ala Arg Leu
            20                  25                  30

Leu Ser Leu Glu Gly Arg Thr Gly Met Ala Glu Lys Lys Leu Ala Asp
        35                  40                  45

Cys Glu Lys Thr Ala Val Glu Phe Ser Asn Gln Leu Glu Gly Lys Trp
    50                  55                  60

Ala Val Leu Gly Thr Leu Leu Gln Glu Tyr Gly Leu Leu Gln Arg Arg
65                  70                  75                  80

Leu Glu Asn Val Glu Asn Leu Leu Arg Asn Arg Asn Phe Trp Ile Leu
                85                  90                  95

Arg Leu Pro Pro Gly Ser Lys Gly Glu Val Pro Lys Glu Trp Gly Lys
```

```
                100             105             110
Leu Glu Asp Trp Gln Lys Glu Leu Tyr Lys His Val Met Arg Gly Asn
            115                 120                 125

Tyr Glu Thr Leu Val Ser Leu Asp Tyr Ala Ile Ser Lys Pro Glu Val
        130                 135                 140

Leu Ser Gln Ile Glu Gln Gly Lys Glu Pro Cys Thr Trp Arg Arg Thr
145                 150                 155                 160

Gly Pro Lys Val Pro Glu Val Pro Val Asp Pro Ser Pro Gly Ser Gly
                165                 170                 175

Ala Pro Val Pro Ala Pro Asp Leu Leu Met Gln Ile Lys Gln Glu Gly
            180                 185                 190

Glu Leu Gln Leu Gln Glu Gln Ala Leu Gly Val Glu Ala Trp Ala
        195                 200                 205

Ala Gly Gln Pro Asp Ile Gly Glu Glu Pro Trp Gly Leu Ser Gln Leu
    210                 215                 220

Asp Ser Gly Ala Gly Asp Ile Ser Thr Asp Ala Thr Ser Gly Val His
225                 230                 235                 240

Ser Asn Phe Ser Thr Thr Ile Pro Pro Thr Ser Trp Gln Ala Asp Leu
                245                 250                 255

Pro Pro His His Pro Ser Ser Ala Cys Ser Asp Gly Thr Leu Lys Leu
            260                 265                 270

Asn Thr Ala Ala Ser Thr Glu Ala Asp Val Lys Ile Val Ile Lys Thr
        275                 280                 285

Glu Val Gln Glu Glu Val Val Ala Thr Pro Val His Pro Thr Asp
    290                 295                 300

Leu Glu Ala His Gly Thr Leu Phe Ala Pro Gly Gln Ala Thr Arg Phe
305                 310                 315                 320

Phe Pro Ser Pro Val Gln Glu Gly Ala Trp Glu Ser Gln Gly Ser Ser
                325                 330                 335

Phe Pro Ser Gln Asp Pro Val Leu Gly Leu Arg Glu Pro Thr Arg Pro
            340                 345                 350

Glu Arg Asp Ile Gly Glu Leu Ser Pro Ala Ile Ala Gln Glu Glu Ala
        355                 360                 365

Pro Ala Gly Asp Trp Leu Phe Gly Gly Val Arg Trp Gly Trp Asn Phe
    370                 375                 380

Arg Cys Lys Pro Pro Val Ser Leu Asn Pro Arg Thr Val Pro Glu Gly
385                 390                 395                 400

Leu Pro Phe Ser Ser Pro Asp Asn Gly Glu Ala Ile Leu Asp Pro Ser
                405                 410                 415

Gln Ala Pro Arg Pro Phe Asn Asp Pro Cys Lys Tyr Pro Gly Arg Thr
            420                 425                 430

Lys Gly Phe Gly His Lys Pro Gly Leu Lys Lys His Pro Ala Ala Pro
        435                 440                 445

Pro Gly Gly Arg Pro Phe Thr Cys Ala Thr Cys Gly Lys Ser Phe Gln
    450                 455                 460

Leu Gln Val Ser Leu Ser Ala His Gln Arg Ser Cys Gly Leu Ser Asp
465                 470                 475                 480

Gly Ala Gly Thr Gly Ala Ala Ser Thr Ala Thr Gly Gly Gly Gly
                485                 490                 495

Gly Gly Gly Gly Gly Ser Ser Ala Gly Gly Ser Ser Ala Arg Asp Ser
            500                 505                 510

Ser Ala Leu Arg Cys Gly Glu Cys Gly Arg Cys Phe Thr Arg Pro Ala
        515                 520                 525
```

```
His Leu Ile Arg His Arg Met Leu His Thr Gly Glu Arg Pro Phe Pro
    530                 535                 540
Cys Thr Glu Cys Glu Lys Arg Phe Thr Glu Arg Ser Lys Leu Ile Asp
545                 550                 555                 560
His Tyr Arg Thr His Thr Gly Val Arg Pro Phe Thr Cys Thr Val Cys
                565                 570                 575
Gly Lys Ser Phe Ile Arg Lys Asp His Leu Arg Lys His Gln Arg Asn
            580                 585                 590
His Pro Ala Val Ala Lys Ala Pro Ala His Gly Gln Pro Leu Pro Pro
        595                 600                 605
Leu Pro Ala Pro Pro Asp Pro Phe Lys Ser Pro Ala Ala Lys Gly Pro
    610                 615                 620
Met Ala Ser Thr Asp Leu Val Thr Asp Trp Thr Cys Gly Leu Ser Val
625                 630                 635                 640
Leu Gly Pro Asn Asp Gly Gly Asp Leu
                645                 650

<210> SEQ ID NO 5
<211> LENGTH: 66
<212> TYPE: DNA
<213> ORGANISM: Artificial Sequence
<220> FEATURE:
<223> OTHER INFORMATION: CAST-26
<220> FEATURE:
<221> NAME/KEY: misc_feature
<222> LOCATION: (21)..(46)
<223> OTHER INFORMATION: any nucleotide

<400> SEQUENCE: 5
ctgtcggaat tcgctgacgt nnnnnnnnnn nnnnnnnnnn nnnnnncgtc ttatcggatc    60
ctacgt                                                                66

<210> SEQ ID NO 6
<211> LENGTH: 20
<212> TYPE: DNA
<213> ORGANISM: Artificial Sequence
<220> FEATURE:
<223> OTHER INFORMATION: CAST-C

<400> SEQUENCE: 6
acgtaggatc cgataagacg                                                 20

<210> SEQ ID NO 7
<211> LENGTH: 19
<212> TYPE: DNA
<213> ORGANISM: Artificial Sequence
<220> FEATURE:
<223> OTHER INFORMATION: CAST-N

<400> SEQUENCE: 7
ctgtcggaat tcgctgacg                                                  19

<210> SEQ ID NO 8
<211> LENGTH: 27
<212> TYPE: DNA
<213> ORGANISM: Artificial sequence
<220> FEATURE:
<223> OTHER INFORMATION: IRS1-WT, 986 - 960

<400> SEQUENCE: 8
agtgtgttgg tattttccc tcagttc                                          27
```

<210> SEQ ID NO 9
<211> LENGTH: 27
<212> TYPE: DNA
<213> ORGANISM: Artificial sequence
<220> FEATURE:
<223> OTHER INFORMATION: IRS1-MT, 986 - 960

<400> SEQUENCE: 9
agtgtgttgg tattgttccc tcagttc                                        27

<210> SEQ ID NO 10
<211> LENGTH: 27
<212> TYPE: DNA
<213> ORGANISM: Artificial sequence
<220> FEATURE:
<223> OTHER INFORMATION: IRS2-WT, 596 - 570

<400> SEQUENCE: 10
acatacaggc tattttgttg attaaac                                        27

<210> SEQ ID NO 11
<211> LENGTH: 27
<212> TYPE: DNA
<213> ORGANISM: Artificial sequence
<220> FEATURE:
<223> OTHER INFORMATION: IRS2-MT, 596 - 570

<400> SEQUENCE: 11
acatacaggc tattgtgttg attaaac                                        27

<210> SEQ ID NO 12
<211> LENGTH: 27
<212> TYPE: DNA
<213> ORGANISM: Artificial sequence
<220> FEATURE:
<223> OTHER INFORMATION: IRS3-WT, 364 - 338

<400> SEQUENCE: 12
gccacttgct tgttttggaa ggaaaat                                        27

<210> SEQ ID NO 13
<211> LENGTH: 27
<212> TYPE: DNA
<213> ORGANISM: Artificial sequence
<220> FEATURE:
<223> OTHER INFORMATION: IRS3-MT, 364 - 338

<400> SEQUENCE: 13
gccacttgct tgttgtggaa ggaaaat                                        27

<210> SEQ ID NO 14
<211> LENGTH: 27
<212> TYPE: DNA
<213> ORGANISM: Artificial sequence
<220> FEATURE:
<223> OTHER INFORMATION: hPGC-1a promoter, forward

<400> SEQUENCE: 14
acatacaggc tattttgttg attaaac                                        27

<210> SEQ ID NO 15
<211> LENGTH: 27
<212> TYPE: DNA
<213> ORGANISM: Artificial sequence
<220> FEATURE:
<223> OTHER INFORMATION: hPGC-1a promoter, reverse

```
<400> SEQUENCE: 15
attttccttc caaaacaagc aagtggc                                              27

<210> SEQ ID NO 16
<211> LENGTH: 28
<212> TYPE: DNA
<213> ORGANISM: Artificial sequence
<220> FEATURE:
<223> OTHER INFORMATION: hG6Pase promoter, forward

<400> SEQUENCE: 16
gtagactctg tcctgtgtct ctggcctg                                             28

<210> SEQ ID NO 17
<211> LENGTH: 28
<212> TYPE: DNA
<213> ORGANISM: Artificial sequence
<220> FEATURE:
<223> OTHER INFORMATION: hG6Pase promoter, reverse

<400> SEQUENCE: 17
ggtcaaccca gccctgatct ttggactc                                             28

<210> SEQ ID NO 18
<211> LENGTH: 30
<212> TYPE: DNA
<213> ORGANISM: Artificial sequence
<220> FEATURE:
<223> OTHER INFORMATION: hPEPCK promoter, forward

<400> SEQUENCE: 18
gactgtgacc tttgactatg gggtgacatc                                           30

<210> SEQ ID NO 19
<211> LENGTH: 27
<212> TYPE: DNA
<213> ORGANISM: Artificial sequence
<220> FEATURE:
<223> OTHER INFORMATION: hPEPCK promoter, reverse

<400> SEQUENCE: 19
ctggatcacg gccagggtca gttatgc                                              27

<210> SEQ ID NO 20
<211> LENGTH: 20
<212> TYPE: DNA
<213> ORGANISM: Artificial sequence
<220> FEATURE:
<223> OTHER INFORMATION: hGAPDH promoter, forward

<400> SEQUENCE: 20
tactagcggt tttacgggcg                                                      20

<210> SEQ ID NO 21
<211> LENGTH: 24
<212> TYPE: DNA
<213> ORGANISM: Artificial sequence
<220> FEATURE:
<223> OTHER INFORMATION: hGAPDH promoter, reverse

<400> SEQUENCE: 21
tcgaacagga ggagcagaga gcga                                                 24

<210> SEQ ID NO 22
```

```
<211> LENGTH: 20
<212> TYPE: DNA
<213> ORGANISM: Artificial sequence
<220> FEATURE:
<223> OTHER INFORMATION: mPGC-1a promoter, forward

<400> SEQUENCE: 22
caaagctggc ttcagtcaca                                                20

<210> SEQ ID NO 23
<211> LENGTH: 20
<212> TYPE: DNA
<213> ORGANISM: Artificial sequence
<220> FEATURE:
<223> OTHER INFORMATION: mPGC-1a promoter, reverse

<400> SEQUENCE: 23
ttgctgcaca aactcctgac                                                20

<210> SEQ ID NO 24
<211> LENGTH: 21
<212> TYPE: DNA
<213> ORGANISM: Artificial sequence
<220> FEATURE:
<223> OTHER INFORMATION: mGAPDH promoter, forward

<400> SEQUENCE: 24
tgggtggagt gtcctttatc c                                              21

<210> SEQ ID NO 25
<211> LENGTH: 20
<212> TYPE: DNA
<213> ORGANISM: Artificial sequence
<220> FEATURE:
<223> OTHER INFORMATION: mGAPDH promoter, reverse

<400> SEQUENCE: 25
tatgcccgag gacaataagg                                                20

<210> SEQ ID NO 26
<211> LENGTH: 19
<212> TYPE: DNA
<213> ORGANISM: Artificial Sequence
<220> FEATURE:
<223> OTHER INFORMATION: short hairpin sequence

<400> SEQUENCE: 26
agttccagta cggctccaa                                                 19

<210> SEQ ID NO 27
<211> LENGTH: 21
<212> TYPE: DNA
<213> ORGANISM: Homo sapiens

<400> SEQUENCE: 27
gcctcaaagg aacttctgct t                                              21

<210> SEQ ID NO 28
<211> LENGTH: 21
<212> TYPE: DNA
<213> ORGANISM: Homo sapiens

<400> SEQUENCE: 28
gccattcaac gaaccctgta a                                              21
```

```
<210> SEQ ID NO 29
<211> LENGTH: 22
<212> TYPE: DNA
<213> ORGANISM: Mus musculus

<400> SEQUENCE: 29
agccgtgacc actgacaacg ag                                             22

<210> SEQ ID NO 30
<211> LENGTH: 23
<212> TYPE: DNA
<213> ORGANISM: Mus musculus

<400> SEQUENCE: 30
gctgcatggt tctgagtgct aag                                            23

<210> SEQ ID NO 31
<211> LENGTH: 21
<212> TYPE: DNA
<213> ORGANISM: Homo sapiens

<400> SEQUENCE: 31
tcctcacaga gacactagac a                                              21

<210> SEQ ID NO 32
<211> LENGTH: 21
<212> TYPE: DNA
<213> ORGANISM: Homo sapiens

<400> SEQUENCE: 32
ctggtgccag taagagcttc t                                              21

<210> SEQ ID NO 33
<211> LENGTH: 21
<212> TYPE: DNA
<213> ORGANISM: Mus musculus

<400> SEQUENCE: 33
ctgcataacg gtctggactt c                                              21

<210> SEQ ID NO 34
<211> LENGTH: 19
<212> TYPE: DNA
<213> ORGANISM: Mus musculus

<400> SEQUENCE: 34
cagcaactgc ccgtactcc                                                 19

<210> SEQ ID NO 35
<211> LENGTH: 21
<212> TYPE: DNA
<213> ORGANISM: Homo sapiens

<400> SEQUENCE: 35
caagacggtt atcgtcaccc a                                              21

<210> SEQ ID NO 36
<211> LENGTH: 20
<212> TYPE: DNA
<213> ORGANISM: Homo sapiens

<400> SEQUENCE: 36
gaacctggca ttgaacgctt                                                20
```

```
<210> SEQ ID NO 37
<211> LENGTH: 21
<212> TYPE: DNA
<213> ORGANISM: Mus musculus

<400> SEQUENCE: 37
cgactcgcta tctccaagtg a                                              21

<210> SEQ ID NO 38
<211> LENGTH: 20
<212> TYPE: DNA
<213> ORGANISM: Mus musculus

<400> SEQUENCE: 38
gttgaaccag tctccgacca                                                20

<210> SEQ ID NO 39
<211> LENGTH: 19
<212> TYPE: DNA
<213> ORGANISM: Homo sapiens

<400> SEQUENCE: 39
gtgtccgtga tcgcagacc                                                 19

<210> SEQ ID NO 40
<211> LENGTH: 20
<212> TYPE: DNA
<213> ORGANISM: Homo sapiens

<400> SEQUENCE: 40
gacgaggttg agccagtctc                                                20

<210> SEQ ID NO 41
<211> LENGTH: 20
<212> TYPE: DNA
<213> ORGANISM: Mus musculus

<400> SEQUENCE: 41
atcagcccat cctgtggaac                                                20

<210> SEQ ID NO 42
<211> LENGTH: 23
<212> TYPE: DNA
<213> ORGANISM: Mus musculus

<400> SEQUENCE: 42
tgcagctaat ctctctagca ctt                                            23

<210> SEQ ID NO 43
<211> LENGTH: 21
<212> TYPE: DNA
<213> ORGANISM: Homo sapiens

<400> SEQUENCE: 43
gagcacggag ataactgagg a                                              21

<210> SEQ ID NO 44
<211> LENGTH: 21
<212> TYPE: DNA
<213> ORGANISM: Homo sapiens

<400> SEQUENCE: 44
gccttcgagc catcataggt a                                              21
```

<210> SEQ ID NO 45
<211> LENGTH: 22
<212> TYPE: DNA
<213> ORGANISM: Mus musculus

<400> SEQUENCE: 45
tacagggcta catggaacaa gc                                              22

<210> SEQ ID NO 46
<211> LENGTH: 22
<212> TYPE: DNA
<213> ORGANISM: Mus musculus

<400> SEQUENCE: 46
cagggatctg aagtgattgt cc                                              22

<210> SEQ ID NO 47
<211> LENGTH: 20
<212> TYPE: DNA
<213> ORGANISM: Homo sapiens

<400> SEQUENCE: 47
ctcccttctc agcttcatgc                                                 20

<210> SEQ ID NO 48
<211> LENGTH: 21
<212> TYPE: DNA
<213> ORGANISM: Homo sapiens

<400> SEQUENCE: 48
tgcagggtta catgaagcac g                                               21

<210> SEQ ID NO 49
<211> LENGTH: 20
<212> TYPE: DNA
<213> ORGANISM: Homo sapiens

<400> SEQUENCE: 49
gtctgacctc agggtccaaa                                                 20

<210> SEQ ID NO 50
<211> LENGTH: 21
<212> TYPE: DNA
<213> ORGANISM: Homo sapiens

<400> SEQUENCE: 50
ctccagtagt ctttcaggga a                                               21

<210> SEQ ID NO 51
<211> LENGTH: 21
<212> TYPE: DNA
<213> ORGANISM: Mus musculus

<400> SEQUENCE: 51
tgctggatgt tcgcgtcaat a                                               21

<210> SEQ ID NO 52
<211> LENGTH: 21
<212> TYPE: DNA
<213> ORGANISM: Mus musculus

<400> SEQUENCE: 52

```
cggcttcacc ttcatgttgt c                                              21

<210> SEQ ID NO 53
<211> LENGTH: 21
<212> TYPE: DNA
<213> ORGANISM: Homo sapiens

<400> SEQUENCE: 53
tgtgtcccca tcttagctga t                                              21

<210> SEQ ID NO 54
<211> LENGTH: 22
<212> TYPE: DNA
<213> ORGANISM: Homo sapiens

<400> SEQUENCE: 54
tacagaccct gaagttaccc ag                                             22

<210> SEQ ID NO 55
<211> LENGTH: 22
<212> TYPE: DNA
<213> ORGANISM: Homo sapiens

<400> SEQUENCE: 55
aatggtacag ggtcccaaaa tg                                             22

<210> SEQ ID NO 56
<211> LENGTH: 21
<212> TYPE: DNA
<213> ORGANISM: Homo sapiens

<400> SEQUENCE: 56
taagaagcaa tctcctcccg a                                              21

<210> SEQ ID NO 57
<211> LENGTH: 20
<212> TYPE: DNA
<213> ORGANISM: Mus musculus

<400> SEQUENCE: 57
ccagtgcagg acctcatttt                                                20

<210> SEQ ID NO 58
<211> LENGTH: 20
<212> TYPE: DNA
<213> ORGANISM: Mus musculus

<400> SEQUENCE: 58
ttgtttctca tggaccacca                                                20

<210> SEQ ID NO 59
<211> LENGTH: 21
<212> TYPE: DNA
<213> ORGANISM: Homo sapiens

<400> SEQUENCE: 59
agggcatcat caatttcgag c                                              21

<210> SEQ ID NO 60
<211> LENGTH: 19
<212> TYPE: DNA
<213> ORGANISM: Homo sapiens

<400> SEQUENCE: 60
```

```
gcccaccgtg ttttctgga                                              19

<210> SEQ ID NO 61
<211> LENGTH: 20
<212> TYPE: DNA
<213> ORGANISM: Mus musculus

<400> SEQUENCE: 61
ccgaggagaa gtaccacgag                                             20

<210> SEQ ID NO 62
<211> LENGTH: 20
<212> TYPE: DNA
<213> ORGANISM: Mus musculus

<400> SEQUENCE: 62
gcttgatagc ctccagcaac                                             20

<210> SEQ ID NO 63
<211> LENGTH: 20
<212> TYPE: DNA
<213> ORGANISM: Homo sapiens

<400> SEQUENCE: 63
ttggccaagg gagatgttac                                             20

<210> SEQ ID NO 64
<211> LENGTH: 20
<212> TYPE: DNA
<213> ORGANISM: Homo sapiens

<400> SEQUENCE: 64
agtcacgttt gatggcttcc                                             20

<210> SEQ ID NO 65
<211> LENGTH: 20
<212> TYPE: DNA
<213> ORGANISM: Mus musculus

<400> SEQUENCE: 65
ccgtgcaatc agttcggaca                                             20

<210> SEQ ID NO 66
<211> LENGTH: 23
<212> TYPE: DNA
<213> ORGANISM: Mus musculus

<400> SEQUENCE: 66
tcacttcgca cttctcaaac aat                                         23

<210> SEQ ID NO 67
<211> LENGTH: 19
<212> TYPE: DNA
<213> ORGANISM: Homo sapiens

<400> SEQUENCE: 67
gcaccctctc ttcgccttc                                              19

<210> SEQ ID NO 68
<211> LENGTH: 21
<212> TYPE: DNA
<213> ORGANISM: Homo sapiens
```

```
<400> SEQUENCE: 68
tcaggctcga tgtcaatggt c                                              21

<210> SEQ ID NO 69
<211> LENGTH: 20
<212> TYPE: DNA
<213> ORGANISM: Mus musculus

<400> SEQUENCE: 69
agcgaccaga tgaagcagtg                                                20

<210> SEQ ID NO 70
<211> LENGTH: 21
<212> TYPE: DNA
<213> ORGANISM: Mus musculus

<400> SEQUENCE: 70
tccgctctct gtcaaagtgt g                                              21

<210> SEQ ID NO 71
<211> LENGTH: 21
<212> TYPE: DNA
<213> ORGANISM: Homo sapiens

<400> SEQUENCE: 71
cgcagaaagc tgatgtcctg a                                              21

<210> SEQ ID NO 72
<211> LENGTH: 22
<212> TYPE: DNA
<213> ORGANISM: Homo sapiens

<400> SEQUENCE: 72
tcatgtgtga cctcaaagta gc                                             22

<210> SEQ ID NO 73
<211> LENGTH: 20
<212> TYPE: DNA
<213> ORGANISM: Mus musculus

<400> SEQUENCE: 73
gttggtacag gggcaacagt                                                20

<210> SEQ ID NO 74
<211> LENGTH: 20
<212> TYPE: DNA
<213> ORGANISM: Mus musculus

<400> SEQUENCE: 74
tcgtctggat ggtcatttca                                                20

<210> SEQ ID NO 75
<211> LENGTH: 20
<212> TYPE: DNA
<213> ORGANISM: Homo sapiens

<400> SEQUENCE: 75
cttacaaggt gggggacaga                                                20

<210> SEQ ID NO 76
<211> LENGTH: 20
<212> TYPE: DNA
<213> ORGANISM: Homo sapiens
```

```
<400> SEQUENCE: 76
ggtgactgcg ctgtctgata                                              20

<210> SEQ ID NO 77
<211> LENGTH: 20
<212> TYPE: DNA
<213> ORGANISM: Mus musculus

<400> SEQUENCE: 77
ccaaaaagac ctcgttcagc                                              20

<210> SEQ ID NO 78
<211> LENGTH: 20
<212> TYPE: DNA
<213> ORGANISM: Mus musculus

<400> SEQUENCE: 78
cttcagccat ctgctcttcc                                              20

<210> SEQ ID NO 79
<211> LENGTH: 20
<212> TYPE: DNA
<213> ORGANISM: Homo sapiens

<400> SEQUENCE: 79
ccgaggtggt tttcatctgt                                              20

<210> SEQ ID NO 80
<211> LENGTH: 19
<212> TYPE: DNA
<213> ORGANISM: Homo sapiens

<400> SEQUENCE: 80
tccgcctata agcatcttg                                               19

<210> SEQ ID NO 81
<211> LENGTH: 20
<212> TYPE: DNA
<213> ORGANISM: Mus musculus

<400> SEQUENCE: 81
actttccctc tggataccgc                                              20

<210> SEQ ID NO 82
<211> LENGTH: 20
<212> TYPE: DNA
<213> ORGANISM: Mus musculus

<400> SEQUENCE: 82
acggaggcaa agctcatctg                                              20

<210> SEQ ID NO 83
<211> LENGTH: 20
<212> TYPE: DNA
<213> ORGANISM: Homo sapiens

<400> SEQUENCE: 83
gcatcggcct gtatgattct                                              20

<210> SEQ ID NO 84
<211> LENGTH: 20
<212> TYPE: DNA
```

```
<213> ORGANISM: Homo sapiens

<400> SEQUENCE: 84
ttggtatctc cgaccacctc                                              20

<210> SEQ ID NO 85
<211> LENGTH: 20
<212> TYPE: DNA
<213> ORGANISM: Mus musculus

<400> SEQUENCE: 85
ctgcaccgcc agatgagttt                                              20

<210> SEQ ID NO 86
<211> LENGTH: 21
<212> TYPE: DNA
<213> ORGANISM: Mus musculus

<400> SEQUENCE: 86
atcatggctt gaaatcggac c                                            21

<210> SEQ ID NO 87
<211> LENGTH: 20
<212> TYPE: DNA
<213> ORGANISM: Homo sapiens

<400> SEQUENCE: 87
agcctcacta cccggatttt                                              20

<210> SEQ ID NO 88
<211> LENGTH: 20
<212> TYPE: DNA
<213> ORGANISM: Homo sapiens

<400> SEQUENCE: 88
cgtccatagt cccgctgtat                                              20

<210> SEQ ID NO 89
<211> LENGTH: 20
<212> TYPE: DNA
<213> ORGANISM: Mus musculus

<400> SEQUENCE: 89
gtctctgtcc agggcatcat                                              20

<210> SEQ ID NO 90
<211> LENGTH: 20
<212> TYPE: DNA
<213> ORGANISM: Mus musculus

<400> SEQUENCE: 90
acgacgaaca gtctcaaacg                                              20

<210> SEQ ID NO 91
<211> LENGTH: 20
<212> TYPE: DNA
<213> ORGANISM: Homo sapiens

<400> SEQUENCE: 91
atggtctggg cgactgtatc                                              20

<210> SEQ ID NO 92
<211> LENGTH: 20
```

<212> TYPE: DNA
<213> ORGANISM: Homo sapiens

<400> SEQUENCE: 92
tcaaaggggt aggacaccag          20

<210> SEQ ID NO 93
<211> LENGTH: 20
<212> TYPE: DNA
<213> ORGANISM: Mus musculus

<400> SEQUENCE: 93
gagggattac cacccatcct          20

<210> SEQ ID NO 94
<211> LENGTH: 20
<212> TYPE: DNA
<213> ORGANISM: Mus musculus

<400> SEQUENCE: 94
catgattctg cccaaggtct          20

<210> SEQ ID NO 95
<211> LENGTH: 20
<212> TYPE: DNA
<213> ORGANISM: Homo sapiens

<400> SEQUENCE: 95
gcacggaaaa tacagcgttt          20

<210> SEQ ID NO 96
<211> LENGTH: 20
<212> TYPE: DNA
<213> ORGANISM: Homo sapiens

<400> SEQUENCE: 96
gccagcttat cagcttttgc          20

<210> SEQ ID NO 97
<211> LENGTH: 21
<212> TYPE: DNA
<213> ORGANISM: Mus musculus

<400> SEQUENCE: 97
ccaaatctcc acggtctgtt c          21

<210> SEQ ID NO 98
<211> LENGTH: 21
<212> TYPE: DNA
<213> ORGANISM: Mus musculus

<400> SEQUENCE: 98
atcagggtat cctctcccca g          21

<210> SEQ ID NO 99
<211> LENGTH: 22
<212> TYPE: DNA
<213> ORGANISM: Homo sapiens

<400> SEQUENCE: 99
ggtgatgttg agaaaaggca ag          22

<210> SEQ ID NO 100

```
<211> LENGTH: 20
<212> TYPE: DNA
<213> ORGANISM: Homo sapiens

<400> SEQUENCE: 100
gttcttattg gcggctgtgt                                              20

<210> SEQ ID NO 101
<211> LENGTH: 20
<212> TYPE: DNA
<213> ORGANISM: Mus musculus

<400> SEQUENCE: 101
acgaaatcaa caaccccgta                                              20

<210> SEQ ID NO 102
<211> LENGTH: 20
<212> TYPE: DNA
<213> ORGANISM: Mus musculus

<400> SEQUENCE: 102
ggcagaacga ctcggttatc                                              20

<210> SEQ ID NO 103
<211> LENGTH: 20
<212> TYPE: DNA
<213> ORGANISM: Homo sapiens

<400> SEQUENCE: 103
ttcatgatca cgccctcata                                              20

<210> SEQ ID NO 104
<211> LENGTH: 20
<212> TYPE: DNA
<213> ORGANISM: Homo sapiens

<400> SEQUENCE: 104
taaaggatgc gtagggatgg                                              20

<210> SEQ ID NO 105
<211> LENGTH: 20
<212> TYPE: DNA
<213> ORGANISM: Mus musculus

<400> SEQUENCE: 105
accaagcgaa tgctggacat                                              20

<210> SEQ ID NO 106
<211> LENGTH: 17
<212> TYPE: DNA
<213> ORGANISM: Mus musculus

<400> SEQUENCE: 106
ggcggagaag ccctgaa                                                 17

<210> SEQ ID NO 107
<211> LENGTH: 19
<212> TYPE: DNA
<213> ORGANISM: Homo sapiens

<400> SEQUENCE: 107
ccgcgctcgt tatcatgtg                                               19
```

```
<210> SEQ ID NO 108
<211> LENGTH: 23
<212> TYPE: DNA
<213> ORGANISM: Homo sapiens

<400> SEQUENCE: 108
cgttcttttc gtagtcccac ttg                                              23

<210> SEQ ID NO 109
<211> LENGTH: 21
<212> TYPE: DNA
<213> ORGANISM: Mus musculus

<400> SEQUENCE: 109
aaacccatca ccatcttcca g                                                21

<210> SEQ ID NO 110
<211> LENGTH: 21
<212> TYPE: DNA
<213> ORGANISM: Mus musculus

<400> SEQUENCE: 110
aggggccatc cacagtcttc t                                                21

<210> SEQ ID NO 111
<211> LENGTH: 21
<212> TYPE: DNA
<213> ORGANISM: Homo sapiens

<400> SEQUENCE: 111
aaacccatca ccatcttcca g                                                21

<210> SEQ ID NO 112
<211> LENGTH: 21
<212> TYPE: DNA
<213> ORGANISM: Homo sapiens

<400> SEQUENCE: 112
aggggccatc cacagtcttc t                                                21

<210> SEQ ID NO 113
<211> LENGTH: 20
<212> TYPE: DNA
<213> ORGANISM: Mus musculus

<400> SEQUENCE: 113
tggaaagctc cgagttcagt                                                  20

<210> SEQ ID NO 114
<211> LENGTH: 20
<212> TYPE: DNA
<213> ORGANISM: Mus musculus

<400> SEQUENCE: 114
ccttgtctga ggttgggtgt                                                  20

<210> SEQ ID NO 115
<211> LENGTH: 20
<212> TYPE: DNA
<213> ORGANISM: Homo sapiens

<400> SEQUENCE: 115
cagcagtatg gtgcagcgga                                                  20
```

```
<210> SEQ ID NO 116
<211> LENGTH: 20
<212> TYPE: DNA
<213> ORGANISM: Homo sapiens

<400> SEQUENCE: 116
tcaaatacgg cactgcactc                                          20

<210> SEQ ID NO 117
<211> LENGTH: 20
<212> TYPE: DNA
<213> ORGANISM: Mus musculus

<400> SEQUENCE: 117
agttggactc tggagcagga                                          20

<210> SEQ ID NO 118
<211> LENGTH: 20
<212> TYPE: DNA
<213> ORGANISM: Mus musculus

<400> SEQUENCE: 118
gctgctgtgt tgagcttcag                                          20

<210> SEQ ID NO 119
<211> LENGTH: 22
<212> TYPE: DNA
<213> ORGANISM: Homo sapiens

<400> SEQUENCE: 119
gctggaattt ccggtgtaaa cc                                       22

<210> SEQ ID NO 120
<211> LENGTH: 19
<212> TYPE: DNA
<213> ORGANISM: Homo sapiens

<400> SEQUENCE: 120
ggggtccaag atggcctct                                           19

<210> SEQ ID NO 121
<211> LENGTH: 27
<212> TYPE: DNA
<213> ORGANISM: Artificial sequence
<220> FEATURE:
<223> OTHER INFORMATION: PARIS C458A - Foward

<400> SEQUENCE: 121
acctgcgcca cggctgggaa gagcttc                                  27

<210> SEQ ID NO 122
<211> LENGTH: 27
<212> TYPE: DNA
<213> ORGANISM: Artificial sequence
<220> FEATURE:
<223> OTHER INFORMATION: PARIS C458A - Reverse

<400> SEQUENCE: 122
gaagctcttc ccagccgtgg cgcaggt                                  27

<210> SEQ ID NO 123
<211> LENGTH: 27
<212> TYPE: DNA
<213> ORGANISM: Artificial sequence
```

```
<220> FEATURE:
<223> OTHER INFORMATION: PARIS C518A - Forward

<400> SEQUENCE: 123
agcctgagcg cggcccagcg cagctgt                                        27

<210> SEQ ID NO 124
<211> LENGTH: 27
<212> TYPE: DNA
<213> ORGANISM: Artificial sequence
<220> FEATURE:
<223> OTHER INFORMATION: PARIS C518A - Reverse

<400> SEQUENCE: 124
acagctgcgc tgggccgcgc tcaggct                                        27

<210> SEQ ID NO 125
<211> LENGTH: 27
<212> TYPE: DNA
<213> ORGANISM: Artificial sequence
<220> FEATURE:
<223> OTHER INFORMATION: PARIS C543A - Forward

<400> SEQUENCE: 125
gagtgcggcc gtgccttcac gcgcccc                                        27

<210> SEQ ID NO 126
<211> LENGTH: 27
<212> TYPE: DNA
<213> ORGANISM: Artificial sequence
<220> FEATURE:
<223> OTHER INFORMATION: PARIS C543A - Reverse

<400> SEQUENCE: 126
ggggcgcgtg aaggcacggc cgcactc                                        27

<210> SEQ ID NO 127
<211> LENGTH: 27
<212> TYPE: DNA
<213> ORGANISM: Artificial sequence
<220> FEATURE:
<223> OTHER INFORMATION: PARIS C571A, forward

<400> SEQUENCE: 127
cacctcatcc gcgctcgcat gctgcac                                        27

<210> SEQ ID NO 128
<211> LENGTH: 27
<212> TYPE: DNA
<213> ORGANISM: Artificial sequence
<220> FEATURE:
<223> OTHER INFORMATION: PARIS C571A, reverse

<400> SEQUENCE: 128
gtgcagcatg cgagcgcgga tgaggtg                                        27

<210> SEQ ID NO 129
<211> LENGTH: 30
<212> TYPE: DNA
<213> ORGANISM: Artificial sequence
<220> FEATURE:
<223> OTHER INFORMATION: PARIS H471A, forward

<400> SEQUENCE: 129
ttcccctgca ccgaggctga gaagcgcttc                                     30
```

<210> SEQ ID NO 130
<211> LENGTH: 30
<212> TYPE: DNA
<213> ORGANISM: Artificial sequence
<220> FEATURE:
<223> OTHER INFORMATION: PARIS H471A, reverse

<400> SEQUENCE: 130
gaagcgcttc tcagcctcgg tgcagggaa                              30

<210> SEQ ID NO 131
<211> LENGTH: 27
<212> TYPE: DNA
<213> ORGANISM: Artificial sequence
<220> FEATURE:
<223> OTHER INFORMATION: PARIS H528A, forward

<400> SEQUENCE: 131
cactaccgaa cggccacggg cgtgcgg                                27

<210> SEQ ID NO 132
<211> LENGTH: 27
<212> TYPE: DNA
<213> ORGANISM: Artificial sequence
<220> FEATURE:
<223> OTHER INFORMATION: PARIS H528A, reverse

<400> SEQUENCE: 132
ccgcacgccc gtggccgttc ggtagtg                                27

<210> SEQ ID NO 133
<211> LENGTH: 27
<212> TYPE: DNA
<213> ORGANISM: Artificial sequence
<220> FEATURE:
<223> OTHER INFORMATION: PARIS H560A, forward

<400> SEQUENCE: 133
acctgcaccg tcgccggcaa aagcttc                                27

<210> SEQ ID NO 134
<211> LENGTH: 27
<212> TYPE: DNA
<213> ORGANISM: Artificial sequence
<220> FEATURE:
<223> OTHER INFORMATION: PARIS H560A, forward

<400> SEQUENCE: 134
gaagcttttg ccggcgacgg tgcaggt                                27

<210> SEQ ID NO 135
<211> LENGTH: 27
<212> TYPE: DNA
<213> ORGANISM: Artificial sequence
<220> FEATURE:
<223> OTHER INFORMATION: PARIS H584A, forward

<400> SEQUENCE: 135
cacctccgca aggcccagcg caaccat                                27

<210> SEQ ID NO 136
<211> LENGTH: 27
<212> TYPE: DNA
<213> ORGANISM: Artificial sequence
<220> FEATURE:
<223> OTHER INFORMATION: PARIS H584A, reverse

```
<400> SEQUENCE: 136
atggttgcgc tgggccttgc ggaggtg                                           27

<210> SEQ ID NO 137
<211> LENGTH: 26
<212> TYPE: DNA
<213> ORGANISM: Homo sapiens

<400> SEQUENCE: 137 ctatatttt atatttttgt tttata                                             26

<210> SEQ ID NO 138
<211> LENGTH: 26
<212> TYPE: DNA
<213> ORGANISM: Homo sapiens

<400> SEQUENCE: 138
atatttatta taatttattt taaata                                            26

<210> SEQ ID NO 139
<211> LENGTH: 26
<212> TYPE: DNA
<213> ORGANISM: Homo sapiens

<400> SEQUENCE: 139
ttatttttaa ttttttttgt ttaata                                            26

<210> SEQ ID NO 140
<211> LENGTH: 26
<212> TYPE: DNA
<213> ORGANISM: Homo sapiens

<400> SEQUENCE: 140
ttatttttat tttttgtta ctaata                                             26

<210> SEQ ID NO 141
<211> LENGTH: 26
<212> TYPE: DNA
<213> ORGANISM: Homo sapiens

<400> SEQUENCE: 141
taatacaaat attattttgt ttaata                                            26

<210> SEQ ID NO 142
<211> LENGTH: 26
<212> TYPE: DNA
<213> ORGANISM: Homo sapiens

<400> SEQUENCE: 142
ttatatttat tttgttttat tttata                                            26

<210> SEQ ID NO 143
<211> LENGTH: 26
<212> TYPE: DNA
<213> ORGANISM: Homo sapiens

<400> SEQUENCE: 143
ttgtatttat tttgttttat tttata                                            26

<210> SEQ ID NO 144
<211> LENGTH: 27
<212> TYPE: DNA
```

<210> SEQ ID NO 145
<211> LENGTH: 26
<212> TYPE: DNA
<213> ORGANISM: Homo sapiens

<400> SEQUENCE: 144
tgttatttat tttttattat ttttata                                    27

<210> SEQ ID NO 145
<211> LENGTH: 26
<212> TYPE: DNA
<213> ORGANISM: Homo sapiens

<400> SEQUENCE: 145
tatttttaat gtattgttac ttatta                                     26

<210> SEQ ID NO 146
<211> LENGTH: 26
<212> TYPE: DNA
<213> ORGANISM: Homo sapiens

<400> SEQUENCE: 146 taatttgta tttttgttat taatta                                      26

<210> SEQ ID NO 147
<211> LENGTH: 26
<212> TYPE: DNA
<213> ORGANISM: Homo sapiens

<400> SEQUENCE: 147
attatatatt ttttgttttt tttata                                     26

<210> SEQ ID NO 148
<211> LENGTH: 26
<212> TYPE: DNA
<213> ORGANISM: Homo sapiens

<400> SEQUENCE: 148
taatgtttat tttttatatt ttatta                                     26

<210> SEQ ID NO 149
<211> LENGTH: 26
<212> TYPE: DNA
<213> ORGANISM: Homo sapiens

<400> SEQUENCE: 149 tattttttgtt aatttatttg ttatta                                    26

<210> SEQ ID NO 150
<211> LENGTH: 26
<212> TYPE: DNA
<213> ORGANISM: Homo sapiens

<400> SEQUENCE: 150
tattgtttgt tattattttt attata                                     26

<210> SEQ ID NO 151
<211> LENGTH: 26
<212> TYPE: DNA
<213> ORGANISM: Homo sapiens

<400> SEQUENCE: 151 taatttttgta tttttgttat taatta                                    26

<210> SEQ ID NO 152
<211> LENGTH: 26

```
<212> TYPE: DNA
<213> ORGANISM: Homo sapiens

<400> SEQUENCE: 152
tattgtttgt tattattttt attata                                              26
```